(12) United States Patent
Loosmore et al.

(10) Patent No.: US 7,118,749 B2
(45) Date of Patent: *Oct. 10, 2006

(54) TRANSFERRIN RECEPTOR GENES

(75) Inventors: Sheena M. Loosmore, Aurora (CA);
Robin E. Harkness, Willowdale (CA);
Anthony B. Schryvers, Calgary (CA);
Pele Chong, Richmond Hill (CA);
Scott Gray-Owen, Calgary (CA);
Yan-Ping Yang, Willowdale (CA);
Andrew D. Murdin, Newmarket (CA);
Michel H. Klein, Willowdale (CA)

(73) Assignee: Connaught Laboratories Limited, Toronto (CA)

( * ) Notice: Subject to any disclaimer, the term of this patent is extended or adjusted under 35 U.S.C. 154(b) by 270 days.

This patent is subject to a terminal disclaimer.

(21) Appl. No.: 10/043,344

(22) Filed: Jan. 14, 2002

(65) Prior Publication Data

US 2003/0088086 A1 May 8, 2003

Related U.S. Application Data

(63) Continuation of application No. 08/649,518, filed on May 17, 1996, now Pat. No. 6,361,779, which is a continuation-in-part of application No. 08/483,577, filed on Jun. 7, 1995, now Pat. No. 6,015,688, which is a continuation-in-part of application No. 08/337,483, filed on Nov. 8, 1994, now Pat. No. 5,922,562, which is a continuation-in-part of application No. 08/175,116, filed on Dec. 29, 1993, now abandoned, which is a continuation-in-part of application No. 08/148,968, filed on Nov. 8, 1993, now abandoned.

(51) Int. Cl.
*A61K 51/00* (2006.01)
*A61K 39/395* (2006.01)
*A61K 39/00* (2006.01)
*A61K 39/02* (2006.01)
*A61K 39/38* (2006.01)

(52) U.S. Cl. ............... 424/190.1; 424/1.11; 424/130.1; 424/178.1; 424/184.1; 424/185.1; 424/190.1; 424/200.1; 424/234.1; 424/256.1; 424/278.1; 424/282.1; 424/404; 435/69.3; 435/71.3; 436/85; 436/86; 514/2; 930/10; 930/200

(58) Field of Classification Search ............... 424/1.11, 424/130.1, 178.1, 184.1, 185.1, 190.1, 200.1, 424/234.1, 256.1, 278.1, 282.1, 404; 435/69.3, 435/71.3; 436/85, 86; 514/2; 930/10, 200
See application file for complete search history.

(56) References Cited

U.S. PATENT DOCUMENTS 4,258,029 A    3/1981   Moloney et al.
(Continued)

FOREIGN PATENT DOCUMENTS

WO    WO 92/17167    10/1992
WO    WO 94/12641    6/1994
WO    WO 95/13370    5/1995

OTHER PUBLICATIONS

Holland et al. 1992. Infect. and Immun. vol. 60, No. 7: 2986-2991.*

(Continued)

*Primary Examiner*—Nita Minnifield
*Assistant Examiner*—J. Hines
(74) *Attorney, Agent, or Firm*—Sanofi Pasteur Inc.

(57) ABSTRACT

Purified and isolated nucleic acid is provided which encodes a transferrin receptor protein of a strain of *Haemophilus* or a fragment or an analog of the transferrin receptor protein. The nucleic acid sequence may be used to produce peptides free of contaminants derived from bacteria normally containing the Tbp1 or Tbp2 proteins for purposes of diagnostics and medical treatment. Furthermore, the nucleic acid molecule may be used in the diagnosis of infection. Also provided are recombinant Tbp1 or Tbp2 and methods for purification of the same. Live vectors expressing epitopes of transferrin receptor protein for vaccination are provided.

6 Claims, 144 Drawing Sheets

U.S. PATENT DOCUMENTS

| | | | |
|---|---|---|---|
| 4,496,538 | A | 1/1985 | Gordon |
| 4,596,792 | A | 6/1986 | Vyas |
| 4,599,230 | A | 7/1986 | Milich et al. |
| 4,599,231 | A | 7/1986 | Milich et al. |
| 4,601,903 | A | 7/1986 | Frasch |
| 4,855,283 | A | 8/1989 | Lockhoff et al. |
| 4,952,496 | A | 8/1990 | Studier et al. |
| 5,141,743 | A * | 8/1992 | Schryvers ................ 424/234.1 |
| 5,194,254 | A | 3/1993 | Barber et al. |

OTHER PUBLICATIONS

Gerlach et al. 1992. Infect. and Immun. vol. 60, No. 8: 3253-3261.*
Barcak et al, (1991) Methods Enzymol. 204: 321-342.
Berkowitz et al, (1987) J. Pediatr. 110:509.
Black et al, (1991) Pediatr. Infect. Dis. J. 10:97.
Bluestone, N. (1982) Engl. J. Med. 306;1399.
Chang et al, (1978) Nature 375:615.
Claesson et al, (1989) J. Pediatr. 114:97.
Cornelissen et al, (1992) J. Bacteriol. 174:5788.
Danve, et al, (1993) Vaccine 11, 1214-1220.
Deres et al, (1989) Nature 342:651.
Gerlach et al. (1992) Infect. Immun. 608:325.
Goeddel et al, (1979) Nature 281:544.
Chou et al, (1978) Annual Reviews of Biochemistry 47, 251-276.
Harkness et al, (1992) J. Bacteriol. 174:2425.
Holland et al, (1992) Infect. Immun. 60:2986.
Hopp, T.P., (1986) Journal of Immunological Methods 88:1-18.
Itakura et al, (1977) Science 198:1056.
Jarosik et al, (1994) Infection and Immunity 62:2470-2477.
Legrain et al, (1993) Gene 130:73.
Lockhoff et al. (1991) Chem. Int. Ed. Engl. 30:1611.
Mickelsen and Sparling, (1981) Infect. Immun. 33:555.
Morton et al, (1993) Infection and Immunity 61: 4033-4037.
Murdin et al, (1992) J. Gen. Viral 73:607.
Murdin et al, (1991) Microbial Pathogenesis 10:27.
Nixon-George et al (1990) J. Immunol. 14:4798.
Ogunnariwo et al, (1992) Avian Dis. 36:655.
O'Hagan (1992) Clin. Pharmokinet. 22:1.
Panezutti et al, (1993) Infection and Immunity, 61:1867-1872.
Roosi-Campos et al, (1992) Vaccine 10,:512-518.
Schryvers, (1988) Molec. Microbiol. 2:467.
Schryvers and Lee, (1989) Can. J. Microbiol. 35:409.
Schryvers and Gray-Owen, (1992) J. Infect. Dis. 165 suppl 1:S103.
Schryvers (1989) Med. Microbiol. 29:121.
Short et al, (1988) Nucl. Acids Res. 16:7583.
Ulmer et al (1993) Curr. Opinion Invest. Drugs. 2(9):983-989.
VanderWerf et al, (1986) Proc. Natl. Acad. Sci. 83:2330.
Weismuller et al, (1989) Vaccine 8:29.
Wilton et al, (1993) FEMS Microbiology Letters 107:59-66.
Sambrook et al, Molecular Cloning, A Lab Manual. vol. 3, p. 16.2, 16.3 and p. 17.2-17.28.
Ghrayeb et al, Embo J. vol. 3, p. 2437-42, (1984).
Thomas et al, Methods in Enzymology, vol. 182, p. 499-520, (1990).
Gray-Owen et al, Infect. Immun., vol. 63; No. 4 (1995) pp. 1201-1210.
Griffiths et al, Fems Microbiol. Lett. vol. 109, No. 1—May 1993, pp. 85-91.

* cited by examiner

FIG. 3A.

TATAACTCA ATG AAA TCT GTA CCT CTT ATC TCT GGT GGA CTT TCC TTT
          Met Lys Ser Val Pro Leu Ile Ser Gly Gly Leu Ser Phe
           1                   5                          10

TTA CTA AGT GCT TGT AGC GGA GGG GGG TCT TTT GAT GTA GAT AAC GTC
Leu Leu Ser Ala Cys Ser Gly Gly Gly Ser Phe Asp Val Asp Asn Val
             15                  20                  25

TCT AAT ACC CCC TCT TCT AAA CCA CGT TAT CAA GAC GAT ACT TCA AGT
Ser Asn Thr Pro Ser Ser Lys Pro Arg Tyr Gln Asp Asp Thr Ser Ser
 30                  35                  40                  45

TCA AGA ACA AAA TCT AAA TTG GAA AAG TTG TCC ATT CCT TCT TTA GGG
Ser Arg Thr Lys Ser Lys Leu Glu Lys Leu Ser Ile Pro Ser Leu Gly
             50                  55                  60

GGA GGG AAG TTA GCG GCT CTG AAT CTT TTT GAT AGG AAC AAA CCT
Gly Gly Met Lys Leu Ala Ala Leu Asn Leu Phe Asp Arg Asn Lys Pro
 65                  70                  75

AGT CTC TTA AAT GAA GAT AGC TAT ATG ATA TTT TCC TCA CGT TCT ACG
Ser Leu Leu Asn Glu Asp Ser Tyr Met Ile Phe Ser Ser Arg Ser Thr
             80                  85                  90

FIG. 3B.

ATT GAA GAG GAT GTT AAA AAT GAC AAT CAA AAC GGC GAG CAC CCT ATT
Ile Glu Glu Asp Val Lys Asn Asp Asn Gln Asn Gly Glu His Pro Ile
95                      100                     105

GAC TCA ATA GTC GAT CCT AGA GCA CCA AAT TCA AAC GAA AAT CGT CAT
Asp Ser Ile Val Asp Pro Arg Ala Pro Asn Ser Asn Glu Asn Arg His
110                     115                     120             125

GGA CAA AAA TAT GTA TAT TCA GGG CTT TAT TAT ATT CAA TCG TGG AGT
Gly Gln Lys Tyr Val Tyr Ser Gly Leu Tyr Tyr Ile Gln Ser Trp Ser
                130                     135                     140

CTA AGA GAT TTA CCA AAT AAA AAG TTT TAT TCA GGT TAC TAT GGA TAT
Leu Arg Asp Leu Pro Asn Lys Lys Phe Tyr Ser Gly Tyr Tyr Gly Tyr
        145                     150                     155

GCG TAT TAC TTT GGC AAT ACA ACT GCC TCT GCA TTA CCT GTA GGT GGC
Ala Tyr Tyr Phe Gly Asn Thr Thr Ala Ser Ala Leu Pro Val Gly Gly
160                     165                     170

GTA GCA ACG TAT AAA GGA ACT TGG AGC TTC ATC ACC GCA GCT GAA AAT
Val Ala Thr Tyr Lys Gly Thr Trp Ser Phe Ile Thr Ala Ala Glu Asn
175                     180                     185

FIG. 3C.

GGC AAG AAT TAT GAA TTG TTA AGA AAT TCT GGT GGC GGT CAA GCT TAT
Gly Lys Asn Tyr Glu Leu Leu Arg Asn Ser Gly Gly Gly Gln Ala Tyr
190                     195                     200                     205

TCT CGA CGT AGT GCT ACT CCA GAA GAT ATT GAT TTA GAT CGT AAG ACG
Ser Arg Arg Ser Ala Thr Pro Glu Asp Ile Asp Leu Asp Arg Lys Thr
210                     215                     220

GGC TTA ACA AGT GAA TTT ACT GTC AAT TTT GGT ACA AAA AAG CTC ACT
Gly Leu Thr Ser Glu Phe Thr Val Asn Phe Gly Thr Lys Lys Leu Thr
225                     230                     235

GGA GGA CTT TAT TAT AAT TTA CGT GAA ACA GAT GCT AAT AAA TCA CAA
Gly Gly Leu Tyr Tyr Asn Leu Arg Glu Thr Asp Ala Asn Lys Ser Gln
240                     245                     250

AAT AGA ACA CAT AAA CTC TAC GAT CTA GAA GCT GAT GTT CAT AGC AAC
Asn Arg Thr His Lys Leu Tyr Asp Leu Glu Ala Asp Val His Ser Asn
255                     260                     265

CGA TTC AGG GGT AAA GTA AAG CCA ACC AAA AAA GAG TCT TCT GAA GAA
Arg Phe Arg Gly Lys Val Lys Pro Thr Lys Lys Glu Ser Ser Glu Glu
270                     275                     280                     285

FIG. 3D.

CAT CCC TTT ACC AGC GAG GGA ACA TTA GAA GGT GGT TTT TAC GGG CCT
His Pro Phe Thr Ser Glu Gly Thr Leu Glu Gly Gly Phe Tyr Gly Pro
              290                         295                         300

GAG GGT CAA GAA TTA GGA GGA AAG TTT TTA GCT CAC GAC AAA AAA GTT
Glu Gly Gln Glu Leu Gly Gly Lys Phe Leu Ala His Asp Lys Lys Val
              305                         310                         315

TTG GGG GTA TTT AGT GCC AAA GAA CAG CAA GAA ACG TCA GAA AAC AAA
Leu Gly Val Phe Ser Ala Lys Glu Gln Glu Thr Ser Glu Asn Lys
              320                         325                         330

AAA TTA CCC AAA GAA ACC TTA ATT GAT GGC AAG CTA ACT ACT TTT AAA
Lys Leu Pro Lys Glu Thr Leu Ile Asp Gly Lys Leu Thr Thr Phe Lys
              335                         340                         345

ACA ACC AAT GCA ACA ACA GCC AAT GCA ACA ACC GAT GCA ACA ACC AGT ACA
Thr Thr Asn Ala Thr Thr Ala Asn Ala Thr Thr Asp Ala Thr Thr Ser Thr
              350                         355                         360                         365

ACA GCC AGT ACA AAA ACC GAT ACA ACC AAT GCA ACA ACA GCC AAT ACA
Thr Ala Ser Thr Lys Thr Asp Thr Thr Asn Ala Thr Thr Ala Asn Thr
              370                         375                         380

FIG. 3E.

GAA AAC TTT ACG ACA AAA GAT ATA CCA AGT TTG GGT GAA GCT GAT TAT
Glu Asn Phe Thr Thr Lys Asp Ile Pro Ser Leu Gly Glu Ala Asp Tyr
                385                 390                 395

CTT TTA ATT GAT AAT TAC CCT GTT CCT GAG TTC CCT GAG AGT GGT GAT
Leu Leu Ile Asp Asn Tyr Pro Val Pro Glu Phe Pro Glu Ser Gly Asp
            400                 405                 410

TTC ATA AGT AGT AAG CAC CAT ACT GTA GGA AAG AAA ACC TAT CAA GTA
Phe Ile Ser Ser Lys His His Thr Val Gly Lys Lys Thr Tyr Gln Val
        415                 420                 425

GAA GCA TGT TGC AGT AAT CTA AGC TAT GTA AAA TTT GGT ATG TAT TAT
Glu Ala Cys Cys Ser Asn Leu Ser Tyr Val Lys Phe Gly Met Tyr Tyr
    430                 435                 440                 445

GAA GCC CCA CCT AAA GAA GAA AAA GAA AAA GAA AAA GAC AAA GAC
Glu Ala Pro Pro Lys Glu Glu Lys Glu Lys Glu Lys Asp Lys Asp
                450                 455                 460

AAA GAA AAA GAA AAA CAA GCG ACA ACA TCT ATC AAG ACT TAT TAT CAA
Lys Glu Lys Glu Lys Gln Ala Thr Thr Ser Ile Lys Thr Tyr Tyr Gln
465                 470                 475

FIG. 3F.

TTC TTA GGT CTC CGT ACT CCC AGT TCT GAA ATA CCT AAA GAA GGA
Phe Leu Gly Leu Arg Thr Pro Ser Ser Glu Ile Pro Lys Glu Gly
480                         485                          490

AGT GCA AAA TAT CAT GGT AAT TGG TTT GGT TAT ATT AGT GAT GGC GAG
Ser Ala Lys Tyr His Gly Asn Trp Phe Gly Tyr Ile Ser Asp Gly Glu
495                         500                          505

ACA TCT TAC TCC GCC AGT GGT GAT AAG GAA CGC AGT AAA AAT GCT GTC
Thr Ser Tyr Ser Ala Ser Gly Asp Lys Glu Arg Ser Lys Asn Ala Val
510                         515                          520                   525

GCC GAG TTT AAT GTA AAT TTT GCC GAG AAA ACA TTA ACA GGC GAA TTA
Ala Glu Phe Asn Val Asn Phe Ala Glu Lys Thr Leu Thr Gly Glu Leu
530                         535                          540

AAA CGA CAC GAT ACT CAA AAT CCC GTA TTT AAA ATT AAT GCA ACC TTT
Lys Arg His Asp Thr Gln Asn Pro Val Phe Lys Ile Asn Ala Thr Phe
545                         550                          555

CAA AGT GGT AAG AAT GAC TTC ACT GGT ACA GCA ACC GCA AAA GAT TTA
Gln Ser Gly Lys Asn Asp Phe Thr Gly Thr Ala Thr Ala Lys Asp Leu
560                         565                          570

FIG. 3G.

GCA ATA GAT GGT AAA AAT ACA CAA GGC ACA TCT AAA GTC AAT TTC ACG
Ala Ile Asp Gly Lys Asn Thr Gln Gly Thr Ser Lys Val Asn Phe Thr
575                     580                     585

GCA ACA GTA AAC GGG GCA TTT TAT GGT CCG CAC GCT ACA GAA TTA GGC
Ala Thr Val Asn Gly Ala Phe Tyr Gly Pro His Ala Thr Glu Leu Gly
590                     595                     600                 605

GGT TAT TTC ACC TAT AAC GGA AAC AAT CCT ACA GAT AAA AAT TCA TCA
Gly Tyr Phe Thr Tyr Asn Gly Asn Asn Pro Thr Asp Lys Asn Ser Ser
610                     615                     620

TCC AAT TCA GAA AAG GCA AGA GCT GCC GTT GTG TTT GGA GCT AAA AAA
Ser Asn Ser Glu Lys Ala Arg Ala Ala Val Val Phe Gly Ala Lys Lys
625                     630                     635

CAA CAA GTA GAA ACA ACC AA  GTAATGAAT ACTAAA A ATG ACT AAA AAA
Gln Gln Val Glu Thr Thr Lys                    Met Thr Lys Lys
640                                             645

CCC TAT TTT CGC CTA AGT ATT ATT TCT TGT CTT TTA ATT TCA TGC TAT
Pro Tyr Phe Arg Leu Ser Ile Ile Ser Cys Leu Leu Ile Ser Cys Tyr
650                     655                     660

FIG. 3H.

GTA AAA GCA GAA ACT CAA AGT ATA AAA GAT ACA AAA GAA GCT ATA TCA
Val Lys Ala Glu Thr Gln Ser Ile Lys Asp Thr Lys Glu Ala Ile Ser
665                     670                 675                 680

TCT GAA GTG GAC ACT CAA AGT ACA GAA GAT TCA GAA TTA GAA ACT ATC
Ser Glu Val Asp Thr Gln Ser Thr Glu Asp Ser Glu Leu Glu Thr Ile
                685                 690                 695

TCA GTC ACT GCA GAA AAA GTT AGA GAT CGT AAA GAT AAT GAA GTA ACT
Ser Val Thr Ala Glu Lys Val Arg Asp Arg Lys Asp Asn Glu Val Thr
            700                 705                 710

GGA CTT GGC AAA ATT ATA AAA ACT AGT GAA AGT ATC AGC CGA GAA CAA
Gly Leu Gly Lys Ile Ile Lys Thr Ser Glu Ser Ile Ser Arg Glu Gln
715                 720                 725

GTA TTA AAT ATT CGT GAT CTA ACA CGC TAT GAT CCA GGG ATT TCA GTT
Val Leu Asn Ile Arg Asp Leu Thr Arg Tyr Asp Pro Gly Ile Ser Val
        730                 735                 740

GTA GAA CAA GGT CGC GGT GCA AGT TCT GGA TAT TCT ATT CGT GGT ATG
Val Glu Gln Gly Arg Gly Ala Ser Ser Gly Tyr Ser Ile Arg Gly Met
745                 750                 755                 760

FIG. 31.

GAC AGA AAT AGA GTT GCT TTA GTA GAT GGT TTA CCT CAA ACG CAA
Asp Arg Asn Arg Val Ala Leu Leu Val Asp Gly Leu Pro Gln Thr Gln
            765                 770                 775

TCT TAT GTA GTG CAA AGC CCT TTA GTT GCT CGT TCA GGA TAT TCT GGC
Ser Tyr Val Val Gln Ser Pro Leu Val Ala Arg Ser Gly Tyr Ser Gly
            780                 785                 790

ACT GGT GCA ATT AAT GAA ATT GAA TAT GAA AAT GTA AAG GCC GTC GAA
Thr Gly Ala Ile Asn Glu Ile Glu Tyr Glu Asn Val Lys Ala Val Glu
            795                 800                 805

ATA AGC AAG GGG AGT TCT TCT GAG TAT GGT GGA GCA CTA GCT
Ile Ser Lys Gly Gly Ser Ser Ser Glu Tyr Gly Asn Gly Ala Leu Ala
            810                 815                 820

GGT TCT GTA ACA TTT CAA AGC AAA TCA GCA GCC GAT ATC TTA GAA GGA
Gly Ser Val Thr Phe Gln Ser Lys Ser Ala Ala Asp Ile Leu Glu Gly
            825                 830                 835                 840

GAC AAA TCA TGG GGA ATT CAA ACT TAT TCA AGC AAA AAT
Asp Lys Ser Trp Gly Ile Gln Thr Lys Asn Ala Tyr Ser Ser Lys Asn
            845                 850                 855

FIG. 3J.

AAA GGC TTT ACC CAT TCT TTA GCT GTA GCA GGA AAA CAA GGT GGA TTT
Lys Gly Phe Thr His Ser Leu Ala Val Ala Gly Lys Gln Gly Gly Phe
860                       865                       870

GAA GGG GTC GCC ATT TAC ACT CAC CGA AAT TCA ATT GAA ACC CAA GTC
Glu Gly Val Ala Ile Tyr Thr His Arg Asn Ser Ile Glu Thr Gln Val
875                       880                       885

CAT AAA GAT GCA TTA AAA GGC GTG CAA AGT TAT GAT CGA TTC ATC GCC
His Lys Asp Ala Leu Lys Gly Val Gln Ser Tyr Asp Arg Phe Ile Ala
890                       895                       900

ACA ACA GAG GAT CAA TCT GCA TAC TTT GTG ATG CAA GAT GAG TGT CTA
Thr Thr Glu Asp Gln Ser Ala Tyr Phe Val Met Gln Asp Glu Cys Leu
905                       910                       915                       920

GAT GGT TAT GAC AAG TGT AAA ACT TCA CCC AAA CGA CCT GCG ACT TTA
Asp Gly Tyr Asp Lys Cys Lys Thr Ser Pro Lys Arg Pro Ala Thr Leu
925                       930                       935

TCC ACC CAA AGA GAA ACC GTT TCA GAT TAT ACG GGG GCT AAC
Ser Thr Gln Arg Glu Thr Val Ser Asp Tyr Thr Gly Ala Asn
940                       945                       950

FIG. 3K.

CGT ATC AAA CCT AAT CCA ATG AAA TAT GAA AGC CAG TCT TGG TTT TTA
Arg Ile Lys Pro Asn Pro Met Lys Tyr Glu Ser Gln Ser Trp Phe Leu
955                     960                     965

AGA GGA GGT TAT CAT TTT TCT GAA CAA CAC TAT ATT GGT GGT ATT TTT
Arg Gly Gly Tyr His Phe Ser Glu Gln His Tyr Ile Gly Gly Ile Phe
970                     975                     980

GAA TTC ACA CAA CAA AAA TTT GAT ATC CGT GAT ATG ACA TTT CCC GCT
Glu Phe Thr Gln Gln Lys Phe Asp Ile Arg Asp Met Thr Phe Pro Ala
985                     990                     995                     1000

TAT TTA AGG CCA ACA GAA GAC AAG GAT TTA CAA AGT CGC CCT TTT TAT
Tyr Leu Arg Pro Thr Glu Asp Lys Asp Leu Gln Ser Arg Pro Phe Tyr
                1005                    1010                    1015

CCA AAG CAA GAT TAT GGT GCA TAT CAA CAT ATT GGT GAT GGC AGA GGC
Pro Lys Gln Asp Tyr Gly Ala Tyr Gln His Ile Gly Asp Gly Arg Gly
                1020                    1025                    1030

GTT AAA TAT GCA AGT GGG CTT TAT TTC GAT GAA CAC CAT AGA AAA CAG
Val Lys Tyr Ala Ser Gly Leu Tyr Phe Asp Glu His His Arg Lys Gln
                1035                    1040                    1045

FIG. 3L.

CGT GTA GGT ATT GAA TAT ATT TAC GAA AAT AAG AAC AAA GCG GCC ATC
Arg Val Gly Ile Glu Tyr Ile Tyr Glu Asn Lys Asn Lys Ala Gly Ile
                1050                    1055                    1060

ATT GAC AAA GCG GTG TTA AGT GCT AAT CAA CAA ACA TAC TTG ACA
Ile Asp Lys Ala Val Leu Ser Ala Asn Gln Gln Thr Ser Tyr Leu Thr
                1065                    1070                    1075                1080

GTT ATA TGC GAC ATA CGC ATT GCA GTC TTT ATC CAT AAT CCA AGT AAG
Val Ile Cys Asp Ile Arg Ile Ala Val Phe Ile His Asn Pro Ser Lys
                1085                    1090                    1095

AAT TGC CGC CCA ACA CTT GAT AAA CCT TAT TCA TAC TAT CAT TCT GAT
Asn Cys Arg Pro Thr Leu Asp Lys Pro Tyr Ser Tyr Tyr His Ser Asp
                1100                    1105                    1110

AGA AAT GTT TAT AAA GAA AAA CAT AAC ATG TTG CAA TTG CTT AAT TTA GAG
Arg Asn Val Tyr Lys Glu Lys His Asn Met Leu Gln Leu Asn Leu Glu
                1115                    1120                    1125

AAA AAA ATT CAA CAA AAT TGG CTT ACT CAT CAA ATT GCC TTC AAT CTT
Lys Lys Ile Gln Gln Asn Trp Leu Thr His Gln Ile Ala Phe Asn Leu
                1130                    1135                    1140

FIG.3M.

GGT TTT GAT GAC TTT ACT TCC GCA CTT CAG CAT AAA GAT TAT TTA ACT
Gly Phe Asp Asp Phe Thr Ser Ala Leu Gln His Lys Asp Tyr Leu Thr
1145                          1150                          1155                     1160

CGA CGT GTT ATC GCT ACG GCA AGT AGT ATT TCA GAG AAA CGT GGT GAA
Arg Arg Val Ile Ala Thr Ala Ser Ser Ile Ser Glu Lys Arg Gly Glu
                    1165                          1170                          1175

GCA AGA AGA AAT GGT TTA CAA TCA AGT CCT TAC TTA TAC CCA ACA CCA
Ala Arg Arg Asn Gly Leu Gln Ser Ser Pro Tyr Leu Tyr Pro Thr Pro
               1180                          1185                          1190

AAA GCA GAG TTG GTA GGA GGA GAT CTT TGT AAT TAT CAA GGT AAG TCC
Lys Ala Glu Leu Val Gly Gly Asp Leu Cys Asn Tyr Gln Gly Lys Ser
                    1195                          1200                     1205

TCT AAT TAC AGT GAC TGT AAA GTG CGG TTA ATT AAA GGG AAA AAT TAT
Ser Asn Tyr Ser Asp Cys Lys Val Arg Leu Ile Lys Gly Lys Asn Tyr
          1210                          1215                          1220

TAT TTC GCA GCA CGC AAT AAT ATG GCA TTA GGG AAA TAC GTT GAT TTA
Tyr Phe Ala Ala Arg Asn Asn Met Ala Leu Gly Lys Tyr Val Asp Leu
     1225                          1230                          1235           1240

FIG. 3N.

GGT TTA GGT ATG AGG TAT GAC GTA TCT CGT ACA AAA GCT AAT GAA TCA
Gly Leu Gly Met Arg Tyr Asp Val Ser Arg Thr Lys Ala Asn Glu Ser
                        1245                        1250                      1255

ACT ATT AGT GTT GGT AAA TTT TCT TGG AAT ACT GTT ATT
Thr Ile Ser Val Gly Lys Phe Ser Trp Asn Thr Gly Ile
                        1260                        1265                      1270

GTC ATA AAA CCA ACG GAA TGG CTT GAT CTT TCT TAT CGC CTT TCT ACT
Val Ile Lys Pro Thr Glu Trp Leu Asp Leu Ser Tyr Arg Leu Ser Thr
                        1275                        1280                      1285

GGA TTT AGA AAT CCT AGT TTT GCT GAA ATG TAT GGT TGG CGG TAT GGT
Gly Phe Arg Asn Pro Ser Phe Ala Glu Met Tyr Gly Trp Arg Tyr Gly
                        1290                        1295                      1300

GGC AAG GAT ACC GAT GTT TAT ATA GGT AAA TTT AAG CCT GAA ACA TCT
Gly Lys Asp Thr Asp Val Tyr Ile Gly Lys Phe Lys Pro Glu Thr Ser
                        1305                        1310                      1315                      1320

CGT AAC CAA GAG TTT GGT CTC GCT CTA AAA GGG GAT TTT GGT AAT ATT
Arg Asn Gln Glu Phe Gly Leu Ala Leu Lys Gly Asp Phe Gly Asn Ile
                        1325                        1330                      1335

FIG. 30.

GAG ATC AGT CAT TTT AGT AAT GCT TAT CGA AAT CTT ATC GCC TTT GCT
Glu Ile Ser His Phe Ser Asn Ala Tyr Arg Asn Leu Ile Ala Phe Ala
                1340                              1345            1350

GAA GAA CTT AGT AAA AAT GGA ACT ACT GGA AAG GGC AAT TAT GGA TAT
Glu Glu Leu Ser Lys Asn Gly Thr Thr Gly Lys Gly Asn Tyr Gly Tyr
                1355                              1360            1365

CAT AAT GCA CAA AAT GCA AAA TTA GTT GGC GTA AAT ATA ACT GCG CAA
His Asn Ala Gln Asn Ala Lys Leu Val Gly Val Asn Ile Thr Ala Gln
                1370                              1375            1380

TTA GAT TTT AAT GGT TTA TGG AAA CGT ATT CCC TAC GGT TGG TAT GCA
Leu Asp Phe Asn Gly Leu Trp Lys Arg Ile Pro Tyr Gly Trp Tyr Ala
                1385                              1390            1395            1400

ACA TTT GCT TAT AAC CGA GTA AAA GTT AAA GAT CAA AAA ATC AAT GCT
Thr Phe Ala Tyr Asn Arg Val Lys Val Lys Asp Gln Lys Ile Asn Ala
                1405                              1410            1415

GGT TTA GCT TCC GTA AGC AGT TAT TTA TTT GAT GCC ATT CAG CCC AGC
Gly Leu Ala Ser Val Ser Ser Tyr Leu Phe Asp Ala Ile Gln Pro Ser
                1420                              1425            1430

FIG. 3P.

```
CGT TAT ATC ATT GGT TTA GGC TAT GAT CAT CCA AGT AAT ACT TGG GGA
Arg Tyr Ile Ile Gly Leu Gly Tyr Asp His Pro Ser Asn Thr Trp Gly
            1435                1440                    1445

ATT AAG ACA ATG TTT ACT CAA TCA AAA GCA AAA TCT CAA AAT GAA TTG
Ile Lys Thr Met Phe Thr Gln Ser Lys Ala Lys Ser Gln Asn Glu Leu
            1450                1455                    1460

CTA GGA AAA CGT GCA TTG GGT AAC AAT TCA AGG AAT GTA AAA TCA ACA
Leu Gly Lys Arg Ala Leu Gly Asn Asn Ser Arg Asn Val Lys Ser Thr
1465                1470                    1475                1480

AGA AAA CTT ACT CGG GCA TGG CAT ATC TTA GAT GTA TCG GGT TAT TAC
Arg Lys Leu Thr Arg Ala Trp His Ile Leu Asp Val Ser Gly Tyr Tyr
            1485                1490                    1495

ATG GTG AAT AGA AGT ATT TTG TTC CGA TTA GGA GTA TAT AAT TTA TTA
Met Val Asn Arg Ser Ile Leu Phe Arg Leu Gly Val Tyr Asn Leu Leu
            1500                1505                    1510

AAC TAT CGC TAT GTC ACT TGG GAA GCG GTG CGT CAA ACA GCA CAA GGT
Asn Tyr Arg Tyr Val Thr Trp Glu Ala Val Arg Gln Thr Ala Gln Gly
1515                1520                    1525
```

FIG. 3Q.

GCG GTC AAT CAA CAT CAA AAT GTT GGT AAC TAT ACT CGC TAC GCA GCA
Ala Val Asn Gln His Gln Asn Val Gly Asn Tyr Thr Arg Tyr Ala Ala
1530                          1535                     1540

TCA GGA CGA AAC TAT ACC TTA ACA TTA GAA ATG AAA TTC TAA
Ser Gly Arg Asn Tyr Thr Leu Thr Leu Glu Met Lys Phe
1545                     1550                1555

FIG. 4A.

```
GCCCAAGCTA CATTGGTTAA TGATAAGCCT ATAAATGATA AGAAGAAAT TTGTTTTACG
                                                       -35
CCATTTTCA TATTTTATCC ATGAACTTAA AAAACTCTAA CTTGACATTA TTACAAAAAA
                                         RBS
AGATCAATAA TGCGAATTAT TATCAATTTT GTATGAGTAT ATAATTCT ATG AAA TCT
                                                        Met Lys Ser
                                                            1

GTA CCT CTT ATC TCT GGT GGA CTT TCC TTT TTA CTA AGT GCT TGT AGC
Val Pro Leu Ile Ser Gly Gly Leu Ser Phe Leu Leu Ser Ala Cys Ser
                    5                      10                  15

GGA GGG GGG TCT TTT GAT GTA GAT AAC GTC TCT AAT ACC CCC TCT TCT
Gly Gly Gly Ser Phe Asp Val Asp Asn Val Ser Asn Thr Pro Ser Ser
                20                      25                      30                  35

AAA CCA CGT TAT CAA GAC GAT ACC TCG AAT CAA AGA AAA AAA TCT AAT
Lys Pro Arg Tyr Gln Asp Asp Thr Ser Asn Gln Arg Lys Lys Ser Asn
                    40                      45                  50

TTG AAA AAG TTG TTC ATT CCT TCT TTA GGA GGA GGG ATG AAA TTG GTG
Leu Lys Lys Leu Phe Ile Pro Ser Leu Gly Gly Gly Met Lys Leu Val
                    55                      60                  65
```

FIG.4B.

GCT CAG AAT CTT CGT GGT AAT AAA GAA CCT AGT TTC TTA AAT GAA GAT
Ala Gln Asn Leu Arg Gly Asn Lys Glu Pro Ser Phe Leu Asn Glu Asp
            70                      75                      80

GAC TAT ATA TCA TAT TTT TCC TCA CTT TCT ACG ATT GAA AAG GAT GTT
Asp Tyr Ile Ser Tyr Phe Ser Ser Leu Ser Thr Ile Glu Lys Asp Val
            85                      90                      95

AAA GAT AAC AAT AAA AAC GGG GCG GAC CTT ATT GGC TCA ATA GAC GAG
Lys Asp Asn Asn Lys Asn Gly Ala Asp Leu Ile Gly Ser Ile Asp Glu
100                     105                     110                 115

CCT AGT ACA ACA AAT CCA CCC GAA AAG CAT CAT GGA CAA AAA TAT GTA
Pro Ser Thr Thr Asn Pro Pro Glu Lys His His Gly Gln Lys Tyr Val
            120                     125                     130

TAT TCA GGG CTT TAT TAT ACT CCA TCG TGG AGT TTA AAC GAT TCT AAA
Tyr Ser Gly Leu Tyr Tyr Thr Pro Ser Trp Ser Leu Asn Asp Ser Lys
            135                     140                     145

AAC AAG TTT TAT TTA GGT TAC TAT GGA TAT GCG TTT TAT TAT GGT AAT
Asn Lys Phe Tyr Leu Gly Tyr Tyr Gly Tyr Ala Phe Tyr Tyr Gly Asn
            150                     155                     160

FIG. 4C.

AAA ACT GCA ACA AAC TTG CCA GTA AAC GGT GTA GCT AAA TAC AAA GGA
Lys Thr Ala Thr Asn Leu Pro Val Asn Gly Val Ala Lys Tyr Lys Gly
165                         170                         175

ACT TGG GAT TTC ATC ACT GCA ACT AAA AAT GGC AAA CGT TAT CCT TTG
Thr Trp Asp Phe Ile Thr Ala Thr Lys Asn Gly Lys Arg Tyr Pro Leu
180                         185                         190                 195

TTA AGT AAT GGC AGT CAC GCT TAT TAT CGA CGT AGT GCA ATT CCA GAA
Leu Ser Asn Gly Ser His Ala Tyr Tyr Arg Arg Ser Ala Ile Pro Glu
                200                         205                         210

GAT ATT GAT TTA GAA AAT GAT TCA AAG AAT GGT GAT ATA GGC TTA ATA
Asp Ile Asp Leu Glu Asn Asp Ser Lys Asn Gly Asp Ile Gly Leu Ile
        215                         220                         225

AGT GAA TTT AGT GCA GAT TTT GGG ACT AAA AAA CTG ACA GGA CAA CTG
Ser Glu Phe Ser Ala Asp Phe Gly Thr Lys Lys Leu Thr Gly Gln Leu
        230                         235                         240

TCT TAC ACC AAA AGA AAA ACT AAT CAA CCA TAT GAA AAG AAA AAA
Ser Tyr Thr Lys Arg Lys Thr Asn Gln Pro Tyr Glu Lys Lys Lys
245                         250                         255

FIG. 4D.

CTC TAT GAT ATA GAT GCC GAT ATT TAT AGT AAT AGA TTC AGG GGT ACA
Leu Tyr Asp Ile Asp Ala Asp Ile Tyr Ser Asn Arg Phe Arg Gly Thr
260                 265                 270                 275

GTA AAG CCA ACC GAA AAA GAT TCT GAA GAA CAT CCC TTT ACC AGC GAG
Val Lys Pro Thr Glu Lys Asp Ser Glu Glu His Pro Phe Thr Ser Glu
            280                 285                 290

GGA ACA TTA GAA GGT GGT TAT GGG CCT AAT GCT GAA GAA CTA GGG
Gly Thr Leu Glu Gly Gly Gly Phe Tyr Gly Pro Asn Ala Glu Leu Gly
        295                 300                 305

GGG AAA TTT TTA GCT ACG GAT AAC CGA GTT TTT GGG GTA TTT AGT GCC
Gly Lys Phe Leu Ala Thr Asp Asn Arg Val Phe Gly Val Phe Ser Ala
    310                 315                 320

AAA GAA ACG GAA GAA ACA AAA AAG GAA GCG TTA TCC AAG GAA ACC TTA
Lys Glu Thr Glu Glu Thr Lys Lys Glu Ala Leu Ser Lys Glu Thr Leu
325                 330                 335

ATT GAT GGC AAG CTA ATT ACT TTC TCT ACT AAA AAA ACC GAT GCA AAA
Ile Asp Gly Lys Leu Ile Thr Phe Ser Thr Lys Lys Thr Asp Ala Lys
340                 345                 350                 355

FIG. 4E.

ACC AAT GCA ACA ACC AGT ACC GCA GCT AAT ACA ACA GAT ACA ACC
Thr Asn Ala Thr Thr Ser Thr Ala Ala Asn Thr Thr Asp Thr Thr
            360                     365                 370

GCC AAT ACA ATA ACC GAT GAA AAA AAC TTT AAG ACG GAA GAT ATA TCA
Ala Asn Thr Ile Thr Asp Glu Lys Asn Phe Lys Thr Glu Asp Ile Ser
            375                     380                 385

AGT TTT GGT GAA GCT GAT TAT CTG TTA ATT GAC AAA TAT CCT ATT CCA
Ser Phe Gly Glu Ala Asp Tyr Leu Leu Ile Asp Lys Tyr Pro Ile Pro
            390                     395                 400

CTT TTA CCT GAT AAA AAT ACT AAT GAT TTC ATA AGT AGT AAG CAT CAT
Leu Leu Pro Asp Lys Asn Thr Asn Asp Phe Ile Ser Ser Lys His His
            405                     410                 415

ACT GTA GGA AAT AAA CGC TAT AAA GTG GAA GCA TGT TGC AGT AAT CTA
Thr Val Gly Asn Lys Arg Tyr Lys Val Glu Ala Cys Cys Ser Asn Leu
            420                     425                 430                 435

AGC TAT GTG AAA TTT GGT ATG TAT TAT GAA GAC CCA CTT AAA GAA AAA
Ser Tyr Val Lys Phe Gly Met Tyr Tyr Glu Asp Pro Leu Lys Glu Lys
            440                     445                 450

FIG. 4F.

```
GAA ACA GAA ACA GAA ACA GAA AAA GAC AAA GAA AAA GAA AAA
Glu Thr Glu Thr Glu Thr Glu Lys Asp Lys Glu Lys Glu Lys
                    455             460             465

GAA AAA GAC AAA GAC AAA GAA AAA CAA ACG GCG GCA ACG AAC ACT
Glu Lys Asp Lys Asp Lys Glu Lys Gln Thr Ala Thr Thr Asn Thr
                    470             475             480

TAT TAT CAA TTC TTA TTA GGT CAC CGT ACT CCC AAG GAC GAC ATA CCT
Tyr Tyr Gln Phe Leu Leu Gly His Arg Thr Pro Lys Asp Asp Ile Pro
                485             490             495

AAA ACA GGA AGT GCA AAA TAT CAT GGT AGT TGG TTT GGT TAT ATT ACT
Lys Thr Gly Ser Ala Lys Tyr His Gly Ser Trp Phe Gly Tyr Ile Thr
            500             505             510             515

GAC GGT AAG ACA TCT TAC TCC CCC AGT GGT GAT AAG AAA CGC GAT AAA
Asp Gly Lys Thr Ser Tyr Ser Pro Ser Gly Asp Lys Lys Arg Asp Lys
            520             525             530

AAT GCT GTC GCC GAG TTT AAT GTT GAT TTT GCC GAG AAA AAG CTA ACA
Asn Ala Val Ala Glu Phe Asn Val Asp Phe Ala Glu Lys Lys Leu Thr
            535             540             545
```

FIG. 4G.

GGC GAA TTA AAA CGA CAC GAT ACT GGA AAT CCC GTA TTT AGT ATT GAG
Gly Glu Leu Lys Arg His Asp Thr Gly Asn Pro Val Phe Ser Ile Glu
550                             555                             560

GCA AAC TTT AAT AAT AGT AGT GCC TTC ACT GGT ACA GCA ACC GCA
Ala Asn Phe Asn Asn Ser Ser Ala Phe Thr Gly Thr Ala Thr Ala
565                             570                             575

ACA AAT TTT GTA ATA GAT GGT AAA AAT AGT CAA AAT AAA AAT ACC CCA
Thr Asn Phe Val Ile Asp Gly Lys Asn Ser Gln Asn Lys Asn Thr Pro
580                             585                             590                             595

ATT AAT ATT ACA ACT AAA GTA AAC GGG GCA TTT TAT GGA CCT AAG GCT
Ile Asn Ile Thr Thr Lys Val Asn Gly Ala Phe Tyr Gly Pro Lys Ala
600                             605                             610

TCT GAA TTA GGC GGT TAT TTC ACT TAT AAC GGA AAT TCT ACA GCT ACA
Ser Glu Leu Gly Gly Tyr Phe Thr Tyr Asn Gly Asn Ser Thr Ala Thr
615                             620                             625

AAT TCT GAA AGT TCC TCA ACC GTA TCT TCA TCC AAT TCA AAA AAT
Asn Ser Glu Ser Ser Ser Thr Val Ser Ser Ser Asn Ser Lys Asn
630                             635                             640

FIG. 4H.

```
GCA AGA GCT GCA GTT GTC TTT GGT GCG AGA CAA CAA GTA GAA ACA ACC
Ala Arg Ala Ala Val Val Phe Gly Ala Arg Gln Gln Val Glu Thr Thr
645                              650                              655

AAA TAATGAATA CTAAAA ATG ACT AAA AAA CCC TAT TTT CGC CTA AGT
Lys                 Met Thr Lys Lys Pro Tyr Phe Arg Leu Ser
660                                    665                    670

ATT ATT TCT TGT CTT TTA ATT TCA TGC TAT GTA AAA GCA GAA ACT CAA
Ile Ile Ser Cys Leu Leu Ile Ser Cys Tyr Val Lys Ala Glu Thr Gln
              675                            680                  685

AGT ATA GAA GAT ACA AAA GAA GCT ATA TCA TCT GAA GTG GAC ACT CAA
Ser Ile Lys Asp Thr Lys Glu Ala Ile Ser Ser Glu Val Asp Thr Gln
          690                          695                    700

AGT ACA GAA GAT TCA GAA TTA GAA ACT ATC TCA GTC ACT GCA GAA AAA
Ser Thr Glu Asp Ser Glu Leu Glu Thr Ile Ser Val Thr Ala Glu Lys
              705                          710                  715

ATA AGA GAT CGT AAA GAT AAT GAA GTA ACT GGA CTT GGC AAA ATT ATC
Ile Arg Asp Arg Lys Asp Asn Glu Val Thr Gly Leu Gly Lys Ile Ile
          720                          725                  730
```

FIG.41.

```
AAA ACT AGT GAA AGT ATC AGC CGA GAA CAA GTA TTA AAT ATT CGT GAT
Lys Thr Ser Glu Ser Ile Ser Arg Glu Gln Val Leu Asn Ile Arg Asp
735                 740                 745                 750

CTA ACA CGC TAT GAT CCA GGG ATT TCA GTT GTA GAA CAA GGT CGC GGT
Leu Thr Arg Tyr Asp Pro Gly Ile Ser Val Val Glu Gln Gly Arg Gly
            755                 760                 765

GCA AGT TCT GGA TAT TCT ATT CGT GGT ATG GAC AGA AAT AGA GTT GCT
Ala Ser Ser Gly Tyr Ser Ile Arg Gly Met Asp Arg Asn Arg Val Ala
770                 775                 780

TTA TTA GTA GAT GGT TTA CCT CAA ACG CAA TCT TAT GTA GTG CAA AGC
Leu Leu Val Asp Gly Leu Pro Gln Thr Gln Ser Tyr Val Val Gln Ser
        785                 790                 795

CCT TTA GTT GCT CGT TCA GGA TAT TCT GGC ACT GGT GCA ATT AAT GAA
Pro Leu Val Ala Arg Ser Gly Tyr Ser Gly Thr Gly Ala Ile Asn Glu
                800                 805                 810

ATT GAA TAT GAA AAT GTA AAG GCC GTC GAA ATA AGC AAG GGG GGG AGT
Ile Glu Tyr Glu Asn Val Lys Ala Val Glu Ile Ser Lys Gly Gly Ser
815                 820                 825                 830
```

FIG. 4J.

TCT TCT GAG TAT GGT AAT GGA GCA CTA GCT GGT TCT GTA ACA TTT CAA
Ser Ser Glu Tyr Gly Asn Gly Ala Leu Ala Gly Ser Val Thr Phe Gln
            835                 840                 845

AGC AAA TCA GCA GCC GAT ATC TTA GAA GGA GAC AAA TCA TGG GGA ATT
Ser Lys Ser Ala Ala Asp Ile Leu Glu Gly Asp Lys Ser Trp Gly Ile
            850                 855                 860

CAA ACT AAA AAT GCT TAT TCA AGC TAT AGC AGC AAA AAT AAA GGC TTT ACC CAT TCT
Gln Thr Lys Asn Ala Tyr Ser Ser Lys Asn Lys Gly Phe Thr His Ser
            865                 870                 875

TTA GCT GTA GCA GGA AAA CAA GGT GGA TTT GAA GGG CTA GCC ATT TAC
Leu Ala Val Ala Gly Lys Gln Gly Gly Phe Glu Gly Leu Ala Ile Tyr
            880                 885                 890

ACT CAA CGA AAT TCA ATT GAA ACC CAA GTC CAT AAA GAT GCA TTA AAA
Thr Gln Arg Asn Ser Ile Glu Thr Gln Val His Lys Asp Ala Leu Lys
            895                 900                 905                 910

GGC GTA CAA AGT TAT GAT CGA TTA ATC GCC ACA ACA GAT AAA TCT TCA
Gly Val Gln Ser Tyr Asp Arg Leu Ile Ala Thr Thr Asp Lys Ser Ser
            915                 920                 925

FIG. 4K.

GGA TAC TTT GTG ATA CAA GGT GAG TGT CCA AAT GGT GAT GAC AAG TGT
Gly Tyr Phe Val Ile Gln Gly Glu Cys Pro Asn Gly Asp Asp Lys Cys
930                              935                             940

GCA GCC AAG CCA CCT GCG ACT TTA TCC ACC CAA AGC GAA ACC GTA AGC
Ala Ala Lys Pro Pro Ala Thr Leu Ser Thr Gln Ser Glu Thr Val Ser
945                              950                             955

GTT TCA GAT TAT ACG GGG GCT AAC CGT ATC AAA CCT AAT CCA ATG AAA
Val Ser Asp Tyr Thr Gly Ala Asn Arg Ile Lys Pro Asn Pro Met Lys
960                              965                             970

TAT GAA AGC CAG TCT TGG TTT TTA AGA GGA GGG TAT CAT TTT TCT GAA
Tyr Glu Ser Gln Ser Trp Phe Leu Arg Gly Gly Tyr His Phe Ser Glu
975                              980                             985                             990

CAA CAT TAT ATT GGT GGT ATT TTT GAA TTC ACA CAA CAA AAA TTT GAT
Gln His Tyr Ile Gly Gly Ile Phe Glu Phe Thr Gln Gln Lys Phe Asp
995                              1000                            1005

ATC CGT GAT ATG ACA TTT CCC GCT TAT TTA AGC CCA ACA GAA AGA CGG
Ile Arg Asp Met Thr Phe Pro Ala Tyr Leu Ser Pro Thr Glu Arg Arg
1010                             1015                            1020

FIG. 4L.

```
GAT GAT AGT AGT CGT TCT TTT TAT CCA ATG CAA GAT CAT GGT GCA TAT
Asp Asp Ser Ser Arg Ser Phe Tyr Pro Met Gln Asp His Gly Ala Tyr
1025                         1030                        1035

CAA CAT ATT GAG GAT GGC AGA GGC GTT AAA TAT GCA AGT GGG CTT TAT
Gln His Ile Glu Asp Gly Arg Gly Val Lys Tyr Ala Ser Gly Leu Tyr
1040                        1045                        1050

TTC GAT GAA CAC CAT AGA AAA CAG CGT GTA GGT ATT GAA TAT ATT TAC
Phe Asp Glu His His Arg Lys Gln Arg Val Gly Ile Glu Tyr Ile Tyr
1055                        1060                        1065                1070

GAA AAT AAG AAC AAA GCG GGC ATC ATT GAC AGT TAT ATG CGA CAT TGC
Glu Asn Lys Asn Lys Ala Gly Ile Ile Asp Ser Tyr Met Arg His Cys
                 1075                       1080                   1085

AAT CAA CAA AAC ATC ATA CTT GAC AGT TAT ATG CGA CAT ACG CAT TGC
Asn Gln Gln Asn Ile Ile Leu Asp Ser Tyr Met Arg His Thr His Cys
                1090                        1095                        1100

AGT CTT TAT CCT AAT CCA AGT AAG AAT TGC CGC CCA ACA CTT GAT AAA
Ser Leu Tyr Pro Asn Pro Ser Lys Asn Cys Arg Pro Thr Leu Asp Lys
1105                        1110                        1115
```

FIG. 4M.

CCT TAT TCA TAC TAT CGT TCT GAT AGA AAT GTT TAT AAA GAA AAA CAT
Pro Tyr Ser Tyr Tyr Arg Ser Asp Arg Asn Val Tyr Lys Glu Lys His
1120                          1125                          1130

AAT ATG TTG CAA TTG AAT TTA GAG AAA AAA ATT CAA CAA AAT TGG CTT
Asn Met Leu Gln Leu Asn Leu Glu Lys Lys Ile Gln Gln Asn Trp Leu
1135                          1140                          1145                 1150

ACT CAT CAA ATT GTC TTC AAT CTT GGT TTT GAT GAC TTT ACT TCA GCG
Thr His Gln Ile Val Phe Asn Leu Gly Phe Asp Asp Phe Thr Ser Ala
1155                          1160                          1165

CTT CAG CAT AAA GAT TAT TTA ACT CGA CGT GTT ATC GCT ACG GCA GAT
Leu Gln His Lys Asp Tyr Leu Thr Arg Arg Val Ile Ala Thr Ala Asp
1170                          1175                          1180

AGT ATT CCA AGG AAA CCT GGT GAA ACT GGT AAA CCA AGA AAT GGT TTG
Ser Ile Pro Arg Lys Pro Gly Glu Thr Gly Lys Pro Arg Asn Gly Leu
1185                          1190                          1195

CAA TCA CAA CCT TAC TTA TAC CCA AAA CCA GAG CCA TAT TTT GCA GGA
Gln Ser Gln Pro Tyr Leu Tyr Pro Lys Pro Glu Pro Tyr Phe Ala Gly
1200                          1205                          1210

FIG. 4N.

```
CAA GAT CAT TGT AAT TAT CAA GGT AGC TCC TCT AAT TAC AGA GAC TGT
Gln Asp His Cys Asn Tyr Gln Gly Ser Ser Ser Asn Tyr Arg Asp Cys
1215                    1220                    1225                1230

AAA GTG CGG TTA ATT AAA GGG AAA AAT TAT TTC GCA GCA CGC AAT
Lys Val Arg Leu Ile Lys Gly Lys Asn Tyr Phe Ala Ala Arg Asn
            1235                    1240                    1245

AAT ATG GCA TTA GGG AAA TAC GTT GAT TTA GGT TTA GGT ATT CGG TAT
Asn Met Ala Leu Gly Lys Tyr Val Asp Leu Gly Leu Gly Ile Arg Tyr
1250                    1255                    1260

GAC GTA TCT CGT ACA AAA GCT AAT GAA TCA ACT ATT AGT GTT GGT AAA
Asp Val Ser Arg Thr Lys Ala Asn Glu Ser Thr Ile Ser Val Gly Lys
            1265                    1270                    1275

TTT AAA AAT TTC TCT TGG AAT ACT GGT ATT GTC ATA AAA CCA ACG GAA
Phe Lys Asn Phe Ser Trp Asn Thr Gly Ile Val Ile Lys Pro Thr Glu
        1280                    1285                    1290

TGG CTT GAT CTT TCT TAT CGC CTT TCT ACT GGA TTT AGA AAT CCT AGT
Trp Leu Asp Leu Ser Tyr Arg Leu Ser Thr Gly Phe Arg Asn Pro Ser
            1295                1300                1305        1310
```

FIG. 40.

TTT TCT GAA ATG TAT GGT TGG CGG TAT GGT GGC AAG AAT GAC GAG GTT
Phe Ser Glu Met Tyr Gly Trp Arg Tyr Gly Gly Lys Asn Asp Glu Val
1315                                                      1325

TAT GTA GGT AAA TTT AAG CCT GAA ACA TCT CGT AAC CAA GAG TTT GGT
Tyr Val Gly Lys Phe Lys Pro Glu Thr Ser Arg Asn Gln Glu Phe Gly
1330                          1335                        1340

CTC GCT CTA AAA GGG GAT TTT GGT AAT ATT GAG ATC AGT CAT TTT AGT
Leu Ala Leu Lys Gly Asp Phe Gly Asn Ile Glu Ile Ser His Phe Ser
1345                          1350                    1355

AAT GCT TAT CGA AAT CTT ATC GCC TTT GCT GAA GAA CTT AGT AAA AAT
Asn Ala Tyr Arg Asn Leu Ile Ala Phe Ala Glu Glu Leu Ser Lys Asn
1360                          1365                        1370

GGA ACT GGA AAG GGC AAT TAT GGA TAT CAT AAT GCA CAA AAT GCA AAA
Gly Thr Gly Lys Gly Asn Tyr Gly Tyr His Asn Ala Gln Asn Ala Lys
1375                          1380                    1385    1390

TTA GTT GGC GTA AAT ATA ACT GCA CAA TTA GAT TTT AAT GGT TTA TGG
Leu Val Gly Val Asn Ile Thr Ala Gln Leu Asp Phe Asn Gly Leu Trp
1395                          1400                        1405

FIG. 4P.

AAA CGT ATT CCC TAC GGT TGG TAT GCA ACA TTT GCT TAT AAC CAA GTA
Lys Arg Ile Pro Tyr Gly Trp Tyr Ala Thr Phe Ala Tyr Asn Gln Val
    1410                    1415                    1420

AAA GTT AAA GAT CAA AAA ATC AAT GCT GGT TTA GCC TCC GTA AGC AGT
Lys Val Lys Asp Gln Lys Ile Asn Ala Gly Leu Ala Ser Val Ser Ser
    1425                    1430                    1435

TAT TTA TTT GAT GCC ATT CAG CCC AGC CGT TAT ATC ATT GGT TTA GGC
Tyr Leu Phe Asp Ala Ile Gln Pro Ser Arg Tyr Ile Ile Gly Leu Gly
    1440                    1445                    1450

TAT GAT CAT CCA AGT AAT ACT TGG GGA ATT AAT ACA ATG TTT ACT CAA
Tyr Asp His Pro Ser Asn Thr Trp Gly Ile Asn Thr Met Phe Thr Gln
    1455                    1460                    1465                    1470

TCA AAA GCA AAA TCT CAA AAT GAA TTG CTA GGA AAA CGT GCA TTA GGT
Ser Lys Ala Lys Ser Gln Asn Glu Leu Leu Gly Lys Arg Ala Leu Gly
    1475                    1480                    1485

AAC AAT TCA AGG GAT GTA AAA TCA ACA AGA AAA CTT ACT CGG GCA TGG
Asn Asn Ser Arg Asp Val Lys Ser Thr Arg Lys Leu Thr Arg Ala Trp
    1490                    1495                    1500

FIG. 4Q.

```
CAT ATC TTA GAT GTA TCG GGT TAT TAC ATG GCG AAT AAA AAT ATT ATG
His Ile Leu Asp Val Ser Gly Tyr Tyr Met Ala Asn Lys Asn Ile Met
        1505                    1510                    1515

CTT CGA TTA GGG ATA TAT AAT TTA TTC AAC TAT CGC TAT GTT ACT TGG
Leu Arg Leu Gly Ile Tyr Asn Leu Phe Asn Tyr Arg Tyr Val Thr Trp
        1520                    1525                    1530

GAA GCG GTC CGT CAA ACA GCA CAA GGT GCG GTC AAT CAA CAT CAA AAT
Glu Ala Val Arg Gln Thr Ala Gln Gly Ala Val Asn Gln His Gln Asn
        1535                    1540                    1545    1550

GTT GGT AGC TAT ACT CGC TAC GCA GCA TCA GGA CGA AAC TAT ACC TTA
Val Gly Ser Tyr Thr Arg Tyr Ala Ala Ser Gly Arg Asn Tyr Thr Leu
        1555                    1560                    1565

ACA TTA GAA ATG AAA TTC TAAATTAAAA TCGCCCAGAT GGACTAGATA
Thr Leu Glu Met Lys Phe
        1570

TGCTATATCT ATACCTTACT GCCGCATCTT TTTCTGTTCT ATAAATCTGCT TAAGTGAAAA

ACCAAACTTG GATTTTTAC AAGATCTTTT CACACATTTA TTG
```

FIG. 5A.

```
                                                          -35
ATTGTTTA CGCCATTTTT CATATTTTAT CCATGAACTT AAAAAACTCT AACTTGACAT
                                              RBS
                    -10
TATTACAAAA AAAGATCAAT AATGCGAATT ATTATCAATT TTGTATGAGT ATATAATTCT

ATG AAA TCT GTA CCT CTT ATC TCT GGT GGA CTT TCC TTT TTA CTA AGT
Met Lys Ser Val Pro Leu Ile Ser Gly Gly Leu Ser Phe Leu Leu Ser
 1                   5                  10                  15

GCT TGT AGC GGA GGG GGG TCT TTT GAT GTA GAT AAC GTC TCT AAT ACC
Ala Cys Ser Gly Gly Gly Ser Phe Asp Val Asp Asn Val Ser Asn Thr
                20                  25                  30

CCC TCT TCT AAA CCA CGT TAT CAA GAC GAT ACC TCG AAT CAA AGA AAA
Pro Ser Ser Lys Pro Arg Tyr Gln Asp Asp Thr Ser Asn Gln Arg Lys
        35                  40                  45

AAA TCT AAT TTG AAA AAG TTG TTC ATT CCT TCT TTA GGA GGA GGG ATG
Lys Ser Asn Leu Lys Lys Leu Phe Ile Pro Ser Leu Gly Gly Gly Met
            50                  55                  60

AAA TTG GTC GCT CAG AAT CTT CGT GGT AAT AAA GAA CCT AGT TTC TTA
Lys Leu Val Ala Gln Asn Leu Arg Gly Asn Lys Glu Pro Ser Phe Leu
65                  70                  75                  80
```

FIG. 5B.

```
AAT GAA GAT GAC TAT ATA TCA TAT TTT TCC TCA CTT TCT ACG ATT GAA
Asn Glu Asp Asp Tyr Ile Ser Tyr Phe Ser Ser Leu Ser Thr Ile Glu
 85                          90                          95

AAG GAT GTT AAA GAT AAC AAT AAA AAC GGG GCG GAC CTT ATT GGC TCA
Lys Asp Val Lys Asp Asn Asn Lys Asn Gly Ala Asp Leu Ile Gly Ser
                100                         105                         110

ATA GAC GAG CCT AGT ACA ACA AAT CCA CCC GAA AAG CAT CAT GGA CAA
Ile Asp Glu Pro Ser Thr Thr Asn Pro Pro Glu Lys His His Gly Gln
                115                         120                         125

AAA TAT GTA TAT TCA GGG CTT TAT TAT TAT ACT CCA TCG TGG AGT TTA AAC
Lys Tyr Val Tyr Ser Gly Leu Tyr Tyr Tyr Thr Pro Ser Trp Ser Leu Asn
                130                         135                         140

GAT TCT AAA AAC AAG TTT TAT TTA GGT TAC TAT GGA TAT GCG TTT TAT
Asp Ser Lys Asn Lys Phe Tyr Leu Gly Tyr Tyr Gly Tyr Ala Phe Tyr
                145                         150                         155                 160

TAT GGT AAT AAA ACT GCA ACA AAC TTG CCA GTA AAC GGT GTA GCT AAA
Tyr Gly Asn Lys Thr Ala Thr Asn Leu Pro Val Asn Gly Val Ala Lys
                165                         170                         175
```

FIG. 5C.

```
TAC AAA GGA ACT TGG GAT TTC ATC ACT GCA ACT AAA AAT GGC AAA CGT
Tyr Lys Gly Thr Trp Asp Phe Ile Thr Ala Thr Lys Asn Gly Lys Arg
            180                 185                 190

TAT CCT TTG TTA AGT AAT GGC AGT CAC GCT TAT TAT CGA CGT AGT GCA
Tyr Pro Leu Leu Ser Asn Gly Ser His Ala Tyr Tyr Arg Arg Ser Ala
            195                 200                 205

ATT CCA GAA GAT ATT GAT TTA GAA AAT GAT TCA AAG AAT GGT GAT ATA
Ile Pro Glu Asp Ile Asp Leu Glu Asn Asp Ser Lys Asn Gly Asp Ile
            210                 215                 220

GGC TTA ATA AGT GAA TTT AGT GCA GAT TTT GGG ACT AAA AAA CTG ACA
Gly Leu Ile Ser Glu Phe Ser Ala Asp Phe Gly Thr Lys Lys Leu Thr
            225                 230                 235                 240

GGA CAA CTG TCT TAC ACC AAA AGA AAA ACT AAT CAA CCA TAT GAA
Gly Gln Leu Ser Tyr Thr Lys Arg Lys Thr Asn Asn Gln Pro Tyr Glu
            245                 250                 255

AAG AAA AAA CTC TAT GAT ATA GAT GCC GAT ATT TAT AGT AAT AGA TTC
Lys Lys Lys Leu Tyr Asp Ile Asp Ala Asp Ile Tyr Ser Asn Arg Phe
            260                 265                 270
```

FIG. 5D.

```
AGG GGT ACA GTA AAG CCA ACC GAA AAA GAT TCT GAA GAA CAT CCC TTT
Arg Gly Thr Val Lys Pro Thr Glu Lys Asp Ser Glu Glu His Pro Phe
            275                 280                 285

ACC AGC GAG GGA ACA TTA GAA GGT GGT TTT TAT GGG CCT AAT GCT GAA
Thr Ser Glu Gly Thr Leu Glu Gly Gly Phe Tyr Gly Pro Asn Ala Glu
            290                 295                 300

GAA CTA GGG GGG AAA TTT TTA GCT ACG GAT AAC CGA GTT TTT GGG GTA
Glu Leu Gly Gly Lys Phe Leu Ala Thr Asp Asn Arg Val Phe Gly Val
            305                 310                 315                 320

TTT AGT GCC AAA GAA ACG GAA GAA ACA AAA AAG GAA GCG TTA TCC AAG
Phe Ser Ala Lys Glu Thr Glu Glu Thr Lys Lys Glu Ala Leu Ser Lys
            325                 330                 335

GAA ACC TTA ATT GAT GGC AAG CTA ATT ACT TTC TCT ACT AAA AAA ACC
Glu Thr Leu Ile Asp Gly Lys Leu Ile Thr Phe Ser Thr Lys Lys Thr
            340                 345                 350

GAT GCA AAA ACC AAT GCA ACA ACC AGT ACC GCA GCT AAT ACA ACA ACC
Asp Ala Lys Thr Asn Ala Thr Thr Ser Thr Ala Ala Asn Thr Thr Thr
            355                 360                 365
```

FIG. 5E.

GAT ACA ACC GCC AAT ACA ATA ACC GAT GAA AAA AAC TTT AAG ACG GAA
Asp Thr Thr Ala Asn Thr Ile Thr Asp Glu Lys Asn Phe Lys Thr Glu
370                              375                         380

GAT ATA TCA AGT TTT GGT GAA GCT GAT TAT CTG TTA ATT GAC AAA TAT
Asp Ile Ser Ser Phe Gly Glu Ala Asp Tyr Leu Leu Ile Asp Lys Tyr
385                              390                         395                    400

CCT ATT CCA CTT TTA CCT GAT AAA AAT ACT AAT GAT TTC ATA AGT AGT
Pro Ile Pro Leu Leu Pro Asp Lys Asn Thr Asn Asp Phe Ile Ser Ser
405                              410                         415

AAG CAT CAT ACT GTA GGA AAT AAA CGC TAT AAA GTG GAA GCA TGT TGC
Lys His His Thr Val Gly Asn Lys Arg Tyr Lys Val Glu Ala Cys Cys
420                              425                         430

AGT AAT CTA AGC TAT GTG AAA TTT GGT ATG TAT TAT GAA GAC CCA CTT
Ser Asn Leu Ser Tyr Val Lys Phe Gly Met Tyr Tyr Glu Asp Pro Leu
435                              440                         445

AAA GAA AAA GAA ACA GAA ACA GAA ACA GAA AAA GAC AAA GAA
Lys Glu Lys Glu Thr Glu Thr Glu Thr Glu Lys Asp Lys Glu
450                              455                         460

FIG. 5F.

AAA GAA AAA GAA AAA GAC AAA GAG AAA GAA AAA CAA ACG GCA ACG
Lys Glu Lys Glu Lys Asp Lys Glu Lys Glu Lys Gln Thr Ala Thr
465                     470                  475                 480

ACC AAC ACT TAT TAT CAA TTC TTA TTA GGT CAC CGT ACT CCC AAG GAC
Thr Asn Thr Tyr Tyr Gln Phe Leu Leu Gly His Arg Thr Pro Lys Asp
             485                  490                  495

GAC ATA CCT AAA ACA GGA AGT GCA AAA TAT CAT GGT AGT TGG TTT GGT
Asp Ile Pro Lys Thr Gly Ser Ala Lys Tyr His Gly Ser Trp Phe Gly
         500                  505                  510

TAT ATT ACT GAC GGT AAG ACA TCT TAC TCC CCC AGT GGT GAT AAG AAA
Tyr Ile Thr Asp Gly Lys Thr Ser Tyr Ser Pro Ser Gly Asp Lys Lys
     515                  520                  525

CGC GAT AAA AAT GCT GTC GCC GAG TTT AAT GTT GAT TTT GCC GAG AAA
Arg Asp Lys Asn Ala Val Ala Glu Phe Asn Val Asp Phe Ala Glu Lys
 530                  535                  540

AAG CTA ACA GGC GAA TTA AAA CGA CAC GAT ACT GGA AAT CCC GTA TTT
Lys Leu Thr Gly Glu Leu Lys Arg His Asp Thr Gly Asn Pro Val Phe
545                  550                  555                  560

FIG. 5G.

AGT ATT GAG GCA AAC TTT AAT AAT AGT AGT AAT GCC TTC ACT GGT ACA
Ser Ile Glu Ala Asn Phe Asn Asn Ser Ser Asn Ala Phe Thr Gly Thr
              565                 570                 575

GCA ACC GCA ACA AAT TTT GTA ATA GAT GGT AAA AAT AGT CAA AAT AAA
Ala Thr Ala Thr Asn Phe Val Ile Asp Gly Lys Asn Ser Gln Asn Lys
              580                 585                 590

AAT ACC CCA ATT AAT ATT ACA ACT AAA GTA AAC GGG GCA TTT TAT GGA
Asn Thr Pro Ile Asn Ile Thr Thr Lys Val Asn Gly Ala Phe Tyr Gly
              595                 600                 605

CCT AAG GCT TCT GAA TTA GGC GGT TAT TTC ACT TAT AAC GGA AAT TCT
Pro Lys Ala Ser Glu Leu Gly Gly Tyr Phe Thr Tyr Asn Gly Asn Ser
              610                 615                 620

ACA GCT ACA AAT TCT GAA AGT TCC TCA ACC GTA TCT TCA TCC AAT
Thr Ala Thr Asn Ser Glu Ser Ser Ser Thr Val Ser Ser Ser Asn
              625                 630                 635                 640

TCA AAA AAT GCA AGA GCT GCA GTT GTC TTT GGT GCG AGA CAA CAA GTA
Ser Lys Asn Ala Arg Ala Ala Val Val Phe Gly Ala Arg Gln Gln Val
              645                 650                 655

FIG. 5H.

```
GAA ACA ACC AAA TAATGAAATA CTAAAA ATG ACT AAA AAA CCC TAT TTT
Glu Thr Thr Lys                  Met Thr Lys Lys Pro Tyr Phe
        660                                      665

CGC CTA AGT ATT TCT TGT CTT TTA ATT TCA TGC TAT GTA AAA GCA
Arg Leu Ser Ile Ile Ser Cys Leu Leu Ile Ser Cys Tyr Val Lys Ala
        670                     675                     680

GAA ACT CAA AGT ATA AAA GAT ACA AAA GAA GCT ATA TCA TCT GAA GTG
Glu Thr Gln Ser Ile Lys Asp Thr Lys Glu Ala Ile Ser Ser Glu Val
        685                     690                     695

GAC ACT CAA AGT ACA GAA GAT TCA GAA TTA GAA ACT ATC TCA GTC ACT
Asp Thr Gln Ser Thr Glu Asp Ser Glu Leu Glu Thr Ile Ser Val Thr
        700                     705                     710                 715

GCA GAA AAA ATA AGA GAT CGT AAA GAT AAT GAA GTA ACT GGA CTT GGC
Ala Glu Lys Ile Arg Asp Arg Lys Asp Asn Glu Val Thr Gly Leu Gly
        720                     725                     730

AAA ATT ATC AAA ACT AGT GAA AGT ATC AGC CGA GAA CAA GTA TTA AAT
Lys Ile Ile Lys Thr Ser Glu Ser Ile Ser Arg Glu Gln Val Leu Asn
        735                     740                     745
```

FIG. 51.

ATT CGT GAT CTA ACA CGC TAT GAT CCA GGG ATT TCA GTT GTA GAA CAA
Ile Arg Asp Leu Thr Arg Tyr Asp Pro Gly Ile Ser Val Val Glu Gln
750                          755                          760

GGT CGC GGT GCA AGT TCT GGA TAT TCT ATT CGT GGT ATG GAC AGA AAT
Gly Arg Gly Ala Ser Ser Gly Tyr Ser Ile Arg Gly Met Asp Arg Asn
765                          770                          775

AGA GTT GCT TTA TTA GTA GAT GGT TTA CCT CAA ACG CAA TCT TAT GTA
Arg Val Ala Leu Leu Val Asp Gly Leu Pro Gln Thr Gln Ser Tyr Val
780                          785                          790                 795

GTG CAA AGC CCT TTA GTT GCT CGT TCA GGA TAT TCT GGC ACT GGT GCA
Val Gln Ser Pro Leu Val Ala Arg Ser Gly Tyr Ser Gly Thr Gly Ala
                800                          805                          810

ATT AAT GAA ATT GAA TAT GAA AAT GTA AAG GCC GTC GAA ATA AGC AAG
Ile Asn Glu Ile Glu Tyr Glu Asn Val Lys Ala Val Glu Ile Ser Lys
815                          820                          825

GGG GGG AGT TCT TCT GAG TAT GGT AAT GGA GCA CTA GCT GGT TCT GTA
Gly Gly Ser Ser Ser Glu Tyr Gly Asn Gly Ala Leu Ala Gly Ser Val
              830                          835                          840

FIG. 5J.

ACA TTT CAA AGC AAA TCA GCA GCC GAT ATC TTA GAA GGA GAC AAA TCA
Thr Phe Gln Ser Lys Ser Ala Ala Asp Ile Leu Glu Gly Asp Lys Ser
845                         850                         855

TGG GGA ATT CAA ACT AAA AAT GCT TAT TCA AGC AAA AAT AAA GGC TTT
Trp Gly Ile Gln Thr Lys Asn Ala Tyr Ser Ser Lys Asn Lys Gly Phe
860                         865                         870                         875

ACC CAT TCT TTA GCT GTA GCA GGA AAA CAA GGT GGA TTT GAA GGG CTA
Thr His Ser Leu Ala Val Ala Gly Lys Gln Gly Gly Phe Glu Gly Leu
880                         885                         890

GCC ATT TAC ACT CAA CGA AAT TCA ATT GAA ACC CAA GTC CAT AAA GAT
Ala Ile Tyr Thr Gln Arg Asn Ser Ile Glu Thr Gln Val His Lys Asp
895                         900                         905

GCA TTA AAA GGC GTA CAA AGT TAT GAT CGA TTA ATC GCC ACA ACA GAT
Ala Leu Lys Gly Val Gln Ser Tyr Asp Arg Leu Ile Ala Thr Thr Asp
910                         915                         920

AAA TCT TCA GGA TAC TTT GTG ATA CAA GGT GAG TGT CCA AAT GGT GAT
Lys Ser Ser Gly Tyr Phe Val Ile Gln Gly Glu Cys Pro Asn Gly Asp
925                         930                         935

FIG. 5K.

GAC AAG TGT GCA GCC AAG CCA CCT GCG ACT TTA TCC ACC CAA AGC GAA
Asp Lys Cys Ala Ala Lys Pro Pro Ala Thr Leu Ser Thr Gln Ser Glu
940                 945                 950                 955

ACC GTA AGC GTT TCA GAT TAT ACG GGG GCT AAC CGT ATC AAA CCT AAT
Thr Val Ser Val Ser Asp Tyr Thr Gly Ala Asn Arg Ile Lys Pro Asn
960                 965                 970

CCA ATG AAA TAT GAA AGC CAG TCT TGG TTT TTA AGA GGA GGG TAT CAT
Pro Met Lys Tyr Glu Ser Gln Ser Trp Phe Leu Arg Gly Gly Tyr His
        975                 980                 985

TTT TCT GAA CAA CAT TAT ATT GGT GGT ATT TTT GAA TTC ACA CAA CAA
Phe Ser Glu Gln His Tyr Ile Gly Gly Ile Phe Glu Phe Thr Gln Gln
990                 995                 1000

AAA TTT GAT ATC CGT GAT ATG ACA TTT CCC GCT TAT TTA AGC CCA ACA
Lys Phe Asp Ile Arg Asp Met Thr Phe Pro Ala Tyr Leu Ser Pro Thr
1005                1010                1015

GAA AGA CGG GAT GAT AGT CGT TTT TAT CCA ATG CAA GAT CAT
Glu Arg Arg Asp Asp Ser Ser Phe Tyr Pro Met Gln Asp His
1020                1025                1030                1035

FIG. 5L.

GGT GCA TAT CAA CAT ATT GAG GAT GGC AGA GGC GTT AAA TAT GCA AGT
Gly Ala Tyr Gln His Ile Glu Asp Gly Arg Gly Val Lys Tyr Ala Ser
            1040                    1045                    1050

GGG CTT TAT TTC GAT GAA CAC CAT AGA AAA CAG CGT GTA GGT ATT GAA
Gly Leu Tyr Phe Asp Glu His His Arg Lys Gln Arg Val Gly Ile Glu
            1055                    1060                    1065

TAT ATT TAC GAA AAT CAA CAA AAC ATC ATT GAC AAA GCA GTG
Tyr Ile Tyr Glu Asn Gln Gln Asn Ile Ile Asp Lys Ala Val
            1070                    1075                    1080

TTA AGT GCT AAT CAA CAA AAC ATC ATA CTT GAC AGT TAT ATG CGA CAT
Leu Ser Ala Asn Gln Gln Asn Ile Ile Leu Asp Ser Tyr Met Arg His
            1085                    1090                    1095

ACG CAT TGC AGT CTT TAT CCT AAT CCA AGT AAG AAT TGC CGC CCA ACA
Thr His Cys Ser Leu Tyr Pro Asn Pro Ser Lys Asn Cys Arg Pro Thr
            1100                    1105                    1110                    1115

CTT GAT AAA CCT TAT TCA TAC TAT CGT TCT GAT AGA AAT GTT TAT AAA
Leu Asp Lys Pro Tyr Ser Tyr Tyr Arg Ser Asp Arg Asn Val Tyr Lys
            1120                    1125                    1130

FIG.5M.

GAA AAA CAT AAT ATG TTG CAA TTG AAT TTA GAG AAA AAA ATT CAA CAA
Glu Lys His Asn Met Leu Gln Leu Asn Leu Glu Lys Lys Ile Gln Gln
                      1135                     1140                    1145

AAT TGG CTT ACT CAT CAA ATT GTC TTC AAT CTT GGT TTT GAT GAC TTT
Asn Trp Leu Thr His Gln Ile Val Phe Asn Leu Gly Phe Asp Asp Phe
                      1150                     1155                    1160

ACT TCA GCG CTT CAG CAT AAA GAT TAT TTA ACT CGA CGT GTT ATC GCT
Thr Ser Ala Leu Gln His Lys Asp Tyr Leu Thr Arg Arg Val Ile Ala
                      1165                     1170                    1175

ACG GCA GAT AGT ATT CCA AGG AAA CCT GGT GAA ACT GGT AAA CCA AGA
Thr Ala Asp Ser Ile Pro Arg Lys Pro Gly Glu Thr Gly Lys Pro Arg
                      1180                     1185                    1190                    1195

AAT GGT TTG CAA TCA CAA CCT TAC TTA TAC CCA AAA CCA GAG CCA TAT
Asn Gly Leu Gln Ser Gln Pro Tyr Leu Tyr Pro Lys Pro Glu Pro Tyr
                      1200                     1205                    1210

TTT GCA GGA CAA GAT CAT TGT AAT TAT CAA GGT AGC TCC TCT AAT TAC
Phe Ala Gly Gln Asp His Cys Asn Tyr Gln Gly Ser Ser Ser Asn Tyr
                      1215                     1220                    1225

FIG. 5N.

AGA GAC TGT AAA GTG CGG TTA ATT AAA GGG AAA AAT TAT TTC GCA
Arg Asp Cys Lys Val Arg Leu Ile Lys Gly Lys Asn Tyr Phe Ala
1230                           1235                      1240

GCA CGC AAT AAT ATG GCA TTA GGG AAA TAC GTT GAT TTA GGT TTA GGT
Ala Arg Asn Asn Met Ala Leu Gly Lys Tyr Val Asp Leu Gly Leu Gly
1245                           1250                      1255

ATT CGG TAT GAC GTA TCT CGT ACA AAA GCT AAT GAA TCA ACT ATT AGT
Ile Arg Tyr Asp Val Ser Arg Thr Lys Ala Asn Glu Ser Thr Ile Ser
1260                           1265                      1270                 1275

GTT GGT AAA TTT AAA AAT TTC TCT TGG AAT ACT GGT ATT GTC ATA AAA
Val Gly Lys Phe Lys Asn Phe Ser Trp Asn Thr Gly Ile Val Ile Lys
1280                           1285                      1290

CCA ACG GAA TGG CTT GAT CTT TCT TAT CGC CTT TCT ACT GGA TTT AGA
Pro Thr Glu Trp Leu Asp Leu Ser Tyr Arg Leu Ser Thr Gly Phe Arg
1295                           1300                      1305

AAT CCT AGT TTT TCT GAA ATG TAT GGT TGG CGG TAT GGT GGC AAG AAT
Asn Pro Ser Phe Ser Glu Met Tyr Gly Trp Arg Tyr Gly Gly Lys Asn
1310                           1315                      1320

FIG. 50.

```
GAC GAG GTT TAT GTA GGT AAA TTT AAG CCT GAA ACA TCT CGT AAC CAA
Asp Glu Val Tyr Val Gly Lys Phe Lys Pro Glu Thr Ser Arg Asn Gln
1325                     1330                    1335

GAG TTT GGT CTC GCT CTA AAA GGG GAT TTT GGT AAT ATT GAG ATC AGT
Glu Phe Gly Leu Ala Leu Lys Gly Asp Phe Gly Asn Ile Glu Ile Ser
1340                     1345                    1350           1355

CAT TTT AGT AAT GCT TAT CGA AAT CTT GCT TTT GCT GAA GAA CTT
His Phe Ser Asn Ala Tyr Arg Asn Leu Ile Ala Phe Ala Glu Glu Leu
          1360                    1365                    1370

AGT AAA AAT GGA ACT GGA AAG GGC AAT TAT GGA TAT GGA TAT CAT AAT GCA CAA
Ser Lys Asn Gly Thr Gly Lys Gly Asn Tyr Gly Tyr His Asn Ala Gln
              1375                    1380                    1385

AAT GCA AAA TTA GTT GGC GTA AAT ATA ACT GCA CAA TTA GAT TTT AAT
Asn Ala Lys Leu Val Gly Val Asn Ile Thr Ala Gln Leu Asp Phe Asn
                  1390                    1395                    1400

GGT TTA TGG AAA CGT ATT CCC TAC GGT TGG TAT GCA ACA TTT GCT TAT
Gly Leu Trp Lys Arg Ile Pro Tyr Gly Trp Tyr Ala Thr Phe Ala Tyr
                      1405                    1410                    1415
```

FIG. 5P.

AAC CAA GTA AAA GAT CAA AAA ATC AAT GCT GGT TTA GCC TCC
Asn Gln Val Lys Asp Gln Lys Ile Asn Ala Gly Leu Ala Ser
1420            1425                1430                1435

GTA AGC AGT TTA TTT GAT GCC ATT CAG CCC AGC CGT TAT ATC ATT
Val Ser Ser Tyr Leu Phe Asp Ala Ile Gln Pro Ser Arg Tyr Ile Ile
            1440                    1445                1450

GGT TTA GGC TAT GAT CAT CCA AGT AAT ACT TGG GGA ATT AAT ACA ATG
Gly Leu Gly Tyr Asp His Pro Ser Asn Thr Trp Gly Ile Asn Thr Met
        1455                    1460                    1465

TTT ACT CAA TCA AAA GCA AAT GAA TTG CTA GGA AAA CGT
Phe Thr Gln Ser Lys Ala Asn Glu Leu Leu Gly Lys Arg
1470                    1475                1480

GCA TTA GGT AAC AAT TCA AGG GAT GTA AAA TCA ACA AGA AAA CTT ACT
Ala Leu Gly Asn Asn Ser Arg Asp Val Lys Ser Thr Arg Lys Leu Thr
        1485                    1490                    1495

CGG GCA TGG CAT ATC TTA GAT GTA TCG GGT TAT TAC ATG GCG AAT AAA
Arg Ala Trp His Ile Leu Asp Val Ser Gly Tyr Tyr Met Ala Asn Lys
    1500                1505                1510                1515

FIG. 5Q.

```
AAT ATT ATG CTT CGA TTA GGG ATA TAT AAT TTA TTC AAC TAT CGC TAT
Asn Ile Met Leu Arg Leu Gly Ile Tyr Asn Leu Phe Asn Tyr Arg Tyr
        1520                    1525                    1530

GTT ACT TGG GAA GCG GTG CGT CAA ACA GCA CAA GGT GCG GTC AAT CAA
Val Thr Trp Glu Ala Val Arg Gln Thr Ala Gln Gly Ala Val Asn Gln
        1535                    1540                    1545

CAT CAA AAT GTT GGT AGC TAT ACT CGC TAC GCA GCA TCA GGA CGA AAC
His Gln Asn Val Gly Ser Tyr Thr Arg Tyr Ala Ala Ser Gly Arg Asn
        1550                    1555                    1560

TAT ACC TTA ACA TTA GAA ATG AAA TTC TAAATTAAAA TCGCCAGAT
Tyr Thr Leu Thr Leu Glu Met Lys Phe
        1565                    1570

GGACTAGATA TGCTATATCT ATACCTTACT GGGCATCTT TTTCTGTTCT ATAATCTGCT

TAAGTGAAAA ACCAAACTTG GATTTTTTAC AAGATCTTTT CACACATTTA TTGTAAAATC

TCCGACAATT TTGACCG
```

FIG. 6A.

AAAATTCGT AATGATAACC CTATAAATGA TAAGAGAGAA AGTGTTTTA CGCCATTTTT

CATATTTAT CCATGAACTT AAAAAATTCT AAGTTGACAT TATTACAAAA AAAGAACAAT
                                   -35

AATGCGAATT ATTATCAATT TTGTATAAGT ATTAATTCT ATG AAA TCT GTA CCT
           RBS                               Met Lys Ser Val Pro
                                              1               5

CTT ATC ACT GGT GGA CTT TCC TTT TTA CTA AGC GCT TGT AGC GGG GGA
Leu Ile Thr Gly Gly Leu Ser Phe Leu Leu Ser Ala Cys Ser Gly Gly
             10                      15                      20

GGT TCT TTT GAT GTA GAT GAC ACC TCG AAT CAA AGA ACA AAA TCT GAT TTG
Gly Ser Phe Asp Val Asp Asp Thr Ser Asn Gln Arg Thr Lys Ser Asp Leu
             25                      30                      35

CCA CGT TAT CAA GAC GAT ACC TCG AAT CAA AGA ACA AAA TCT GAT TTG
Pro Arg Tyr Gln Asp Asp Thr Ser Asn Gln Arg Thr Lys Ser Asp Leu
             40                      45                      50

GAA AAG TTG TTC ATT CCT TCT TTA GGG GGA GGG ATG AAG TTA GTG GCT
Glu Lys Leu Phe Ile Pro Ser Leu Gly Gly Gly Met Lys Leu Val Ala
             55                      60                      65

FIG.6B.

```
CAA AAT TTT ATT GGT GCT AGA GAA CCT AGT TTC TTA AAT GAA GAT GGC
Gln Asn Phe Ile Gly Ala Arg Glu Pro Ser Phe Leu Asn Glu Asp Gly
         70                  75                  80              85

TAT ATG ATA TTT TCC TCA CTT TCT ACG ATT GAA GAG GAT GTT GAA AAA
Tyr Met Ile Phe Ser Ser Leu Ser Thr Ile Glu Glu Asp Val Glu Lys
                         90                  95                 100

GTT AAA AAT AAC AAT AAA AAC GGG AGG CTT ATT GGC TCA ATT GAG
Val Lys Asn Asn Asn Lys Asn Gly Gly Arg Leu Ile Gly Ser Ile Glu
                 105                 110                 115

GAA CCT AAT GGA ACA TCA CAA AAT TCT AAT TCA CAA GAA TAC GTT TAT
Glu Pro Asn Gly Thr Ser Gln Asn Ser Asn Ser Gln Glu Tyr Val Tyr
                         120                 125                 130

TCT GGT TTG TAT TAT ATC GAT AGT TGG CGT GAT TAT AAG AAG GAA GAG
Ser Gly Leu Tyr Tyr Ile Asp Ser Trp Arg Asp Tyr Lys Lys Glu Glu
         135                 140                 145

CAA AAA GCT TAT ACT GGC TAT TAT TAT TAT GCA TTT TAT TAT GGT AAT
Gln Lys Ala Tyr Thr Gly Tyr Tyr Tyr Tyr Ala Phe Tyr Tyr Gly Asn
150                 155                 160                 165
```

FIG.6C.

```
GAA ACT GCA AAA AAC TTG CCA GTA AAA GGT GTA GCT AAA TAC AAA GGA
Glu Thr Ala Lys Asn Leu Pro Val Lys Gly Val Ala Lys Tyr Lys Gly
        170                 175                 180

ACG TGG AAC TTC ATC ACT GAA ACT GCA ACT GAA AAT GGC AAA CGT TAT TCT TTG
Thr Trp Asn Phe Ile Thr Ala Thr Glu Asn Gly Lys Arg Tyr Ser Leu
        185                 190                 195

TTC AGT AAT TCT ATC GGT CAA GCT TAT TCC AGA CGC AGC GCT ATT TCA
Phe Ser Asn Ser Ile Gly Gln Ala Tyr Ser Arg Arg Ser Ala Ile Ser
        200                 205                 210

GAA GAT ATC TAT AAT TTA GAA AAC GGT GAC GCG GGC TTA ATA AGT GAA
Glu Asp Ile Tyr Asn Leu Glu Asn Gly Asp Ala Gly Leu Ile Ser Glu
        215                 220                 225

TTT AGT GTA GAT TTT GGT AAG AAA GAG CTC ACT GGA GAA CTT TAT TAT
Phe Ser Val Asp Phe Gly Lys Lys Glu Leu Thr Gly Glu Leu Tyr Tyr
        230                 235                 240                 245

AAT GAA AGG AAA ACA AGT GTT AAT GAA TCA CAA AAT ACA ACA CAT AAA
Asn Glu Arg Lys Thr Ser Val Asn Glu Ser Gln Asn Thr Thr His Lys
        250                 255                 260
```

FIG. 6D.

CTC TAC ACT CTA GAA GCT AAA GTG TAT AGC AAC CGA TTC AGA GGT AAA
Leu Tyr Thr Leu Glu Ala Lys Val Tyr Ser Asn Arg Phe Arg Gly Lys
265                         270                         275

GTA AAG CCA ACC AAA ACA AAG TCT GAA GAT CAT CCC TTT ACC AGC GAG
Val Lys Pro Thr Lys Thr Lys Ser Glu Asp His Pro Phe Thr Ser Glu
280                         285                         290

GGA ACA TTA GAA GGT GGT TAT GGG CCT AAT GCT GAA GAA CTA GGG
Gly Thr Leu Glu Gly Gly Phe Tyr Gly Pro Asn Ala Glu Glu Leu Gly
295                         300                         305

GGA AAG TTT TTA GCT AAC GAC GAA AAA GTT TTT GGG GTA TTT AGT GCC
Gly Lys Phe Leu Ala Asn Asp Glu Lys Val Phe Gly Val Phe Ser Ala
310                         315                         320                         325

AAA GAA GAC CCA CAA AAC CAA GAA AAC CAA AAA TTA TCC ACA GAA ACC
Lys Glu Asp Pro Gln Asn Gln Glu Asn Gln Lys Leu Ser Thr Glu Thr
330                         335                         340

TTA ATT GAT GGC AAG CTA ATT ACT TTT AAA AGA ACT GAT GCA ACA ACC
Leu Ile Asp Gly Lys Leu Ile Thr Phe Lys Arg Thr Asp Ala Thr Thr
345                         350                         355

FIG.6E.

AAT GCA ACA ACC GAT GCA AAA ACC AGT GCA ACA ACC GAT GCA ACC AGT
Asn Ala Thr Thr Asp Ala Lys Thr Ser Ala Thr Thr Asp Ala Thr Ser
                360                 365                 370

ACA ACA GCC AAT AAA AAA ACC GAT GCA GAA AAC TTT AAG ACG GAA GAT
Thr Thr Ala Asn Lys Lys Thr Asp Ala Glu Asn Phe Lys Thr Glu Asp
                375                 380                 385

ATA CCA AGT TTT GGT GAA GCT GAT TAC CTT TTA ATT GGC AAT CAG CCT
Ile Pro Ser Phe Gly Glu Ala Asp Tyr Leu Leu Ile Gly Asn Gln Pro
                390                 395                 400                 405

ATT CCT CTT TTA CCT GAA AAA AAT ACT GAT GAT TTC ATA AGT AGT AAG
Ile Pro Leu Leu Pro Glu Lys Asn Thr Asp Asp Phe Ile Ser Ser Lys
                410                 415                 420

CAC CAT ACG GTA GGA GGT AAA ACC TAT AAA GTA GAA GCA TGT TGC AAG
His His Thr Val Gly Gly Lys Thr Tyr Lys Val Glu Ala Cys Cys Lys
                425                 430                 435

AAT CTA AGC TAT GTG AAA TTT GGT ATG TAT TAT GAG GAT AAA GAT AAG
Asn Leu Ser Tyr Val Lys Phe Gly Met Tyr Tyr Glu Asp Lys Asp Lys
                440                 445                 450

FIG. 6F.

GAC AAC AAA AAT GAA ACA GAC AAA GAA AAA GGC AAA GAA AAA CCA ACG
Asp Asn Lys Asn Glu Thr Asp Lys Glu Lys Gly Lys Glu Lys Pro Thr
455                     460                     465

ACG ACA ACA TCT ATC AAC ACT TAT TAT CAA TTC TTA TTA GGT CTC CGT
Thr Thr Thr Ser Ile Asn Thr Tyr Tyr Gln Phe Leu Leu Gly Leu Arg
470                     475                     480                 485

ACT CCC AAG GAC GAA ATA CCT AAA GAA GGA AGT GCA AAA TAT CAT GGT
Thr Pro Lys Asp Glu Ile Pro Lys Glu Gly Ser Ala Lys Tyr His Gly
            490                     495                     500

AAT TGG TTT GGT TAT ATT AGT GAT GGC GAG ACA TCT TAC TCC GCC AGT
Asn Trp Phe Gly Tyr Ile Ser Asp Gly Glu Thr Ser Tyr Ser Ala Ser
                505                     510                     515

GGT GAT AAG GAA CGC AGT AAA AAT GCT GTC GCC GAG TTT GAT GTA AGT
Gly Asp Lys Glu Arg Ser Lys Asn Ala Val Ala Glu Phe Asp Val Ser
        520                     525                     530

TTT GCC AAT AAA ACA TTA ACA GGC GAA TTA AAA CGA CAC GAT AAT GGA
Phe Ala Asn Lys Thr Leu Thr Gly Glu Leu Lys Arg His Asp Asn Gly
            535                     540                     545

FIG. 6G.

```
AAT ACC GTA TTT AAA ATT AAT GCA GAA TTA AAT GGT AGT AAT GAC TTC
Asn Thr Val Phe Lys Ile Asn Ala Glu Leu Asn Gly Ser Asn Asp Phe
550                 555                 560                 565

ACT GGT ACA GCA ACC GCA ACA AAT TTT GTA ATA GAT GGT AAC AAT AGT
Thr Gly Thr Ala Thr Ala Thr Asn Phe Val Ile Asp Gly Asn Asn Ser
                570                 575                 580

CAA ACT TCA AAT GCC AAA ATT AAT ATT ACA ACT AAA GTA AAT GGG GCA
Gln Thr Ser Asn Ala Lys Ile Asn Ile Thr Thr Lys Val Asn Gly Ala
            585                 590                 595

TTT TAT GGA CCT AAG GCT TCT GAA TTA GGA GGG TAT TTC ACC TAT AAC
Phe Tyr Gly Pro Lys Ala Ser Glu Leu Gly Gly Tyr Phe Thr Tyr Asn
        600                 605                 610

GGA AAA AAT CCT ACA GCT ACA AAT TCT GAA AGT TCC TCA ACC GTA CCT
Gly Lys Asn Pro Thr Ala Thr Asn Ser Glu Ser Ser Thr Val Pro
    615                 620                 625

TCA CCA CCC AAT TCA CCA AAT GCA AGC GCT GCA GTT GTC TTT GGT GCT
Ser Pro Pro Asn Ser Pro Asn Ala Ser Ala Ala Val Val Phe Gly Ala
630                 635                 640                 645
```

FIG. 6H.

```
AAA AAA CAA GTA GAA ACA ACC AAC AAG TAAAAACAAC CAAGTAATGG
Lys Lys Gln Val Glu Thr Thr Asn Lys
                650

AATACTAAAA ATG ACT AAA AAA CCC TAT TTT CGC CTA AGT ATT ATT TCT
           Met Thr Lys Lys Pro Tyr Phe Arg Leu Ser Ile Ile Ser
               655                 660                     665

TGT CTT TTA ATT TCA TGC TAT GTA AAA GCA GAA ACT CAA AGT ATA AAA
Cys Leu Leu Ile Ser Cys Tyr Val Lys Ala Glu Thr Gln Ser Ile Lys
                670                 675                     680

GAT ACA AAA GAA GCT ATA TCA TCT GAA GTG GAC ACT CAA AGT ACA GAA
Asp Thr Lys Glu Ala Ile Ser Ser Glu Val Asp Thr Gln Ser Thr Glu
            685                 690                     695

GAT TCA GAA TTA GAA ACT ATC TCA GTC ACT ATC GCA GAA AAA ATA GAT
Asp Ser Glu Leu Glu Thr Ile Ser Val Thr Ile Ala Glu Lys Ile Arg Asp
        700                 705                     710         715

CGT AAA GAT AAT GAA GTA ACT GGA CTT GGC AAA ATT ATC AAA ACT AGT
Arg Lys Asp Asn Glu Val Thr Gly Leu Gly Lys Ile Ile Lys Thr Ser
        720                     725                         730
```

FIG.61.

GAA AGT ATC AGC CGA GAA CAA GTA TTA AAT ATT CGT GAT CTA ACA CGC
Glu Ser Ile Ser Arg Glu Gln Val Leu Asn Ile Arg Asp Leu Thr Arg
                735                     740                 745

TAT GAT CCA GGC ATT TCA GTT GTA GAA CAA GGC CGT GGT GCA AGT TCT
Tyr Asp Pro Gly Ile Ser Val Val Glu Gln Gly Arg Gly Ala Ser Ser
            750                     755                 760

GGA TAT TCT ATT CGT GGT ATG GAC AGA AAT AGA GTT GCT TTA TTA GTA
Gly Tyr Ser Ile Arg Gly Met Asp Arg Asn Arg Val Ala Leu Leu Val
        765                     770                 775

GAT GGT TTA CCT CAA ACG CAA TCT TAT GTA GTG CAA AGC CCT TTA GTT
Asp Gly Leu Pro Gln Thr Gln Ser Tyr Val Val Gln Ser Pro Leu Val
    780                     785                 790                 795

GCT CGT TCA GGA TAT TCT GGC ACT GGT GCA ATT AAT GAA ATT GAA TAT
Ala Arg Ser Gly Tyr Ser Gly Thr Gly Ala Ile Asn Glu Ile Glu Tyr
                800                     805                 810

GAA AAT GTA AAG GCC GTC GAA ATA AGC AAG GGG GGG AGT TCT TCT GAG
Glu Asn Val Lys Ala Val Glu Ile Ser Lys Gly Gly Ser Ser Ser Glu
            815                     820                 825

FIG.6J.

TAT GGT AAT GGA GCA CTA GCT GGT TCT GTA ACA TTT CAA AGC AAA TCA
Tyr Gly Asn Gly Ala Leu Ala Gly Ser Val Thr Phe Gln Ser Lys Ser
              830                 835                 840

GCA GCC GAT ATC TTA GAA GGA GAC AAA GGA ATT CAA ACT AAA
Ala Ala Asp Ile Leu Glu Gly Asp Lys Gly Ile Gln Thr Lys
          845                 850                 855

AAT GCT TAT TCA AGC AAA AAT AAA GGC TTT ACC CAT TCT TTA GCT GTA
Asn Ala Tyr Ser Ser Lys Asn Lys Gly Phe Thr His Ser Leu Ala Val
              860                 865                 870                 875

GCT GGA AAA CAA GGG GGA TTT GAC GGG GTC GCC ATT TAT ACT CAA CGA
Ala Gly Lys Gln Gly Gly Phe Asp Gly Val Ala Ile Tyr Thr Gln Arg
              880                 885                 890

AAT TCA ATT GAA ACC CAA GTC CAT AAA GAT GCA TTA AAA GGC GTA CAA
Asn Ser Ile Glu Thr Gln Val His Lys Asp Ala Leu Lys Gly Val Gln
              895                 900                 905

AGT TAT CAT CGA TTA ATC GCC AAA CCA GAG GAT CAA TCT GCA TAC TTT
Ser Tyr His Arg Leu Ile Ala Lys Pro Glu Asp Gln Ser Ala Tyr Phe
              910                 915                 920

FIG.6K.

GTG ATG CAA GAT GAG TGT CCA AAG CCA GAT GAT TAT AAC AGT TGT TTA
Val Met Gln Asp Glu Cys Pro Lys Pro Asp Asp Tyr Asn Ser Cys Leu
925                              930                         935

CCT TTC GCC AAA CGA CCT GCG ATT TTA TCC CAA AGA GAA ACC GTA
Pro Phe Ala Lys Arg Pro Ala Ile Leu Ser Ser Gln Arg Glu Thr Val
940                         945                         950                955

AGC GTT TCA GAT TAT ACG GGG GCT AAC CGT ATC AAA CCT AAT CCA ATG
Ser Val Ser Asp Tyr Thr Gly Ala Asn Arg Ile Lys Pro Asn Pro Met
            960                         965                         970

AAA TAT GAA AGC CAG TCT TGG TTT TTA AGA GGA GGG TAT CAT TTT TCT
Lys Tyr Glu Ser Gln Ser Trp Phe Leu Arg Gly Gly Tyr His Phe Ser
975                         980                         985

GAA CAA CAT TAT ATT GGT GGT ATT TTT GAA TTC ACA CAA CAA AAA TTT
Glu Gln His Tyr Ile Gly Gly Ile Phe Glu Phe Thr Gln Gln Lys Phe
            990                         995                         1000

GAT ATC CGT GAT ATG ACA TTT CCC GCT TAT TTA AGA TCA ACA GAA AAA
Asp Ile Arg Asp Met Thr Phe Pro Ala Tyr Leu Arg Ser Thr Glu Lys
1005                        1010                        1015

FIG.6L.

CGG GAT GAT AGC AGT GGC TCT TTT TAT CCA AAG CAA GAT TAT GGT GCA
Arg Asp Asp Ser Ser Gly Ser Phe Tyr Pro Lys Gln Asp Tyr Gly Ala
1020                    1025                   1030              1035

TAT CAA CGT ATT GAG GAT GGC CGA GGC GTT AAC TAT GCA AGT GGG CTT
Tyr Gln Arg Ile Glu Asp Gly Arg Gly Val Asn Tyr Ala Ser Gly Leu
              1040                   1045                   1050

TAT TTC GAT GAA CAC CAT AGA AAA CAG CGT GTA GGT ATT GAA TAT ATT
Tyr Phe Asp Glu His His Arg Lys Gln Arg Val Gly Ile Glu Tyr Ile
         1055                   1060                   1065

TAC GAA AAT AAG AAC AAA GCG ATC ATT GAC AAA GCA GTG TTA AGT
Tyr Glu Asn Lys Asn Lys Ala Gly Ile Ile Asp Lys Ala Val Leu Ser
                 1070                   1075                   1080

GCT AAT CAA CAA AAC ATC ATA CTT GAC AGT TAT ATG CAA CAT ACG CAT
Ala Asn Gln Gln Asn Ile Ile Leu Asp Ser Tyr Met Gln His Thr His
            1085                   1090                   1095

TGC AGT CTT TAT CCT AAT CCA AGT AAG AAT TGC CGC CCA ACA CGT GAT
Cys Ser Leu Tyr Pro Asn Pro Ser Lys Asn Cys Arg Pro Thr Arg Asp
1100                   1105                    1110              1115

FIG.6M.

AAA CCT TAT TCA TAC TAT CAT TCT GAT AGA AAT GTT TAT AAA GAA AAA
Lys Pro Tyr Ser Tyr Tyr His Ser Asp Arg Asn Val Tyr Lys Glu Lys
                    1120                    1125                    1130

CAT AAT ATG TTG CAA TTG AAT TTA GAG AAA AAA ATT CAA CAA AAT TGG
His Asn Met Leu Gln Leu Asn Leu Glu Lys Lys Ile Gln Gln Asn Trp
        1135                    1140                    1145

CTT ACT CAT CAA ATT GTC TTC AAT CTT GGT TTT GAT GAC TTT ACT TCA
Leu Thr His Gln Ile Val Phe Asn Leu Gly Phe Asp Asp Phe Thr Ser
                    1150                    1155                    1160

GCG CTT CAG CAT AAA GAT TAT TTA ACT CGA CGT GTT ACC GCT ACG GCA
Ala Leu Gln His Lys Asp Tyr Leu Thr Arg Arg Val Thr Ala Thr Ala
        1165                    1170                    1175

AAG AGT ATT TCA GAG AAA GCT AAT GAA ACA AGA AGA AAT GGT TAC AAA
Lys Ser Ile Ser Glu Lys Ala Asn Glu Thr Arg Arg Asn Gly Tyr Lys
                    1180                    1185                    1190                    1195

AAA CAA CCT TAC TTA TAC CCA AAA CCA ACA GTA GGT TTT GTA GTA CAA
Lys Gln Pro Tyr Leu Tyr Pro Lys Pro Thr Val Gly Phe Val Val Gln
        1200                    1205                    1210

FIG. 6N.

GAT CAT TGT GAT TAT AAA GGT AAC TCC TCT AAT TAC AGA GAC TGT AAA
Asp His Cys Asp Tyr Lys Gly Asn Ser Ser Asn Tyr Arg Asp Cys Lys
                1215                    1220                    1225

GTG CGG TTA ATT AAA GGG AAA AAT TAT TTC GCA GCA CGC AAT AAT
Val Arg Leu Ile Lys Gly Lys Asn Tyr Phe Ala Ala Arg Asn Asn
                1230                    1235                    1240

ATG GCA TTA GGG AAA TAC GTT GAT TTA GGT TTA GGT ATT CGG TAT GAC
Met Ala Leu Gly Lys Tyr Val Asp Leu Gly Leu Gly Ile Arg Tyr Asp
                1245                    1250                    1255

GTA TCT CGC ACA AAA GCT AAT ACT GGT ATT AGT GTT GGT AAA TTT
Val Ser Arg Thr Lys Ala Asn Thr Gly Ile Ser Val Gly Lys Phe
                1260                    1265                    1270                1275

AAA AAT TTC TCT TGG AAT ACT GGT ATT GTC ATA AAA CCA ACG GAA TGG
Lys Asn Phe Ser Trp Asn Thr Gly Ile Val Ile Lys Pro Thr Glu Trp
                1280                    1285                    1290

CTT GAT CTT TCT TAT CGC CTT TCT ACT GGA TTT AGA AAT CCT AGT TTT
Leu Asp Leu Ser Tyr Arg Leu Ser Thr Gly Phe Arg Asn Pro Ser Phe
                1295                    1300                    1305

FIG. 60.

GCT GAA ATG TAT GGT TGG CGG TAT GGT GGC AAT AAT AGC GAG GTT TAT
Ala Glu Met Tyr Gly Trp Arg Tyr Gly Gly Asn Asn Ser Glu Val Tyr
         1310                          1315                    1320

GTA GGT AAA TTT AAG CCT GAA ACA TCT CGT AAC CAA GAG TTT GGT CTC
Val Gly Lys Phe Lys Pro Glu Thr Ser Arg Asn Gln Glu Phe Gly Leu
         1325                          1330                    1335

GCT CTA AAA GGG GAT TTT GGT AAT ATT GAG ATC AGT CAT TTT AGT AAT
Ala Leu Lys Gly Asp Phe Gly Asn Ile Glu Ile Ser His Phe Ser Asn
         1340                          1345                    1350                    1355

GCT TAT CGA AAT CTT ATC GCC TTT GCT GAA GAA CTT AAT AAA AAT GGA
Ala Tyr Arg Asn Leu Ile Ala Phe Ala Glu Glu Leu Asn Lys Asn Gly
         1360                          1365                    1370

ACT GGA AAG GCC AAT TAT GGA TAT CAT AAT GCA CAA AAT GCA AAA TTA
Thr Gly Lys Ala Asn Tyr Gly Tyr His Asn Ala Gln Asn Ala Lys Leu
         1375                          1380                    1385

GTT GGC GTA AAT ATA ACT GCG CAA TTA GAT TTT AAT GGT TTA TGG AAA
Val Gly Val Asn Ile Thr Ala Gln Leu Asp Phe Asn Gly Leu Trp Lys
         1390                          1395                    1400

FIG.6P.

CGT ATT CCC TAC GGT TGG TAT GCA ACA TTT GCT TAT AAC CGA GTA AAA
Arg Ile Pro Tyr Gly Trp Tyr Ala Thr Phe Ala Tyr Asn Arg Val Lys
    1405                        1410                    1415

GTT AAA GAT CAA AAA ATC AAT GCT GGT TTG GCC TCC GTA AGC AGT TAT
Val Lys Asp Gln Lys Ile Asn Ala Gly Leu Ala Ser Val Ser Ser Tyr
    1420                    1425                    1430         1435

TTA TTT GAT GCC ATT CAG CCC AGC CGT TAT ATC ATT GGT TTA GGC TAT
Leu Phe Asp Ala Ile Gln Pro Ser Arg Tyr Ile Ile Gly Leu Gly Tyr
    1440                    1445                        1450

GAT CAT CCA AGT AAT ACT TGG GGA ATT AAT ACA ATG TTT ACT CAA TCA
Asp His Pro Ser Asn Thr Trp Gly Ile Asn Thr Met Phe Thr Gln Ser
        1455                    1460                    1465

AAA GCA AAA TCT CAA AAT GAA TTG CTA GGA AAA CGT GCA TTG GGT AAC
Lys Ala Lys Ser Gln Asn Glu Leu Leu Gly Lys Arg Ala Leu Gly Asn
    1470                    1475                        1480

AAT TCA AGG GAT GTA AAA TCA ACA AGA AAA CTT ACT CGG GCA TGG CAT
Asn Ser Arg Asp Val Lys Ser Thr Arg Lys Leu Thr Arg Ala Trp His
        1485                    1490                        1495

FIG. 6Q.

ATC TTA GAT GTA TCG GGT TAT TAC ATG GCG AAT AAA AAT ATT ATG CTT
Ile Leu Asp Val Ser Gly Tyr Tyr Met Ala Asn Lys Asn Ile Met Leu
1500                         1505                         1510                    1515

CGA TTA GGG ATA TAT AAT TTA TTC TAC AAC TAT CGC TAT GTT ACT TCG GAA
Arg Leu Gly Ile Tyr Asn Leu Phe Tyr Asn Tyr Arg Tyr Val Thr Trp Glu
                    1520                         1525                    1530

GCG GTG CGT CAA ACA GCA CAA GGT GCG GTC AAT CAA CAT CAA AAT GTT
Ala Val Arg Gln Thr Ala Gln Gly Ala Val Asn Gln His Gln Asn Val
               1535                         1540                    1545

GGT AGC TAT ACT CGC TAC GCA GCA TCA GGA CGA AAC TAT ACC TTA ACA
Gly Ser Tyr Thr Arg Tyr Ala Ser Gly Arg Asn Tyr Thr Leu Thr
          1550                         1555                    1560

TTA GAA ATG AAA TTCTAAATTA AAATGCGCCA GATGGACTAG ACATGCTATA
Leu Glu Met Lys
          1565

TCTATACCTT ACTGGCGCAT CTTTTTCTGT TCTATAATCT GGTTAAGTGA AAAACCAAAC

TTGGATTTTT TAGAAGATCT TTCCACGCAT TTATTGTAAA ATCTCCGACA ATTTTTACCG

CACTTTTCTC TATTACAAAA ACAATAAGGA TCCTTTTGTG AATCTCTCA

FIG.7A.

```
CAACATCTGC CCAAGCTATA TTCGTTAATG ATAAGCCTAT TAATGATAAG CCTATTAATG

ATAAGAAAGA AATTGTTTT ACGCCATTT TCATATTTA TCCATGAACT TAAAAAATTC

TAAGTTGACA TTATTACAAA AAAAGAACAA TAATGCGAAT TATTATCAAT TTTGTATAAG

AATATAATTC T ATG AAA TCT GTA CCT CTT ATC TCT GGT GGA CTT TCC TTT
             Met Lys Ser Val Pro Leu Ile Ser Gly Gly Leu Ser Phe
             1                 5                      10

TTA TTA AGT GCT TGT AGC GGA GGG TCT TTT GAT GTA GAT AAC GTC
Leu Leu Ser Ala Cys Ser Gly Gly Ser Phe Asp Val Asp Asn Val
             15                  20                  25

TCT AAT CCC TCC TCT TCT AAA CCA CGT TAT CAA GAC GAT ACC TCG AAT
Ser Asn Pro Ser Ser Ser Lys Pro Arg Tyr Gln Asp Asp Thr Ser Asn
         30                  35                  40              45

CAA AGA ACA AAA TCT GAT TTG CAA AAG TTG TCC ATT CCT TCT TTA GGG
Gln Arg Thr Lys Ser Asp Leu Gln Lys Leu Ser Ile Pro Ser Leu Gly
         50                  55                      60
```

FIG. 7B.

GGA GGG ATG AAG TTA GTG GCT CAG AAT CTT CTT GGT AAG AAA GAA CCT
Gly Gly Met Lys Leu Val Ala Gln Asn Leu Leu Gly Lys Lys Glu Pro
65                                      70                              75

AGT CTC TTA AAT AAT GAA GAT GGC TAT ATG ATA TTT TCC TCA CTT TCT
Ser Leu Leu Asn Asn Glu Asp Gly Tyr Met Ile Phe Ser Ser Leu Ser
        80                              85                              90

ACG ATT GAA GAG GAT GTT ACA AAA GAA AAT AAA TCT CAG GAA CCC ACT
Thr Ile Glu Glu Asp Val Thr Lys Glu Asn Lys Ser Gln Glu Pro Thr
95                              100                             105

ATT GGC TCA ATA GAC GAG CCT AGC AAA ACA AAT TCA CCC CAA AAT CAT
Ile Gly Ser Ile Asp Glu Pro Ser Lys Thr Asn Ser Pro Gln Asn His
110                             115                             120                 125

CAT GGC AAT ATG TAT ATT CGG GTC TTT ATT ATA TTC AAT CGT GGC GTA
His Gly Asn Met Tyr Ile Arg Val Phe Ile Ile Phe Asn Arg Gly Val
        130                             135                             140

ATT CCT CAA ATG GCA AGT TTT ATT CAG ATG GTT ACT ATG GAT ATG CGT ATT
Ile Pro Gln Met Ala Ser Phe Ile Gln Met Val Thr Met Asp Met Arg Ile
145                             150                             155

FIG. 7C.

```
ACT TTG GCA AGC AAA CAG CCA CTA CAT TAC CTG TAGATGGCGA AGCAAGGTAT
Thr Leu Ala Ser Lys Gln Pro Leu His Tyr Leu
               160                         165

AAAGGAACTT GGCACTTCAT CACGGCAACT GAAAATGGCA AAAAGTATTC TTTGTTCAGT
AATGATAGCG GTCAAGCTTA TCGCAGACGT AGTGCAATTC CAGAAGATAT TGATTTAGAA
AAAAATGATT CAACTAATGG TGACAAGGGC TTAATAAGTG AATTTAGTGT CAATTTTGT
ACAAAAAAGC TCACTGGAAA ACTTTATTAT AATGAAAGAG AAACAGAACT TAATAAATCA
AAAGATAGAA AACATACACT CTACAATCTA GAAGCTGAAG TGTATAGTAA CCGATTCAGG
GGTACAGTAA AGCCAACCGA AAAAGATTCT ACAGATCATC CCTTTACCAG CGAGGGAACA
TTAGAAGGTG GTTTTTATGG GCCTAAAGGT GAAGAACTAG GAGGAAAGTT TTTAGCTGGC
GATAAAAAAG TTTTTGGGGT ATTTAGTGCC AAAGAAACGG AAGAAACAAA AAAGAAAGCG
TTATCCAAGG AAACCTTAAT TGATGGCAAG CTAACTACTT TTAAAACAAC CAATGCAACA
ACCAATGCAA CAGCCAATGC AACAACCAGT AACAACAGCA GTACAACAAC CGATGCAGAA
```

FIG.7D.

AACTTTACGA CGAAAGATAT ACCAAGTTTT GGTGAAGCTG ATTACCTTTT AATTGATAAT
TACCCTGTTC CTCTTTTACC TGAGAGTGGT GATTTCATAA GTAGTAAGCA CCATACTGTA
GGAAAGAAAA CCTATCAAGT AGAAGCATGT TGCAGTAATC TAAGCTATGT GAAATTTGGT
ATGTTTTATG AAGACCCACT TAAAGAAGAA AAAAGAAGAA AGACAAAGAA
AAACAAACGG CGGCAAGGAC CAACACTTAT TATCAATTCT TATTAGGTCT CCGTACTGCC
AGTTCTGAAA TCCCTAAAAT GGGAAACGTG GAATATGCGG GTAATTGGTT TGTTTATATT
AGTGATGGCA CGACATCTTA CTCCCCCAGT GGTGATAAGG AACGCAATAA AAATGCTCCC
GCCGATTTTA ATGTTGATTT TGTCAATAAA AAGCTAACAG GCACATTAAA ACGACACGAT
AATGAAATAA CCGTATTTAG TATTGAGGCA AACTTTAACA GTGGGAATGA CTTCACTGGT
AAAGCAACCG CAAAAGATTT AGTAATAGAT GGTAAAAGTA CACAAGCCAC ATCTAAAGTC
AATTCACGGC AACAGTAAAA GGGGCATTTT TATGGACCTG ATGCTTCTGA ATTAGCGGT
TATTTCACCT ATAACGGAAA AAATCCTACA GCTACAAATT CCCAACCGT ATCTTCACCA

FIG. 7E.

TCCAATTCAG CAAATGCTCG TGCTGCCGTT GTGTTTGGAG CTAAAAAACA AGTAGACACA

ACCAACAAGT AGAAAAAACC AAATAATGGA ATACTAAAA ATG ACT AAA AAA CCC
                                                                     Met Thr Lys Lys Pro
                                                                         170

TAT TTT CGC CTA AGT ATT ATT TCT TGT CTT TTA ATT TCA TGC TAT GTA
Tyr Phe Arg Leu Ser Ile Ile Ser Cys Leu Leu Ile Ser Cys Tyr Val
175                         180                         185

AAA GCA GAA ACT CAA AGT ATA AAA GAT ACA AAA GAA GCT ATA TCA TCT
Lys Ala Glu Thr Gln Ser Ile Lys Asp Thr Lys Glu Ala Ile Ser Ser
190                         195                         200                        205

GAA GTG GAC ACT CAA AGT ACA GAA GAT TCA GAA TTA GAA ACT ATC TCA
Glu Val Asp Thr Gln Ser Thr Glu Asp Ser Glu Leu Glu Thr Ile Ser
                         210                         215                         220

GTC ACT GCA GAA AAA ATA AGA GAT CGT AAA GAT AAT GAA GTA ACT GGA
Val Thr Ala Glu Lys Ile Arg Asp Arg Lys Asp Asn Glu Val Thr Gly
                         225                         230                         235

CTT GGC AAA ATT ATA AAA ACG AGT GAA AGT ATC AGC CGA GAA CAA GTA
Leu Gly Lys Ile Ile Lys Thr Ser Glu Ser Ile Ser Arg Glu Gln Val
                         240                         245                         250

FIG. 7F.

TTA AAT ATT CGT GAT CTA ACA CGC TAT GAT CCA GGC ATT TCA GTT GTA
Leu Asn Ile Arg Asp Leu Thr Arg Tyr Asp Pro Gly Ile Ser Val Val
255                             260                             265

GAA CAA GGT CGC GGT GCA AGT TCT GGA TAT TCT ATT CGT GGT ATG GAC
Glu Gln Gly Arg Gly Ala Ser Ser Gly Tyr Ser Ile Arg Gly Met Asp
270                             275                             280                             285

AGA AAT AGA GTT GCT TTA TTA GTA GAT GGT TTA CCT CAA ACG CAA TCT
Arg Asn Arg Val Ala Leu Leu Val Asp Gly Leu Pro Gln Thr Gln Ser
290                             295                             300

TAT GTA GTG CAA AGC CCT TTA GTT GCT CGT TCA GGA TAT TCT GGC ACT
Tyr Val Val Gln Ser Pro Leu Val Ala Arg Ser Gly Tyr Ser Gly Thr
305                             310                             315

GGT GCA ATT AAT GAA ATT GAA TAT GAA AAT GTA AAG GCC GTC GAA ATA
Gly Ala Ile Asn Glu Ile Glu Tyr Glu Asn Val Lys Ala Val Glu Ile
320                             325                             330

AGC AAG GGG AGT TCT TCT GAG TAT GGT AAT GGA GCA GCT GGT
Ser Lys Gly Gly Ser Ser Glu Tyr Gly Asn Gly Ala Leu Ala Gly
335                             340                             345

FIG. 7G.

```
TCT GTA ACA TTT CAA AGC AAA TCC GCA GCC GAT ATC TTA GAA GGA GAC
Ser Val Thr Phe Gln Ser Lys Ser Ala Ala Asp Ile Leu Glu Gly Asp
350                 355                 360                 365

AAA TCA TGG GGA ATT CAA ACT AAA AAT GCT TCA AGC AAA AAT AAA
Lys Ser Trp Gly Ile Gln Thr Lys Asn Ala Ser Ser Lys Asn Lys
        370                 375                 380

GGC TTT ACC CAT TCT TTA GCT GTA GCA GGA AAA CAA GGT GGA TTT GAA
Gly Phe Thr His Ser Leu Ala Val Ala Gly Lys Gln Gly Gly Phe Glu
            385                 390                 395

GGG GTC GCC ATT TAC ACT CAA CGA AAT TCG GAG GAA ACC CAA GTC CAT
Gly Val Ala Ile Tyr Thr Gln Arg Asn Ser Glu Glu Thr Gln Val His
400                 405                 410

AAA GAT GCA TTA AAA GGC GTA CAA GGT GTT GAG CGA TTC ATC GCC ACA
Lys Asp Ala Leu Lys Gly Val Gln Ser Tyr Glu Arg Phe Ile Ala Thr
            415                 420                 425

ACA GAT AAA TCT TCA GGA TAC TTT GTG ATA CAA GGT GAG TGT CCA AAT
Thr Asp Lys Ser Ser Gly Tyr Phe Val Ile Gln Gly Glu Cys Pro Asn
430                 435                 440                 445
```

FIG. 7H.

GGT GAT GAC AAG TGT GCA GCC AAA CCA CCT GCA AAG TTA TCC CCC CAA
Gly Asp Asp Lys Cys Ala Ala Lys Pro Pro Ala Lys Leu Ser Pro Gln
　　　　　　　450　　　　　　　　　　455　　　　　　　　　460

AGC GAA ACC GTA AGC GTT TCA GAT TAT ACG GGG GCT AAC CGT ATC AAA
Ser Glu Thr Val Ser Val Ser Asp Tyr Thr Gly Ala Asn Arg Ile Lys
　　　　　　　465　　　　　　　　　　470　　　　　　　　　475

CCT AAT CCA ATG AAA TAT GAA AGC CAG TCT TGG TTT TTA AGA GGA GGG
Pro Asn Pro Met Lys Tyr Glu Ser Gln Ser Trp Phe Leu Arg Gly Gly
　　　　　　　480　　　　　　　　　　485　　　　　　　　　490

TAT CAT TTT TCT GAA CAA CAC TAT ATT GGT GGT ATT TTT GAA TTC ACA
Tyr His Phe Ser Glu Gln His Tyr Ile Gly Gly Ile Phe Glu Phe Thr
　　　　　　　495　　　　　　　　　　500　　　　　　　　　505

CAA CAA AAA TTT GAT ATC CGT GAT ATG ACA TTT CCC GCT TAT TTA AGA
Gln Gln Lys Phe Asp Ile Arg Asp Met Thr Phe Pro Ala Tyr Leu Arg
　　　　　　　510　　　　　　　　　　515　　　　　　　　　520　　　　　　　　　525

TCA ACA GAA AAA CCG GAT GAT AGA ACT GGC CCT TTT TAT CCA AAG CAA
Ser Thr Glu Lys Arg Asp Asp Arg Thr Gly Pro Phe Tyr Pro Lys Gln
　　　　　　　530　　　　　　　　　　535　　　　　　　　　540

FIG. 71.

GAT TAT GGT GCA TAT CAA CGT ATT GAG GAT GGC CGA GGC GTT AAC TAT
Asp Tyr Gly Ala Tyr Gln Arg Ile Glu Asp Gly Arg Gly Val Asn Tyr
545                          550                          555

GCA AGT GGG CTT TAT TTC GAT GAA CAC CAT AGA AAA CAG CGT GTA GGT
Ala Ser Gly Leu Tyr Phe Asp Glu His His Arg Lys Gln Arg Val Gly
         560                          565                          570

ATT GAA ATT TAC GAA AAT CAA CAA AAC ATC ATA CTT GAC AGT TAT ATG
Ile Glu Ile Tyr Glu Asn Gln Gln Asn Ile Ile Leu Asp Ser Tyr Met
575                          580                          585

GCA GTG TTA AGT GCT AAT CAA CAA AAC ATC ATA CTT GAC AGT TAT ATG
Ala Val Leu Ser Ala Asn Gln Gln Asn Ile Ile Leu Asp Ser Tyr Met
590                          595                          600                          605

CGA CAT ACG CAT TGC AGT CTT TAT CCT AAT CCA AGT AAG AAT TGC CGC
Arg His Thr His Cys Ser Leu Tyr Pro Asn Pro Ser Lys Asn Cys Arg
         610                          615                          620

CCG ACA CTT GAT AAA CCT TAT TCA TAC TAT CGT TCT GAT AGA AAT GTT
Pro Thr Leu Asp Lys Pro Tyr Ser Tyr Tyr Arg Ser Asp Arg Asn Val
625                          630                          635

FIG. 7J.

TAT AAA GAA AAA CAT AAT ATG TTC CAA TTG AAT TTA GAG AAA AAA ATT
Tyr Lys Glu Lys His Asn Met Leu Gln Leu Asn Leu Glu Lys Lys Ile
                              640                    645                    650

CAA CAA AAT TGG CTT ACT CAT CAA TTC CAT CAA ATT GTC TTC AAT CTT GGT TTT GAT
Gln Gln Asn Trp Leu Thr His Gln Phe His Gln Ile Val Phe Asn Leu Gly Phe Asp
              655                    660                    665

GAC TTT ACT TCA GCG CTT CAG CAT AAA GAT TAT TTA ACT CGA CGT GTT
Asp Phe Thr Ser Ala Leu Gln His Lys Asp Tyr Leu Thr Arg Arg Val
              670                    675                    680                    685

ACC GCT ACG GCA AAT ATT ATT TCA GGG ACA GTT GCT GGT AAA CGA AGA
Thr Ala Thr Ala Asn Ile Ile Ser Gly Thr Val Ala Gly Lys Arg Arg
                      690                    695                    700

AAT GGT TAC GAA AAA CAA CCT TAC TTA TAC TCA AAA CCA AAA GTA GAT
Asn Gly Tyr Glu Lys Gln Pro Tyr Leu Tyr Ser Lys Pro Lys Val Asp
              705                    710                    715

TTT GTA GGA CAA GAT CAT TGT AAT TAT AAA GGT AGC TCC TCT AAT TAC
Phe Val Gly Gln Asp His Cys Asn Tyr Lys Gly Ser Ser Ser Asn Tyr
              720                    725                    730

FIG. 7K.

AGC GAC TGT AAA GTG CGG TTA ATT AAA GGG AAA AAT TAT TTC GCA
Ser Asp Cys Lys Val Arg Leu Ile Lys Gly Lys Asn Tyr Tyr Phe Ala
735                    740                    745

GCA CGC AAT AAT ATG GCA TTA GGG AAA TAC ATT GAT TTA GGT TTA GGT
Ala Arg Asn Asn Met Ala Leu Gly Lys Tyr Ile Asp Leu Gly Leu Gly
750                    755                    760                    765

ATT CGG TAT GAC GTA TCT CGT ACA AAA GCT AAT GAA TCA ACT ATT AGT
Ile Arg Tyr Asp Val Ser Arg Thr Lys Ala Asn Glu Ser Thr Ile Ser
770                    775                    780

GTT GGT AAA TTT AAA AAT TTC TCT TGG AAT ACT GGT ATT GTC ATA AAA
Val Gly Lys Phe Lys Asn Phe Ser Trp Asn Thr Gly Ile Val Ile Lys
785                    790                    795

CCA ACG GAA TGG CTT GAT CTT TCT TAT CGC CTT TCT ACT GGA TTT AGA
Pro Thr Glu Trp Leu Asp Leu Ser Tyr Arg Leu Ser Thr Gly Phe Arg
800                    805                    810

AAT CCT AGT TTT GCT GAA ATG TAT GGT TGG CGG TAT GGT GGC AAT AAT
Asn Pro Ser Phe Ala Glu Met Tyr Gly Trp Arg Tyr Gly Gly Asn Asn
815                    820                    825

FIG. 7L.

AGC GAT GTT TAT GTA GGT AAA TTT AAG CCT GAA ACA TCT CGT AAC CAA
Ser Asp Val Tyr Val Gly Lys Phe Lys Pro Glu Thr Ser Arg Asn Gln
830                     835                 840                 845

GAG TTT GGT CTC GCT CTA AAA GGG GAT TTT GGT AAT ATT GAG ATC AGT
Glu Phe Gly Leu Ala Leu Lys Gly Asp Phe Gly Asn Ile Glu Ile Ser
             850                 855                 860

CAT TTT AGT AAT GCT TAT CGA AAT CTT ATC GCC TTT GCT GAA GAA CTT
His Phe Ser Asn Ala Tyr Arg Asn Leu Ile Ala Phe Ala Glu Glu Leu
865                 870                 875

AGT AAA AAT GGA ACT ACT GGA AAG GGC AAT TAT GGA TAT CAT AAT GCA
Ser Lys Asn Gly Thr Thr Gly Lys Gly Asn Tyr Gly Tyr His Asn Ala
        880                 885                 890

CAA AAT GCA AAA TTA GTT GGC GTA AAT ATA ACT GCG CAA TTA GAT TTT
Gln Asn Ala Lys Leu Val Gly Val Asn Ile Thr Ala Gln Leu Asp Phe
             895                 900                 905

AAT GGT TTA TGG AAA CGT ATT CCC TAC GGT TGG TAT GCA ACA TTT GCT
Asn Gly Leu Trp Lys Arg Ile Pro Tyr Gly Trp Tyr Ala Thr Phe Ala
910                 915                 920                 925

FIG. 7M.

TAT AAC CGA GTA AAA GTT AAA GAT CAA AAA ATC AAT GCT GGT TTG GCC
Tyr Asn Arg Val Lys Val Lys Asp Gln Lys Ile Asn Ala Gly Leu Ala
930                                935                            940

TCC GTA AGC AGT TAT TTA TTT GAT GCC ATT CAG CCC AGC CGT TAT ATC
Ser Val Ser Ser Tyr Leu Phe Asp Ala Ile Gln Pro Ser Arg Tyr Ile
945                                950                            955

ATT GGT TTA GGC TAT GAT CAT CCA AGT AAT ACT TGG GGA ATT AAT ACA
Ile Gly Leu Gly Tyr Asp His Pro Ser Asn Thr Trp Gly Ile Asn Thr
960                                965                            970

ATG TTT ACT CAA TCA AAA GCA AAA TCT CAA AAT GAA TTG CTA GGA CAA
Met Phe Thr Gln Ser Lys Ala Lys Ser Gln Asn Glu Leu Leu Gly Gln
975                                980                            985

CGT GCA TTG GGT AAC AAT TCA AGG AAT GTA AAA TCA ACA AGA AAA CTT
Arg Ala Leu Gly Asn Asn Ser Arg Asn Val Lys Ser Thr Arg Lys Leu
990                                995                      1000                1005

ACT CGG GCA TGG CAT ATC TTA GAT GTA TCG GGT TAT TAC ATG GCG AAT
Thr Arg Ala Trp His Ile Leu Asp Val Ser Gly Tyr Tyr Met Ala Asn
            1010                            1015                     1020

FIG.7N.

AAA AAT ATT ATG CTT CGA TTA GGG ATA TAT AAT TTA TTC AAC TAT CGC
Lys Asn Ile Met Leu Arg Leu Gly Ile Tyr Asn Leu Phe Asn Tyr Arg
              1025                    1030                   1035

TAT GTT ACT TGG GAA GCG GTG CGT CAA ACA GCA CAA GGT GCG GTC AAT
Tyr Val Thr Trp Glu Ala Val Arg Gln Thr Ala Gln Gly Ala Val Asn
              1040                    1045                   1050

CAA CAT CAA AAT GTT GGT AGC TAT TAT ACT CGC TAC GCA GCA TCA GGA CGA
Gln His Gln Asn Val Gly Ser Tyr Tyr Thr Arg Tyr Ala Ala Ser Gly Arg
              1055                    1060                      1065

AAC TAT ACC TTA ACA TTA GAA ATG AAA TTC TAAATTAAAA TGCGCCAGAT
Asn Tyr Thr Leu Thr Leu Glu Met Lys Phe
              1070                   1075

GGACTAGATA TGCTATATCT ATACCTTACT GGGCCATCTT TTTCTGTTCT ATAATCTGCT

TAAGTGAAAA ACCAAACTTG GATTTTTAC AAGATCTTTT CACGCATTTA TTGTAAAATC

TCCGACAATT TTTACGCAC TTTTCTCTAT TACAAAAACA ATAAGGATCC TTTTGTGACT

CTCTCAATCT TTGGCAAGTT GCTGTTACAA CTTCAGATCA AGTTTCAGCC AGGGATCTTA

GGCACTTGGG TTCGGCC

FIG. 8A.

```
AT ATG AAA TCT GTA CCT CTT ATC TCT GGT GGA CTT TCC TTT TTA TTA
   Met Lys Ser Val Pro Leu Ile Ser Gly Gly Leu Ser Phe Leu Leu
   1                     5                  10                 15

AGT GCT TGT AGC GGG GGA GGT GGT TCT TTT GAT GTA GAT GAC GTC TCT
Ser Ala Cys Ser Gly Gly Gly Gly Ser Phe Asp Val Asp Asp Val Ser
             20                  25                  30

AAT CCC TCC TCT TCT AAA CCA CGT TAT CAA GAC GAT ACT TCA AGT TCA
Asn Pro Ser Ser Ser Lys Pro Arg Tyr Gln Asp Asp Thr Ser Ser Ser
                 35                  40                  45

AGA ACA AAA TCT AAA TTG GAA AAT TTG TCC ATT CCT TCT TTA GGG GGA
Arg Thr Lys Ser Lys Leu Glu Asn Leu Ser Ile Pro Ser Leu Gly Gly
             50                  55                  60

GGG ATG AAG TTA GTG GCT CAG AAT CTT CGT GAT AGG ACA AAA CCT AGT
Gly Met Lys Leu Val Ala Gln Asn Leu Arg Asp Arg Thr Lys Pro Ser
         65                  70                  75

CTC TTA AAT GAA GAT GAC TAT ATG ATA TTT TCC TCA CTT TCA ACG ATT
Leu Leu Asn Glu Asp Asp Tyr Met Ile Phe Ser Ser Leu Ser Thr Ile
     80                  85                  90                 95
```

FIG. 8B.

AAA GCT GAT GTT GAA AAA GAA AAT AAA CAC TAT ACA AGT CCA GTT GGC
Lys Ala Asp Val Glu Lys Glu Asn Lys His Tyr Thr Ser Pro Val Gly
                100                 105                 110

TCA ATA GAC GAG CCT AGT ACA ACA AAT CCA AAA GAA AAT GAT CAT GGA
Ser Ile Asp Glu Pro Ser Thr Thr Asn Pro Lys Glu Asn Asp His Gly
                115                 120                 125

CAA AGA TAT GTA TAT TCA GGA CTT TAT TAT TAT ATT CCA TCG TGG AAT TTA
Gln Arg Tyr Val Tyr Ser Gly Leu Tyr Tyr Tyr Ile Pro Ser Trp Asn Leu
                130                 135                 140

AAC GAT CTT AAA AAT AAC AAG TAT TAT TAT TCT GGT TAC TAT GGA TAT
Asn Asp Leu Lys Asn Asn Lys Tyr Tyr Tyr Ser Gly Tyr Tyr Gly Tyr
                145                 150                 155

GCG TAT TAC TTT GGC AAG CAA ACA GCC ACT ACA TTA CCT GTA AAT GGC
Ala Tyr Tyr Phe Gly Lys Gln Thr Ala Thr Thr Leu Pro Val Asn Gly
                160                 165                 170                 175

AAA GTA ACG TAT AAA GGA ACT TGG AGC TTC ATC ACC GCA GCT GAA AAT
Lys Val Thr Tyr Lys Gly Thr Trp Ser Phe Ile Thr Ala Ala Glu Asn
                180                 185                 190

FIG. 8C.

GGC AAA AGG TAT CCT TTG TTA AGT AAT GGC AGT CAA GCT TAT TTT CGA
Gly Lys Arg Tyr Pro Leu Leu Ser Asn Gly Ser Gln Ala Tyr Phe Arg
195                              200                          205

CGT AGT GCA ATT CCA GAA GAT ATT GAT TTA GAA GTT AAA AAT GAT GAG
Arg Ser Ala Ile Pro Glu Asp Ile Asp Leu Glu Val Lys Asn Asp Glu
210                              215                          220

AAT AGA GAA AAA GGG CTA GTG AGT GAA TTT AGT GCA GAT TTT GGG ACT
Asn Arg Glu Lys Gly Leu Val Ser Glu Phe Ser Ala Asp Phe Gly Thr
225                              230                          235

AAA AAA CTG ACA GGA GGA CTG TTT TAC ACC AAA AGA CAA ACT CAT ATT
Lys Lys Leu Thr Gly Gly Leu Phe Tyr Thr Lys Arg Gln Thr His Ile
240                              245                          255
                                                              250

CAA AAC CAT GAA AAG AAA CTC TAT GAT ATA GAT GCC CAT ATT TAT
Gln Asn His Glu Lys Lys Leu Tyr Asp Ile Asp Ala His Ile Tyr
260                              265                          270

AGT AAT AGA TTC AGA GGT AAA GTA AAT CCT ACC CAA AAA GAT TCT AAA
Ser Asn Arg Phe Arg Gly Lys Val Asn Pro Thr Gln Lys Asp Ser Lys
275                              280                          285

FIG. 8D.

```
GAA CAT CCC TTT ACC AGC GAG GGA ACA TTA GAA GGT GGT TTT TAC GGG
Glu His Pro Phe Thr Ser Glu Gly Thr Leu Glu Gly Gly Phe Tyr Gly
        290                 295                 300

CCT GAA GGT CAA GAA TTA GGA GGA AAG TTT TTA GCT GGC GAC AAA AAA
Pro Glu Gly Gln Glu Leu Gly Gly Lys Phe Leu Ala Gly Asp Lys Lys
        305                 310                 315

GTT TTT GGG GTA TTT AGT GCC AAA GGA ACG GAA GAA AAC AAA AAA TTA
Val Phe Gly Val Phe Ser Ala Lys Gly Thr Glu Glu Asn Lys Lys Leu
        320                 325                 330                 335

CCC AAA GAA ACC TTA ATT GAT GGC AAG CTA ACT ACT TTC TCT ACT AAA
Pro Lys Glu Thr Leu Ile Asp Gly Lys Leu Thr Thr Phe Ser Thr Lys
        340                 345                 350

ACA ACC GAT GCA AAA ACC AAT GCA ACA GCC AAT GCA ACA ACC AGT ACC
Thr Thr Asp Ala Lys Thr Asn Ala Thr Ala Asn Ala Thr Thr Ser Thr
        355                 360                 365

GCA GCC AAT ACA ACA ACC GAT ACA ACC GAT ACA ACA GCC AAT ACA GAT GCA
Ala Ala Asn Thr Thr Thr Asp Thr Thr Asp Thr Thr Ala Asn Thr Ile Thr Asp Ala
        370                 375                 380
```

FIG. 8E.

```
GAA AAC TTT AAG ACG AAA GAT ATA TCA AGT TTT GGT GAA GCT GAT TAC
Glu Asn Phe Lys Thr Lys Asp Ile Ser Ser Phe Gly Glu Ala Asp Tyr
385                 390                 395

CTT TTA ATT GAT AAT TAC CCT GTT CCT CTT TTA CCT GAG AGT GGT GAT
Leu Leu Ile Asp Asn Tyr Pro Val Pro Leu Leu Pro Glu Ser Gly Asp
400                 405                 410                 415

TTC ATA AGT AGT AAG CAC CAT ACT GTA GGA AAG AAA ACC TAT CAA GTA
Phe Ile Ser Ser Lys His His Thr Val Gly Lys Lys Thr Tyr Gln Val
420                 425                 430

AAA GCA TGT TGC AGT AAT CTA AGC TAT GTG AAA TTT GGT ATG TAT TAT
Lys Ala Cys Cys Ser Asn Leu Ser Tyr Val Lys Phe Gly Met Tyr Tyr
435                 440                 445

GAA GTC CCA CCT AAA GAA GAA GAA AAA GAC AAA GAA AAA GAA AAA AAA
Glu Val Pro Pro Lys Glu Glu Glu Lys Asp Lys Glu Lys Lys Glu Lys
450                 455                 460

GAA AAA GAA AAA CAA GCG ACA AAT CTA TCG AAC ACT TAT TAT CAA TTC
Glu Lys Glu Lys Gln Ala Thr Asn Leu Ser Asn Thr Tyr Tyr Gln Phe
465                 470                 475
```

FIG. 8F.

```
TTA TTA GGT CTC CGT ACT CCC AGT TCT GAA ATT CCT AAA GGA GGA AGT
Leu Leu Gly Leu Arg Thr Pro Ser Ser Glu Ile Pro Lys Gly Gly Ser
480                     485                     490                 495

GCA AAA TAT CTC CGT AGT TGG TTT GGT TAT CTG AGC GAT GGT TCA ACA
Ala Lys Tyr Leu Gly Ser Trp Phe Gly Tyr Leu Ser Asp Gly Ser Thr
              500                     505                     510

TCT TAC TCC CCC AGT GGT GAT AAG AAA CGC GAG AAC AAT GCT CTC GCC
Ser Tyr Ser Pro Ser Gly Asp Lys Lys Arg Glu Asn Asn Ala Leu Ala
          515                     520                     525

GAG TTT AAT GTA AAT TTT GTC GAT AAA ACA TTA AAA GGC CAA TTA ATA
Glu Phe Asn Val Asn Phe Val Asp Lys Thr Leu Lys Gly Gln Leu Ile
      530                     535                     540

CGA CAC GAT AAT CAA AAT ACC GTT TTT ACA ATT GAT GCA ACC TTT AAA
Arg His Asp Asn Gln Asn Thr Val Phe Thr Ile Asp Ala Thr Phe Lys
  545                     550                     555

GGT GGT AAG AAT AAC TTC ACT GGT ACA GCA ACC GCA AAC AAT GTA GCG
Gly Gly Lys Asn Asn Phe Thr Gly Thr Ala Thr Ala Asn Asn Val Ala
560                     565                     570                 575
```

FIG. 8G.

ATT GAT CCC CAA AGT ACA CAA GGC ACA TCT AAC GTC AAT TTC ACG GCA
Ile Asp Pro Gln Ser Thr Gln Gly Thr Ser Asn Val Asn Phe Thr Ala
         580                     585                     590

ACA GTA AAT GGG GCA TTT TAT GGG CCG AAC GCT ACA GAA TTA GGC GGT
Thr Val Asn Gly Ala Phe Tyr Gly Pro Asn Ala Thr Glu Leu Gly Gly
             595                     600                     605

TAT TTC ACC TAT AAC GGA AAT CCT ACA GAT AAA AGT TCC TCA ACC GTA
Tyr Phe Thr Tyr Asn Gly Asn Pro Thr Asp Lys Ser Ser Ser Thr Val
         610                     615                     620

CCT TCA TCA TCC AAT TCA AAA AAT GCA AGA GCT GCA GTT GTC TTT GGT
Pro Ser Ser Ser Asn Ser Lys Asn Ala Arg Ala Ala Val Val Phe Gly
         625                     630                     635

GCG AGA CAA CAA GTA GAA ACA ACC AAA TAATGCAATA CTAAAAATGA
Ala Arg Gln Gln Val Glu Thr Thr Lys
         640                     645

CTAAAAAAGC TTCTAGAAGC CGAATTC

FIG. 9A.

GAATTCGGCT TGGATCCAT ATG AAA TCT GTA CCT CTT ATC TCT GGT GGA CTT
                     Met Lys Ser Val Pro Leu Ile Ser Gly Gly Leu
                      1                   5                   10

TCC TTT TTA CTA AGT GCT TGT AGC GGA GGG TCT TTT GAT GTA GAT
Ser Phe Leu Leu Ser Ala Cys Ser Gly Gly Ser Phe Asp Val Asp
             15                  20                  25

AAC GTC TCT AAT CCA TCC TCT TCT AAA CCA CGT TAT CAA GAC GAT ACT
Asn Val Ser Asn Pro Ser Ser Ser Lys Pro Arg Tyr Gln Asp Asp Thr
                 30                  35                  40

TCA AGT TCA AGA ACA AAA TCT AAT TTG AAA AAG TTG TCC ATT CCT TCT
Ser Ser Ser Arg Thr Lys Ser Asn Leu Lys Lys Leu Ser Ile Pro Ser
             45                  50                  55

TTA GGG GGA GGG ATG AAG TTA GTG GCT CAG AAT CTT AGT GAT AAG AAC
Leu Gly Gly Gly Met Lys Leu Val Ala Gln Asn Leu Ser Asp Lys Asn
             60                  65                  70                  75

AAA CCT AGT CTC TTA AAT GAA GAT GAC TAT ATA TCA TAT TTT TCC TCA
Lys Pro Ser Leu Leu Asn Glu Asp Asp Tyr Ile Ser Tyr Phe Ser Ser
                 80                  85                  90

FIG. 9B.

CTT TCT ACA ATT CAA GAT GAT GTT AAA AAA GAA AAT AAA CGC CAT ACA
Leu Ser Thr Ile Gln Asp Asp Val Lys Lys Glu Asn Lys Arg His Thr
                    95                    100                   105

AAT CCA GTT GGC TCA ATA GAC GAG CCT AAC GCA ACA AAT CCA CCC GAA
Asn Pro Val Gly Ser Ile Asp Glu Pro Asn Ala Thr Asn Pro Pro Glu
                    110                   115                   120

AAG CAT CAT GGA CAA AGA TAT GTA TAT TCA GGG CTT TAT TAT ATT CCA
Lys His His Gly Gln Arg Tyr Val Tyr Ser Gly Leu Tyr Tyr Ile Pro
                    125                   130                   135

TCG TGG AGT CAT TCC TCA AAT GGC AAG CTT TAT TTA GGT TAC TAT GGA
Ser Trp Ser His Ser Ser Asn Gly Lys Leu Tyr Leu Gly Tyr Tyr Gly
                    140                   145                   150                   155

TAT GCG TTT TAT TAT GGT AAT AAA ACT GCA ACA AAC TTG CCA GTA AGC
Tyr Ala Phe Tyr Tyr Gly Asn Lys Thr Ala Thr Asn Leu Pro Val Ser
                    160                   165                   170

GGC ATA GCT AAA TAC AAA GGA ACT TGG GAT TTT ATT ACT GCA ACT AAA
Gly Ile Ala Lys Tyr Lys Gly Thr Trp Asp Phe Ile Thr Ala Thr Lys
                    175                   180                   185

FIG. 9C.

AAT GGC CAA CGT TAT TCT TTA TTT GGT AGC GCT TTT GGA GCT TAT AAT
Asn Gly Gln Arg Tyr Ser Leu Phe Gly Ser Ala Phe Gly Ala Tyr Asn
        190                 195                 200

AGA CGC AGT GCT ATT TCA GAA GAT ATA GAT AAT TTA GAA AAT AAT CTA
Arg Arg Ser Ala Ile Ser Glu Asp Ile Asp Asn Leu Glu Asn Asn Leu
        205                 210                 215

AAG AAT GGT GCG GGA TTA ACT AGT GAA TTT ACT GTC AAT TTT GGT ACG
Lys Asn Gly Ala Gly Leu Thr Ser Glu Phe Thr Val Asn Phe Gly Thr
        220                 225                 230                 235

AAA AAG CTC ACT GGA AAA CTT TAT TAT AAT GAA AGG GAA ACA AAT CTT
Lys Lys Leu Thr Gly Lys Leu Tyr Tyr Asn Glu Arg Glu Thr Asn Leu
        240                 245                 250

AAT AAA TTA CAA AAG AGA AAA CAT GAA CTC TAT GAT ATA GAT GCC GAT
Asn Lys Leu Gln Lys Arg Lys His Glu Leu Tyr Asp Ile Asp Ala Asp
        255                 260                 265

ATT TAT AGT AAT AGA TTC AGA GGT AAA GTA AAG CCA ACA ACC CAA AAA
Ile Tyr Ser Asn Arg Phe Arg Gly Lys Val Lys Pro Thr Thr Gln Lys
        270                 275                 280

FIG. 9D.

```
GAT TCT CAA GAA CAT CCC TTT ACC AGC GAG GGA ACA TTA GAA GGT GGT
Asp Ser Gln Glu His Pro Phe Thr Ser Glu Gly Thr Leu Glu Gly Gly
285                     290                     295

TTT TAT GGG CCT AAC GGT GAA GAA TTA GGA GGA AAG TTT TTA GCT GGC
Phe Tyr Gly Pro Asn Gly Glu Glu Leu Gly Gly Lys Phe Leu Ala Gly
300                     305                     310                 315

GAT AAC CGA GTT TTT GGG GTA TTT AGT GCC AAA GAA GAA ACA AAA
Asp Asn Arg Val Phe Gly Val Phe Ser Ala Lys Glu Glu Thr Lys
            320                     325                     330

GAC AAA AAA TTA TCC AGA GAA ACC TTA ATT GAT GGC AAG CTA ATT ACT
Asp Lys Lys Leu Ser Arg Glu Thr Leu Ile Asp Gly Lys Leu Ile Thr
335                     340                     345

TTT AAA AGA ACT GAT GCA ACA ACC AAT ACA GCA GCC AAT GCA AAA ACC
Phe Lys Arg Thr Asp Ala Thr Thr Asn Thr Ala Ala Asn Ala Lys Thr
            350                     355                     360

GAT GAA AAA AAC TTT ACG ACG AAA GAT ATA CCA AGT TTT GGT GAA GCT
Asp Glu Lys Asn Phe Thr Thr Lys Asp Ile Pro Ser Phe Gly Glu Ala
365                     370                     375
```

FIG. 9E.

GAT TAC CTT TTA ATT GAT AAT TAC CCT GTT CCT CTT TTC CCT GAA GAA
Asp Tyr Leu Leu Ile Asp Asn Tyr Pro Val Pro Leu Phe Pro Glu Glu
380                        385                        390                395

AAT ACT AAT GAT TTC ATA ACT AGT AGG CAC CAT AAG GTA GGA GAT AAA
Asn Thr Asn Asp Phe Ile Thr Ser Arg His His Lys Val Gly Asp Lys
             400                        405                        410

ACC TAT AAA GTA GAA GCA TGT TGC AAG AAT CTA AGC TAT GTG AAA TTT
Thr Tyr Lys Val Glu Ala Cys Cys Lys Asn Leu Ser Tyr Val Lys Phe
             415                        420                        425

GGT ATG TAT TAT GAA GAC CCA TTA AAT GGA GAA AAT GGC AAA GAA AAA
Gly Met Tyr Tyr Glu Asp Pro Leu Asn Gly Glu Asn Gly Lys Glu Lys
430                        435                        440

GAA AAA GAA AAA GAC AAA GAA AAA CAA GCG AAA ACA ACA TCT ATC
Glu Lys Glu Lys Asp Lys Glu Lys Gln Ala Thr Thr Ser Ile
445                        450                        455

AAG ACT TAT TAT CAA TTC TTA TTA GGT CAC CGT ACT GCC AAG GCC GAC
Lys Thr Tyr Tyr Gln Phe Leu Leu Gly His Arg Thr Ala Lys Ala Asp
460                        465                        470                475

FIG. 9F.

ATA CCT GCA ACG GGA AAC GTG AAA TAT CGC GGT AAT TGG TTT GGT TAT
Ile Pro Ala Thr Gly Asn Val Lys Tyr Arg Gly Asn Trp Phe Gly Tyr
480                             485                             490

ATT GGT GAT GAC AAG ACA TCT TAC TCC ACT ACT GGA GAT AAA AAT GCT
Ile Gly Asp Asp Lys Thr Ser Tyr Ser Thr Thr Gly Asp Lys Asn Ala
495                             500                             505

GTC GCC GAG TTT GAT GTA AAT TTT GCC GAT AAA ACA TTA ACA GGC ACA
Val Ala Glu Phe Asp Val Asn Phe Ala Asp Lys Thr Leu Thr Gly Thr
510                             515                             520

TTA AAA CGA CAC GAT AAT GGA AAT CCC GTA TTT ACA ATT AAT GCA AGC
Leu Lys Arg His Asp Asn Gly Asn Pro Val Phe Thr Ile Asn Ala Ser
525                             530                             535

TTT CAA AGT GGT AAG AAT GAC TTC ACT GGT ACA GCA ACC GCA AAC AAT
Phe Gln Ser Gly Lys Asn Asp Phe Thr Gly Thr Ala Thr Ala Asn Asn
540                             545                             550                             555

GTA GCG ATT GAT CCC CAA AAT ACA CAA ACC ACA TCT AGA GTC AAT TTC
Val Ala Ile Asp Pro Gln Asn Thr Gln Thr Thr Ser Arg Val Asn Phe
560                             565                             570

FIG. 9G.

```
ACG GCA ACA GTA AAC GGG GCA TTT TAT GGA CCT AAG GCT ACA GAA TTA
Thr Ala Thr Val Asn Gly Ala Phe Tyr Gly Pro Lys Ala Thr Glu Leu
        575                 580                 585

GGC GGT TAT TTC ACT TAT AAC GGA AAC AAT CCT ACA GAT AAA AAT TCC
Gly Gly Tyr Phe Thr Tyr Asn Gly Asn Asn Pro Thr Asp Lys Asn Ser
        590                 595                 600

TCA ACC GTT TCA CCA TCC AAT GCT TCA GCA AAT GCT CGT GCC GTT GTG
Ser Thr Val Ser Pro Ser Asn Ala Ser Ala Asn Ala Arg Ala Ala Val Val
        605                 610                 615

TTT GGC GCT AAA AAA CAA GTA GAA ACA ACC AAC AAG TAAAAACAAC
Phe Gly Ala Lys Lys Gln Val Glu Thr Thr Asn Lys
        620                 625                 630

CAAGTAATGG AATACTAAAA ATGACTAAAA AAGCTTCTAG AAAGCGGAAT TC
```

FIG.10A.

ATG AAA TCT GTA CCT CTT ATC TCT GGT GGA CTT TCC CTT TTA TTA AGT
Met Lys Ser Val Pro Leu Ile Ser Gly Gly Leu Ser Leu Leu Leu Ser
1                   5                   10                  15

GCT TGT AGC GGG GGA GGT GGT TCT TTT GAT GTA GAT GAC GTC TCT AAT
Ala Cys Ser Gly Gly Gly Gly Ser Phe Asp Val Asp Asp Val Ser Asn
            20                  25                  30

CCC TCC TCT AAA CCA CGT TAT CGT CAA GAC GAT ACC TCG AGT CAA AGA
Pro Ser Ser Lys Pro Arg Tyr Arg Gln Asp Asp Thr Ser Ser Gln Arg
        35                  40                  45

ACA AAA TCT AAT TTG GAA AAG TTG TCC ATT CCT TCT TTA GGA GGA GGG
Thr Lys Ser Asn Leu Glu Lys Leu Ser Ile Pro Ser Leu Gly Gly Gly
    50                  55                  60

ATG AAA TTG GTG GCT CAG AAT CTG AGT GGT AAT AAA GAA CCT AGT TTC
Met Lys Leu Val Ala Gln Asn Leu Ser Gly Asn Lys Glu Pro Ser Phe
65                  70                  75                  80

TTA AAT GGA AAT GAC TAT ATG ATA TTT TCC TCA CGT TCT ACG ATT AAA
Leu Asn Gly Asn Asp Tyr Met Ile Phe Ser Ser Arg Ser Thr Ile Lys
            85                  90                  95

FIG.10B.

```
GAT GAT GTT GAA AAT AAC AAT ACA AAC GGG GGG GAC TAT ATT GGC TCA
Asp Asp Val Glu Asn Asn Thr Asn Gly Gly Asp Tyr Ile Gly Ser
                            105                          110

ATA GAC GAG CCT AGT ACA ACA AAT CCA CTC GAA AAG CAT GGA CAA
Ile Asp Glu Pro Ser Thr Thr Asn Pro Leu Glu Lys His Gly Gln
            115                          120                125

AGG TAT GTA TAT TCA GGG CTT TAT TAT ATT CAA TCG TGG AGT CTA AGA
Arg Tyr Val Tyr Ser Gly Leu Tyr Tyr Ile Gln Ser Trp Ser Leu Arg
        130                          135                      140

GAT TTA CCA AAG AAG TTT TAT TCA GGT TAC TAT TAT GGA TAT GCG TAT TAC
Asp Leu Pro Lys Lys Phe Tyr Ser Gly Tyr Tyr Tyr Gly Tyr Ala Tyr Tyr
145                         150                         155           160

TTT GGC AAG GAA ACA ACA GCC ACT ACA CCT GTA AAT GGC GAA GCA ACG
Phe Gly Lys Glu Thr Thr Ala Thr Thr Leu Pro Val Asn Gly Glu Ala Thr
                165                         170                      175

TAT AAA GGA ACT TGG GAT TTC ATC ACT GCA ACT AGA AAT GGC AAA AGT
Tyr Lys Gly Thr Trp Asp Phe Ile Thr Ala Thr Arg Asn Gly Lys Ser
            180                         185                    190
```

FIG. 10C.

TAT TCT TTG TTA AGT AAT AAC CGA CAA GCT TAT TCC AAA CGT AGT GCA
Tyr Ser Leu Leu Ser Asn Asn Arg Gln Ala Tyr Ser Lys Arg Ser Ala
195                              200                         205

ATT CCA GAA GAC ATT GAT TTA GAA AAT GAT CCA AAG AAT GGT GAG ACG
Ile Pro Glu Asp Ile Asp Leu Glu Asn Asp Pro Lys Asn Gly Glu Thr
210                              215                         220

AGA TTA ACT AGT GAA TTT ACT GTG AAT TTT GGT ACG AAA AAG CTC ACA
Arg Leu Thr Ser Glu Phe Thr Val Asn Phe Gly Thr Lys Lys Leu Thr
225                              230                         235                         240

GGT GGA CTT TAT TAC CAT TTA CGT AAA ACA AAT GCT AAT GAA AAC CAA
Gly Gly Leu Tyr Tyr His Leu Arg Lys Thr Asn Ala Asn Glu Asn Gln
245                              250                         255

AAT AGA AAA CAT AAA CTC TAC AAT CTA GAA GCT GAT GTG TAT AGC AAC
Asn Arg Lys His Lys Leu Tyr Asn Leu Glu Ala Asp Val Tyr Ser Asn
260                              265                         270

CGA TTC AGA GGT AAA GTA AAG CCA ACC AAA GAG TCT TCT GAA GAA CAT
Arg Phe Arg Gly Lys Val Lys Pro Thr Lys Glu Ser Ser Glu Glu His
275                              280                         285

FIG.10D.

CCC TTT ACC AGC GAG GGA ACA TTA GAA GGT GGT TTT TAT GGG CCT AAT
Pro Phe Thr Ser Glu Gly Thr Leu Glu Gly Gly Phe Tyr Gly Pro Asn
290                          295                         300

GCT GAA GAA CTA GGG GGA AAA TTT TTA GCT AGC GAT AAA AAA GTT TTT
Ala Glu Glu Leu Gly Gly Lys Phe Leu Ala Ser Asp Lys Lys Val Phe
305                          310                         315                         320

GGG GTA TTT AGT GCC AAA GAA CAG CAA GAA ACG GAA GAA AAC AAA AAA
Gly Val Phe Ser Ala Lys Glu Gln Gln Glu Thr Glu Glu Asn Lys Lys
325                          330                         335

TTA CTC AAA GAA ACC TTA ATT GAT GGC AAG CTA ACT TTC TCT ACT
Leu Leu Lys Glu Thr Leu Ile Asp Gly Lys Leu Thr Thr Phe Ser Thr
340                          345                         350

AAA AAA ACC AAT GCA ACA ACC GAT GCA ACA ACC AGT ACA ACA ACC AGT
Lys Lys Thr Asn Ala Thr Thr Asp Ala Thr Thr Ser Thr Thr Thr Ser
355                          360                         365

ACA GCA ACC AAT GCA ACA GCC GAT GCA GAA AAC TTT ACG ACA AAA GAT
Thr Ala Thr Asn Ala Thr Ala Asp Ala Glu Asn Phe Thr Thr Lys Asp
370                          375                         380

FIG.10E.

ATA TCA AGT TTT GGT GAA GCT GAT TAT CTT TTA ATT GAT AAT TAC CCT
Ile Ser Ser Phe Gly Glu Ala Asp Tyr Leu Leu Ile Asp Asn Tyr Pro
385                          390                          395                    400

GTT CCT CTT TTA CCT GAA AAT ACT AAT GAT TTC ATA AGC AGT AAG CAC
Val Pro Leu Leu Pro Glu Asn Thr Asn Asp Phe Ile Ser Ser Lys His
          405                          410                          415

CAT GAG GTA GGA GGT AAA CAC TAT AAA GTG GAA GCA TGT TGC AAG AAT
His Glu Val Gly Gly Lys His Tyr Lys Val Glu Ala Cys Cys Lys Asn
420                          425                          430

CTA AGC TAT GTG AAA TTT GGT ATA TAT GAG GAT AAT GAG AAG AAC
Leu Ser Tyr Val Lys Phe Gly Ile Tyr Glu Asp Asn Glu Lys Asn
435                          440                          445

ACC AAA ATT GAA ACA GAA CAA TAC CAC CAA TTT TTG TTA GGT CTC CGT
Thr Lys Ile Glu Thr Glu Gln Tyr His Gln Phe Leu Leu Gly Leu Arg
450                          455                          460

ACT CCC AGT TCT CAA ATT CCT GCA ACG GGA AAC GTG AAA TAT CCC GGT
Thr Pro Ser Ser Gln Ile Pro Ala Thr Gly Asn Val Lys Tyr Arg Gly
465                          470                          475                    480

FIG.10F.

AGT TGG TTT GGT TAT ATT GGT GAT GAC AAG ACA TCT TAC TCC ACT ACT
Ser Trp Phe Gly Tyr Ile Gly Asp Asp Lys Thr Ser Tyr Ser Thr Thr
485                                490                          495

GGA GAT AAA AAT GCT CTC GCC GAG TTT GAT GTA AAT TTT ACC GAT AAA
Gly Asp Lys Asn Ala Leu Ala Glu Phe Asp Val Asn Phe Thr Asp Lys
500                                505                          510

AAG CTA ACA GGC GAA TTA AAA CGA GCC GAT AAT CAA GCC GTA TTT
Lys Leu Thr Gly Glu Leu Lys Arg Ala Asp Asn Gln Asn Thr Val Phe
515                                520                          525

AGA ATT AAT GCA GAC TTT AAA AAT AAT GAT AAT GCC TTC AAA GGT ACA
Arg Ile Asn Ala Asp Phe Lys Asn Asn Asp Asn Ala Phe Lys Gly Thr
530                                535                          540

GCA ACC GCA GAA AAT TTT GTA ATA GAT GGT AAC AAT AGT CAA ACT GGA
Ala Thr Ala Glu Asn Phe Val Ile Asp Gly Asn Asn Ser Gln Thr Gly
545                                550                          555                          560

AAT ACC CAA ATT AAT ATT AAA ACT GAA GTA AAT GGG GCA TTT TAT GGT
Asn Thr Gln Ile Asn Ile Lys Thr Glu Val Asn Gly Ala Phe Tyr Gly
565                                570                          575

FIG.10G.

```
CCG AAC GCT ACA GAA TTA GGC GGT TAT TTC ACT TAT AAC GGA AAA AAT
Pro Asn Ala Thr Glu Leu Gly Gly Tyr Phe Thr Tyr Asn Gly Lys Asn
        580                     585                     590

CCT ACA GAT AAA AAT TCT GAA AGT TCC TCA ACC GTA CCT TCA CCA CCC
Pro Thr Asp Lys Asn Ser Glu Ser Ser Ser Thr Val Pro Ser Pro Pro
        595                     600                     605

AAT TCA CCA AAT GCA AGA GCT GCA GTT GTC TTT GGT GCT AAA AAA CAA
Asn Ser Pro Asn Ala Arg Ala Ala Val Val Phe Gly Ala Lys Lys Gln
        610                     615                     620

GTA GAA AAA AAC AAC AAG TAAAAACAAC CAAGTAATGG AATACTAAAA
Val Glu Lys Asn Asn Lys
        625                     630

ATGACTAAAA AAGCTTCTAG AAGCCGAATT C
```

FIG. 11A.

```
ATG AAA TCT GTA CCT CTT ATC TCT GGT GGA CTT TCC TTT TTA CTA AGT
Met Lys Ser Val Pro Leu Ile Ser Gly Gly Leu Ser Phe Leu Leu Ser
 1               5                  10                  15

GCT TGT AGC GGA GGG GGG TCT TTT GAT GTA GAT AAC GTC TCT AAT ACC
Ala Cys Ser Gly Gly Gly Ser Phe Asp Val Asp Asn Val Ser Asn Thr
            20                  25                  30

CCC TCT TCT AAA CCA CGT TAT CAA GAC GAT ACC TCG AAT CAA AGA ACA
Pro Ser Ser Lys Pro Arg Tyr Gln Asp Asp Thr Ser Asn Gln Arg Thr
        35                  40                  45

AAA TCT AAA TTG GAA AAG TTG TCC ATT CCT TCT TTA GGA GGA GGG ATG
Lys Ser Lys Leu Glu Lys Leu Ser Ile Pro Ser Leu Gly Gly Gly Met
    50                  55                  60

AAG TTA GTT GTG CAA AAT TTT GCT GGT GCT AAA GAA CCT AGT TTC TTA
Lys Leu Val Val Gln Asn Phe Ala Gly Ala Lys Glu Pro Ser Phe Leu
65                  70                  75                  80

AAT GAA AAT GAC TAT ATA TCA TAT TTT TCC TCA CTT TCT ATG ATT AAA
Asn Glu Asn Asp Tyr Ile Ser Tyr Phe Ser Ser Leu Ser Met Ile Lys
                85                  90                  95
```

FIG. 11B.

GAT GAT GTT GAA AAT AAC AAT AAA AAT AAG GAT ACT CCA ATT GGC TCA
Asp Asp Val Glu Asn Asn Asn Lys Asn Lys Asp Thr Pro Ile Gly Ser
100                       105                       110

ATA GAC GAG CCT AGA GCA CCA AAT TCA AAC GAA AAT CAT CAA AAT CAT
Ile Asp Glu Pro Arg Ala Pro Asn Ser Asn Glu Asn His Gln Asn His
       115                       120                       125

CAT GGA CAG CAA TAT GTA TAT TCG GGT CTT TAT TAT ATT CCA TCG TGG
His Gly Gln Gln Tyr Val Tyr Ser Gly Leu Tyr Tyr Ile Pro Ser Trp
               130                       135                       140

CGT CTA ATA AAT TTA CCA AAT AAG TTT TAT TCA GGT TAC TAT GGA TAT
Arg Leu Ile Asn Leu Pro Asn Lys Phe Tyr Ser Gly Tyr Tyr Gly Tyr
145                       150                       155                       160

GCG TAT TAC TTT GGC AAG CAA ACT GCC ACT ACA TTA CCT GTA AAT GGC
Ala Tyr Tyr Phe Gly Lys Gln Thr Ala Thr Thr Leu Pro Val Asn Gly
       165                       170                       175

GAA GCA ACG TAT AAA GGA ACT TGG AGC TTC ATC ACC GCA ACT GAA AGA
Glu Ala Thr Tyr Lys Gly Thr Trp Ser Phe Ile Thr Ala Thr Glu Arg
               180                       185                       190

FIG.11C.

```
GGC AAA AAT TAT TCT TTG TTC AAT AAT AGA GGT CAA GCT TAT TCT CGA
Gly Lys Asn Tyr Ser Leu Phe Asn Asn Arg Gly Gln Ala Tyr Ser Arg
    195                     200                     205

CGT AGT GCT ACT CCA GGA GAT ATT GAT TTA GAA AAC GGT GAC GCA GGC
Arg Ser Ala Thr Pro Gly Asp Ile Asp Leu Glu Asn Gly Asp Ala Gly
    210                     215                     220

TTA ACA AGT GAA TTT ACT GTC AAT TTT GGT ACA AAA AAG CTC ACT GGA
Leu Thr Ser Glu Phe Thr Val Asn Phe Gly Thr Lys Lys Leu Thr Gly
    225                     230                     235         240

GAA CCT TAT TAT AAT GAA AGG GAA ACA AAT CTT AAT CAA TCA AAA GAT
Glu Pro Tyr Tyr Asn Glu Arg Glu Thr Asn Leu Asn Gln Ser Lys Asp
    245                     250                     255

AGA AAA CAT AAA CTC TAC GAT CTA GAA GCT GAT GTG TAT AGC AAC CGA
Arg Lys His Lys Leu Tyr Asp Leu Glu Ala Asp Val Tyr Ser Asn Arg
    260                     265                     270

TTC AGA GGT ACA GTA AAG CCA ACC AAA GAG TCT TCT GAA GAA CAT
Phe Arg Gly Thr Val Lys Pro Thr Lys Glu Ser Ser Glu Glu His
    275                     280                     285
```

FIG.11D.

```
CCC TTT ACC AGC GAG GGA ACA TTA GAA GGT GGT TTT TAT GGG CCT AAT
Pro Phe Thr Ser Glu Gly Thr Leu Glu Gly Gly Phe Tyr Gly Pro Asn
290                     295                     300

GCT GAA GAA CTA GGG GGA AAA TTT TTA GCT AGC GAT AAA AAA GTT TTT
Ala Glu Glu Leu Gly Gly Lys Phe Leu Ala Ser Asp Lys Lys Val Phe
305                     310                     315                 320

GGG GTA TTT AGT GCC AAA GAA ACG GAA GAA CCA AAA TTA CCC AAA
Gly Val Phe Ser Ala Lys Glu Thr Glu Glu Pro Lys Leu Pro Lys
            325                     330                     335

GAA ACC TTA ATT GAT GGC AAG CTA ACT TTC TCT AAA ACA ACC GAT
Glu Thr Leu Ile Asp Gly Lys Leu Thr Phe Ser Lys Thr Thr Asp
            340                     345                     350

ACA ACA AAT AAA ACA AGT GCA AAA ACC AAT ACA GAA AAC TTT
Thr Thr Asn Lys Thr Ser Ala Lys Thr Asn Thr Glu Asn Phe
        355                     360                     365

ACG ACA AAA GAT ATA CCA AGT TTT GGT GAA GCT GAT TAT CTT TTA ATT
Thr Thr Lys Asp Ile Pro Ser Phe Gly Glu Ala Asp Tyr Leu Leu Ile
370                     375                     380
```

FIG. 11E.

GAT AAT TAC CCT ATT CCG CTT TTA CCT GAG AGT GGT GAT TTC ATA AGT
Asp Asn Tyr Pro Ile Pro Leu Leu Pro Glu Ser Gly Asp Phe Ile Ser
385                 390                 395                 400

AGT AAG CAC CAT GAG GTA GGA GGT AAA CGC TAT AAA GTG GAA GCA TGT
Ser Lys His His Glu Val Gly Gly Lys Arg Tyr Lys Val Glu Ala Cys
            405                 410                 415

TGC AAG AAT CTA TGC TAT GTG AAA TTT GGT ATG TAT TAT GAG GAT AAA
Cys Lys Asn Leu Cys Tyr Val Lys Phe Gly Met Tyr Tyr Glu Asp Lys
        420                 425                 430

GAG AAC AAC AAA AAT GAA ACA GAC AAA GAA AAA GAA AAA CAA ACG ACA
Glu Asn Asn Lys Asn Glu Thr Asp Lys Glu Lys Glu Lys Gln Thr Thr
    435                 440                 445

ACA TCT ATC AAG ACT TAT TAT CAA TTC TTA GGT CTC CGG ACT CCC
Thr Ser Ile Lys Thr Tyr Tyr Gln Phe Leu Gly Leu Leu Arg Thr Pro
450                 455                 460

AGT TCT GAA ATT CCT AAA ATG GGA AAC GTG ACA TAT CGC GGT AGT TGG
Ser Ser Glu Ile Pro Lys Met Gly Asn Val Thr Tyr Arg Gly Ser Trp
465                 470                 475                 480

FIG. 11F.

TTT GGT TAT ATT GGT GAT GAC AAG ACA TCT TAC TCC GCT ACA GGA GAT
Phe Gly Tyr Ile Gly Asp Asp Lys Thr Ser Tyr Ser Ala Thr Gly Asp
485                          490                         495

AAA CGA CAA GAT AAA AAT GCT CCC GCC GAG TTT AAT GCT GAT TTT AAC
Lys Arg Gln Asp Lys Asn Ala Pro Ala Glu Phe Asn Ala Asp Phe Asn
500                          505                         510

AAT AAA AAG CTA ACA GGC ACA TCA AAA CGA CAC GAT AAT CAA AAT CCC
Asn Lys Lys Leu Thr Gly Thr Ser Lys Arg His Asp Asn Gln Asn Pro
515                          520                         525

GTG TTT AAC ATT AAG GCA ACC TTT CAA AAT GGT CGG AAT GAC TTT GAA
Val Phe Asn Ile Lys Ala Thr Phe Gln Asn Gly Arg Asn Asp Phe Glu
530                          535                         540

GGT ACA ACC GCA GAA AAT TTT GTA ATA GAT GGT AAA GAT AGT CAA
Gly Thr Ala Thr Ala Glu Asn Phe Val Ile Asp Gly Lys Asp Ser Gln
545                          550                         555                         560

GGA AAT ACC CCA ATT AAT ATT ACA ACT AAA GTA AAC GGG GCA TTT TAT
Gly Asn Thr Pro Ile Asn Ile Thr Thr Lys Val Asn Gly Ala Phe Tyr
565                          570                         575

FIG. 11G.

```
GGA CCT GAT GCT TCT GAA TTA GGC GGT TAT TTC ACC TAT AAC GGA AAA
Gly Pro Asp Ala Ser Glu Leu Gly Gly Tyr Phe Thr Tyr Asn Gly Lys
            580                     585                     590

GAC ACT ATA ACT AAA AAT ACT GAA AGT TCC TCA ACC GTA CCT TCA CCA
Asp Thr Ile Thr Lys Asn Thr Glu Ser Ser Thr Val Pro Ser Pro
            595                     600                     605

CCC AAT TCA CCA AAT GCA AGA GCT GCA GTT GTG TTT GGA GCT AAA AAA
Pro Asn Ser Pro Asn Ala Arg Ala Ala Val Val Phe Gly Ala Lys Lys
            610                     615                     620

CAA GTA GAA ACA ACC AAC AAG TAGAAAAAAA CAAATAATGG AATACTAAAA
Gln Val Glu Thr Thr Asn Lys
            625                 630

ATGACTAAAA AAGCTTCTAG AAAGCCGAAT TC
```

FIG.12A

```
         -35                                    -10                    RBS
TCTAACTTGACATTATTACAAAAAAGATCAATAATGCGAATTATTATCAATTTTGTATGAG...
TCTAACTTGACATTATTACAAAAAAGATCAATAATGCGAATTATCAATTTTGTATGAG...
TCTAAGTTGACATTATTACAAAAAAGAACAATAATGCGAATTATTATCAATTTTGTATGAG...
TCTAAGTTGACATTATTACAAAAAAGAACAATAATCCGAATTATTATCAATTTTGTATAAG...
                   fur-binding site          ATAATGATAATCATTATC ...5'GGATCCAT\ATGAAATCTGTACCTCTTATCTCTCTGGT 3'
                       M  K  S  V  P  L  I  S  G
         ...TATATAATTCTATGAAATCTGTACCTCTTATCTCTCTCGT      EAGAN
         ...TATATAATTCTATGAAATCTGTACCTCTTATCTCTCTCGT      MINNA
         ...TAT-TAATTCTATGAAATCTGTACCTCTTATCTCTCTCGT      PAK
         ...AATATAATTCTATGAAATCTGTACCTCTTATCTCTCTCGT      SB33
```

FIG. 12B

```
3' tbp2                                                                              5' tbp1
                                                                                     M T K K
GTAGAAACAACCAACCAAATAA--------------TGGAATACTAAAAATGACTAAAAACCCTATTTTCGCCTAAGT       EAGAN
GTAGAAACAACCAACCAAATAA--------------TGGAATACTAAAAATGACTAAAAACCCTATTTTCGCCTAAGT       MINNA
GTAGAAACAACCAACCAAGTAA--------------TGGAATACTAAAAATGACTAAAAACCCTATTTTCGCCTAAGT       DL63

GTAGAAACAACCAACCAAGTAAAAAAACAACCAAGTAATGGAATACTAAAAATGACTAAAAACCCTATTTTCGCCTAAGT    PAK
                                 3'TACTTATGATTTTTACTGATTTTT
                                                            \CGAAGATCT 5'
                                                              M T K K
GTAGAAACAACCAACCAAATAA--------------TGGAATACTAAAAATGACTAAAAA                        SB12

GTAGAAACAACCAACCAAGTAAAAAACAACCAAGTAATGGAATACTAAAAATGACTAAAAA                       SB29

GTAGAAACAACCAACTAGTAAAAAACAACCAAGTAATGGAATACTAAAAATGACTAAAAA                        SB30

GTAGAAACAACCAACCAAGTAAAAAAAACAACCAAGTAATGGAATACTAAAAATGACTAAAAA                     SB32
```

FIG. 14A.

Comparison of TBP1 amino acid sequences

```
MTKKPYFRLSIISCLLISCYVKAETQSIKDTKEAISSEVDTQSTEDSELETISVTAEKIRDRKDNEVTGLGKIIKTSESISREQVLNIRDLTRYDPGISV         EAGAN
..............................................................................................         DL63
.............................................................V..................................         PAK
..............................................................................................         SB33
...QQQHL...N.L-..SLMTALPVYAENTQAEQAQEKQ------.D..Q.K.K.QKT.R............LV.S.DTL.K..............A.         B16B6
...QQQHL...N.L-..SLMTALP.YAENTQAGQAQEKQ------.D..Q.K.K.QKT.R............LV..ADTL.K....D..........A.         M982
...QQQHL...N.L-..SLMTALP.YAENTQAGQAQEKQ------.D..Q.K.K.QKT.R............LV..ADTL.K....D..........A.         FA19

VEQGRGASSGYSIRGMDRNRVALLVDGLPQTQSYVVVQSPLVARSGYSGTGAINEIEYENVKAVEISKGGSSEYGNCALAGSVTFQSKSAADILEGDKSW         EAGAN
....................................................................................................         DL63
....................................................................................................         PAK
....................................................................................................         SB33
....K...S.T...VS.I...TA.AA.GGTRTAGSS..........................SN..........A..TT....IGEG.Q........         B16B6
....K...S.T....A.I...TA.AA.GGTRTAGSS..........................SN.V.Q.S....A..T.T.D.VIGEGRQ........         M982
....K...S.T....A.I...TA.AA.GGTRTAGSS..........................SN.V.Q.S....A..T.T.D.VIGEGRQ........         FA19

GIQTKNAYSSKNKGFTHSLAVAGKQGGFEGLAIYTQRNSIETQVHKDALKGVQSYDRLIATTDKSSGYFVIQG-----ECPNGDDK--CAA--KPPATLS         EAGAN
.............V...H...................................F....EDQ.A...M.D------..LD.Y...-.KTSP.R.....         DL63
.............D.V.......................................................H...KPEDQ.A...M.D------....KP..YNS.LPFA.R..I..         PAK
.............V.....E...................................E.F.................--------......----.KV.         SB33
...S.T..G.DHAL.Q...L..RS..A.A.L...K.RGR.IHA....G.....FN..VLDE..KE.GSQYRYFIVEE..H..YAA--.KNKL.ED.SVK         B16B6
...S.T..G.R.L.Q.I.L..RI..A.A.L.H.K.RGG.IRA.E..GR.....FN..VLVE.----SSEYAYFIVED..EGKNYET-.KSKP.KDVVGK         M982
...S.T..G.R.L.Q.I.L..RI..A.A.L.H.K.RGG.IRA.EA.GR.....FN..APVD.----GSKYAYFIVEE..K..GHEK-.K..NP.KDVVGE         FA19
```

FIG. 14B.

```
TQSETVSVSDYTGANRIKPNPMKYESQSWFLRGGYHFSE-QHYIGGIFEFTQQKFDIRDMTFPAYLSPTERRDDSSRSFYPMQDHGAYQHIEDGR----   EAGAN
..R...............................................-.........................R..DK.LQ..P...K..Y......G......--   DL63
S.R...............................................-.........................RS.K....G...K.Y......R.........--   PAK
P.................................................-.........................RS.K...RTGP..K..Y......R.........--   SB33
DERK...TQ....S..LLA..LE.G.........LF.P.W.LDN-R..V.AVL.R....T..T.....V..FTSEDYVP----GSLKGLGKYSGDNKAE..LFVQG   B16B6
DERQ...TR....P..FLAD.LS....R..LF.P.FR.ENKRR......L.H...T..T.....V..F.TKAVFDAN..KQAGSLPGNGKYAGNHKY.GLFTNG   M982
DERQ...TR....P..FLAD.LS....R..LF.P.FR.ENKRR......L.H...T..T.....V..F.TKAVFDANQKQAGSLPGNGKYAGNHKY.GLFTSG   FA19

------GVKYASGLYFDEHHRKQRVGIEYIYENKNKAGIIDKAVLSANQQNIILDSYMRHTCSLYPNPSKNCRPTLDKPYSYRSDRNVYKEKHNMLQL   EAGAN
................................................................H.............................   DL63
................................................Q.............H.............................    PAK
..N................................................................................................   SB33
..N................................................................................................
EGSTLQ.IG.GT.VFY..R.T.N.Y.V..V.H.AD.DTWA.Y.R..YDR.G.D..NRLQQ.....HDGSD-......DGN....F.K....MI.E.SR.LF.A   B16B6
ENGALV.AE.GT.VFY..T.T.S.Y.L..V.T.AD.DTWA.Y.R..YDR.G.D..NHFQQ.....ADGSD-..Y....SA....F....K....VI.G.S.RL..A   M982
ENNAPV.AE.GT.VFY..T.T.S.Y.L..V.T.AD.DTWA.Y.R..YDR.G.D..NHFQQ.....ADG...Y....SA....F....K....VI.G.S.KL..A   FA19

NLEKKIQQNWLTHQIVFNLGFDDFTSALQHKDYLTRRVIATADSIPRKPGETGKPRNGLQSQ-PYLYPKPEPYFAGQDHCNYQGSSNYRDCKVRLIKGK   EAGAN
..............A.................................S..SE.R..A--R......S-.....T.KAELV.G.L....K.....S........   DL63
.................................................T...K..SE.AN...-R...YKK.-......TVG.VV....D.K.N..........   PAK
.................................................T...NI.SGTVA--..R...YEK.-.....S..KVG.V.....K.....S........   SB33
VFK.AFDTAKIR.NLSI...Y.R.K.Q.S.S..YLQNAVQAY.L.TP.KPPFP----.SKDN-..RVSIGKTVNTSPI.RFGNNT--.Y..TP.N.G.N   B16B6
AFK.SFDTAKIR.NLSV......R.D.N.R.Q..YYQHANRAYS..KTPPKTANP----..DK.K-..WVSIGGNVVTGQI.LFGNNT--.Y..TP.S.N..   M982
AFK.SFDTAKIR.NLSV...Y.R.G.N.R.Q..YYQSANRAYSLKTPPQNNGK.TSPNGREKN..WVSIGRGNVVTRQI.LFGNNT--.Y..TP.S.N..   FA19

NYYFAARNNMALGKYVDLGLGIRYDVSRTKANESTISVGKFKNFSWNTGIVIKPTEWLDLSYRLSTGFRNPSFSEMYGWRYGGKNDEVYVGKFKPETSRN   EAGAN
...................................................................................A.........DTD.I..........   DL63
...................M....................................................................A.............N.S......   PAK
```

FIG. 14C.

```
                 I.........................A................N.SD............  SB33
G..A.VQD.VR..RWA.V.A....YRS.HSEDKSV.T.THR.L...A.V.L.FT.M..T.A......L..A....A.---ESLKTLDL...K.F.  B16B6
G..A.V.D.VR..RWA.V.A.L..YRS.HSDDGSV.T.THRTL...A...L.AD....T.A......L..A.....S.---VQSKAV.ID..K.F.  M982
S..A.V.D.VR..RWA.V.A.L..YRS.HSDDGSV.T.THRTL...A...L.AD....T.A......L..A.....S.---.KIKAV.ID..K.F.  FA19

QEFGLALKGDFGNIEISHFSNAYRNLIAFAEELSKNG-TGKGNY--GYHNAQNAKLVGVNITAQLDFNGLMWKRIPYGWVATFAYNQVKVKDQKINAGLAS  EAGAN
.............................T.......-----.......................R...........................  DL63
.............................T.......-----.N..-A.....................R........................  PAK
......................................-----..........................R........................  SB33
R.A.IVF......L.A.Y.N....D....GY.TRTQNGQTSASGDP..R....RIA.I..LGKI.WH.V.GGL.D.L.S.L...RI....AD.R.DRTF  B16B6
K.A.IVF......L.A.W.N....D..VRGY.AQIKNGKEEAKGDPA.L...S.RIT.I..LGKI.W..V.DKL.E...S......R.H.R.I.KR.DRTD  M982
K.A.IVF......L.A.W.N....D..VRGY.AQIKDGKEQVKGNPA.L...S.RIT.I..LGKI.W..V.DKL.E...S......R.R.R.I.KR.DRTD  FA19

VSSYLFDAIQPSRYIIGLGYDHPSNTWGINTMFTQSKAKSQNELLGKRALGNNSRD-VKSTRKLTRAWHILDVSGYYMANKNIMLRLGIYNLFNYRYVTW  EAGAN
...................................................N--.................V.RS.LF..V...L........  DL63
.......................................................Q..........-N..........................  PAK
.......................................................Q..........-N..........................  SB33
.T.....V.....VL......DGI......Y.....VD....SQ..L.GNANAK.AASRR..P.YVT....NIK.HLT..A.V...L........  B16B6
IQ.H.........VV......Q.EGK..V.G.L.Y....EIT.....S...L.GNSRNT.A.ARR..P.Y.V......TIK.HFT..A.V...L........  M982
IQ.H.........VV.S....Q.EGK..V.G.L.Y....EIT.....S...L.GNSRNT.A.ARR..P.Y.V......TVK.HFT..A.V...L.H......  FA19

EAVRQTAQGAVNQHQNVGSYTRYAASGRNYTLTLEMKF*  EAGAN
.....................N..............*  DL63
.....................................*  PAK
.....................................*  SB33
.N......G........K...V.N....P.....FS.*  B16B6
.N......G...G.K..V.N........P.....FS.*  M982
.N......A........K...V.N....P.....FS.*  FA19
```

FIG. 15A.

Comparison of TNP2 amino acid sequences

```
MKSVPLISGGLSFLLSACSGGG-SFDVDNVSNTPS--SKPRYQDDTS----NQRKKS-NLKKLFIPSLGGGMKLVAQNLRGNREPSFLNEDDYISYFSS    EAGAN
..........................................................SS.T..-K.E..S............A.L.FDRNK.L....S.M-I..    DL63
...T....................G......D..PS.-.................-......T..-D.E.................FI.AR......G.M-I..    PAK
........................G......D..PS.-.................--SS.T..-K.EN.S................DRTK.L......M-I..    SB12
...........................-...........................--SS.T..-...S..................FDRNK.L.........    SB19
........................G......D..PS.-.................---S..T..-...E..S........................GN.M-I..    SB30
...L....................-..............................----.T..-K.E..S..............V.FA.A....N........    SB32
MNNPLVNQAAMVLPV.........L...G...L.S.ETVODMH...K.E.EK.Q-PES.QDV.E.SGAAYGFAVKLPRRNAHF.PKYKFKHKP.GSM.WKKLO-R    B16B6
MNNPLVNQAAMVLPV.........L...G...L.S.DT-EAPRPA.K..VS.EKPQA.KD----QG-GYGFAMRLKRRN--WYPGAEESEVK...S.WEATGLP    M982
MNNPLVNQAAMVLPV.........L...G...L.S.DT-EAPRPA.K..VP.KKPEARKD----QG-GYGFAMRFKRRNQHPSANPKEDEVK.KN..WEATGLP    FA19
MHFKINPYALAFTSL..-V.....KG...LED.RPNKTTGVSKEEYK.VETAKKEKEQ----..GE.ME.A..YVV.V-------.VSSF.NKKVDI---    AP205
MHFKINPYALAFTSL..-V.....KG...LED.RPNQTAKAEKATTSYQDEETKKKT.--EE.D..ME.A..YET----.I..R..A.KTETGEKRNREV--    AP37

L---------STIEKDVK---DNNKNGADLIGSIDEPSTTNPPEK---HHGQF-----------YVYSGLYYTPSWSLNDSKN-KF--------YLGYYGYAFY    EAGAN
R----...E.----ND.Q..EHP.D..VD.RAP.SN.N---R......-----IQ...R.LP.K..........S........Y.......    DL63
.-----..E..EKVKN.....GR.....E..NG.SQNSN---S--.E-----ID..RDYKKEEQ.A---------T---.....Y.......    PAK
.-----...KA..EK---E..HYTSPV.........K.N---.D..R--------.I...N...L..N.Y----------Y.S........Y.......    SB12
.-----...QD...K---E..RHTNPV.........NA........-----.I....HSSNGKL-----------------------.......    SB29
R-----...KD.E---N..T.G.Y...........L..R.............R-----IQ...R.LPK-.............S.......Y.......    SB30
.-----..M.KD.E---N...KDTP......RAP.SN.NHQN...Q-----------.I..R.INLP.-.-.-------.S.......Y.......    SB32
GEPNSFSERDE--L..KRG----SSE-..E.KW.DG-----------QSRVVGYTNFT..R..YV.LNK-NNI.I..NIV--LFGPDG..Y.K.KEPS    B16B6
TKPKEL.PKRQK.V...VETDGDSDIYSSPY.TR.NHQNGSAGNGVN---QPKNQATGHENFQ....WF.KHAA.EK.FS.K.I--KSGDDG.IF.H.EKPS    M982
TEPKKL.PLKQQ.V.SEVETNGNSKMYTSPY.SQDA.SSH---ANGAN---QPKNEVTDYKKFK....WF.KHAK.EVKNE.GLVSAKRGDDG.IF.H.DKPS    FA19
------...D..VITNGNL.DVPYK.NSSKYNYPDI..........KTKDSSLQ..R..YVIDGEH.GSNE-------.VY.........    AP205
-------VELSED.IT.LYQESVEIIPH.DELNGKTTSNDVYHS---DSKRLDKNRDLK..R..YV.DG.FNEIRRNDSG.HVFKQGID-----.VY.    AP37
```

FIG.15B.

```
YGNKTATNLPVNGVAKYKGTWDFITATKNGKRYPLLSNGS---HAYYRRSAIPEDIDLENDSKNGDI-GLISEFSADFGTKKLTGQLSYTKRKT------N        EAGAN
F..T..SA...G....T......S....AE...N.E..R.SGGG-Q..S....T.....DRKT-----.T...TVN........G.Y.NL.E.DAN----K        DL63
...E..K...K......N......E......S.F..SIG-Q..S.....S..YNLENGDA----.....V..K.E..E.Y.NE...SVN----E                PAK
F.KQ...T....KVT......S....AE.........---Q.F..........VKNDENREK..V..............G.F....Q.------H               SB12
.......S.I.............Q..S.FGSAF---G..N........S....NLENNLKNGA-..T...TVN..........K.Y.NE.------N             SB29
F.KE....T.....E.T...........R..S..S...NR----Q..SK...........P...ETR-.T....TVN..........G.Y.HL...NAN----E      SB30
F.KQ...T.....E.T......S......ER..N.S.FN.RG---Q..S...T.G......A-.T...TVN.........EPY.NE.E.N------L              SB32
KELP-SEKITYK..TWD.VTDAMEKQRFEGL.-GSAAGGFKSGALSALEEGVLRNQAEAS--SGHT.F-.MT..EV..SD.TIK.T.YRNN.I.QNNSENKQ          B16B6
RQLPASGKVIYK..WHFVTDTKKGQDFREIIQPSKKQGDRYSGFSGDGSEEYSNKNESTLKDDHEGY-.FT.NLEV...N....K.IRNNASLNNNTNNDK           M982
RQLPASEAVIYK..WHFVTDTKQGQKFNDILETSKGQGDKYSGFSGDDEGETSNRT.SNLND.HEGY-.FT.N.KV..NN....K.IRNNKVINTAASDG-          FA19
K..SP.KE....QLLT.T.S...TSNANLNNEEGRPNYLN---DD..TKFIGKRVGLVSG.A.PAKH-KYT.Q.EV..A..M.KJ.-D.E..........           AP205
L.VTPSKE..KGK.IS.....VSNINLEREIDGKDTSGDGKNVSATSITETVNR.HKVGE.L..N-EVKGVAHSSEFAVDFDNKKLTGSLYRNGYINRNK           AP37

NQ--PYEKKLYDIDADIYSNRFRGTVKPTEKD-SEEHPFTSEGT-LEGGFYGPNAEELGGKFLATNDRVFGVFSAKETEETKKEA-LSKETLIDGLITFFS          EAGAN
S.--NRTH-....LE..VH.......K.....K.ES........EGQ.........H.KK.L.....QQ..SENKK.P........T..K                    DL63
S.--NTTH-...TLE.KV........K...KTK-..D........................N.EK......DPQNPENQK..T.........K                 PAK
I.--NH......H.........K.N..Q..-.K.........................EGQ.........G.KK......G...N.---.P..T........        SB12
.NKLQKR.HE...........K....TQKD.Q.........................G.............G.........-....DKK-...R........K      SB29
...--NR.H...NLE..V........K....KES-.........................................................T.........        SB30
...;SKDR.H....LE..V...........K.ES-..........................................QQ..EENKK.L.....T........        SB32
IK--TTRYTIQATLHGNRFKGKALAAD.GATNG-----...I.DSDS.........KG...A....SN..K.AA...G..QKDKKDG.NAAGPA.E------         B16B6
HT--TQYYSLDAQ.TGNRFNGTATA.D.KENET-KL-....V.DSSS.S....F..QG.....FR..SD.QK.AV.G...TKDKLENG.AA.GS.GAAASGGAAG      M982
YT--TEYYSLDATLRGNRF.GKAIA.D..NTGGTKL-....VFDSSS.S....F..QG.....FR..SD.GK.AV.G...TKDSTANGNAPAASSG------         FA19
IY--TV----NA..RGNRFTGAATASD.NKG.GE.YNF-.SADSQS........K...MA...V.N.KSL.A............                           AP205
A.----.VT.R.S.E...AG.....KA.A-...AGD----..IFTDSNY.......K...MA...FTNNKSL.A..A....                              AP37

TKKTDAKT----NATTSTAANTTTDTTANTITDEKNFKTEDISSFGEADYLLIDKY-------------------PIPLLPDKNTNDFI                      EAGAN
.TNAT.NATT--D.....T.S.K...T.ATANTE..T.K.P.L........N-----------------------V..F.--ESG...                       DL63
RTDATTNATT--D.K..ATTDA.S-....KK..AE......P...............GNQ--------------.....E...D....                       PAK
..T......NATA............AE.....K..........................N.----------------V......-ESG...                   SB12
```

FIG.15C.

```
                                                                                       T----------A..AK......T.K..P............N.-------------------------V..F.EE........  SB29
....N.T.----D.....-----..S.ATNATA,AE.T.K.....................N.-------------------------V....-E........  SB30
-----------------KTTD..NK.TSAK.NTE.T.K..P............N.-------------------------.....-ESG...  SB32
.------------.VID.YRI.GEEFKKEQIDSFGDVKKLLVD.VELS..PSEGNKAA------------------------FQHEIE-----------------  B16B6
.S-----SENS--KL..VLD.VEL.LNDKKIKNLDNFSNAAQLVVD.IMIP..PKDSESGNTQADKGKNGGTEFTRKFEHTPESDKKDAQAGTQNGAQTASN  M982
PGAATMPSET--RL..VLD.VEL.PDGKEIKNLDNFSNATRLVD.IMIP..PT--ESGNGQADKGKNGGTDFTYETTYPESDKKDTKAQTGAGGMQTASG  FA19
------------HNGSNVN.VRIIDASKI LT..SISELNN..D.SV.I..------------------------------GKKIKLAGSG.T  AP205
--------SENG--ET.E-------RIIDA.KI.LTQ.NAKELNN..D.SV.I..------------------------------GQKI.LAGVN.K  AP37

SSKHHTVGNKR--YKVEACCSNLSYVKFGMYYEDPLKEKETETETEKDKEKEKEKDKDKEKQTAATTNTYQFLLGHRTPKDDIPK--TGSAKYHGSWFG  EAGAN
.....K.T--..Q..............A.P..--E.K.K.KD..-------------..ATTSIK...........L...SSE.......N......  DL63
....G.T--..........K........................-----------KDKDN.NETDKEKGKEKPT.TTSI.........L...--E...---N......  PAK
....K.T--..Q.K..............V.P..E.-----------------KE.E....ATNLS.........L...SSE...--G......L...  SB12
T.R..K..D.T--..........K.....................-----NG.NG........E......ATTSIK...........A.A...A---..NV..R.N......  SB29
...........E..G.H--..........K......I.........--------------------------------N..N.KIE.EQ.H......L...SSQ.A---..NV..R......  SB30
...........E..G..--..........K..C.............--------------------KENNKN.T..E......TTSIK.......L...SSE......M.NVT.R......  SB32
----QNGVKAT-------V......D MS..KLSKEN--------------------------------------DDM..Q.V...VS.VAARTEAN...R.T.Y.  B16B6
TAGDTNGKT.T--..E..V......N.L.Y..LTRKNS.---------------------SAMQAGGNSSQADAKTEQVEQSM..Q.E..DEKE..--TDQNVV.R...Y.  M982
TAGVNGGQVGTKT...QV......N.L.Y.LLTREN-------------------NNSVMQAVKNSS.AD.K.KQIE..SMFLQGERT..ENKIPQEQGIV.L.F.Y.  FA19
NKHTIEING.T--MVAV......E.M...QLW------------QQAEGGKPENNSL..Q.E..AT.KM..--G.NY..I.T.D--  AP205
N..TVEING.T--MVAV......E.M...QLW--------------------Q.EGKQQVKDNSL..Q.E..AT.KM.A--G.NY..V.T.D--  AP37

YITDGKTSYSPSGDKKRDKNAVAEFNVDFAEKKLTGELKRHDTG-NPVFSIEANFNNSSNAFTGTATATN--FVIDGKNSQNKNTPINITTKVNGAFYCPKA  EAGAN
..S..E...A.....E.S..........N......T..........Q--..K.N.T.QSGK.D........KD--LA....T.GTSKVNFTA.-----  DL63
..S..E...A.....E.S..........D.S..N.T..........N--..T..K.N.EL.G.--D........--.....N..TS.AK........  PAK
LS..S...........EN..L......N.VD.T.KGQ.I...NQ--T..T.D.T.KGGK.N......N.--VA..PQSTQGTSNVNFTA.......N..  SB12
..G.D......TT..........D.N..D.T..T......N.--.....T.N.S.QSGK.D......N.--VA..PQ.T.TTSRVNFTA.-----  SB29
..G.D......TT--......L...D.N.TD.........A.NQ--T..R.N.D.K.ND...K.....E--......N..TG..Q..K.E......N.  SB30
..G.D......AT...RQ......P...A..NN....TS......NQ--.....N.K.T.Q.GR.D.E........E--.......D..G-  SB32
```

FIG. 15D.

```
..AN.-..W.GEASNQEGG.-R...D...ST..IS.T.TAK.RT-S.A.T.T.MIKD--..G.S.V.KTGENG.AL.PQ.TG.SHYTHI-EAT.S.G...KN.      B16B6
.H.AN.-..W.GNASD.EGG.-R...T.N..D.I..K.TAENRQ-AQT.T..GMIQG--..G.E...KTAESG.DL.Q..TTRTPKAYITDA..K.G......      M982
.R.AN.-..W.GKASNAT.G.-R.K.T.N.DR.EI..T.TAENRS-EAT.T.D.MIEG--..G.K...KTG.DG.AP.QN.TVTHKVHIANAE.Q.G....N.      FA19
AQVSKENNWVATA.DD.KSGYRT..D...GN.N.S.K.LFDKN.V....TVD.KIDG---..G...K.KTSDEG.AL.SGS.RYE.VKF.DVA-.S.G....T.     AP205
ALVSKG.NWIAEA.NN.ESGYRT.D.N.SD..VN.K.-FDKG.V....TVD.TI.G---.G.I.S.KTSDSG.AL.AGS..HG.AVFSDI-.....G....T.      AP37

SELGGYFTYNGN-STATNSESSTVSSSSNSKNARAAVVFGAR-QQVETT-K*       EAGAN
T.............---------NPTDKN....EK........KK.......-..*   DL63
...............KNP........P.PP.P..S.........KK......N.*    PAK
.T........----PTDK........P.................-........-.*   SB12
.T.........---NPTDKN......P.-...A...........KK......N.*    SB29
.T.........KNP.DK........P.PP..P............KK....KNN.*    SB30
............KDTITK.T......P.PP..P............KK......N.*   SB32
.I.M..S.SFP..APEGKQE----------------.K.S.....KR..LVQ*      B16B6
.E....W.A.P.DKQ.EKAT-----AT..DGNSASS.T.....KR..PVQ*         M982
.E....W.A.P..EQ.KNA------..E.GNGNSASS.T.....KR.KLVK*        FA19
.A......Q.HHKSENGSVGA------------------------K-...KK*       AP205
.G......Q.HHKSDDNGSVGA-----------------------K-R.I.K*       AP37
```

FIG.16A".

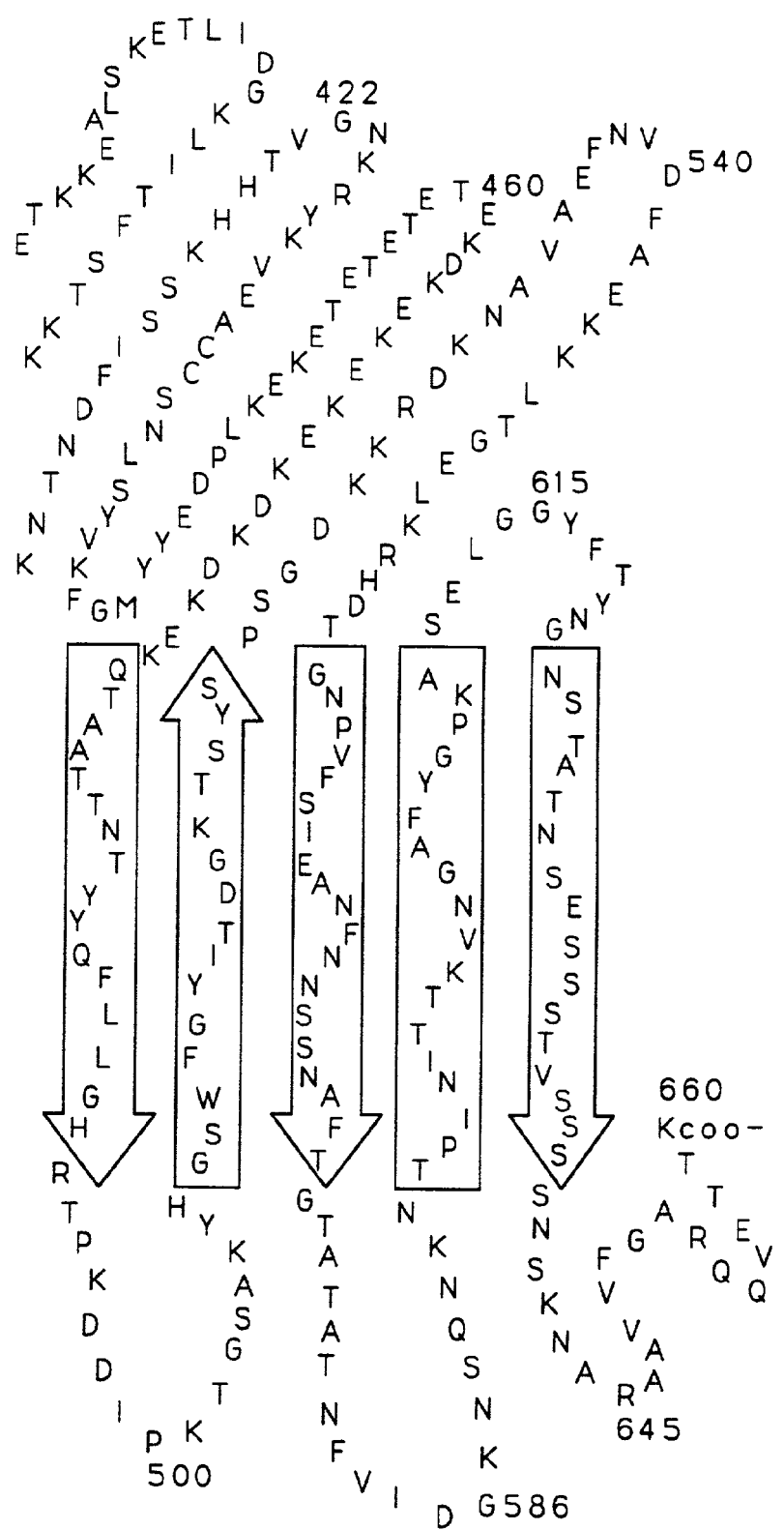
FIG.16B".

FIG.19. Oligonucleotides to expresss TBP2 with no signal sequence.

```
Nde I                                                    Ear I
TATGTGTTCTGGTGGTGGTTCTTTCGACGTTGACAACGTTCTAACACTCCCTCTTCT
ACACAAGACCACCACCAAGAAAGCTGCAACTGTTGCAAAGATTGTGAGGAGAAGATTT
```

ATG start codon is enderlined
TGT cysteinr of mature protein is double underlined

FIG. 20A.

Sequence of oligonucleotide pairs (A, B, C and D) for constructing TBP1 and TBP2 expression plasmids Oligonucleotide pair A (Seq. ID 86 and 87) to join the T7 promoter and Eagan TBP1 gene

```
Nde I                                                                    Pst I
TATGAAACTCAAAGTATAAAGATACAAAAGAAGCTATATCATCTGAAGT....
    ACTTTGAGTTTCATATTTCTATGTTTTCTTCGATATAGTAGACTTCA...
        ...GGACACTCAAAGTACAGAAGATTCAGAATTAGAAACTATCTCAGTCACTGCA
        ...CCTGTGAGTTTCATGTCTTCTAAGTCTTAATCTTTGATAGAGTCAGTG
```

Oligonucleotide pair B (Seq. ID 88 and 89) to join the T7 promoter and Eagan TBP2 genes throught the E. coli lpp leader

```
Nde I                                                                              Ear I
TATGAAAGCTACTAAACTGGTTCTGGGTGCTGTTATCCTGGGTTCCACTCTG...
    ACTTTCGATGATTTGACCAAGACCCACGACAATAGGACCCAAGGTGAGAC...
        ...CTGGCTGGTTGTAGCCGGAGGTGTTGTTTTGATGTAGATAACGTCTCTAATACCCCCTCTTCT
        ...GACCCACCAACATGCGCCTCCACAACAAAACTACATCTATTGCAGAGATTATGGGGGAGAAGATTT
```

FIG. 20B.

Oligonucleotide pair C (Seq. ID 90 and 91) to join the T7 promoter and Eagan TBP2 genes throught the *E. coli* rlp B leader Nde I
T<u>ATG</u>CGATATCTGGCAACATTGTTGTTATCTCTGGCGGTGTTAATCACCGCTG...
ACGCTATAGACCGTTGTAACAACAATAGAGACCGCCACAATTAGTGGCGAC...

Ear I
...GTTGTAGCGGAGGTGGTTCTTTTGATGTAGATAACGTCTCTAATACCCCCTCTTCT
...CAACATCGCCTCCACCAAGAAAACTACATCTATTGCAGAGATTATGGGGGAGAAGATTT

Oligonucleotide pair D (Seq. ID 92 and 93) to join the T7 promoter and Eagan TBP2 genes throught the *E. coli* pal leader Nde I
T<u>ATG</u>CAACTGAACAAAGTGCTGAAAGGGCTGATGATTGCTCTGCCTGTTATGGCAA...
ACGTTGACTTGTTTCACGACTTTCCCGACTACTAACGAGACGGACAATACCGTT...

Ear I
...TTGCTGGTTGTAGCGGAGGTGGTTCTTTTGATGTAGATAACGTCTCTAATACCCCCTCTTCT
... AACGACCAACATCGCCTCCTACCAAGAAAACTACATCTATTGCAGAGATTATGGGGGAGAAGATTT

ATG start codons are underlined
TGT coding for Cys of lipoproteins are double underlined
TGT may be replaced by TCC coding for Ser to secrete non-lipoprotein

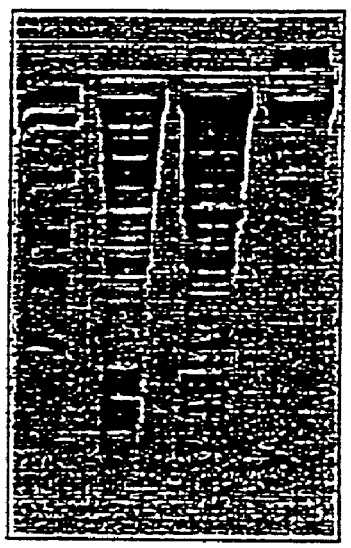
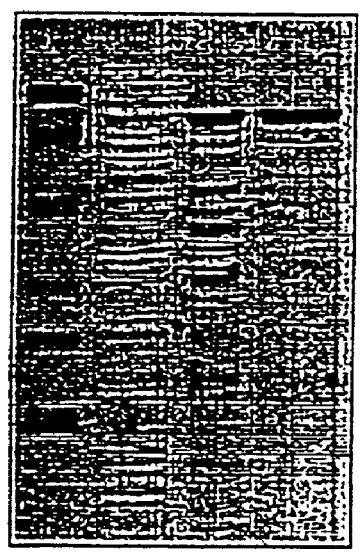
1 2 3 4      1 2 3 4
FIG 24

Kinetics of Antibody Response to TBP1/TBP2 in Mice

FIG. 31A

Eagan Tbp2

MKSVPLISGGLSFLLSACSGGGSFDVDNVSNTPSSKPRYQDDTSNQRKKS
Signal Sequence                              → DS-1466-1-18

NLKKLFIPSLGGMKLVAQNLRGNKEPSFLNEDDYISYFSSLSTIEKDVK
                              → DS-1466-4-3

DNNKNGADLIGSIDEPSTTNPPEKHHGQKYVVYSGLYYTPSWSLNDSKNKF

YLGYYGYAFYYGNKTATNLPVNGVAKYKGTWDFITATKNGKRYPLLSNGS

HAYYRRSAIPEDIDLENDSKNGDIGLISEFSADFGTKKLTGQLSYTKRKT
                    → DS-1466-5-1

NNQPYEKKLYDIDADIYSNRFRGTVKPTEKDSEEHPFTSEGTLEGGFYG
                  → DS-1466-4-1

PNAEELGGKFLATDNRVFGVFSAKETEETKKEALSKETLIDGKLITFSTK

FIG. 31B

KTDAKTNATTSTAANTTSTAANTTTDTTANTITDEKNFKTEDISSFGEADYLLIDKY

PIPLLPDKNTNDFISSKHHTVGNKRYKVEACCSNLSYVKFGMYYEDPLKE

KETETETETEKDKEKEKEKDKDKEKQTAATTNTYYQFLLGHRTPKDDIPK

TGSAKYHGSWFGYITDGKTSYSPSGDKKRDKNAVAEFNVDFAEKKLTGEL

KRHDTGNPVFSIEANFNNSSNAFTGTATATNFVIDGKNSQNKNTPINITT

KVNGAFYGPKASELGGYFTYNGNSTATNSESSSTVSSSSNSKNARAAVVF

GARQQVETTK*

(Arrows mark positions of DS-1457-3-1, DS-1466-1-4, DS-1466-7-9, DS-1466-3-1, DS-1466-3-4, DS-1466-2-6, DS-1461-1-1, DS-1466-1-1, DS-1466-1-14, DS-1461-8-1)

SEQUENCE LISTING

```
<160> NUMBER OF SEQ ID NOS: 160

<210> SEQ ID NO 1
<211> LENGTH: 4699
<212> TYPE: DNA
<213> ORGANISM: Haemophilus influenzae
<220> FEATURE:
<221> NAME/KEY: CDS
<222> LOCATION: (10)..(1940)
<220> FEATURE:
<221> NAME/KEY: CDS
<222> LOCATION: (1957)..(4696)

<400> SEQUENCE: 1 tataactca atg aaa tct gta cct ctt atc tct ggt gga ctt tcc ttt tta      51
          Met Lys Ser Val Pro Leu Ile Ser Gly Gly Leu Ser Phe Leu
            1               5                  10 cta agt gct tgt agc gga ggg ggg tct ttt gat gta gat aac gtc tct        99
Leu Ser Ala Cys Ser Gly Gly Gly Ser Phe Asp Val Asp Asn Val Ser
 15                  20                  25                  30 aat acc ccc tct tct aaa cca cgt tat caa gac gat act tca agt tca       147
Asn Thr Pro Ser Ser Lys Pro Arg Tyr Gln Asp Asp Thr Ser Ser Ser
                 35                  40                  45 aga aca aaa tct aaa ttg gaa aag ttg tcc att cct tct tta ggg gga       195
Arg Thr Lys Ser Lys Leu Glu Lys Leu Ser Ile Pro Ser Leu Gly Gly
             50                  55                  60 ggg atg aag tta gcg gct ctg aat ctt ttt gat agg aac aaa cct agt       243
Gly Met Lys Leu Ala Ala Leu Asn Leu Phe Asp Arg Asn Lys Pro Ser
 65                  70                  75
```

-continued

| | |
|---|---|
| ctc tta aat gaa gat agc tat atg ata ttt tcc tca cgt tct acg att<br>Leu Leu Asn Glu Asp Ser Tyr Met Ile Phe Ser Ser Arg Ser Thr Ile<br>    80                         85                    90 | 291 |
| gaa gag gat gtt aaa aat gac aat caa aac ggc gag cac cct att gac<br>Glu Glu Asp Val Lys Asn Asp Asn Gln Asn Gly Glu His Pro Ile Asp<br>95                    100                   105                 110 | 339 |
| tca ata gtc gat cct aga gca cca aat tca aac gaa aat cgt cat gga<br>Ser Ile Val Asp Pro Arg Ala Pro Asn Ser Asn Glu Asn Arg His Gly<br>                   115                   120                 125 | 387 |
| caa aaa tat gta tat tca ggg ctt tat tat att caa tcg tgg agt cta<br>Gln Lys Tyr Val Tyr Ser Gly Leu Tyr Tyr Ile Gln Ser Trp Ser Leu<br>               130                   135               140 | 435 |
| aga gat tta cca aat aaa aag ttt tat tca ggt tac tat gga tat gcg<br>Arg Asp Leu Pro Asn Lys Lys Phe Tyr Ser Gly Tyr Tyr Gly Tyr Ala<br>               145                   150               155 | 483 |
| tat tac ttt ggc aat aca act gcc tct gca tta cct gta ggt ggc gta<br>Tyr Tyr Phe Gly Asn Thr Thr Ala Ser Ala Leu Pro Val Gly Gly Val<br>160                   165                   170 | 531 |
| gca acg tat aaa gga act tgg agc ttc atc acc gca gct gaa aat ggc<br>Ala Thr Tyr Lys Gly Thr Trp Ser Phe Ile Thr Ala Ala Glu Asn Gly<br>175                   180                   185               190 | 579 |
| aag aat tat gaa ttg tta aga aat tct ggt ggc ggt caa gct tat tct<br>Lys Asn Tyr Glu Leu Leu Arg Asn Ser Gly Gly Gly Gln Ala Tyr Ser<br>               195                   200               205 | 627 |
| cga cgt agt gct act cca gaa gat att gat tta gat cgt aag acg ggc<br>Arg Arg Ser Ala Thr Pro Glu Asp Ile Asp Leu Asp Arg Lys Thr Gly<br>               210                   215               220 | 675 |
| tta aca agt gaa ttt act gtc aat ttt ggt aca aaa aag ctc act gga<br>Leu Thr Ser Glu Phe Thr Val Asn Phe Gly Thr Lys Lys Leu Thr Gly<br>             225                   230               235 | 723 |
| gga ctt tat tat aat tta cgt gaa aca gat gct aat aaa tca caa aat<br>Gly Leu Tyr Tyr Asn Leu Arg Glu Thr Asp Ala Asn Lys Ser Gln Asn<br>240                   245                   250 | 771 |
| aga aca cat aaa ctc tac gat cta gaa gct gat gtt cat agc aac cga<br>Arg Thr His Lys Leu Tyr Asp Leu Glu Ala Asp Val His Ser Asn Arg<br>255                   260                   265               270 | 819 |
| ttc agg ggt aaa gta aag cca acc aaa aaa gag tct tct gaa gaa cat<br>Phe Arg Gly Lys Val Lys Pro Thr Lys Lys Glu Ser Ser Glu Glu His<br>               275                   280               285 | 867 |
| ccc ttt acc agc gag gga aca tta gaa ggt ggt ttt tac ggg cct gag<br>Pro Phe Thr Ser Glu Gly Thr Leu Glu Gly Gly Phe Tyr Gly Pro Glu<br>290                   295                   300 | 915 |
| ggt caa gaa tta gga gga aag ttt tta gct cac gac aaa aaa gtt ttg<br>Gly Gln Glu Leu Gly Gly Lys Phe Leu Ala His Asp Lys Lys Val Leu<br>               305                   310               315 | 963 |
| ggg gta ttt agt gcc aaa gaa cag caa gaa acg tca gaa aac aaa aaa<br>Gly Val Phe Ser Ala Lys Glu Gln Gln Glu Thr Ser Glu Asn Lys Lys<br>320                   325                   330 | 1011 |
| tta ccc aaa gaa acc tta att gat ggc aag cta act act ttt aaa aca<br>Leu Pro Lys Glu Thr Leu Ile Asp Gly Lys Leu Thr Thr Phe Lys Thr<br>335                   340                   345               350 | 1059 |
| acc aat gca aca gcc aat gca aca acc gat gca aca acc agt aca aca<br>Thr Asn Ala Thr Ala Asn Ala Thr Thr Asp Ala Thr Thr Ser Thr Thr<br>               355                   360               365 | 1107 |
| gcc agt aca aaa acc gat aca aca acc aat gca aca gcc aat aca gaa<br>Ala Ser Thr Lys Thr Asp Thr Thr Thr Asn Ala Thr Ala Asn Thr Glu<br>               370                   375               380 | 1155 |
| aac ttt acg aca aaa gat ata cca agt ttg ggt gaa gct gat tat ctt<br>Asn Phe Thr Thr Lys Asp Ile Pro Ser Leu Gly Glu Ala Asp Tyr Leu<br>385                   390                   395 | 1203 |

```
tta att gat aat tac cct gtt cct ctt ttc cct gag agt ggt gat ttc    1251
Leu Ile Asp Asn Tyr Pro Val Pro Leu Phe Pro Glu Ser Gly Asp Phe
    400                 405                 410 ata agt agt aag cac cat act gta gga aag aaa acc tat caa gta gaa    1299
Ile Ser Ser Lys His His Thr Val Gly Lys Lys Thr Tyr Gln Val Glu
415                 420                 425                 430 gca tgt tgc agt aat cta agc tat gta aaa ttt ggt atg tat tat gaa    1347
Ala Cys Cys Ser Asn Leu Ser Tyr Val Lys Phe Gly Met Tyr Tyr Glu
                435                 440                 445 gcc cca cct aaa gaa gaa gaa aaa gaa aaa gaa aaa gac aaa gac aaa    1395
Ala Pro Pro Lys Glu Glu Glu Lys Glu Lys Glu Lys Asp Lys Asp Lys
            450                 455                 460 gaa aaa gaa aaa caa gcg aca aca tct atc aag act tat tat caa ttc    1443
Glu Lys Glu Lys Gln Ala Thr Thr Ser Ile Lys Thr Tyr Tyr Gln Phe
                465                 470                 475 tta tta ggt ctc cgt act ccc agt tct gaa ata cct aaa gaa gga agt    1491
Leu Leu Gly Leu Arg Thr Pro Ser Ser Glu Ile Pro Lys Glu Gly Ser
    480                 485                 490 gca aaa tat cat ggt aat tgg ttt ggt tat att agt gat ggc gag aca    1539
Ala Lys Tyr His Gly Asn Trp Phe Gly Tyr Ile Ser Asp Gly Glu Thr
495                 500                 505                 510 tct tac tcc gcc agt ggt gat aag gaa cgc agt aaa aat gct gtc gcc    1587
Ser Tyr Ser Ala Ser Gly Asp Lys Glu Arg Ser Lys Asn Ala Val Ala
                515                 520                 525 gag ttt aat gta aat ttt gcc gag aaa aca tta aca ggc gaa tta aaa    1635
Glu Phe Asn Val Asn Phe Ala Glu Lys Thr Leu Thr Gly Glu Leu Lys
            530                 535                 540 cga cac gat act caa aat ccc gta ttt aaa att aat gca acc ttt caa    1683
Arg His Asp Thr Gln Asn Pro Val Phe Lys Ile Asn Ala Thr Phe Gln
                545                 550                 555 agt ggt aag aat gac ttc act ggt aca gca acc gca aaa gat tta gca    1731
Ser Gly Lys Asn Asp Phe Thr Gly Thr Ala Thr Ala Lys Asp Leu Ala
    560                 565                 570 ata gat ggt aaa aat aca caa ggc aca tct aaa gtc aat ttc acg gca    1779
Ile Asp Gly Lys Asn Thr Gln Gly Thr Ser Lys Val Asn Phe Thr Ala
575                 580                 585                 590 aca gta aac ggg gca ttt tat ggt ccg cac gct aca gaa tta ggc ggt    1827
Thr Val Asn Gly Ala Phe Tyr Gly Pro His Ala Thr Glu Leu Gly Gly
                595                 600                 605 tat ttc acc tat aac gga aac aat cct aca gat aaa aat tca tca tcc    1875
Tyr Phe Thr Tyr Asn Gly Asn Asn Pro Thr Asp Lys Asn Ser Ser Ser
            610                 615                 620 aat tca gaa aag gca aga gct gcc gtt gtg ttt gga gct aaa aaa caa    1923
Asn Ser Glu Lys Ala Arg Ala Ala Val Val Phe Gly Ala Lys Lys Gln
                625                 630                 635 caa gta gaa aca acc aa gtaatggaat actaaa a atg act aaa aaa ccc    1972
Gln Val Glu Thr Thr Lys                    Met Thr Lys Lys Pro
            640                                    645 tat ttt cgc cta agt att att tct tgt ctt tta att tca tgc tat gta    2020
Tyr Phe Arg Leu Ser Ile Ile Ser Cys Leu Leu Ile Ser Cys Tyr Val
650                 655                 660                 665 aaa gca gaa act caa agt ata aaa gat aca aaa gaa gct ata tca tct    2068
Lys Ala Glu Thr Gln Ser Ile Lys Asp Thr Lys Glu Ala Ile Ser Ser
                670                 675                 680 gaa gtg gac act caa agt aca gaa gat tca gaa tta gaa act atc tca    2116
Glu Val Asp Thr Gln Ser Thr Glu Asp Ser Glu Leu Glu Thr Ile Ser
            685                 690                 695 gtc act gca gaa aaa gtt aga gat cgt aaa gat aat gaa gta act gga    2164
Val Thr Ala Glu Lys Val Arg Asp Arg Lys Asp Asn Glu Val Thr Gly
```

```
                700                 705                 710
ctt ggc aaa att ata aaa act agt gaa agt atc agc cga gaa caa gta   2212
Leu Gly Lys Ile Ile Lys Thr Ser Glu Ser Ile Ser Arg Glu Gln Val
    715                 720                 725 tta aat att cgt gat cta aca cgc tat gat cca ggg att tca gtt gta   2260
Leu Asn Ile Arg Asp Leu Thr Arg Tyr Asp Pro Gly Ile Ser Val Val
730                 735                 740                 745 gaa caa ggt cgc ggt gca agt tct gga tat tct att cgt ggt atg gac   2308
Glu Gln Gly Arg Gly Ala Ser Ser Gly Tyr Ser Ile Arg Gly Met Asp
                750                 755                 760 aga aat aga gtt gct tta tta gta gat ggt tta cct caa acg caa tct   2356
Arg Asn Arg Val Ala Leu Leu Val Asp Gly Leu Pro Gln Thr Gln Ser
            765                 770                 775 tat gta gtg caa agc cct tta gtt gct cgt tca gga tat tct ggc act   2404
Tyr Val Val Gln Ser Pro Leu Val Ala Arg Ser Gly Tyr Ser Gly Thr
        780                 785                 790 ggt gca att aat gaa att gaa tat gaa aat gta aag gcc gtc gaa ata   2452
Gly Ala Ile Asn Glu Ile Glu Tyr Glu Asn Val Lys Ala Val Glu Ile
    795                 800                 805 agc aag ggg ggg agt tct tct gag tat ggt aat gga gca cta gct ggt   2500
Ser Lys Gly Gly Ser Ser Ser Glu Tyr Gly Asn Gly Ala Leu Ala Gly
810                 815                 820                 825 tct gta aca ttt caa agc aaa tca gca gcc gat atc tta gaa gga gac   2548
Ser Val Thr Phe Gln Ser Lys Ser Ala Ala Asp Ile Leu Glu Gly Asp
                830                 835                 840 aaa tca tgg gga att caa act aaa aat gct tat tca agc aaa aat aaa   2596
Lys Ser Trp Gly Ile Gln Thr Lys Asn Ala Tyr Ser Ser Lys Asn Lys
            845                 850                 855 ggc ttt acc cat tct tta gct gta gca gga aaa caa ggt gga ttt gaa   2644
Gly Phe Thr His Ser Leu Ala Val Ala Gly Lys Gln Gly Gly Phe Glu
        860                 865                 870 ggg gtc gcc att tac act cac cga aat tca att gaa acc caa gtc cat   2692
Gly Val Ala Ile Tyr Thr His Arg Asn Ser Ile Glu Thr Gln Val His
    875                 880                 885 aaa gat gca tta aaa ggc gtg caa agt tat gat cga ttc atc gcc aca   2740
Lys Asp Ala Leu Lys Gly Val Gln Ser Tyr Asp Arg Phe Ile Ala Thr
890                 895                 900                 905 aca gag gat caa tct gca tac ttt gtg atg caa gat gag tgt cta gat   2788
Thr Glu Asp Gln Ser Ala Tyr Phe Val Met Gln Asp Glu Cys Leu Asp
                910                 915                 920 ggt tat gac aag tgt aaa act tca ccc aaa cga cct gcg act tta tcc   2836
Gly Tyr Asp Lys Cys Lys Thr Ser Pro Lys Arg Pro Ala Thr Leu Ser
            925                 930                 935 acc caa aga gaa acc gta agc gtt tca gat tat acg ggg gct aac cgt   2884
Thr Gln Arg Glu Thr Val Ser Val Ser Asp Tyr Thr Gly Ala Asn Arg
        940                 945                 950 atc aaa cct aat cca atg aaa tat gaa agc cag tct tgg ttt tta aga   2932
Ile Lys Pro Asn Pro Met Lys Tyr Glu Ser Gln Ser Trp Phe Leu Arg
    955                 960                 965 gga ggt tat cat ttt tct gaa caa cac tat att ggt ggt att ttt gaa   2980
Gly Gly Tyr His Phe Ser Glu Gln His Tyr Ile Gly Gly Ile Phe Glu
970                 975                 980                 985 ttc aca caa caa aaa ttt gat atc cgt gat atg aca ttt ccc gct tat   3028
Phe Thr Gln Gln Lys Phe Asp Ile Arg Asp Met Thr Phe Pro Ala Tyr
                990                 995                 1000 tta agg cca aca gaa gac aag gat tta caa agt cgc cct ttt tat cca   3076
Leu Arg Pro Thr Glu Asp Lys Asp Leu Gln Ser Arg Pro Phe Tyr Pro
            1005                1010                1015 aag caa gat tat ggt gca tat caa cat att ggt gat ggc aga ggc gtt   3124
Lys Gln Asp Tyr Gly Ala Tyr Gln His Ile Gly Asp Gly Arg Gly Val
```

-continued

```
Lys Gln Asp Tyr Gly Ala Tyr Gln His Ile Gly Asp Gly Arg Gly Val
    1020                1025                1030 aaa tat gca agt ggg ctt tat ttc gat gaa cac cat aga aaa cag cgt      3172
Lys Tyr Ala Ser Gly Leu Tyr Phe Asp Glu His His Arg Lys Gln Arg
    1035                1040                1045 gta ggt att gaa tat att tac gaa aat aag aac aaa gcg ggc atc att      3220
Val Gly Ile Glu Tyr Ile Tyr Glu Asn Lys Asn Lys Ala Gly Ile Ile
1050                1055                1060                1065 gac aaa gcg gtg tta agt gct aat caa caa aca tca tac ttg aca gtt      3268
Asp Lys Ala Val Leu Ser Ala Asn Gln Gln Thr Ser Tyr Leu Thr Val
                1070                1075                1080 ata tgc gac ata cgc att gca gtc ttt atc cat aat cca agt aag aat      3316
Ile Cys Asp Ile Arg Ile Ala Val Phe Ile His Asn Pro Ser Lys Asn
            1085                1090                1095 tgc cgc cca aca ctt gat aaa cct tat tca tac tat cat tct gat aga      3364
Cys Arg Pro Thr Leu Asp Lys Pro Tyr Ser Tyr Tyr His Ser Asp Arg
        1100                1105                1110 aat gtt tat aaa gaa aaa cat aac atg ttg caa ttg aat tta gag aaa      3412
Asn Val Tyr Lys Glu Lys His Asn Met Leu Gln Leu Asn Leu Glu Lys
    1115                1120                1125 aaa att caa caa aat tgg ctt act cat caa att gcc ttc aat ctt ggt      3460
Lys Ile Gln Gln Asn Trp Leu Thr His Gln Ile Ala Phe Asn Leu Gly
1130                1135                1140                1145 ttt gat gac ttt act tcc gca ctt cag cat aaa gat tat tta act cga      3508
Phe Asp Asp Phe Thr Ser Ala Leu Gln His Lys Asp Tyr Leu Thr Arg
                1150                1155                1160 cgt gtt atc gct acg gca agt agt att tca gag aaa cgt ggt gaa gca      3556
Arg Val Ile Ala Thr Ala Ser Ser Ile Ser Glu Lys Arg Gly Glu Ala
            1165                1170                1175 aga aga aat ggt tta caa tca agt cct tac tta tac cca aca cca aaa      3604
Arg Arg Asn Gly Leu Gln Ser Ser Pro Tyr Leu Tyr Pro Thr Pro Lys
        1180                1185                1190 gca gag ttg gta gga gga gat ctt tgt aat tat caa ggt aag tcc tct      3652
Ala Glu Leu Val Gly Gly Asp Leu Cys Asn Tyr Gln Gly Lys Ser Ser
    1195                1200                1205 aat tac agt gac tgt aaa gtg cgg tta att aaa ggg aaa aat tat tat      3700
Asn Tyr Ser Asp Cys Lys Val Arg Leu Ile Lys Gly Lys Asn Tyr Tyr
1210                1215                1220                1225 ttc gca gca cgc aat aat atg gca tta ggg aaa tac gtt gat tta ggt      3748
Phe Ala Ala Arg Asn Asn Met Ala Leu Gly Lys Tyr Val Asp Leu Gly
                1230                1235                1240 tta ggt atg agg tat gac gta tct cgt aca aaa gct aat gaa tca act      3796
Leu Gly Met Arg Tyr Asp Val Ser Arg Thr Lys Ala Asn Glu Ser Thr
            1245                1250                1255 att agt gtt ggt aaa ttt aaa aat ttc tct tgg aat act ggt att gtc      3844
Ile Ser Val Gly Lys Phe Lys Asn Phe Ser Trp Asn Thr Gly Ile Val
        1260                1265                1270 ata aaa cca acg gaa tgg ctt gat ctt tct tat cgc ctt tct act gga      3892
Ile Lys Pro Thr Glu Trp Leu Asp Leu Ser Tyr Arg Leu Ser Thr Gly
    1275                1280                1285 ttt aga aat cct agt ttt gct gaa atg tat ggt tgg cgg tat ggt ggc      3940
Phe Arg Asn Pro Ser Phe Ala Glu Met Tyr Gly Trp Arg Tyr Gly Gly
1290                1295                1300                1305 aag gat acc gat gtt tat ata ggt aaa ttt aag cct gaa aca tct cgt      3988
Lys Asp Thr Asp Val Tyr Ile Gly Lys Phe Lys Pro Glu Thr Ser Arg
                1310                1315                1320 aac caa gag ttt ggt ctc gct cta aaa ggg gat ttt ggt aat att gag      4036
Asn Gln Glu Phe Gly Leu Ala Leu Lys Gly Asp Phe Gly Asn Ile Glu
            1325                1330                1335
```

-continued

| | |
|---|---|
| atc agt cat ttt agt aat gct tat cga aat ctt atc gcc ttt gct gaa<br>Ile Ser His Phe Ser Asn Ala Tyr Arg Asn Leu Ile Ala Phe Ala Glu<br>1340                       1345                    1350 | 4084 |
| gaa ctt agt aaa aat gga act act gga aag ggc aat tat gga tat cat<br>Glu Leu Ser Lys Asn Gly Thr Thr Gly Lys Gly Asn Tyr Gly Tyr His<br>       1355                   1360                1365 | 4132 |
| aat gca caa aat gca aaa tta gtt ggc gta aat ata act gcg caa tta<br>Asn Ala Gln Asn Ala Lys Leu Val Gly Val Asn Ile Thr Ala Gln Leu<br>1370                    1375                  1380                  1385 | 4180 |
| gat ttt aat ggt tta tgg aaa cgt att ccc tac ggt tgg tat gca aca<br>Asp Phe Asn Gly Leu Trp Lys Arg Ile Pro Tyr Gly Trp Tyr Ala Thr<br>           1390                   1395                 1400 | 4228 |
| ttt gct tat aac cga gta aaa gtt aaa gat caa aaa atc aat gct ggt<br>Phe Ala Tyr Asn Arg Val Lys Val Lys Asp Gln Lys Ile Asn Ala Gly<br>1405                       1410                    1415 | 4276 |
| tta gct tcc gta agc agt tat tta ttt gat gcc att cag ccc agc cgt<br>Leu Ala Ser Val Ser Ser Tyr Leu Phe Asp Ala Ile Gln Pro Ser Arg<br>        1420                   1425                1430 | 4324 |
| tat atc att ggt tta ggc tat gat cat cca agt aat act tgg gga att<br>Tyr Ile Ile Gly Leu Gly Tyr Asp His Pro Ser Asn Thr Trp Gly Ile<br>1435                       1440                    1445 | 4372 |
| aag aca atg ttt act caa tca aaa gca aaa tct caa aat gaa ttg cta<br>Lys Thr Met Phe Thr Gln Ser Lys Ala Lys Ser Gln Asn Glu Leu Leu<br>1450                       1455                    1460                  1465 | 4420 |
| gga aaa cgt gca ttg ggt aac aat tca agg aat gta aaa tca aca aga<br>Gly Lys Arg Ala Leu Gly Asn Asn Ser Arg Asn Val Lys Ser Thr Arg<br>           1470                   1475                 1480 | 4468 |
| aaa ctt act cgg gca tgg cat atc tta gat gta tcg ggt tat tac atg<br>Lys Leu Thr Arg Ala Trp His Ile Leu Asp Val Ser Gly Tyr Tyr Met<br>1485                       1490                    1495 | 4516 |
| gtg aat aga agt att ttg ttc cga tta gga gta tat aat tta tta aac<br>Val Asn Arg Ser Ile Leu Phe Arg Leu Gly Val Tyr Asn Leu Leu Asn<br>        1500                   1505                1510 | 4564 |
| tat cgc tat gtc act tgg gaa gcg gtg cgt caa aca gca caa ggt gcg<br>Tyr Arg Tyr Val Thr Trp Glu Ala Val Arg Gln Thr Ala Gln Gly Ala<br>1515                       1520                    1525 | 4612 |
| gtc aat caa cat caa aat gtt ggt aac tat act cgc tac gca gca tca<br>Val Asn Gln His Gln Asn Val Gly Asn Tyr Thr Arg Tyr Ala Ala Ser<br>1530                       1535                    1540                  1545 | 4660 |
| gga cga aac tat acc tta aca tta gaa atg aaa ttc taa<br>Gly Arg Asn Tyr Thr Leu Thr Leu Glu Met Lys Phe<br>           1550                   1555 | 4699 |

<210> SEQ ID NO 2
<211> LENGTH: 5033
<212> TYPE: DNA
<213> ORGANISM: Haemophilus influenzae
<220> FEATURE:
<221> NAME/KEY: CDS
<222> LOCATION: (169)..(2148)
<220> FEATURE:
<221> NAME/KEY: CDS
<222> LOCATION: (2165)..(4900)

<400> SEQUENCE: 2

| | |
|---|---|
| gcccaagcta cattggttaa tgataagcct ataatgata agaaagaaat ttgttttacg | 60 |
| ccatttttca tattttatcc atgaacttaa aaaactctaa cttgacatta ttacaaaaaa | 120 |
| agatcaataa tgcgaattat tatcaatttt gtatgagtat ataattct atg aaa tct<br>                                                                                     Met Lys Ser<br>                                                                                         1 | 177 |
| gta cct ctt atc tct ggt gga ctt tcc ttt tta cta agt gct tgt agc<br>Val Pro Leu Ile Ser Gly Gly Leu Ser Phe Leu Leu Ser Ala Cys Ser | 225 |

| | | | | | | | | | | | | | | |
|---|---|---|---|---|---|---|---|---|---|---|---|---|---|---|
| Val | Pro | Leu | Ile | Ser | Gly | Gly | Leu | Ser | Phe | Leu | Leu | Ser | Ala | Cys | Ser |
| | 5 | | | | 10 | | | | 15 | | | | | |

| gga | ggg | ggg | tct | ttt | gat | gta | gat | aac | gtc | tct | aat | acc | ccc | tct | tct | 273 |
|---|---|---|---|---|---|---|---|---|---|---|---|---|---|---|---|---|
| Gly | Gly | Gly | Ser | Phe | Asp | Val | Asp | Asn | Val | Ser | Asn | Thr | Pro | Ser | Ser | |
| 20 | | | | | 25 | | | | | 30 | | | | | 35 | |

| aaa | cca | cgt | tat | caa | gac | gat | acc | tcg | aat | caa | aga | aaa | aaa | tct | aat | 321 |
|---|---|---|---|---|---|---|---|---|---|---|---|---|---|---|---|---|
| Lys | Pro | Arg | Tyr | Gln | Asp | Asp | Thr | Ser | Asn | Gln | Arg | Lys | Lys | Ser | Asn | |
| | | | | 40 | | | | | 45 | | | | | 50 | | |

| ttg | aaa | aag | ttg | ttc | att | cct | tct | tta | gga | gga | ggg | atg | aaa | ttg | gtg | 369 |
|---|---|---|---|---|---|---|---|---|---|---|---|---|---|---|---|---|
| Leu | Lys | Lys | Leu | Phe | Ile | Pro | Ser | Leu | Gly | Gly | Gly | Met | Lys | Leu | Val | |
| | | | | 55 | | | | | 60 | | | | | 65 | | |

| gct | cag | aat | ctt | cgt | ggt | aat | aaa | gaa | cct | agt | ttc | tta | aat | gaa | gat | 417 |
|---|---|---|---|---|---|---|---|---|---|---|---|---|---|---|---|---|
| Ala | Gln | Asn | Leu | Arg | Gly | Asn | Lys | Glu | Pro | Ser | Phe | Leu | Asn | Glu | Asp | |
| | | 70 | | | | | 75 | | | | | 80 | | | | |

| gac | tat | ata | tca | tat | ttt | tcc | tca | ctt | tct | acg | att | gaa | aag | gat | gtt | 465 |
|---|---|---|---|---|---|---|---|---|---|---|---|---|---|---|---|---|
| Asp | Tyr | Ile | Ser | Tyr | Phe | Ser | Ser | Leu | Ser | Thr | Ile | Glu | Lys | Asp | Val | |
| | | 85 | | | | | 90 | | | | | 95 | | | | |

| aaa | gat | aac | aat | aaa | aac | ggg | gcg | gac | ctt | att | ggc | tca | ata | gac | gag | 513 |
|---|---|---|---|---|---|---|---|---|---|---|---|---|---|---|---|---|
| Lys | Asp | Asn | Asn | Lys | Asn | Gly | Ala | Asp | Leu | Ile | Gly | Ser | Ile | Asp | Glu | |
| 100 | | | | | 105 | | | | | 110 | | | | | 115 | |

| cct | agt | aca | aca | aat | cca | ccc | gaa | aag | cat | cat | gga | caa | aaa | tat | gta | 561 |
|---|---|---|---|---|---|---|---|---|---|---|---|---|---|---|---|---|
| Pro | Ser | Thr | Thr | Asn | Pro | Pro | Glu | Lys | His | His | Gly | Gln | Lys | Tyr | Val | |
| | | | | 120 | | | | | 125 | | | | | 130 | | |

| tat | tca | ggg | ctt | tat | tat | act | cca | tcg | tgg | agt | tta | aac | gat | tct | aaa | 609 |
|---|---|---|---|---|---|---|---|---|---|---|---|---|---|---|---|---|
| Tyr | Ser | Gly | Leu | Tyr | Tyr | Thr | Pro | Ser | Trp | Ser | Leu | Asn | Asp | Ser | Lys | |
| | | | | 135 | | | | | 140 | | | | | 145 | | |

| aac | aag | ttt | tat | tta | ggt | tac | tat | gga | tat | gcg | ttt | tat | tat | ggt | aat | 657 |
|---|---|---|---|---|---|---|---|---|---|---|---|---|---|---|---|---|
| Asn | Lys | Phe | Tyr | Leu | Gly | Tyr | Tyr | Gly | Tyr | Ala | Phe | Tyr | Tyr | Gly | Asn | |
| | | | 150 | | | | | 155 | | | | | 160 | | | |

| aaa | act | gca | aca | aac | ttg | cca | gta | aac | ggt | gta | gct | aaa | tac | aaa | gga | 705 |
|---|---|---|---|---|---|---|---|---|---|---|---|---|---|---|---|---|
| Lys | Thr | Ala | Thr | Asn | Leu | Pro | Val | Asn | Gly | Val | Ala | Lys | Tyr | Lys | Gly | |
| | 165 | | | | | 170 | | | | | 175 | | | | | |

| act | tgg | gat | ttc | atc | act | gca | act | aaa | aat | ggc | aaa | cgt | tat | cct | ttg | 753 |
|---|---|---|---|---|---|---|---|---|---|---|---|---|---|---|---|---|
| Thr | Trp | Asp | Phe | Ile | Thr | Ala | Thr | Lys | Asn | Gly | Lys | Arg | Tyr | Pro | Leu | |
| 180 | | | | | 185 | | | | | 190 | | | | | 195 | |

| tta | agt | aat | ggc | agt | cac | gct | tat | tat | cga | cgt | agt | gca | att | cca | gaa | 801 |
|---|---|---|---|---|---|---|---|---|---|---|---|---|---|---|---|---|
| Leu | Ser | Asn | Gly | Ser | His | Ala | Tyr | Tyr | Arg | Arg | Ser | Ala | Ile | Pro | Glu | |
| | | | 200 | | | | | 205 | | | | | 210 | | | |

| gat | att | gat | tta | gaa | aat | gat | tca | aag | aat | ggt | gat | ata | ggc | tta | ata | 849 |
|---|---|---|---|---|---|---|---|---|---|---|---|---|---|---|---|---|
| Asp | Ile | Asp | Leu | Glu | Asn | Asp | Ser | Lys | Asn | Gly | Asp | Ile | Gly | Leu | Ile | |
| | | | | 215 | | | | | 220 | | | | | 225 | | |

| agt | gaa | ttt | agt | gca | gat | ttt | ggg | act | aaa | aaa | ctg | aca | gga | caa | ctg | 897 |
|---|---|---|---|---|---|---|---|---|---|---|---|---|---|---|---|---|
| Ser | Glu | Phe | Ser | Ala | Asp | Phe | Gly | Thr | Lys | Lys | Leu | Thr | Gly | Gln | Leu | |
| | | | 230 | | | | | 235 | | | | | 240 | | | |

| tct | tac | acc | aaa | aga | aaa | act | aat | aat | caa | cca | tat | gaa | aag | aaa | aaa | 945 |
|---|---|---|---|---|---|---|---|---|---|---|---|---|---|---|---|---|
| Ser | Tyr | Thr | Lys | Arg | Lys | Thr | Asn | Asn | Gln | Pro | Tyr | Glu | Lys | Lys | Lys | |
| | 245 | | | | | 250 | | | | | 255 | | | | | |

| ctc | tat | gat | ata | gat | gcc | gat | att | tat | agt | aat | aga | ttc | agg | ggt | aca | 993 |
|---|---|---|---|---|---|---|---|---|---|---|---|---|---|---|---|---|
| Leu | Tyr | Asp | Ile | Asp | Ala | Asp | Ile | Tyr | Ser | Asn | Arg | Phe | Arg | Gly | Thr | |
| 260 | | | | | 265 | | | | | 270 | | | | | 275 | |

| gta | aag | cca | acc | gaa | aaa | gat | tct | gaa | gaa | cat | ccc | ttt | acc | agc | gag | 1041 |
|---|---|---|---|---|---|---|---|---|---|---|---|---|---|---|---|---|
| Val | Lys | Pro | Thr | Glu | Lys | Asp | Ser | Glu | Glu | His | Pro | Phe | Thr | Ser | Glu | |
| | | | | 280 | | | | | 285 | | | | | 290 | | |

| gga | aca | tta | gaa | ggt | ggt | ttt | tat | ggg | cct | aat | gct | gaa | gaa | cta | ggg | 1089 |
|---|---|---|---|---|---|---|---|---|---|---|---|---|---|---|---|---|
| Gly | Thr | Leu | Glu | Gly | Gly | Phe | Tyr | Gly | Pro | Asn | Ala | Glu | Glu | Leu | Gly | |
| | | | | 295 | | | | | 300 | | | | | 305 | | |

| ggg | aaa | ttt | tta | gct | acg | gat | aac | cga | gtt | ttt | ggg | gta | ttt | agt | gcc | 1137 |
|---|---|---|---|---|---|---|---|---|---|---|---|---|---|---|---|---|
| Gly | Lys | Phe | Leu | Ala | Thr | Asp | Asn | Arg | Val | Phe | Gly | Val | Phe | Ser | Ala | |
| | | | 310 | | | | | 315 | | | | | 320 | | | |

```
aaa gaa acg gaa gaa aca aaa aag gaa gcg tta tcc aag gaa acc tta        1185
Lys Glu Thr Glu Glu Thr Lys Lys Glu Ala Leu Ser Lys Glu Thr Leu
    325                 330                 335 att gat ggc aag cta att act ttc tct act aaa aaa acc gat gca aaa        1233
Ile Asp Gly Lys Leu Ile Thr Phe Ser Thr Lys Lys Thr Asp Ala Lys
340                 345                 350                 355 acc aat gca aca acc agt acc gca gct aat aca aca acc gat aca acc        1281
Thr Asn Ala Thr Thr Ser Thr Ala Ala Asn Thr Thr Thr Asp Thr Thr
                    360                 365                 370 gcc aat aca ata acc gat gaa aaa aac ttt aag acg gaa gat ata tca        1329
Ala Asn Thr Ile Thr Asp Glu Lys Asn Phe Lys Thr Glu Asp Ile Ser
            375                 380                 385 agt ttt ggt gaa gct gat tat ctg tta att gac aaa tat cct att cca        1377
Ser Phe Gly Glu Ala Asp Tyr Leu Leu Ile Asp Lys Tyr Pro Ile Pro
        390                 395                 400 ctt tta cct gat aaa aat act aat gat ttc ata agt agt aag cat cat        1425
Leu Leu Pro Asp Lys Asn Thr Asn Asp Phe Ile Ser Ser Lys His His
405                 410                 415 act gta gga aat aaa cgc tat aaa gtg gaa gca tgt tgc agt aat cta        1473
Thr Val Gly Asn Lys Arg Tyr Lys Val Glu Ala Cys Cys Ser Asn Leu
420                 425                 430                 435 agc tat gtg aaa ttt ggt atg tat tat gaa gac cca ctt aaa gaa aaa        1521
Ser Tyr Val Lys Phe Gly Met Tyr Tyr Glu Asp Pro Leu Lys Glu Lys
                    440                 445                 450 gaa aca gaa aca gaa aca gaa aca gaa aaa gac aaa gaa aaa gaa aaa        1569
Glu Thr Glu Thr Glu Thr Glu Thr Glu Lys Asp Lys Glu Lys Glu Lys
            455                 460                 465 gaa aaa gac aaa gac aaa gaa aaa caa acg gcg gca acg acc aac act        1617
Glu Lys Asp Lys Asp Lys Glu Lys Gln Thr Ala Ala Thr Thr Asn Thr
        470                 475                 480 tat tat caa ttc tta tta ggt cac cgt act ccc aag gac gac ata cct        1665
Tyr Tyr Gln Phe Leu Leu Gly His Arg Thr Pro Lys Asp Asp Ile Pro
485                 490                 495 aaa aca gga agt gca aaa tat cat ggt agt tgg ttt ggt tat att act        1713
Lys Thr Gly Ser Ala Lys Tyr His Gly Ser Trp Phe Gly Tyr Ile Thr
500                 505                 510                 515 gac ggt aag aca tct tac tcc ccc agt ggt gat aag aaa cgc gat aaa        1761
Asp Gly Lys Thr Ser Tyr Ser Pro Ser Gly Asp Lys Lys Arg Asp Lys
                    520                 525                 530 aat gct gtc gcc gag ttt aat gtt gat ttt gcc gag aaa aag cta aca        1809
Asn Ala Val Ala Glu Phe Asn Val Asp Phe Ala Glu Lys Lys Leu Thr
            535                 540                 545 ggc gaa tta aaa cga cac gat act gga aat ccc gta ttt agt att gag        1857
Gly Glu Leu Lys Arg His Asp Thr Gly Asn Pro Val Phe Ser Ile Glu
        550                 555                 560 gca aac ttt aat aat agt agt aat gcc ttc act ggt aca gca acc gca        1905
Ala Asn Phe Asn Asn Ser Ser Asn Ala Phe Thr Gly Thr Ala Thr Ala
565                 570                 575 aca aat ttt gta ata gat ggt aaa aat agt caa aat aaa aat acc cca        1953
Thr Asn Phe Val Ile Asp Gly Lys Asn Ser Gln Asn Lys Asn Thr Pro
580                 585                 590                 595 att aat att aca act aaa gta aac ggg gca ttt tat gga cct aag gct        2001
Ile Asn Ile Thr Thr Lys Val Asn Gly Ala Phe Tyr Gly Pro Lys Ala
                    600                 605                 610 tct gaa tta ggc ggt tat ttc act tat aac gga aat tct aca gct aca        2049
Ser Glu Leu Gly Gly Tyr Phe Thr Tyr Asn Gly Asn Ser Thr Ala Thr
            615                 620                 625 aat tct gaa agt tcc tca acc gta tct tca tca tcc aat tca aaa aat        2097
Asn Ser Glu Ser Ser Ser Thr Val Ser Ser Ser Ser Asn Ser Lys Asn
        630                 635                 640
```

-continued

| | | |
|---|---|---|
| gca aga gct gca gtt gtc ttt ggt gcg aga caa caa gta gaa aca acc<br>Ala Arg Ala Ala Val Val Phe Gly Ala Arg Gln Gln Val Glu Thr Thr<br>645                        650                        655 | 2145 | |
| aaa taatggaata ctaaaa atg act aaa aaa ccc tat ttt cgc cta agt att<br>Lys                        Met Thr Lys Lys Pro Tyr Phe Arg Leu Ser Ile<br>660                                           665               670 | 2197 | |
| att tct tgt ctt tta att tca tgc tat gta aaa gca gaa act caa agt<br>Ile Ser Cys Leu Leu Ile Ser Cys Tyr Val Lys Ala Glu Thr Gln Ser<br>               675                        680                        685 | 2245 | |
| ata aaa gat aca aaa gaa gct ata tca tct gaa gtg gac act caa agt<br>Ile Lys Asp Thr Lys Glu Ala Ile Ser Ser Glu Val Asp Thr Gln Ser<br>               690                        695                        700 | 2293 | |
| aca gaa gat tca gaa tta gaa act atc tca gtc act gca gaa aaa ata<br>Thr Glu Asp Ser Glu Leu Glu Thr Ile Ser Val Thr Ala Glu Lys Ile<br>705                        710                        715 | 2341 | |
| aga gat cgt aaa gat aat gaa gta act gga ctt ggc aaa att atc aaa<br>Arg Asp Arg Lys Asp Asn Glu Val Thr Gly Leu Gly Lys Ile Ile Lys<br>720                        725                        730               735 | 2389 | |
| act agt gaa agt atc agc cga gaa caa gta tta aat att cgt gat cta<br>Thr Ser Glu Ser Ile Ser Arg Glu Gln Val Leu Asn Ile Arg Asp Leu<br>                      740                        745               750 | 2437 | |
| aca cgc tat gat cca ggg att tca gtt gta gaa caa ggt cgc ggt gca<br>Thr Arg Tyr Asp Pro Gly Ile Ser Val Val Glu Gln Gly Arg Gly Ala<br>               755                        760                        765 | 2485 | |
| agt tct gga tat tct att cgt ggt atg gac aga aat aga gtt gct tta<br>Ser Ser Gly Tyr Ser Ile Arg Gly Met Asp Arg Asn Arg Val Ala Leu<br>               770                        775                        780 | 2533 | |
| tta gta gat ggt tta cct caa acg caa tct tat gta gtg caa agc cct<br>Leu Val Asp Gly Leu Pro Gln Thr Gln Ser Tyr Val Val Gln Ser Pro<br>785                        790                        795 | 2581 | |
| tta gtt gct cgt tca gga tat tct ggc act ggt gca att aat gaa att<br>Leu Val Ala Arg Ser Gly Tyr Ser Gly Thr Gly Ala Ile Asn Glu Ile<br>800                        805                        810               815 | 2629 | |
| gaa tat gaa aat gta aag gcc gtc gaa ata agc aag ggg ggg agt tct<br>Glu Tyr Glu Asn Val Lys Ala Val Glu Ile Ser Lys Gly Gly Ser Ser<br>                      820                        825               830 | 2677 | |
| tct gag tat ggt aat gga gca cta gct ggt tct gta aca ttt caa agc<br>Ser Glu Tyr Gly Asn Gly Ala Leu Ala Gly Ser Val Thr Phe Gln Ser<br>               835                        840                        845 | 2725 | |
| aaa tca gca gcc gat atc tta gaa gga gac aaa tca tgg gga att caa<br>Lys Ser Ala Ala Asp Ile Leu Glu Gly Asp Lys Ser Trp Gly Ile Gln<br>               850                        855                        860 | 2773 | |
| act aaa aat gct tat tca agc aaa aat aaa ggc ttt acc cat tct tta<br>Thr Lys Asn Ala Tyr Ser Ser Lys Asn Lys Gly Phe Thr His Ser Leu<br>865                        870                        875 | 2821 | |
| gct gta gca gga aaa caa ggt gga ttt gaa ggg cta gcc att tac act<br>Ala Val Ala Gly Lys Gln Gly Gly Phe Glu Gly Leu Ala Ile Tyr Thr<br>880                        885                        890               895 | 2869 | |
| caa cga aat tca att gaa acc caa gtc cat aaa gat gca tta aaa ggc<br>Gln Arg Asn Ser Ile Glu Thr Gln Val His Lys Asp Ala Leu Lys Gly<br>                      900                        905               910 | 2917 | |
| gta caa agt tat gat cga tta atc gcc aca aca gat aaa tct tca gga<br>Val Gln Ser Tyr Asp Arg Leu Ile Ala Thr Thr Asp Lys Ser Ser Gly<br>               915                        920                        925 | 2965 | |
| tac ttt gtg ata caa ggt gag tgt cca aat ggt gat gac aag tgt gca<br>Tyr Phe Val Ile Gln Gly Glu Cys Pro Asn Gly Asp Asp Lys Cys Ala<br>               930                        935                        940 | 3013 | |
| gcc aag cca cct gcg act tta tcc acc caa agc gaa acc gta agc gtt<br>Ala Lys Pro Pro Ala Thr Leu Ser Thr Gln Ser Glu Thr Val Ser Val | 3061 | |

-continued

|  |  |
|---|---|
| tca gat tat acg ggg gct aac cgt atc aaa cct aat cca atg aaa tat<br>Ser Asp Tyr Thr Gly Ala Asn Arg Ile Lys Pro Asn Pro Met Lys Tyr<br>960                965              970              975 | 3109 |
| gaa agc cag tct tgg ttt tta aga gga ggg tat cat ttt tct gaa caa<br>Glu Ser Gln Ser Trp Phe Leu Arg Gly Gly Tyr His Phe Ser Glu Gln<br>              980              985              990 | 3157 |
| cat tat att ggt ggt att ttt gaa ttc aca caa caa aaa ttt gat atc<br>His Tyr Ile Gly Gly Ile Phe Glu Phe Thr Gln Gln Lys Phe Asp Ile<br>995                1000            1005 | 3205 |
| cgt gat atg aca ttt ccc gct tat tta agc cca aca gaa aga cgg gat<br>Arg Asp Met Thr Phe Pro Ala Tyr Leu Ser Pro Thr Glu Arg Arg Asp<br>    1010              1015            1020 | 3253 |
| gat agt agt cgt tct ttt tat cca atg caa gat cat ggt gca tat caa<br>Asp Ser Ser Arg Ser Phe Tyr Pro Met Gln Asp His Gly Ala Tyr Gln<br>1025            1030            1035 | 3301 |
| cat att gag gat ggc aga ggc gtt aaa tat gca agt ggg ctt tat ttc<br>His Ile Glu Asp Gly Arg Gly Val Lys Tyr Ala Ser Gly Leu Tyr Phe<br>1040           1045            1050           1055 | 3349 |
| gat gaa cac cat aga aaa cag cgt gta ggt att gaa tat att tac gaa<br>Asp Glu His His Arg Lys Gln Arg Val Gly Ile Glu Tyr Ile Tyr Glu<br>    1060              1065           1070 | 3397 |
| aat aag aac aaa gcg ggc atc att gac aaa gca gtg tta agt gct aat<br>Asn Lys Asn Lys Ala Gly Ile Ile Asp Lys Ala Val Leu Ser Ala Asn<br>        1075            1080           1085 | 3445 |
| caa caa aac atc ata ctt gac agt tat atg cga cat acg cat tgc agt<br>Gln Gln Asn Ile Ile Leu Asp Ser Tyr Met Arg His Thr His Cys Ser<br>1090           1095            1100 | 3493 |
| ctt tat cct aat cca agt aag aat tgc cgc cca aca ctt gat aaa cct<br>Leu Tyr Pro Asn Pro Ser Lys Asn Cys Arg Pro Thr Leu Asp Lys Pro<br>    1105              1110           1115 | 3541 |
| tat tca tac tat cgt tct gat aga aat gtt tat aaa gaa aaa cat aat<br>Tyr Ser Tyr Tyr Arg Ser Asp Arg Asn Val Tyr Lys Glu Lys His Asn<br>1120           1125            1130           1135 | 3589 |
| atg ttg caa ttg aat tta gag aaa aaa att caa caa aat tgg ctt act<br>Met Leu Gln Leu Asn Leu Glu Lys Lys Ile Gln Gln Asn Trp Leu Thr<br>        1140            1145           1150 | 3637 |
| cat caa att gtc ttc aat ctt ggt ttt gat gac ttt act tca gcg ctt<br>His Gln Ile Val Phe Asn Leu Gly Phe Asp Asp Phe Thr Ser Ala Leu<br>    1155              1160           1165 | 3685 |
| cag cat aaa gat tat tta act cga cgt gtt atc gct acg gca gat agt<br>Gln His Lys Asp Tyr Leu Thr Arg Arg Val Ile Ala Thr Ala Asp Ser<br>1170           1175            1180 | 3733 |
| att cca agg aaa cct ggt gaa act ggt aaa cca aga aat ggt ttg caa<br>Ile Pro Arg Lys Pro Gly Glu Thr Gly Lys Pro Arg Asn Gly Leu Gln<br>1185           1190            1195 | 3781 |
| tca caa cct tac tta tac cca aaa cca gag cca tat ttt gca gga caa<br>Ser Gln Pro Tyr Leu Tyr Pro Lys Pro Glu Pro Tyr Phe Ala Gly Gln<br>1200           1205            1210           1215 | 3829 |
| gat cat tgt aat tat caa ggt agc tcc tct aat tac aga gac tgt aaa<br>Asp His Cys Asn Tyr Gln Gly Ser Ser Ser Asn Tyr Arg Asp Cys Lys<br>        1220            1225           1230 | 3877 |
| gtg cgg tta att aaa ggg aaa aat tat tat ttc gca gca cgc aat aat<br>Val Arg Leu Ile Lys Gly Lys Asn Tyr Tyr Phe Ala Ala Arg Asn Asn<br>    1235              1240           1245 | 3925 |
| atg gca tta ggg aaa tac gtt gat tta ggt tta ggt att cgg tat gac<br>Met Ala Leu Gly Lys Tyr Val Asp Leu Gly Leu Gly Ile Arg Tyr Asp<br>1250           1255            1260 | 3973 |
| gta tct cgt aca aaa gct aat gaa tca act att agt gtt ggt aaa ttt | 4021 |

```
                                                 -continued

Val Ser Arg Thr Lys Ala Asn Glu Ser Thr Ile Ser Val Gly Lys Phe
   1265                1270                1275 aaa aat ttc tct tgg aat act ggt att gtc ata aaa cca acg gaa tgg      4069
Lys Asn Phe Ser Trp Asn Thr Gly Ile Val Ile Lys Pro Thr Glu Trp
1280                1285                1290                1295 ctt gat ctt tct tat cgc ctt tct act gga ttt aga aat cct agt ttt      4117
Leu Asp Leu Ser Tyr Arg Leu Ser Thr Gly Phe Arg Asn Pro Ser Phe
                1300                1305                1310 tct gaa atg tat ggt tgg cgg tat ggt ggc aag aat gac gag gtt tat      4165
Ser Glu Met Tyr Gly Trp Arg Tyr Gly Gly Lys Asn Asp Glu Val Tyr
            1315                1320                1325 gta ggt aaa ttt aag cct gaa aca tct cgt aac caa gag ttt ggt ctc      4213
Val Gly Lys Phe Lys Pro Glu Thr Ser Arg Asn Gln Glu Phe Gly Leu
        1330                1335                1340 gct cta aaa ggg gat ttt ggt aat att gag atc agt cat ttt agt aat      4261
Ala Leu Lys Gly Asp Phe Gly Asn Ile Glu Ile Ser His Phe Ser Asn
    1345                1350                1355 gct tat cga aat ctt atc gcc ttt gct gaa gaa ctt agt aaa aat gga      4309
Ala Tyr Arg Asn Leu Ile Ala Phe Ala Glu Glu Leu Ser Lys Asn Gly
1360                1365                1370                1375 act gga aag ggc aat tat gga tat cat aat gca caa aat gca aaa tta      4357
Thr Gly Lys Gly Asn Tyr Gly Tyr His Asn Ala Gln Asn Ala Lys Leu
                1380                1385                1390 gtt ggc gta aat ata act gca caa tta gat ttt aat ggt tta tgg aaa      4405
Val Gly Val Asn Ile Thr Ala Gln Leu Asp Phe Asn Gly Leu Trp Lys
            1395                1400                1405 cgt att ccc tac ggt tgg tat gca aca ttt gct tat aac caa gta aaa      4453
Arg Ile Pro Tyr Gly Trp Tyr Ala Thr Phe Ala Tyr Asn Gln Val Lys
        1410                1415                1420 gtt aaa gat caa aaa atc aat gct ggt tta gcc tcc gta agc agt tat      4501
Val Lys Asp Gln Lys Ile Asn Ala Gly Leu Ala Ser Val Ser Ser Tyr
    1425                1430                1435 tta ttt gat gcc att cag ccc agc cgt tat atc att ggt tta ggc tat      4549
Leu Phe Asp Ala Ile Gln Pro Ser Arg Tyr Ile Ile Gly Leu Gly Tyr
1440                1445                1450                1455 gat cat cca agt aat act tgg gga att aat aca atg ttt act caa tca      4597
Asp His Pro Ser Asn Thr Trp Gly Ile Asn Thr Met Phe Thr Gln Ser
                1460                1465                1470 aaa gca aaa tct caa aat gaa ttg cta gga aaa cgt gca tta ggt aac      4645
Lys Ala Lys Ser Gln Asn Glu Leu Leu Gly Lys Arg Ala Leu Gly Asn
            1475                1480                1485 aat tca agg gat gta aaa tca aca aga aaa ctt act cgg gca tgg cat      4693
Asn Ser Arg Asp Val Lys Ser Thr Arg Lys Leu Thr Arg Ala Trp His
        1490                1495                1500 atc tta gat gta tcg ggt tat tac atg gcg aat aaa aat att atg ctt      4741
Ile Leu Asp Val Ser Gly Tyr Tyr Met Ala Asn Lys Asn Ile Met Leu
    1505                1510                1515 cga tta ggg ata tat aat tta ttc aac tat cgc tat gtt act tgg gaa      4789
Arg Leu Gly Ile Tyr Asn Leu Phe Asn Tyr Arg Tyr Val Thr Trp Glu
1520                1525                1530                1535 gcg gtg cgt caa aca gca caa ggt gcg gtc aat caa cat caa aat gtt      4837
Ala Val Arg Gln Thr Ala Gln Gly Ala Val Asn Gln His Gln Asn Val
                1540                1545                1550 ggt agc tat act cgc tac gca gca tca gga cga aac tat acc tta aca      4885
Gly Ser Tyr Thr Arg Tyr Ala Ala Ser Gly Arg Asn Tyr Thr Leu Thr
            1555                1560                1565 tta gaa atg aaa ttc taaattaaaa tgcgccagat ggactagata tgctatatct      4940
Leu Glu Met Lys Phe
        1570
```

```
                                                                        -continued atacettact ggcgcatctt tttctgttct ataatctgct taagtgaaaa accaaacttg        5000 gatttttac aagatctttt cacacattta ttg                                     5033

<210> SEQ ID NO 3
<211> LENGTH: 5009
<212> TYPE: DNA
<213> ORGANISM: Haemophilus influenzae
<220> FEATURE:
<221> NAME/KEY: CDS
<222> LOCATION: (121)..(2100)
<220> FEATURE:
<221> NAME/KEY: CDS
<222> LOCATION: (2117)..(4852)

<400> SEQUENCE: 3
atttgtttta cgccattttt catattttat ccatgaactt aaaaaactct aacttgacat        60
tattacaaaa aaagatcaat aatgcgaatt attatcaatt ttgtatgagt ataataattct      120 atg aaa tct gta cct ctt atc tct ggt gga ctt tcc ttt tta cta agt        168
Met Lys Ser Val Pro Leu Ile Ser Gly Gly Leu Ser Phe Leu Leu Ser
1               5                  10                  15 gct tgt agc gga ggg ggg tct ttt gat gta gat aac gtc tct aat acc        216
Ala Cys Ser Gly Gly Gly Ser Phe Asp Val Asp Asn Val Ser Asn Thr
            20                  25                  30 ccc tct tct aaa cca cgt tat caa gac gat acc tcg aat caa aga aaa        264
Pro Ser Ser Lys Pro Arg Tyr Gln Asp Asp Thr Ser Asn Gln Arg Lys
        35                  40                  45 aaa tct aat ttg aaa aag ttg ttc att cct tct tta gga gga ggg atg        312
Lys Ser Asn Leu Lys Lys Leu Phe Ile Pro Ser Leu Gly Gly Gly Met
    50                  55                  60 aaa ttg gtg gct cag aat ctt cgt ggt aat aaa gaa cct agt ttc tta        360
Lys Leu Val Ala Gln Asn Leu Arg Gly Asn Lys Glu Pro Ser Phe Leu
65                  70                  75                  80 aat gaa gat gac tat ata tca tat ttt tcc tca ctt tct acg att gaa        408
Asn Glu Asp Asp Tyr Ile Ser Tyr Phe Ser Ser Leu Ser Thr Ile Glu
                85                  90                  95 aag gat gtt aaa gat aac aat aaa aac ggg gcg gac ctt att ggc tca        456
Lys Asp Val Lys Asp Asn Asn Lys Asn Gly Ala Asp Leu Ile Gly Ser
            100                 105                 110 ata gac gag cct agt aca aca aat cca ccc gaa aag cat cat gga caa        504
Ile Asp Glu Pro Ser Thr Thr Asn Pro Pro Glu Lys His His Gly Gln
        115                 120                 125 aaa tat gta tat tca ggg ctt tat tat act cca tcg tgg agt tta aac        552
Lys Tyr Val Tyr Ser Gly Leu Tyr Tyr Thr Pro Ser Trp Ser Leu Asn
    130                 135                 140 gat tct aaa aac aag ttt tat tta ggt tac tat gga tat gcg ttt tat        600
Asp Ser Lys Asn Lys Phe Tyr Leu Gly Tyr Tyr Gly Tyr Ala Phe Tyr
145                 150                 155                 160 tat ggt aat aaa act gca aca aac ttg cca gta aac ggt gta gct aaa        648
Tyr Gly Asn Lys Thr Ala Thr Asn Leu Pro Val Asn Gly Val Ala Lys
                165                 170                 175 tac aaa gga act tgg gat ttc atc act gca act aaa aat ggc aaa cgt        696
Tyr Lys Gly Thr Trp Asp Phe Ile Thr Ala Thr Lys Asn Gly Lys Arg
            180                 185                 190 tat cct ttg tta agt aat ggc agt cac gct tat tat cga cgt agt gca        744
Tyr Pro Leu Leu Ser Asn Gly Ser His Ala Tyr Tyr Arg Arg Ser Ala
        195                 200                 205 att cca gaa gat att gat tta gaa aat gat tca aag aat ggt gat ata        792
Ile Pro Glu Asp Ile Asp Leu Glu Asn Asp Ser Lys Asn Gly Asp Ile
    210                 215                 220 ggc tta ata agt gaa ttt agt gca gat ttt ggg act aaa aaa ctg aca        840
```

|     |     |     |     |     |     |     |     |     |     |     |     |     |     |      |
|-----|-----|-----|-----|-----|-----|-----|-----|-----|-----|-----|-----|-----|-----|------|
|     |     | Gly | Leu | Ile | Ser | Glu | Phe | Ser | Ala | Asp | Phe | Gly | Thr | Lys Lys Leu Thr |
|     |     | 225 |     |     |     | 230 |     |     |     | 235 |     |     |     | 240 |

| gga | caa | ctg | tct | tac | acc | aaa | aga | aaa | act | aat | aat | caa | cca | tat | gaa | 888 |
|-----|-----|-----|-----|-----|-----|-----|-----|-----|-----|-----|-----|-----|-----|-----|-----|-----|
| Gly | Gln | Leu | Ser | Tyr | Thr | Lys | Arg | Lys | Thr | Asn | Asn | Gln | Pro | Tyr | Glu |     |
|     |     |     |     | 245 |     |     |     | 250 |     |     |     |     | 255 |     |     |     |

| aag | aaa | aaa | ctc | tat | gat | ata | gat | gcc | gat | att | tat | agt | aat | aga | ttc | 936 |
|-----|-----|-----|-----|-----|-----|-----|-----|-----|-----|-----|-----|-----|-----|-----|-----|-----|
| Lys | Lys | Lys | Leu | Tyr | Asp | Ile | Asp | Ala | Asp | Ile | Tyr | Ser | Asn | Arg | Phe |     |
|     |     |     |     | 260 |     |     |     | 265 |     |     |     | 270 |     |     |     |     |

| agg | ggt | aca | gta | aag | cca | acc | gaa | aaa | gat | tct | gaa | gaa | cat | ccc | ttt | 984 |
|-----|-----|-----|-----|-----|-----|-----|-----|-----|-----|-----|-----|-----|-----|-----|-----|-----|
| Arg | Gly | Thr | Val | Lys | Pro | Thr | Glu | Lys | Asp | Ser | Glu | Glu | His | Pro | Phe |     |
|     |     |     | 275 |     |     |     | 280 |     |     |     |     | 285 |     |     |     |     |

| acc | agc | gag | gga | aca | tta | gaa | ggt | ggt | ttt | tat | ggg | cct | aat | gct | gaa | 1032 |
|-----|-----|-----|-----|-----|-----|-----|-----|-----|-----|-----|-----|-----|-----|-----|-----|------|
| Thr | Ser | Glu | Gly | Thr | Leu | Glu | Gly | Gly | Phe | Tyr | Gly | Pro | Asn | Ala | Glu |      |
|     |     | 290 |     |     |     | 295 |     |     |     | 300 |     |     |     |     |     |      |

| gaa | cta | ggg | ggg | aaa | ttt | tta | gct | acg | gat | aac | cga | gtt | ttt | ggg | gta | 1080 |
|-----|-----|-----|-----|-----|-----|-----|-----|-----|-----|-----|-----|-----|-----|-----|-----|------|
| Glu | Leu | Gly | Gly | Lys | Phe | Leu | Ala | Thr | Asp | Asn | Arg | Val | Phe | Gly | Val |      |
| 305 |     |     |     |     | 310 |     |     |     |     | 315 |     |     |     |     | 320 |      |

| ttt | agt | gcc | aaa | gaa | acg | gaa | gaa | aca | aaa | aag | gaa | gcg | tta | tcc | aag | 1128 |
|-----|-----|-----|-----|-----|-----|-----|-----|-----|-----|-----|-----|-----|-----|-----|-----|------|
| Phe | Ser | Ala | Lys | Glu | Thr | Glu | Glu | Thr | Lys | Lys | Glu | Ala | Leu | Ser | Lys |      |
|     |     |     |     | 325 |     |     |     |     | 330 |     |     |     |     | 335 |     |      |

| gaa | acc | tta | att | gat | ggc | aag | cta | att | act | ttc | tct | act | aaa | aaa | acc | 1176 |
|-----|-----|-----|-----|-----|-----|-----|-----|-----|-----|-----|-----|-----|-----|-----|-----|------|
| Glu | Thr | Leu | Ile | Asp | Gly | Lys | Leu | Ile | Thr | Phe | Ser | Thr | Lys | Lys | Thr |      |
|     |     |     |     | 340 |     |     |     |     | 345 |     |     |     |     | 350 |     |      |

| gat | gca | aaa | acc | aat | gca | aca | acc | agt | acc | gca | gct | aat | aca | aca | acc | 1224 |
|-----|-----|-----|-----|-----|-----|-----|-----|-----|-----|-----|-----|-----|-----|-----|-----|------|
| Asp | Ala | Lys | Thr | Asn | Ala | Thr | Thr | Ser | Thr | Ala | Ala | Asn | Thr | Thr | Thr |      |
|     |     |     | 355 |     |     |     |     | 360 |     |     |     |     | 365 |     |     |      |

| gat | aca | acc | gcc | aat | aca | ata | acc | gat | gaa | aaa | aac | ttt | aag | acg | gaa | 1272 |
|-----|-----|-----|-----|-----|-----|-----|-----|-----|-----|-----|-----|-----|-----|-----|-----|------|
| Asp | Thr | Thr | Ala | Asn | Thr | Ile | Thr | Asp | Glu | Lys | Asn | Phe | Lys | Thr | Glu |      |
| 370 |     |     |     |     | 375 |     |     |     |     | 380 |     |     |     |     |     |      |

| gat | ata | tca | agt | ttt | ggt | gaa | gct | gat | tat | ctg | tta | att | gac | aaa | tat | 1320 |
|-----|-----|-----|-----|-----|-----|-----|-----|-----|-----|-----|-----|-----|-----|-----|-----|------|
| Asp | Ile | Ser | Ser | Phe | Gly | Glu | Ala | Asp | Tyr | Leu | Leu | Ile | Asp | Lys | Tyr |      |
| 385 |     |     |     |     | 390 |     |     |     |     | 395 |     |     |     |     | 400 |      |

| cct | att | cca | ctt | tta | cct | gat | aaa | aat | act | aat | gat | ttc | ata | agt | agt | 1368 |
|-----|-----|-----|-----|-----|-----|-----|-----|-----|-----|-----|-----|-----|-----|-----|-----|------|
| Pro | Ile | Pro | Leu | Leu | Pro | Asp | Lys | Asn | Thr | Asn | Asp | Phe | Ile | Ser | Ser |      |
|     |     |     |     | 405 |     |     |     |     | 410 |     |     |     |     | 415 |     |      |

| aag | cat | cat | act | gta | gga | aat | aaa | cgc | tat | aaa | gtg | gaa | gca | tgt | tgc | 1416 |
|-----|-----|-----|-----|-----|-----|-----|-----|-----|-----|-----|-----|-----|-----|-----|-----|------|
| Lys | His | His | Thr | Val | Gly | Asn | Lys | Arg | Tyr | Lys | Val | Glu | Ala | Cys | Cys |      |
|     |     |     | 420 |     |     |     |     | 425 |     |     |     |     | 430 |     |     |      |

| agt | aat | cta | agc | tat | gtg | aaa | ttt | ggt | atg | tat | tat | gaa | gac | cca | ctt | 1464 |
|-----|-----|-----|-----|-----|-----|-----|-----|-----|-----|-----|-----|-----|-----|-----|-----|------|
| Ser | Asn | Leu | Ser | Tyr | Val | Lys | Phe | Gly | Met | Tyr | Tyr | Glu | Asp | Pro | Leu |      |
|     |     |     | 435 |     |     |     |     | 440 |     |     |     |     | 445 |     |     |      |

| aaa | gaa | aaa | gaa | aca | gaa | aca | gaa | aca | gaa | aca | gaa | aaa | gac | aaa | gaa | 1512 |
|-----|-----|-----|-----|-----|-----|-----|-----|-----|-----|-----|-----|-----|-----|-----|-----|------|
| Lys | Glu | Lys | Glu | Thr | Glu | Thr | Glu | Thr | Glu | Thr | Glu | Lys | Asp | Lys | Glu |      |
|     | 450 |     |     |     |     | 455 |     |     |     |     | 460 |     |     |     |     |      |

| aaa | gaa | aaa | gaa | aaa | gac | aaa | gac | aaa | gaa | aaa | caa | acg | gcg | gca | acg | 1560 |
|-----|-----|-----|-----|-----|-----|-----|-----|-----|-----|-----|-----|-----|-----|-----|-----|------|
| Lys | Glu | Lys | Glu | Lys | Asp | Lys | Asp | Lys | Glu | Lys | Gln | Thr | Ala | Ala | Thr |      |
| 465 |     |     |     | 470 |     |     |     |     | 475 |     |     |     |     | 480 |     |      |

| acc | aac | act | tat | tat | caa | ttc | tta | tta | ggt | cac | cgt | act | ccc | aag | gac | 1608 |
|-----|-----|-----|-----|-----|-----|-----|-----|-----|-----|-----|-----|-----|-----|-----|-----|------|
| Thr | Asn | Thr | Tyr | Tyr | Gln | Phe | Leu | Leu | Gly | His | Arg | Thr | Pro | Lys | Asp |      |
|     |     |     |     | 485 |     |     |     |     | 490 |     |     |     |     | 495 |     |      |

| gac | ata | cct | aaa | aca | gga | agt | gca | aaa | tat | cat | ggt | agt | tgg | ttt | ggt | 1656 |
|-----|-----|-----|-----|-----|-----|-----|-----|-----|-----|-----|-----|-----|-----|-----|-----|------|
| Asp | Ile | Pro | Lys | Thr | Gly | Ser | Ala | Lys | Tyr | His | Gly | Ser | Trp | Phe | Gly |      |
|     |     |     | 500 |     |     |     |     | 505 |     |     |     |     | 510 |     |     |      |

| tat | att | act | gac | ggt | aag | aca | tct | tac | tcc | ccc | agt | ggt | gat | aag | aaa | 1704 |
|-----|-----|-----|-----|-----|-----|-----|-----|-----|-----|-----|-----|-----|-----|-----|-----|------|
| Tyr | Ile | Thr | Asp | Gly | Lys | Thr | Ser | Tyr | Ser | Pro | Ser | Gly | Asp | Lys | Lys |      |
|     |     |     |     | 515 |     |     |     |     | 520 |     |     |     |     | 525 |     |      |

| cgc | gat | aaa | aat | gct | gtc | gcc | gag | ttt | aat | gtt | gat | ttt | gcc | gag | aaa | 1752 |
|-----|-----|-----|-----|-----|-----|-----|-----|-----|-----|-----|-----|-----|-----|-----|-----|------|
| Arg | Asp | Lys | Asn | Ala | Val | Ala | Glu | Phe | Asn | Val | Asp | Phe | Ala | Glu | Lys |      |
|     |     | 530 |     |     |     |     | 535 |     |     |     |     | 540 |     |     |     |      |

```
                                                            -continued aag cta aca ggc gaa tta aaa cga cac gat act gga aat ccc gta ttt       1800
Lys Leu Thr Gly Glu Leu Lys Arg His Asp Thr Gly Asn Pro Val Phe
545                 550                 555                 560 agt att gag gca aac ttt aat aat agt agt aat gcc ttc act ggt aca       1848
Ser Ile Glu Ala Asn Phe Asn Asn Ser Ser Asn Ala Phe Thr Gly Thr
                565                 570                 575 gca acc gca aca aat ttt gta ata gat ggt aaa aat agt caa aat aaa       1896
Ala Thr Ala Thr Asn Phe Val Ile Asp Gly Lys Asn Ser Gln Asn Lys
            580                 585                 590 aat acc cca att aat att aca act aaa gta aac ggg gca ttt tat gga       1944
Asn Thr Pro Ile Asn Ile Thr Thr Lys Val Asn Gly Ala Phe Tyr Gly
        595                 600                 605 cct aag gct tct gaa tta ggc ggt tat ttc act tat aac gga aat tct       1992
Pro Lys Ala Ser Glu Leu Gly Gly Tyr Phe Thr Tyr Asn Gly Asn Ser
    610                 615                 620 aca gct aca aat tct gaa agt tcc tca acc gta tct tca tca tcc aat       2040
Thr Ala Thr Asn Ser Glu Ser Ser Ser Thr Val Ser Ser Ser Ser Asn
625                 630                 635                 640 tca aaa aat gca aga gct gca gtt gtc ttt ggt gcg aga caa caa gta       2088
Ser Lys Asn Ala Arg Ala Ala Val Val Phe Gly Ala Arg Gln Gln Val
                645                 650                 655 gaa aca acc aaa taatggaata ctaaaa atg act aaa aaa ccc tat ttt cgc     2140
Glu Thr Thr Lys                       Met Thr Lys Lys Pro Tyr Phe Arg
            660                                   665 cta agt att att tct tgt ctt tta att tca tgc tat gta aaa gca gaa       2188
Leu Ser Ile Ile Ser Cys Leu Leu Ile Ser Cys Tyr Val Lys Ala Glu
        670                 675                 680 act caa agt ata aaa gat aca aaa gaa gct ata tca tct gaa gtg gac       2236
Thr Gln Ser Ile Lys Asp Thr Lys Glu Ala Ile Ser Ser Glu Val Asp
685                 690                 695                 700 act caa agt aca gaa gat tca gaa tta gaa act atc tca gtc act gca       2284
Thr Gln Ser Thr Glu Asp Ser Glu Leu Glu Thr Ile Ser Val Thr Ala
                705                 710                 715 gaa aaa ata aga gat cgt aaa gat aat gaa gta act gga ctt ggc aaa       2332
Glu Lys Ile Arg Asp Arg Lys Asp Asn Glu Val Thr Gly Leu Gly Lys
            720                 725                 730 att atc aaa act agt gaa agt atc agc cga gaa caa gta tta aat att       2380
Ile Ile Lys Thr Ser Glu Ser Ile Ser Arg Glu Gln Val Leu Asn Ile
        735                 740                 745 cgt gat cta aca cgc tat gat cca ggg att tca gtt gta gaa caa ggt       2428
Arg Asp Leu Thr Arg Tyr Asp Pro Gly Ile Ser Val Val Glu Gln Gly
    750                 755                 760 cgc ggt gca agt tct gga tat tct att cgt ggt atg gac aga aat aga       2476
Arg Gly Ala Ser Ser Gly Tyr Ser Ile Arg Gly Met Asp Arg Asn Arg
765                 770                 775                 780 gtt gct tta tta gta gat ggt tta cct caa acg caa tct tat gta gtg       2524
Val Ala Leu Leu Val Asp Gly Leu Pro Gln Thr Gln Ser Tyr Val Val
                785                 790                 795 caa agc cct tta gtt gct cgt tca gga tat tct ggc act ggt gca att       2572
Gln Ser Pro Leu Val Ala Arg Ser Gly Tyr Ser Gly Thr Gly Ala Ile
            800                 805                 810 aat gaa att gaa tat gaa aat gta aag gcc gtc gaa ata agc aag ggg       2620
Asn Glu Ile Glu Tyr Glu Asn Val Lys Ala Val Glu Ile Ser Lys Gly
        815                 820                 825 ggg agt tct tct gag tat ggt aat gga gca cta gct ggt tct gta aca       2668
Gly Ser Ser Ser Glu Tyr Gly Asn Gly Ala Leu Ala Gly Ser Val Thr
    830                 835                 840 ttt caa agc aaa tca gca gcc gat atc tta gaa gga gac aaa tca tgg       2716
Phe Gln Ser Lys Ser Ala Ala Asp Ile Leu Glu Gly Asp Lys Ser Trp
845                 850                 855                 860
```

-continued

| | |
|---|---|
| gga att caa act aaa aat gct tat tca agc aaa aat aaa ggc ttt acc<br>Gly Ile Gln Thr Lys Asn Ala Tyr Ser Ser Lys Asn Lys Gly Phe Thr<br>                  865                    870                    875 | 2764 |
| cat tct tta gct gta gca gga aaa caa ggt gga ttt gaa ggg cta gcc<br>His Ser Leu Ala Val Ala Gly Lys Gln Gly Gly Phe Glu Gly Leu Ala<br>       880                    885                    890 | 2812 |
| att tac act caa cga aat tca att gaa acc caa gtc cat aaa gat gca<br>Ile Tyr Thr Gln Arg Asn Ser Ile Glu Thr Gln Val His Lys Asp Ala<br>                895                    900                    905 | 2860 |
| tta aaa ggc gta caa agt tat gat cga tta atc gcc aca aca gat aaa<br>Leu Lys Gly Val Gln Ser Tyr Asp Arg Leu Ile Ala Thr Thr Asp Lys<br>910                    915                    920 | 2908 |
| tct tca gga tac ttt gtg ata caa ggt gag tgt cca aat ggt gat gac<br>Ser Ser Gly Tyr Phe Val Ile Gln Gly Glu Cys Pro Asn Gly Asp Asp<br>925                    930                    935                    940 | 2956 |
| aag tgt gca gcc aag cca cct gcg act tta tcc acc caa agc gaa acc<br>Lys Cys Ala Ala Lys Pro Pro Ala Thr Leu Ser Thr Gln Ser Glu Thr<br>                945                    950                    955 | 3004 |
| gta agc gtt tca gat tat acg ggg gct aac cgt atc aaa cct aat cca<br>Val Ser Val Ser Asp Tyr Thr Gly Ala Asn Arg Ile Lys Pro Asn Pro<br>       960                    965                    970 | 3052 |
| atg aaa tat gaa agc cag tct tgg ttt tta aga gga ggg tat cat ttt<br>Met Lys Tyr Glu Ser Gln Ser Trp Phe Leu Arg Gly Gly Tyr His Phe<br>975                    980                    985 | 3100 |
| tct gaa caa cat tat att ggt ggt att ttt gaa ttc aca caa caa aaa<br>Ser Glu Gln His Tyr Ile Gly Gly Ile Phe Glu Phe Thr Gln Gln Lys<br>       990                    995                  1000 | 3148 |
| ttt gat atc cgt gat atg aca ttt ccc gct tat tta agc cca aca gaa<br>Phe Asp Ile Arg Asp Met Thr Phe Pro Ala Tyr Leu Ser Pro Thr Glu<br>1005               1010                 1015                 1020 | 3196 |
| aga cgg gat gat agt agt cgt tct ttt tat cca atg caa gat cat ggt<br>Arg Arg Asp Asp Ser Ser Arg Ser Phe Tyr Pro Met Gln Asp His Gly<br>               1025                 1030                 1035 | 3244 |
| gca tat caa cat att gag gat ggc aga ggc gtt aaa tat gca agt ggg<br>Ala Tyr Gln His Ile Glu Asp Gly Arg Gly Val Lys Tyr Ala Ser Gly<br>               1040                 1045                 1050 | 3292 |
| ctt tat ttc gat gaa cac cat aga aaa cag cgt gta ggt att gaa tat<br>Leu Tyr Phe Asp Glu His His Arg Lys Gln Arg Val Gly Ile Glu Tyr<br>               1055                 1060                 1065 | 3340 |
| att tac gaa aat aag aac aaa gcg ggc atc att gac aaa gca gtg tta<br>Ile Tyr Glu Asn Lys Asn Lys Ala Gly Ile Ile Asp Lys Ala Val Leu<br>       1070                 1075                 1080 | 3388 |
| agt gct aat caa caa aac atc ata ctt gac agt tat atg cga cat acg<br>Ser Ala Asn Gln Gln Asn Ile Ile Leu Asp Ser Tyr Met Arg His Thr<br>1085             1090                 1095                 1100 | 3436 |
| cat tgc agt ctt tat cct aat cca agt aag aat tgc cgc cca aca ctt<br>His Cys Ser Leu Tyr Pro Asn Pro Ser Lys Asn Cys Arg Pro Thr Leu<br>               1105                 1110                 1115 | 3484 |
| gat aaa cct tat tca tac tat cgt tct gat aga aat gtt tat aaa gaa<br>Asp Lys Pro Tyr Ser Tyr Tyr Arg Ser Asp Arg Asn Val Tyr Lys Glu<br>               1120                 1125                 1130 | 3532 |
| aaa cat aat atg ttg caa ttg aat tta gag aaa aaa att caa caa aat<br>Lys His Asn Met Leu Gln Leu Asn Leu Glu Lys Lys Ile Gln Gln Asn<br>               1135                 1140                 1145 | 3580 |
| tgg ctt act cat caa att gtc ttc aat ctt ggt ttt gat gac ttt act<br>Trp Leu Thr His Gln Ile Val Phe Asn Leu Gly Phe Asp Asp Phe Thr<br>1150             1155                 1160 | 3628 |
| tca gcg ctt cag cat aaa gat tat tta act cga cgt gtt atc gct acg<br>Ser Ala Leu Gln His Lys Asp Tyr Leu Thr Arg Arg Val Ile Ala Thr | 3676 |

-continued

| | |
|---|---|
| gca gat agt att cca agg aaa cct ggt gaa act ggt aaa cca aga aat<br>Ala Asp Ser Ile Pro Arg Lys Pro Gly Glu Thr Gly Lys Pro Arg Asn<br>    1185                    1190                  1195 | 3724 |
| ggt ttg caa tca caa cct tac tta tac cca aaa cca gag cca tat ttt<br>Gly Leu Gln Ser Gln Pro Tyr Leu Tyr Pro Lys Pro Glu Pro Tyr Phe<br>        1200                  1205                  1210 | 3772 |
| gca gga caa gat cat tgt aat tat caa ggt agc tcc tct aat tac aga<br>Ala Gly Gln Asp His Cys Asn Tyr Gln Gly Ser Ser Ser Asn Tyr Arg<br>    1215                    1220                  1225 | 3820 |
| gac tgt aaa gtg cgg tta att aaa ggg aaa aat tat tat ttc gca gca<br>Asp Cys Lys Val Arg Leu Ile Lys Gly Lys Asn Tyr Tyr Phe Ala Ala<br>    1230                    1235                  1240 | 3868 |
| cgc aat aat atg gca tta ggg aaa tac gtt gat tta ggt tta ggt att<br>Arg Asn Asn Met Ala Leu Gly Lys Tyr Val Asp Leu Gly Leu Gly Ile<br>1245                  1250                  1255                  1260 | 3916 |
| cgg tat gac gta tct cgt aca aaa gct aat gaa tca act att agt gtt<br>Arg Tyr Asp Val Ser Arg Thr Lys Ala Asn Glu Ser Thr Ile Ser Val<br>        1265                  1270                  1275 | 3964 |
| ggt aaa ttt aaa aat ttc tct tgg aat act ggt att gtc ata aaa cca<br>Gly Lys Phe Lys Asn Phe Ser Trp Asn Thr Gly Ile Val Ile Lys Pro<br>    1280                    1285                  1290 | 4012 |
| acg gaa tgg ctt gat ctt tct tat cgc ctt tct act gga ttt aga aat<br>Thr Glu Trp Leu Asp Leu Ser Tyr Arg Leu Ser Thr Gly Phe Arg Asn<br>        1295                  1300                  1305 | 4060 |
| cct agt ttt tct gaa atg tat ggt tgg cgg tat ggt ggc aag aat gac<br>Pro Ser Phe Ser Glu Met Tyr Gly Trp Arg Tyr Gly Gly Lys Asn Asp<br>    1310                    1315                  1320 | 4108 |
| gag gtt tat gta ggt aaa ttt aag cct gaa aca tct cgt aac caa gag<br>Glu Val Tyr Val Gly Lys Phe Lys Pro Glu Thr Ser Arg Asn Gln Glu<br>1325                  1330                  1335                  1340 | 4156 |
| ttt ggt ctc gct cta aaa ggg gat ttt ggt aat att gag atc agt cat<br>Phe Gly Leu Ala Leu Lys Gly Asp Phe Gly Asn Ile Glu Ile Ser His<br>        1345                  1350                  1355 | 4204 |
| ttt agt aat gct tat cga aat ctt atc gcc ttt gct gaa gaa ctt agt<br>Phe Ser Asn Ala Tyr Arg Asn Leu Ile Ala Phe Ala Glu Glu Leu Ser<br>    1360                    1365                  1370 | 4252 |
| aaa aat gga act gga aag ggc aat tat gga tat cat aat gca caa aat<br>Lys Asn Gly Thr Gly Lys Gly Asn Tyr Gly Tyr His Asn Ala Gln Asn<br>        1375                  1380                  1385 | 4300 |
| gca aaa tta gtt ggc gta aat ata act gca caa tta gat ttt aat ggt<br>Ala Lys Leu Val Gly Val Asn Ile Thr Ala Gln Leu Asp Phe Asn Gly<br>    1390                    1395                  1400 | 4348 |
| tta tgg aaa cgt att ccc tac ggt tgg tat gca aca ttt gct tat aac<br>Leu Trp Lys Arg Ile Pro Tyr Gly Trp Tyr Ala Thr Phe Ala Tyr Asn<br>1405                  1410                  1415                  1420 | 4396 |
| caa gta aaa gtt aaa gat caa aaa atc aat gct ggt tta gcc tcc gta<br>Gln Val Lys Val Lys Asp Gln Lys Ile Asn Ala Gly Leu Ala Ser Val<br>        1425                  1430                  1435 | 4444 |
| agc agt tat tta ttt gat gcc att cag ccc agc cgt tat atc att ggt<br>Ser Ser Tyr Leu Phe Asp Ala Ile Gln Pro Ser Arg Tyr Ile Ile Gly<br>    1440                    1445                  1450 | 4492 |
| tta ggc tat gat cat cca agt aat act tgg gga att aat aca atg ttt<br>Leu Gly Tyr Asp His Pro Ser Asn Thr Trp Gly Ile Asn Thr Met Phe<br>        1455                  1460                  1465 | 4540 |
| act caa tca aaa gca aaa tct caa aat gaa ttg cta gga aaa cgt gca<br>Thr Gln Ser Lys Ala Lys Ser Gln Asn Glu Leu Leu Gly Lys Arg Ala<br>    1470                    1475                  1480 | 4588 |
| tta ggt aac aat tca agg gat gta aaa tca aca aga aaa ctt act cgg | 4636 |

-continued

| | | |
|---|---|---|
| Leu Gly Asn Asn Ser Arg Asp Val Lys Ser Thr Arg Lys Leu Thr Arg<br>1485                      1490                   1495                   1500 | |

```
gca tgg cat atc tta gat gta tcg ggt tat tac atg gcg aat aaa aat        4684
Ala Trp His Ile Leu Asp Val Ser Gly Tyr Tyr Met Ala Asn Lys Asn
                1505                1510                1515 att atg ctt cga tta ggg ata tat aat tta ttc aac tat cgc tat gtt        4732
Ile Met Leu Arg Leu Gly Ile Tyr Asn Leu Phe Asn Tyr Arg Tyr Val
            1520                1525                1530 act tgg gaa gcg gtg cgt caa aca gca caa ggt gcg gtc aat caa cat        4780
Thr Trp Glu Ala Val Arg Gln Thr Ala Gln Gly Ala Val Asn Gln His
        1535                1540                1545 caa aat gtt ggt agc tat act cgc tac gca gca tca gga cga aac tat        4828
Gln Asn Val Gly Ser Tyr Thr Arg Tyr Ala Ala Ser Gly Arg Asn Tyr
    1550                1555                1560 acc tta aca tta gaa atg aaa ttc taaattaaaa tgcgccagat ggactagata       4882
Thr Leu Thr Leu Glu Met Lys Phe
1565            1570 tgctatatct ataccttact ggcgcatctt tttctgttct ataatctgct taagtgaaaa      4942
accaaacttg gattttttac aagatctttt cacacattta ttgtaaaatc tccgacaatt      5002
ttgaccg                                                                5009

<210> SEQ ID NO 4
<211> LENGTH: 5099
<212> TYPE: DNA
<213> ORGANISM: Haemophilus influenzae
<220> FEATURE:
<221> NAME/KEY: CDS
<222> LOCATION: (160)..(2121)
<220> FEATURE:
<221> NAME/KEY: CDS
<222> LOCATION: (2152)..(4890)

<400> SEQUENCE: 4
aaaattcggt aatgataacc ctataaatga taagagagaa agttgtttta cgccattttt       60
catattttat ccatgaactt aaaaaattct aagttgacat tattacaaaa aaagaacaat      120
aatgcgaatt attatcaatt ttgtataagt attaattct atg aaa tct gta cct        174
                                            Met Lys Ser Val Pro
                                              1               5 ctt atc act ggt gga ctt tcc ttt tta cta agc gct tgt agc ggg gga        222
Leu Ile Thr Gly Gly Leu Ser Phe Leu Leu Ser Ala Cys Ser Gly Gly
             10                  15                  20 ggt ggt tct ttt gat gta gat gac gtc tct aat ccc tcc tct tct aaa        270
Gly Gly Ser Phe Asp Val Asp Asp Val Ser Asn Pro Ser Ser Ser Lys
         25                  30                  35 cca cgt tat caa gac gat acc tcg aat caa aga aca aaa tct gat ttg        318
Pro Arg Tyr Gln Asp Asp Thr Ser Asn Gln Arg Thr Lys Ser Asp Leu
     40                  45                  50 gaa aag ttg ttc att cct tct tta ggg gga ggg atg aag tta gtg gct        366
Glu Lys Leu Phe Ile Pro Ser Leu Gly Gly Gly Met Lys Leu Val Ala
 55                  60                  65 caa aat ttt att ggt gct aga gaa cct agt ttc tta aat gaa gat ggc        414
Gln Asn Phe Ile Gly Ala Arg Glu Pro Ser Phe Leu Asn Glu Asp Gly
 70                  75                  80                  85 tat atg ata ttt tcc tca ctt tct acg att gaa gag gat gtt gaa aaa        462
Tyr Met Ile Phe Ser Ser Leu Ser Thr Ile Glu Glu Asp Val Glu Lys
             90                  95                 100 gtt aaa aat aac aat aaa aac ggg ggg agg ctt att ggc tca att gag        510
Val Lys Asn Asn Asn Lys Asn Gly Gly Arg Leu Ile Gly Ser Ile Glu
        105                 110                 115
```

-continued

| | | |
|---|---|---|
| gaa cct aat gga aca tca caa aat tct aat tca caa gaa tac gtt tat<br>Glu Pro Asn Gly Thr Ser Gln Asn Ser Asn Ser Gln Glu Tyr Val Tyr<br>      120                        125                    130 | | 558 |
| tct ggt ttg tat tat atc gat agt tgg cgt gat tat aag aag gaa gag<br>Ser Gly Leu Tyr Tyr Ile Asp Ser Trp Arg Asp Tyr Lys Lys Glu Glu<br>      135                        140                    145 | | 606 |
| caa aaa gct tat act ggc tat tat ggt tat gca ttt tat tat ggt aat<br>Gln Lys Ala Tyr Thr Gly Tyr Tyr Gly Tyr Ala Phe Tyr Tyr Gly Asn<br>150                    155                    160                    165 | | 654 |
| gaa act gca aaa aac ttg cca gta aaa ggt gta gct aaa tac aaa gga<br>Glu Thr Ala Lys Asn Leu Pro Val Lys Gly Val Ala Lys Tyr Lys Gly<br>                    170                    175                    180 | | 702 |
| acg tgg aac ttc atc act gca act gaa aat ggc aaa cgt tat tct ttg<br>Thr Trp Asn Phe Ile Thr Ala Thr Glu Asn Gly Lys Arg Tyr Ser Leu<br>              185                        190 | | 750 |
| ttc agt aat tct atc ggt caa gct tat tcc aga cgc agc gct att tca<br>Phe Ser Asn Ser Ile Gly Gln Ala Tyr Ser Arg Arg Ser Ala Ile Ser<br>                    200                    205                    210 | | 798 |
| gaa gat atc tat aat tta gaa aac ggt gac gcg ggc tta ata agt gaa<br>Glu Asp Ile Tyr Asn Leu Glu Asn Gly Asp Ala Gly Leu Ile Ser Glu<br>      215                        220                    225 | | 846 |
| ttt agt gta gat ttt ggt aag aaa gag ctc act gga gaa ctt tat tat<br>Phe Ser Val Asp Phe Gly Lys Lys Glu Leu Thr Gly Glu Leu Tyr Tyr<br>230                    235                    240                    245 | | 894 |
| aat gaa agg aaa aca agt gtt aat gaa tca caa aat aca aca cat aaa<br>Asn Glu Arg Lys Thr Ser Val Asn Glu Ser Gln Asn Thr Thr His Lys<br>                    250                    255                    260 | | 942 |
| ctc tac act cta gaa gct aaa gtg tat agc aac cga ttc aga ggt aaa<br>Leu Tyr Thr Leu Glu Ala Lys Val Tyr Ser Asn Arg Phe Arg Gly Lys<br>              265                        270                    275 | | 990 |
| gta aag cca acc aaa aca aag tct gaa gat cat ccc ttt acc agc gag<br>Val Lys Pro Thr Lys Thr Lys Ser Glu Asp His Pro Phe Thr Ser Glu<br>            280                    285                    290 | | 1038 |
| gga aca tta gaa ggt ggt ttt tat ggg cct aat gct gaa gaa cta ggg<br>Gly Thr Leu Glu Gly Gly Phe Tyr Gly Pro Asn Ala Glu Glu Leu Gly<br>295                    300                    305 | | 1086 |
| gga aag ttt tta gct aac gac gaa aaa gtt ttt ggg gta ttt agt gcc<br>Gly Lys Phe Leu Ala Asn Asp Glu Lys Val Phe Gly Val Phe Ser Ala<br>310                    315                    320                    325 | | 1134 |
| aaa gaa gac cca caa aac cca gaa aac caa aaa tta tcc aca gaa acc<br>Lys Glu Asp Pro Gln Asn Pro Glu Asn Gln Lys Leu Ser Thr Glu Thr<br>                    330                    335                    340 | | 1182 |
| tta att gat ggc aag cta att act ttt aaa aga act gat gca aca acc<br>Leu Ile Asp Gly Lys Leu Ile Thr Phe Lys Arg Thr Asp Ala Thr Thr<br>              345                        350                    355 | | 1230 |
| aat gca aca acc gat gca aaa acc agt gca aca acc gat gca acc agt<br>Asn Ala Thr Thr Asp Ala Lys Thr Ser Ala Thr Thr Asp Ala Thr Ser<br>            360                        365                    370 | | 1278 |
| aca aca gcc aat aaa aaa acc gat gca gaa aac ttt aag acg gaa gat<br>Thr Thr Ala Asn Lys Lys Thr Asp Ala Glu Asn Phe Lys Thr Glu Asp<br>375                    380                    385 | | 1326 |
| ata cca agt ttt ggt gaa gct gat tac ctt tta att ggc aat cag cct<br>Ile Pro Ser Phe Gly Glu Ala Asp Tyr Leu Leu Ile Gly Asn Gln Pro<br>390                    395                    400                    405 | | 1374 |
| att cct ctt tta cct gaa aaa aat act gat gat ttc ata agt agt aag<br>Ile Pro Leu Leu Pro Glu Lys Asn Thr Asp Asp Phe Ile Ser Ser Lys<br>                    410                    415                    420 | | 1422 |
| cac cat acg gta gga ggt aaa acc tat aaa gta gaa gca tgt tgc aag<br>His His Thr Val Gly Gly Lys Thr Tyr Lys Val Glu Ala Cys Cys Lys<br>              425                        430                    435 | | 1470 |

```
aat cta agc tat gtg aaa ttt ggt atg tat tat gag gat aaa gat aag      1518
Asn Leu Ser Tyr Val Lys Phe Gly Met Tyr Tyr Glu Asp Lys Asp Lys
        440                 445                 450 gac aac aaa aat gaa aca gac aaa gaa aaa ggc aaa gaa aaa cca acg      1566
Asp Asn Lys Asn Glu Thr Asp Lys Glu Lys Gly Lys Glu Lys Pro Thr
455                 460                 465 acg aca aca tct atc aac act tat tat caa ttc tta tta ggt ctc cgt      1614
Thr Thr Thr Ser Ile Asn Thr Tyr Tyr Gln Phe Leu Leu Gly Leu Arg
470                 475                 480                 485 act ccc aag gac gaa ata cct aaa gaa gga agt gca aaa tat cat ggt      1662
Thr Pro Lys Asp Glu Ile Pro Lys Glu Gly Ser Ala Lys Tyr His Gly
                490                 495                 500 aat tgg ttt ggt tat att agt gat ggc gag aca tct tac tcc gcc agt      1710
Asn Trp Phe Gly Tyr Ile Ser Asp Gly Glu Thr Ser Tyr Ser Ala Ser
        505                 510                 515 ggt gat aag gaa cgc agt aaa aat gct gtc gcc gag ttt gat gta agt      1758
Gly Asp Lys Glu Arg Ser Lys Asn Ala Val Ala Glu Phe Asp Val Ser
        520                 525                 530 ttt gcc aat aaa aca tta aca ggc gaa tta aaa cga cac gat aat gga      1806
Phe Ala Asn Lys Thr Leu Thr Gly Glu Leu Lys Arg His Asp Asn Gly
535                 540                 545 aat acc gta ttt aaa att aat gca gaa tta aat ggt agt aat gac ttc      1854
Asn Thr Val Phe Lys Ile Asn Ala Glu Leu Asn Gly Ser Asn Asp Phe
550                 555                 560                 565 act ggt aca gca acc gca aca aat ttt gta ata gat ggt aac aat agt      1902
Thr Gly Thr Ala Thr Ala Thr Asn Phe Val Ile Asp Gly Asn Asn Ser
                570                 575                 580 caa act tca aat gcc aaa att aat att aca act aaa gta aat ggg gca      1950
Gln Thr Ser Asn Ala Lys Ile Asn Ile Thr Thr Lys Val Asn Gly Ala
        585                 590                 595 ttt tat gga cct aag gct tct gaa tta gga ggg tat ttc acc tat aac      1998
Phe Tyr Gly Pro Lys Ala Ser Glu Leu Gly Gly Tyr Phe Thr Tyr Asn
        600                 605                 610 gga aaa aat cct aca gct aca aat tct gaa agt tcc tca acc gta cct      2046
Gly Lys Asn Pro Thr Ala Thr Asn Ser Glu Ser Ser Ser Thr Val Pro
615                 620                 625 tca cca ccc aat tca cca aat gca agc gct gca gtt gtc ttt ggt gct      2094
Ser Pro Pro Asn Ser Pro Asn Ala Ser Ala Ala Val Val Phe Gly Ala
630                 635                 640                 645 aaa aaa caa gta gaa aca acc aac aag taaaaacaac caagtaatgg            2141
Lys Lys Gln Val Glu Thr Thr Asn Lys
                650 aatactaaaa atg act aaa aaa ccc tat ttt cgc cta agt att att tct      2190
           Met Thr Lys Lys Pro Tyr Phe Arg Leu Ser Ile Ile Ser
               655                 660                 665 tgt ctt tta att tca tgc tat gta aaa gca gaa act caa agt ata aaa      2238
Cys Leu Leu Ile Ser Cys Tyr Val Lys Ala Glu Thr Gln Ser Ile Lys
        670                 675                 680 gat aca aaa gaa gct ata tca tct gaa gtg gac act caa agt aca gaa      2286
Asp Thr Lys Glu Ala Ile Ser Ser Glu Val Asp Thr Gln Ser Thr Glu
685                 690                 695 gat tca gaa tta gaa act atc tca gtc act gca gaa aaa ata aga gat      2334
Asp Ser Glu Leu Glu Thr Ile Ser Val Thr Ala Glu Lys Ile Arg Asp
700                 705                 710                 715 cgt aaa gat aat gaa gta act gga ctt ggc aaa att atc aaa act agt      2382
Arg Lys Asp Asn Glu Val Thr Gly Leu Gly Lys Ile Ile Lys Thr Ser
                720                 725                 730 gaa agt atc agc cga gaa caa gta tta aat att cgt gat cta aca cgc      2430
Glu Ser Ile Ser Arg Glu Gln Val Leu Asn Ile Arg Asp Leu Thr Arg
```

-continued

|   |   |   |   |   |   |   |   |   |   |   |   |   |   |   |   |   |
|---|---|---|---|---|---|---|---|---|---|---|---|---|---|---|---|---|
|   |   | 735 |   |   |   | 740 |   |   |   | 745 |   |   |   |   |   |   |
| tat | gat | cca | ggc | att | tca | gtt | gta | gaa | caa | ggc | cgt | ggt | gca | agt | tct | 2478 |
| Tyr | Asp | Pro | Gly | Ile | Ser | Val | Val | Glu | Gln | Gly | Arg | Gly | Ala | Ser | Ser |   |
|   |   | 750 |   |   |   | 755 |   |   |   | 760 |   |   |   |   |   |   |
| gga | tat | tct | att | cgt | ggt | atg | gac | aga | aat | aga | gtt | gct | tta | tta | gta | 2526 |
| Gly | Tyr | Ser | Ile | Arg | Gly | Met | Asp | Arg | Asn | Arg | Val | Ala | Leu | Leu | Val |   |
|   | 765 |   |   |   | 770 |   |   |   | 775 |   |   |   |   |   |   |   |
| gat | ggt | tta | cct | caa | acg | caa | tct | tat | gta | gtg | caa | agc | cct | tta | gtt | 2574 |
| Asp | Gly | Leu | Pro | Gln | Thr | Gln | Ser | Tyr | Val | Val | Gln | Ser | Pro | Leu | Val |   |
| 780 |   |   |   | 785 |   |   |   | 790 |   |   |   | 795 |   |   |   |   |
| gct | cgt | tca | gga | tat | tct | ggc | act | ggt | gca | att | aat | gaa | att | gaa | tat | 2622 |
| Ala | Arg | Ser | Gly | Tyr | Ser | Gly | Thr | Gly | Ala | Ile | Asn | Glu | Ile | Glu | Tyr |   |
|   |   |   |   | 800 |   |   |   |   | 805 |   |   |   |   | 810 |   |   |
| gaa | aat | gta | aag | gcc | gtc | gaa | ata | agc | aag | ggg | ggg | agt | tct | tct | gag | 2670 |
| Glu | Asn | Val | Lys | Ala | Val | Glu | Ile | Ser | Lys | Gly | Gly | Ser | Ser | Ser | Glu |   |
|   |   |   | 815 |   |   |   |   | 820 |   |   |   |   | 825 |   |   |   |
| tat | ggt | aat | gga | gca | cta | gct | ggt | tct | gta | aca | ttt | caa | agc | aaa | tca | 2718 |
| Tyr | Gly | Asn | Gly | Ala | Leu | Ala | Gly | Ser | Val | Thr | Phe | Gln | Ser | Lys | Ser |   |
|   |   | 830 |   |   |   |   | 835 |   |   |   |   | 840 |   |   |   |   |
| gca | gcc | gat | atc | tta | gaa | gga | gac | aaa | tca | tgg | gga | att | caa | act | aaa | 2766 |
| Ala | Ala | Asp | Ile | Leu | Glu | Gly | Asp | Lys | Ser | Trp | Gly | Ile | Gln | Thr | Lys |   |
|   | 845 |   |   |   |   | 850 |   |   |   |   | 855 |   |   |   |   |   |
| aat | gct | tat | tca | agc | aaa | aat | aaa | ggc | ttt | acc | cat | tct | tta | gct | gta | 2814 |
| Asn | Ala | Tyr | Ser | Ser | Lys | Asn | Lys | Gly | Phe | Thr | His | Ser | Leu | Ala | Val |   |
| 860 |   |   |   |   | 865 |   |   |   |   | 870 |   |   |   |   | 875 |   |
| gct | gga | aaa | caa | ggg | gga | ttt | gac | ggg | gtc | gcc | att | tat | act | caa | cga | 2862 |
| Ala | Gly | Lys | Gln | Gly | Gly | Phe | Asp | Gly | Val | Ala | Ile | Tyr | Thr | Gln | Arg |   |
|   |   |   |   | 880 |   |   |   |   | 885 |   |   |   |   | 890 |   |   |
| aat | tca | att | gaa | acc | caa | gtc | cat | aaa | gat | gca | tta | aaa | ggc | gta | caa | 2910 |
| Asn | Ser | Ile | Glu | Thr | Gln | Val | His | Lys | Asp | Ala | Leu | Lys | Gly | Val | Gln |   |
|   |   |   | 895 |   |   |   |   | 900 |   |   |   |   | 905 |   |   |   |
| agt | tat | cat | cga | tta | atc | gcc | aaa | cca | gag | gat | caa | tct | gca | tac | ttt | 2958 |
| Ser | Tyr | His | Arg | Leu | Ile | Ala | Lys | Pro | Glu | Asp | Gln | Ser | Ala | Tyr | Phe |   |
|   |   | 910 |   |   |   |   | 915 |   |   |   |   | 920 |   |   |   |   |
| gtg | atg | caa | gat | gag | tgt | cca | aag | cca | gat | gat | tat | aac | agt | tgt | tta | 3006 |
| Val | Met | Gln | Asp | Glu | Cys | Pro | Lys | Pro | Asp | Asp | Tyr | Asn | Ser | Cys | Leu |   |
| 925 |   |   |   |   | 930 |   |   |   |   | 935 |   |   |   |   |   |   |
| cct | ttc | gcc | aaa | cga | cct | gcg | att | tta | tcc | tcc | caa | aga | gaa | acc | gta | 3054 |
| Pro | Phe | Ala | Lys | Arg | Pro | Ala | Ile | Leu | Ser | Ser | Gln | Arg | Glu | Thr | Val |   |
| 940 |   |   |   |   | 945 |   |   |   |   | 950 |   |   |   |   | 955 |   |
| agc | gtt | tca | gat | tat | acg | ggg | gct | aac | cgt | atc | aaa | cct | aat | cca | atg | 3102 |
| Ser | Val | Ser | Asp | Tyr | Thr | Gly | Ala | Asn | Arg | Ile | Lys | Pro | Asn | Pro | Met |   |
|   |   |   | 960 |   |   |   |   | 965 |   |   |   |   | 970 |   |   |   |
| aaa | tat | gaa | agc | cag | tct | tgg | ttt | tta | aga | gga | ggg | tat | cat | ttt | tct | 3150 |
| Lys | Tyr | Glu | Ser | Gln | Ser | Trp | Phe | Leu | Arg | Gly | Gly | Tyr | His | Phe | Ser |   |
|   |   | 975 |   |   |   |   | 980 |   |   |   |   | 985 |   |   |   |   |
| gaa | caa | cat | tat | att | ggt | ggt | att | ttt | gaa | ttc | aca | caa | caa | aaa | ttt | 3198 |
| Glu | Gln | His | Tyr | Ile | Gly | Gly | Ile | Phe | Glu | Phe | Thr | Gln | Gln | Lys | Phe |   |
|   | 990 |   |   |   |   | 995 |   |   |   |   | 1000 |   |   |   |   |   |
| gat | atc | cgt | gat | atg | aca | ttt | ccc | gct | tat | tta | aga | tca | aca | gaa | aaa | 3246 |
| Asp | Ile | Arg | Asp | Met | Thr | Phe | Pro | Ala | Tyr | Leu | Arg | Ser | Thr | Glu | Lys |   |
| 1005 |   |   |   |   | 1010 |   |   |   |   | 1015 |   |   |   |   |   |   |
| cgg | gat | gat | agc | agt | ggc | tct | ttt | tat | cca | aag | caa | gat | tat | ggt | gca | 3294 |
| Arg | Asp | Asp | Ser | Ser | Gly | Ser | Phe | Tyr | Pro | Lys | Gln | Asp | Tyr | Gly | Ala |   |
| 1020 |   |   |   |   | 1025 |   |   |   |   | 1030 |   |   |   |   | 1035 |   |
| tat | caa | cgt | att | gag | gat | ggc | cga | ggc | gtt | aac | tat | gca | agt | ggg | ctt | 3342 |
| Tyr | Gln | Arg | Ile | Glu | Asp | Gly | Arg | Gly | Val | Asn | Tyr | Ala | Ser | Gly | Leu |   |
|   |   |   |   | 1040 |   |   |   |   | 1045 |   |   |   |   | 1050 |   |   |
| tat | ttc | gat | gaa | cac | cat | aga | aaa | cag | cgt | gta | ggt | att | gaa | tat | att | 3390 |

```
Tyr Phe Asp Glu His His Arg Lys Gln Arg Val Gly Ile Glu Tyr Ile
        1055                1060                1065 tac gaa aat aag aac aaa gcg ggc atc att gac aaa gca gtg tta agt    3438
Tyr Glu Asn Lys Asn Lys Ala Gly Ile Ile Asp Lys Ala Val Leu Ser
    1070                1075                1080 gct aat caa caa aac atc ata ctt gac agt tat atg caa cat acg cat    3486
Ala Asn Gln Gln Asn Ile Ile Leu Asp Ser Tyr Met Gln His Thr His
1085                1090                1095 tgc agt ctt tat cct aat cca agt aag aat tgc cgc cca aca cgt gat    3534
Cys Ser Leu Tyr Pro Asn Pro Ser Lys Asn Cys Arg Pro Thr Arg Asp
1100                1105                1110                1115 aaa cct tat tca tac tat cat tct gat aga aat gtt tat aaa gaa aaa    3582
Lys Pro Tyr Ser Tyr Tyr His Ser Asp Arg Asn Val Tyr Lys Glu Lys
        1120                1125                1130 cat aat atg ttg caa ttg aat tta gag aaa aaa att caa caa aat tgg    3630
His Asn Met Leu Gln Leu Asn Leu Glu Lys Lys Ile Gln Gln Asn Trp
    1135                1140                1145 ctt act cat caa att gtc ttc aat ctt ggt ttt gat gac ttt act tca    3678
Leu Thr His Gln Ile Val Phe Asn Leu Gly Phe Asp Asp Phe Thr Ser
        1150                1155                1160 gcg ctt cag cat aaa gat tat tta act cga cgt gtt acc gct acg gca    3726
Ala Leu Gln His Lys Asp Tyr Leu Thr Arg Arg Val Thr Ala Thr Ala
1165                1170                1175 aag agt att tca gag aaa gct aat gaa aca aga aga aat ggt tac aaa    3774
Lys Ser Ile Ser Glu Lys Ala Asn Glu Thr Arg Arg Asn Gly Tyr Lys
1180                1185                1190                1195 aaa caa cct tac tta tac cca aaa cca aca gta ggt ttt gta gta caa    3822
Lys Gln Pro Tyr Leu Tyr Pro Lys Pro Thr Val Gly Phe Val Val Gln
        1200                1205                1210 gat cat tgt gat tat aaa ggt aac tcc tct aat tac aga gac tgt aaa    3870
Asp His Cys Asp Tyr Lys Gly Asn Ser Ser Asn Tyr Arg Asp Cys Lys
    1215                1220                1225 gtg cgg tta att aaa ggg aaa aat tat tat ttc gca gca cgc aat aat    3918
Val Arg Leu Ile Lys Gly Lys Asn Tyr Tyr Phe Ala Ala Arg Asn Asn
        1230                1235                1240 atg gca tta ggg aaa tac gtt gat tta ggt tta ggt att cgg tat gac    3966
Met Ala Leu Gly Lys Tyr Val Asp Leu Gly Leu Gly Ile Arg Tyr Asp
    1245                1250                1255 gta tct cgc aca aaa gct aat gaa tca act att agt gtt ggt aaa ttt    4014
Val Ser Arg Thr Lys Ala Asn Glu Ser Thr Ile Ser Val Gly Lys Phe
1260                1265                1270                1275 aaa aat ttc tct tgg aat act ggt att gtc ata aaa cca acg gaa tgg    4062
Lys Asn Phe Ser Trp Asn Thr Gly Ile Val Ile Lys Pro Thr Glu Trp
        1280                1285                1290 ctt gat ctt tct tat cgc ctt tct act gga ttt aga aat cct agt ttt    4110
Leu Asp Leu Ser Tyr Arg Leu Ser Thr Gly Phe Arg Asn Pro Ser Phe
    1295                1300                1305 gct gaa atg tat ggt tgg cgg tat ggt ggc aat aat agc gag gtt tat    4158
Ala Glu Met Tyr Gly Trp Arg Tyr Gly Gly Asn Asn Ser Glu Val Tyr
        1310                1315                1320 gta ggt aaa ttt aag cct gaa aca tct cgt aac caa gag ttt ggt ctc    4206
Val Gly Lys Phe Lys Pro Glu Thr Ser Arg Asn Gln Glu Phe Gly Leu
    1325                1330                1335 gct cta aaa ggg gat ttt ggt aat att gag atc agt cat ttt agt aat    4254
Ala Leu Lys Gly Asp Phe Gly Asn Ile Glu Ile Ser His Phe Ser Asn
1340                1345                1350                1355 gct tat cga aat ctt atc gcc ttt gct gaa gaa ctt aat aaa aat gga    4302
Ala Tyr Arg Asn Leu Ile Ala Phe Ala Glu Glu Leu Asn Lys Asn Gly
        1360                1365                1370
```

```
act gga aag gcc aat tat gga tat cat aat gca caa aat gca aaa tta      4350
Thr Gly Lys Ala Asn Tyr Gly Tyr His Asn Ala Gln Asn Ala Lys Leu
        1375                1380                1385 gtt ggc gta aat ata act gcg caa tta gat ttt aat ggt tta tgg aaa      4398
Val Gly Val Asn Ile Thr Ala Gln Leu Asp Phe Asn Gly Leu Trp Lys
    1390                1395                1400 cgt att ccc tac ggt tgg tat gca aca ttt gct tat aac cga gta aaa      4446
Arg Ile Pro Tyr Gly Trp Tyr Ala Thr Phe Ala Tyr Asn Arg Val Lys
1405                1410                1415 gtt aaa gat caa aaa atc aat gct ggt ttg gcc tcc gta agc agt tat      4494
Val Lys Asp Gln Lys Ile Asn Ala Gly Leu Ala Ser Val Ser Ser Tyr
1420                1425                1430                1435 tta ttt gat gcc att cag ccc agc cgt tat atc att ggt tta ggc tat      4542
Leu Phe Asp Ala Ile Gln Pro Ser Arg Tyr Ile Ile Gly Leu Gly Tyr
        1440                1445                1450 gat cat cca agt aat act tgg gga att aat aca atg ttt act caa tca      4590
Asp His Pro Ser Asn Thr Trp Gly Ile Asn Thr Met Phe Thr Gln Ser
    1455                1460                1465 aaa gca aaa tct caa aat gaa ttg cta gga aaa cgt gca ttg ggt aac      4638
Lys Ala Lys Ser Gln Asn Glu Leu Leu Gly Lys Arg Ala Leu Gly Asn
1470                1475                1480 aat tca agg gat gta aaa tca aca aga aaa ctt act cgg gca tgg cat      4686
Asn Ser Arg Asp Val Lys Ser Thr Arg Lys Leu Thr Arg Ala Trp His
    1485                1490                1495 atc tta gat gta tcg ggt tat tac atg gcg aat aaa aat att atg ctt      4734
Ile Leu Asp Val Ser Gly Tyr Tyr Met Ala Asn Lys Asn Ile Met Leu
1500                1505                1510                1515 cga tta ggg ata tat aat tta ttc aac tat cgc tat gtt act tgg gaa      4782
Arg Leu Gly Ile Tyr Asn Leu Phe Asn Tyr Arg Tyr Val Thr Trp Glu
            1520                1525                1530 gcg gtg cgt caa aca gca caa ggt gcg gtc aat caa cat caa aat gtt      4830
Ala Val Arg Gln Thr Ala Gln Gly Ala Val Asn Gln His Gln Asn Val
        1535                1540                1545 ggt agc tat act cgc tac gca gca tca gga cga aac tat acc tta aca      4878
Gly Ser Tyr Thr Arg Tyr Ala Ala Ser Gly Arg Asn Tyr Thr Leu Thr
    1550                1555                1560 tta gaa atg aaa ttctaaatta aaatgcgcca gatggactag acatgctata         4930
Leu Glu Met Lys
1565 tctataccctt actggcgcat ctttttctgt tctataatct ggttaagtga aaaaccaaac   4990
ttggattttt tagaagatct ttccacgcat ttattgtaaa atctccgaca attttttaccg  5050 cactttctc tattacaaaa acaataagga tccttttgtg aatctctca                5099

<210> SEQ ID NO 5
<211> LENGTH: 913
<212> TYPE: PRT
<213> ORGANISM: Haemophilus influenzae

<400> SEQUENCE: 5

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
            20                  25                  30

Glu Ala Ile Ser Ser Glu Val Asp Thr Gln Ser Thr Glu Asp Ser Glu
        35                  40                  45

Leu Glu Thr Ile Ser Val Thr Ala Glu Lys Val Arg Asp Arg Lys Asp
    50                  55                  60

Asn Glu Val Thr Gly Leu Gly Lys Ile Ile Lys Thr Ser Glu Ser Ile
```

-continued

```
            65                  70                  75                  80
Ser Arg Glu Gln Val Leu Asn Ile Arg Asp Leu Thr Arg Tyr Asp Pro
                    85                  90                  95
Gly Ile Ser Val Val Glu Gln Gly Arg Gly Ala Ser Ser Gly Tyr Ser
                   100                 105                 110
Ile Arg Gly Met Asp Arg Asn Arg Val Ala Leu Leu Val Asp Gly Leu
                   115                 120                 125
Pro Gln Thr Gln Ser Tyr Val Val Gln Ser Pro Leu Val Ala Arg Ser
                   130                 135                 140
Gly Tyr Ser Gly Thr Gly Ala Ile Asn Glu Ile Glu Tyr Glu Asn Val
145                 150                 155                 160
Lys Ala Val Glu Ile Ser Lys Gly Ser Ser Glu Tyr Gly Asn
                   165                 170                 175
Gly Ala Leu Ala Gly Ser Val Thr Phe Gln Ser Lys Ser Ala Ala Asp
                   180                 185                 190
Ile Leu Glu Gly Asp Lys Ser Trp Gly Ile Gln Thr Lys Asn Ala Tyr
                   195                 200                 205
Ser Ser Lys Asn Lys Gly Phe Thr His Ser Leu Ala Val Ala Gly Lys
210                 215                 220
Gln Gly Gly Phe Glu Gly Val Ala Ile Tyr Thr His Arg Asn Ser Ile
225                 230                 235                 240
Glu Thr Gln Val His Lys Asp Ala Leu Lys Gly Val Gln Ser Tyr Asp
                   245                 250                 255
Arg Phe Ile Ala Thr Thr Glu Asp Gln Ser Ala Tyr Phe Val Met Gln
                   260                 265                 270
Asp Glu Cys Leu Asp Gly Tyr Asp Lys Cys Lys Thr Ser Pro Lys Arg
                   275                 280                 285
Pro Ala Thr Leu Ser Thr Gln Arg Glu Thr Val Ser Val Ser Asp Tyr
                   290                 295                 300
Thr Gly Ala Asn Arg Ile Lys Pro Asn Pro Met Lys Tyr Glu Ser Gln
305                 310                 315                 320
Ser Trp Phe Leu Arg Gly Gly Tyr His Phe Ser Glu Gln His Tyr Ile
                   325                 330                 335
Gly Gly Ile Phe Glu Phe Thr Gln Gln Lys Phe Asp Ile Arg Asp Met
                   340                 345                 350
Thr Phe Pro Ala Tyr Leu Arg Pro Thr Glu Asp Lys Asp Leu Gln Ser
                   355                 360                 365
Arg Pro Phe Tyr Pro Lys Gln Asp Tyr Gly Ala Tyr Gln His Ile Gly
                   370                 375                 380
Asp Gly Arg Gly Val Lys Tyr Ala Ser Gly Leu Tyr Phe Asp Glu His
385                 390                 395                 400
His Arg Lys Gln Arg Val Gly Ile Glu Tyr Ile Tyr Glu Asn Lys Asn
                   405                 410                 415
Lys Ala Gly Ile Ile Asp Lys Ala Val Leu Ser Ala Asn Gln Gln Asn
                   420                 425                 430
Ile Ile Leu Asp Ser Tyr Met Arg His Thr His Cys Ser Leu Tyr Pro
                   435                 440                 445
Asn Pro Ser Lys Asn Cys Arg Pro Thr Leu Asp Lys Pro Tyr Ser Tyr
                   450                 455                 460
Tyr His Ser Asp Arg Asn Val Tyr Lys Glu Lys His Asn Met Leu Gln
465                 470                 475                 480
Leu Asn Leu Glu Lys Lys Ile Gln Gln Asn Trp Leu Thr His Gln Ile
                   485                 490                 495
```

-continued

```
Ala Phe Asn Leu Gly Phe Asp Asp Phe Thr Ser Ala Leu Gln His Lys
            500                 505                 510
Asp Tyr Leu Thr Arg Arg Val Ile Ala Thr Ala Ser Ser Ile Ser Glu
            515                 520                 525
Lys Arg Gly Glu Ala Arg Arg Asn Gly Leu Gln Ser Ser Pro Tyr Leu
            530                 535                 540
Tyr Pro Thr Pro Lys Ala Glu Leu Val Gly Gly Asp Leu Cys Asn Tyr
545                 550                 555                 560
Gln Gly Lys Ser Ser Asn Tyr Ser Asp Cys Lys Val Arg Leu Ile Lys
                565                 570                 575
Gly Lys Asn Tyr Tyr Phe Ala Ala Arg Asn Asn Met Ala Leu Gly Lys
            580                 585                 590
Tyr Val Asp Leu Gly Leu Gly Met Arg Tyr Asp Val Ser Arg Thr Lys
            595                 600                 605
Ala Asn Glu Ser Thr Ile Ser Val Gly Lys Phe Lys Asn Phe Ser Trp
            610                 615                 620
Asn Thr Gly Ile Val Ile Lys Pro Thr Glu Trp Leu Asp Leu Ser Tyr
625                 630                 635                 640
Arg Leu Ser Thr Gly Phe Arg Asn Pro Ser Phe Ala Glu Met Tyr Gly
                645                 650                 655
Trp Arg Tyr Gly Gly Lys Asp Thr Asp Val Tyr Ile Gly Lys Phe Lys
            660                 665                 670
Pro Glu Thr Ser Arg Asn Gln Glu Phe Gly Leu Ala Leu Lys Gly Asp
            675                 680                 685
Phe Gly Asn Ile Glu Ile Ser His Phe Ser Asn Ala Tyr Arg Asn Leu
            690                 695                 700
Ile Ala Phe Ala Glu Glu Leu Ser Lys Asn Gly Thr Thr Gly Lys Gly
705                 710                 715                 720
Asn Tyr Gly Tyr His Asn Ala Gln Asn Ala Lys Leu Val Gly Val Asn
                725                 730                 735
Ile Thr Ala Gln Leu Asp Phe Asn Gly Leu Trp Lys Arg Ile Pro Tyr
            740                 745                 750
Gly Trp Tyr Ala Thr Phe Ala Tyr Asn Arg Val Lys Val Lys Asp Gln
            755                 760                 765
Lys Ile Asn Ala Gly Leu Ala Ser Val Ser Ser Tyr Leu Phe Asp Ala
            770                 775                 780
Ile Gln Pro Ser Arg Tyr Ile Ile Gly Leu Gly Tyr Asp His Pro Ser
785                 790                 795                 800
Asn Thr Trp Gly Ile Lys Thr Met Phe Thr Gln Ser Lys Ala Lys Ser
                805                 810                 815
Gln Asn Glu Leu Leu Gly Lys Arg Ala Leu Gly Asn Asn Ser Arg Asn
            820                 825                 830
Val Lys Ser Thr Arg Lys Leu Thr Arg Ala Trp His Ile Leu Asp Val
            835                 840                 845
Ser Gly Tyr Tyr Met Val Asn Arg Ser Ile Leu Phe Arg Leu Gly Val
            850                 855                 860
Tyr Asn Leu Leu Asn Tyr Arg Tyr Val Thr Trp Glu Ala Val Arg Gln
865                 870                 875                 880
Thr Ala Gln Gly Ala Val Asn Gln His Gln Asn Val Gly Asn Tyr Thr
                885                 890                 895
Arg Tyr Ala Ala Ser Gly Arg Asn Tyr Thr Leu Thr Leu Glu Met Lys
            900                 905                 910
```

Phe

<210> SEQ ID NO 6
<211> LENGTH: 644
<212> TYPE: PRT
<213> ORGANISM: Haemophilus influenzae

<400> SEQUENCE: 6

| | | | | | | | | | | | | | | |
|---|---|---|---|---|---|---|---|---|---|---|---|---|---|---|
| Met | Lys | Ser | Val | Pro | Leu | Ile | Ser | Gly | Gly | Leu | Ser | Phe | Leu | Leu | Ser |
| 1 | | | | 5 | | | | | 10 | | | | | 15 | |
| Ala | Cys | Ser | Gly | Gly | Gly | Ser | Phe | Asp | Val | Asp | Asn | Val | Ser | Asn | Thr |
| | | | 20 | | | | | 25 | | | | | 30 | | |
| Pro | Ser | Ser | Lys | Pro | Arg | Tyr | Gln | Asp | Asp | Thr | Ser | Ser | Ser | Arg | Thr |
| | | 35 | | | | | 40 | | | | | 45 | | | |
| Lys | Ser | Lys | Leu | Glu | Lys | Leu | Ser | Ile | Pro | Ser | Leu | Gly | Gly | Gly | Met |
| | 50 | | | | | 55 | | | | | 60 | | | | |
| Lys | Leu | Ala | Ala | Leu | Asn | Leu | Phe | Asp | Arg | Asn | Lys | Pro | Ser | Leu | Leu |
| 65 | | | | | 70 | | | | | 75 | | | | | 80 |
| Asn | Glu | Asp | Ser | Tyr | Met | Ile | Phe | Ser | Arg | Ser | Thr | Ile | Glu | Glu | |
| | | | | 85 | | | | | 90 | | | | | 95 | |
| Asp | Val | Lys | Asn | Asp | Asn | Gln | Asn | Gly | Glu | His | Pro | Ile | Asp | Ser | Ile |
| | | | 100 | | | | | 105 | | | | | 110 | | |
| Val | Asp | Pro | Arg | Ala | Pro | Asn | Ser | Asn | Glu | Asn | Arg | His | Gly | Gln | Lys |
| | | | 115 | | | | | 120 | | | | | 125 | | |
| Tyr | Val | Tyr | Ser | Gly | Leu | Tyr | Tyr | Ile | Gln | Ser | Trp | Ser | Leu | Arg | Asp |
| | 130 | | | | | 135 | | | | | 140 | | | | |
| Leu | Pro | Asn | Lys | Lys | Phe | Tyr | Ser | Gly | Tyr | Tyr | Gly | Tyr | Ala | Tyr | Tyr |
| 145 | | | | | 150 | | | | | 155 | | | | | 160 |
| Phe | Gly | Asn | Thr | Thr | Ala | Ser | Ala | Leu | Pro | Val | Gly | Gly | Val | Ala | Thr |
| | | | | 165 | | | | | 170 | | | | | 175 | |
| Tyr | Lys | Gly | Thr | Trp | Ser | Phe | Ile | Thr | Ala | Ala | Glu | Asn | Gly | Lys | Asn |
| | | | 180 | | | | | 185 | | | | | 190 | | |
| Tyr | Glu | Leu | Leu | Arg | Asn | Ser | Gly | Gly | Gln | Ala | Tyr | Ser | Arg | Arg | |
| | | | 195 | | | | | 200 | | | | | 205 | | |
| Ser | Ala | Thr | Pro | Glu | Asp | Ile | Asp | Leu | Asp | Arg | Lys | Thr | Gly | Leu | Thr |
| | 210 | | | | | 215 | | | | | 220 | | | | |
| Ser | Glu | Phe | Thr | Val | Asn | Phe | Gly | Thr | Lys | Lys | Leu | Thr | Gly | Gly | Leu |
| 225 | | | | | 230 | | | | | 235 | | | | | 240 |
| Tyr | Tyr | Asn | Leu | Arg | Glu | Thr | Asp | Ala | Asn | Lys | Ser | Gln | Asn | Arg | Thr |
| | | | | 245 | | | | | 250 | | | | | 255 | |
| His | Lys | Leu | Tyr | Asp | Leu | Glu | Ala | Asp | Val | His | Ser | Asn | Arg | Phe | Arg |
| | | | 260 | | | | | 265 | | | | | 270 | | |
| Gly | Lys | Val | Lys | Pro | Thr | Lys | Lys | Glu | Ser | Ser | Glu | Glu | His | Pro | Phe |
| | | 275 | | | | | 280 | | | | | 285 | | | |
| Thr | Ser | Glu | Gly | Thr | Leu | Glu | Gly | Gly | Phe | Tyr | Gly | Pro | Glu | Gly | Gln |
| | 290 | | | | | 295 | | | | | 300 | | | | |
| Glu | Leu | Gly | Gly | Lys | Phe | Leu | Ala | His | Asp | Lys | Lys | Val | Leu | Gly | Val |
| 305 | | | | | 310 | | | | | 315 | | | | | 320 |
| Phe | Ser | Ala | Lys | Glu | Gln | Gln | Glu | Thr | Ser | Glu | Asn | Lys | Lys | Leu | Pro |
| | | | | 325 | | | | | 330 | | | | | 335 | |
| Lys | Glu | Thr | Leu | Ile | Asp | Gly | Lys | Leu | Thr | Thr | Phe | Lys | Thr | Thr | Asn |
| | | | 340 | | | | | 345 | | | | | 350 | | |
| Ala | Thr | Ala | Asn | Ala | Thr | Thr | Asp | Ala | Thr | Thr | Ser | Thr | Thr | Ala | Ser |
| | | | 355 | | | | | 360 | | | | | 365 | | |

```
Thr Lys Thr Asp Thr Thr Thr Asn Ala Thr Ala Asn Thr Glu Asn Phe
        370                 375                 380

Thr Thr Lys Asp Ile Pro Ser Leu Gly Glu Ala Asp Tyr Leu Leu Ile
385                 390                 395                 400

Asp Asn Tyr Pro Val Pro Leu Phe Pro Glu Ser Gly Asp Phe Ile Ser
                405                 410                 415

Ser Lys His His Thr Val Gly Lys Lys Thr Tyr Gln Val Glu Ala Cys
            420                 425                 430

Cys Ser Asn Leu Ser Tyr Val Lys Phe Gly Met Tyr Tyr Glu Ala Pro
        435                 440                 445

Pro Lys Glu Glu Glu Lys Glu Lys Lys Asp Lys Asp Lys Glu Lys
    450                 455                 460

Glu Lys Gln Ala Thr Thr Ser Ile Lys Thr Tyr Tyr Gln Phe Leu Leu
465                 470                 475                 480

Gly Leu Arg Thr Pro Ser Ser Glu Ile Pro Lys Glu Gly Ser Ala Lys
                485                 490                 495

Tyr His Gly Asn Trp Phe Gly Tyr Ile Ser Asp Gly Glu Thr Ser Tyr
            500                 505                 510

Ser Ala Ser Gly Asp Lys Glu Arg Ser Lys Asn Ala Val Ala Glu Phe
        515                 520                 525

Asn Val Asn Phe Ala Glu Lys Thr Leu Thr Gly Glu Leu Lys Arg His
530                 535                 540

Asp Thr Gln Asn Pro Val Phe Lys Ile Asn Ala Thr Phe Gln Ser Gly
545                 550                 555                 560

Lys Asn Asp Phe Thr Gly Thr Ala Thr Ala Lys Asp Leu Ala Ile Asp
                565                 570                 575

Gly Lys Asn Thr Gln Gly Thr Ser Lys Val Asn Phe Thr Ala Thr Val
            580                 585                 590

Asn Gly Ala Phe Tyr Gly Pro His Ala Thr Glu Leu Gly Gly Tyr Phe
        595                 600                 605

Thr Tyr Asn Gly Asn Asn Pro Thr Asp Lys Asn Ser Ser Asn Ser
610                 615                 620

Glu Lys Ala Arg Ala Ala Val Val Phe Gly Ala Lys Lys Gln Gln Val
625                 630                 635                 640

Glu Thr Thr Lys

<210> SEQ ID NO 7
<211> LENGTH: 912
<212> TYPE: PRT
<213> ORGANISM: Haemophilus influenzae

<400> SEQUENCE: 7

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
                20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
    50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95
```

```
Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
            115                 120                 125

Pro Gln Thr Gln Ser Tyr Val Val Gln Ser Pro Leu Val Ala Arg Ser
            130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Ser Ser Ser Glu Tyr Gly Asn
            165                 170                 175

Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
            195                 200                 205

Ser Ser Lys Asn Lys Gly Phe Thr His Ser Leu Ala Val Ala Gly Lys
            210                 215                 220

Gln Gly Gly Phe Glu Gly Leu Ala Ile Tyr Thr Gln Arg Asn Ser Ile
225                 230                 235                 240

Glu Thr Gln Val His Lys Asp Ala Leu Lys Gly Val Gln Ser Tyr Asp
            245                 250                 255

Arg Leu Ile Ala Thr Thr Asp Lys Ser Ser Gly Tyr Phe Val Ile Gln
            260                 265                 270

Gly Glu Cys Pro Asn Gly Asp Lys Cys Ala Ala Lys Pro Pro Ala
            275                 280                 285

Thr Leu Ser Thr Gln Ser Glu Thr Val Ser Val Ser Asp Tyr Thr Gly
            290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
            325                 330                 335

Ile Phe Glu Phe Thr Gln Gln Lys Phe Asp Ile Arg Asp Met Thr Phe
            340                 345                 350

Pro Ala Tyr Leu Ser Pro Thr Glu Arg Arg Asp Asp Ser Ser Arg Ser
            355                 360                 365

Phe Tyr Pro Met Gln Asp His Gly Ala Tyr Gln His Ile Glu Asp Gly
            370                 375                 380

Arg Gly Val Lys Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
            405                 410                 415

Gly Ile Ile Asp Lys Ala Val Leu Ser Ala Asn Gln Asn Ile Ile
            420                 425                 430

Leu Asp Ser Tyr Met Arg His Thr His Cys Ser Leu Tyr Pro Asn Pro
            435                 440                 445

Ser Lys Asn Cys Arg Pro Thr Leu Asp Lys Pro Tyr Ser Tyr Tyr Arg
            450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
            485                 490                 495

Asn Leu Gly Phe Asp Asp Phe Thr Ser Ala Leu Gln His Lys Asp Tyr
            500                 505                 510

Leu Thr Arg Arg Val Ile Ala Thr Ala Asp Ser Ile Pro Arg Lys Pro
```

```
            515                 520                 525
Gly Glu Thr Gly Lys Pro Arg Asn Gly Leu Gln Ser Gln Pro Tyr Leu
            530                 535                 540
Tyr Pro Lys Pro Glu Pro Tyr Phe Ala Gly Gln Asp His Cys Asn Tyr
545                 550                 555                 560
Gln Gly Ser Ser Asn Tyr Arg Asp Cys Lys Val Arg Leu Ile Lys
                565                 570                 575
Gly Lys Asn Tyr Tyr Phe Ala Ala Arg Asn Asn Met Ala Leu Gly Lys
                580                 585                 590
Tyr Val Asp Leu Gly Leu Gly Ile Arg Tyr Asp Val Ser Arg Thr Lys
            595                 600                 605
Ala Asn Glu Ser Thr Ile Ser Val Gly Lys Phe Lys Asn Phe Ser Trp
            610                 615                 620
Asn Thr Gly Ile Val Ile Lys Pro Thr Glu Trp Leu Asp Leu Ser Tyr
625                 630                 635                 640
Arg Leu Ser Thr Gly Phe Arg Asn Pro Ser Phe Ser Glu Met Tyr Gly
                645                 650                 655
Trp Arg Tyr Gly Gly Lys Asn Asp Glu Val Tyr Val Gly Lys Phe Lys
                660                 665                 670
Pro Glu Thr Ser Arg Asn Gln Glu Phe Gly Leu Ala Leu Lys Gly Asp
                675                 680                 685
Phe Gly Asn Ile Glu Ile Ser His Phe Ser Asn Ala Tyr Arg Asn Leu
            690                 695                 700
Ile Ala Phe Ala Glu Glu Leu Ser Lys Asn Gly Thr Gly Lys Gly Asn
705                 710                 715                 720
Tyr Gly Tyr His Asn Ala Gln Asn Ala Lys Leu Val Gly Val Asn Ile
                725                 730                 735
Thr Ala Gln Leu Asp Phe Asn Gly Leu Trp Lys Arg Ile Pro Tyr Gly
                740                 745                 750
Trp Tyr Ala Thr Phe Ala Tyr Asn Gln Val Lys Val Lys Asp Gln Lys
            755                 760                 765
Ile Asn Ala Gly Leu Ala Ser Val Ser Ser Tyr Leu Phe Asp Ala Ile
            770                 775                 780
Gln Pro Ser Arg Tyr Ile Ile Gly Leu Gly Tyr Asp His Pro Ser Asn
785                 790                 795                 800
Thr Trp Gly Ile Asn Thr Met Phe Thr Gln Ser Lys Ala Lys Ser Gln
                805                 810                 815
Asn Glu Leu Leu Gly Lys Arg Ala Leu Gly Asn Ser Arg Asp Val
                820                 825                 830
Lys Ser Thr Arg Lys Leu Thr Arg Ala Trp His Ile Leu Asp Val Ser
            835                 840                 845
Gly Tyr Tyr Met Ala Asn Lys Asn Ile Met Leu Arg Leu Gly Ile Tyr
            850                 855                 860
Asn Leu Phe Asn Tyr Arg Tyr Val Thr Trp Glu Ala Val Arg Gln Thr
865                 870                 875                 880
Ala Gln Gly Ala Val Asn Gln His Gln Asn Val Gly Ser Tyr Thr Arg
                885                 890                 895
Tyr Ala Ala Ser Gly Arg Asn Tyr Thr Leu Thr Leu Glu Met Lys Phe
                900                 905                 910

<210> SEQ ID NO 8
<211> LENGTH: 660
<212> TYPE: PRT
<213> ORGANISM: Haemophilus influenzae
```

```
<400> SEQUENCE: 8

Met Lys Ser Val Pro Leu Ile Ser Gly Gly Leu Ser Phe Leu Leu Ser
 1               5                  10                  15

Ala Cys Ser Gly Gly Ser Phe Asp Val Asp Asn Val Ser Asn Thr
             20                  25                  30

Pro Ser Ser Lys Pro Arg Tyr Gln Asp Asp Thr Ser Asn Gln Arg Lys
             35                  40                  45

Lys Ser Asn Leu Lys Lys Leu Phe Ile Pro Ser Leu Gly Gly Gly Met
 50                  55                  60

Lys Leu Val Ala Gln Asn Leu Arg Gly Asn Lys Glu Pro Ser Phe Leu
 65                  70                  75                  80

Asn Glu Asp Asp Tyr Ile Ser Tyr Phe Ser Ser Leu Ser Thr Ile Glu
                 85                  90                  95

Lys Asp Val Lys Asp Asn Asn Lys Asn Gly Ala Asp Leu Ile Gly Ser
             100                 105                 110

Ile Asp Glu Pro Ser Thr Thr Asn Pro Pro Glu Lys His His Gly Gln
         115                 120                 125

Lys Tyr Val Tyr Ser Gly Leu Tyr Tyr Thr Pro Ser Trp Ser Leu Asn
 130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                 165                 170                 175

Tyr Lys Gly Thr Trp Asp Phe Ile Thr Ala Thr Lys Asn Gly Lys Arg
             180                 185                 190

Tyr Pro Leu Leu Ser Asn Gly Ser His Ala Tyr Tyr Arg Arg Ser Ala
         195                 200                 205

Ile Pro Glu Asp Ile Asp Leu Glu Asn Asp Ser Lys Asn Gly Asp Ile
 210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                 245                 250                 255

Lys Lys Lys Leu Tyr Asp Ile Asp Ala Asp Ile Tyr Ser Asn Arg Phe
             260                 265                 270

Arg Gly Thr Val Lys Pro Thr Glu Lys Asp Ser Glu His Pro Phe
         275                 280                 285

Thr Ser Glu Gly Thr Leu Glu Gly Phe Tyr Gly Pro Asn Ala Glu
290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                 325                 330                 335

Glu Thr Leu Ile Asp Gly Lys Leu Ile Thr Phe Ser Thr Lys Lys Thr
             340                 345                 350

Asp Ala Lys Thr Asn Ala Thr Ser Thr Ala Ala Asn Thr Thr Thr
         355                 360                 365

Asp Thr Thr Ala Asn Thr Ile Thr Asp Glu Lys Asn Phe Lys Thr Glu
         370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
```

```
                        405                 410                 415
Lys His His Thr Val Gly Asn Lys Arg Tyr Lys Val Glu Ala Cys Cys
                420                 425                 430

Ser Asn Leu Ser Tyr Val Lys Phe Gly Met Tyr Tyr Glu Asp Pro Leu
            435                 440                 445

Lys Glu Lys Glu Thr Glu Thr Glu Thr Glu Thr Glu Lys Asp Lys Glu
        450                 455                 460

Lys Glu Lys Glu Lys Asp Lys Asp Lys Glu Lys Gln Thr Ala Ala Thr
465                 470                 475                 480

Thr Asn Thr Tyr Tyr Gln Phe Leu Leu Gly His Arg Thr Pro Lys Asp
                485                 490                 495

Asp Ile Pro Lys Thr Gly Ser Ala Lys Tyr His Gly Ser Trp Phe Gly
            500                 505                 510

Tyr Ile Thr Asp Gly Lys Thr Ser Tyr Ser Pro Ser Gly Asp Lys Lys
        515                 520                 525

Arg Asp Lys Asn Ala Val Ala Glu Phe Asn Val Asp Phe Ala Glu Lys
    530                 535                 540

Lys Leu Thr Gly Glu Leu Lys Arg His Asp Thr Gly Asn Pro Val Phe
545                 550                 555                 560

Ser Ile Glu Ala Asn Phe Asn Asn Ser Ser Asn Ala Phe Thr Gly Thr
                565                 570                 575

Ala Thr Ala Thr Asn Phe Val Ile Asp Gly Lys Asn Ser Gln Asn Lys
            580                 585                 590

Asn Thr Pro Ile Asn Ile Thr Thr Lys Val Asn Gly Ala Phe Tyr Gly
        595                 600                 605

Pro Lys Ala Ser Glu Leu Gly Gly Tyr Phe Thr Tyr Asn Gly Asn Ser
    610                 615                 620

Thr Ala Thr Asn Ser Glu Ser Ser Ser Thr Val Ser Ser Ser Ser Asn
625                 630                 635                 640

Ser Lys Asn Ala Arg Ala Ala Val Val Phe Gly Ala Arg Gln Gln Val
                645                 650                 655

Glu Thr Thr Lys
            660

<210> SEQ ID NO 9
<211> LENGTH: 912
<212> TYPE: PRT
<213> ORGANISM: Haemophilus influenzae

<400> SEQUENCE: 9

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
                20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
        50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
            100                 105                 110
```

```
Ile Arg Gly Met Asp Arg Asn Arg Val Ala Leu Leu Val Asp Gly Leu
        115                 120                 125

Pro Gln Thr Gln Ser Tyr Val Val Gln Ser Pro Leu Val Ala Arg Ser
        130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Ser Ser Ser Glu Tyr Gly Asn
                165                 170                 175

Gly Ala Leu Ala Gly Ser Val Thr Phe Gln Ser Lys Ser Ala Ala Asp
                180                 185                 190

Ile Leu Glu Gly Asp Lys Ser Trp Gly Ile Gln Thr Lys Asn Ala Tyr
        195                 200                 205

Ser Ser Lys Asn Lys Gly Phe Thr His Ser Leu Ala Val Ala Gly Lys
        210                 215                 220

Gln Gly Gly Phe Glu Gly Leu Ala Ile Tyr Thr Gln Arg Asn Ser Ile
225                 230                 235                 240

Glu Thr Gln Val His Lys Asp Ala Leu Lys Gly Val Gln Ser Tyr Asp
                245                 250                 255

Arg Leu Ile Ala Thr Thr Asp Lys Ser Ser Gly Tyr Phe Val Ile Gln
                260                 265                 270

Gly Glu Cys Pro Asn Gly Asp Lys Cys Ala Ala Lys Pro Pro Ala
        275                 280                 285

Thr Leu Ser Thr Gln Ser Glu Thr Val Ser Val Ser Asp Tyr Thr Gly
        290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
                325                 330                 335

Ile Phe Glu Phe Thr Gln Gln Lys Phe Asp Ile Arg Asp Met Thr Phe
                340                 345                 350

Pro Ala Tyr Leu Ser Pro Thr Glu Arg Arg Asp Asp Ser Ser Arg Ser
        355                 360                 365

Phe Tyr Pro Met Gln Asp His Gly Ala Tyr Gln His Ile Glu Asp Gly
370                 375                 380

Arg Gly Val Lys Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
                405                 410                 415

Gly Ile Ile Asp Lys Ala Val Leu Ser Ala Asn Gln Gln Asn Ile Ile
                420                 425                 430

Leu Asp Ser Tyr Met Arg His Thr His Cys Ser Leu Tyr Pro Asn Pro
        435                 440                 445

Ser Lys Asn Cys Arg Pro Thr Leu Asp Lys Pro Tyr Ser Tyr Arg
450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
                485                 490                 495

Asn Leu Gly Phe Asp Asp Phe Thr Ser Ala Leu Gln His Lys Asp Tyr
                500                 505                 510

Leu Thr Arg Arg Val Ile Ala Thr Ala Asp Ser Ile Pro Arg Lys Pro
        515                 520                 525

Gly Glu Thr Gly Lys Pro Arg Asn Gly Leu Gln Ser Gln Pro Tyr Leu
```

```
                530               535               540
Tyr Pro Lys Pro Glu Pro Tyr Phe Ala Gly Gln Asp His Cys Asn Tyr
545                 550                 555                 560

Gln Gly Ser Ser Ser Asn Tyr Arg Asp Cys Lys Val Arg Leu Ile Lys
                565                 570                 575

Gly Lys Asn Tyr Tyr Phe Ala Ala Arg Asn Asn Met Ala Leu Gly Lys
                580                 585                 590

Tyr Val Asp Leu Gly Leu Gly Ile Arg Tyr Asp Val Ser Arg Thr Lys
                595                 600                 605

Ala Asn Glu Ser Thr Ile Ser Val Gly Lys Phe Lys Asn Phe Ser Trp
610                 615                 620

Asn Thr Gly Ile Val Ile Lys Pro Thr Glu Trp Leu Asp Leu Ser Tyr
625                 630                 635                 640

Arg Leu Ser Thr Gly Phe Arg Asn Pro Ser Phe Ser Glu Met Tyr Gly
                645                 650                 655

Trp Arg Tyr Gly Gly Lys Asn Asp Glu Val Tyr Val Gly Lys Phe Lys
                660                 665                 670

Pro Glu Thr Ser Arg Asn Gln Glu Phe Gly Leu Ala Leu Lys Gly Asp
                675                 680                 685

Phe Gly Asn Ile Glu Ile Ser His Phe Ser Asn Ala Tyr Arg Asn Leu
690                 695                 700

Ile Ala Phe Ala Glu Glu Leu Ser Lys Asn Gly Thr Gly Lys Gly Asn
705                 710                 715                 720

Tyr Gly Tyr His Asn Ala Gln Asn Ala Lys Leu Val Gly Val Asn Ile
                725                 730                 735

Thr Ala Gln Leu Asp Phe Asn Gly Leu Trp Lys Arg Ile Pro Tyr Gly
                740                 745                 750

Trp Tyr Ala Thr Phe Ala Tyr Asn Gln Val Lys Val Lys Asp Gln Lys
                755                 760                 765

Ile Asn Ala Gly Leu Ala Ser Val Ser Ser Tyr Leu Phe Asp Ala Ile
770                 775                 780

Gln Pro Ser Arg Tyr Ile Ile Gly Leu Gly Tyr Asp His Pro Ser Asn
785                 790                 795                 800

Thr Trp Gly Ile Asn Thr Met Phe Thr Gln Ser Lys Ala Lys Ser Gln
                805                 810                 815

Asn Glu Leu Leu Gly Lys Arg Ala Leu Gly Asn Asn Ser Arg Asp Val
                820                 825                 830

Lys Ser Thr Arg Lys Leu Thr Arg Ala Trp His Ile Leu Asp Val Ser
                835                 840                 845

Gly Tyr Tyr Met Ala Asn Lys Asn Ile Met Leu Arg Leu Gly Ile Tyr
850                 855                 860

Asn Leu Phe Asn Tyr Arg Tyr Val Thr Trp Glu Ala Val Arg Gln Thr
865                 870                 875                 880

Ala Gln Gly Ala Val Asn Gln His Gln Asn Val Gly Ser Tyr Thr Arg
                885                 890                 895

Tyr Ala Ala Ser Gly Arg Asn Tyr Thr Leu Thr Leu Glu Met Lys Phe
                900                 905                 910

<210> SEQ ID NO 10
<211> LENGTH: 660
<212> TYPE: PRT
<213> ORGANISM: Haemophilus influenzae

<400> SEQUENCE: 10
```

-continued

```
Met Lys Ser Val Pro Leu Ile Ser Gly Gly Leu Ser Phe Leu Leu Ser
 1               5                  10                  15

Ala Cys Ser Gly Gly Ser Phe Asp Val Asp Asn Val Ser Asn Thr
                20                  25                  30

Pro Ser Ser Lys Pro Arg Tyr Gln Asp Thr Ser Asn Gln Arg Lys
            35                  40                  45

Lys Ser Asn Leu Lys Lys Leu Phe Ile Pro Ser Leu Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
            100                 105                 110

Ile Asp Glu Pro Ser Thr Thr Asn Pro Pro Glu Lys His His Gly Gln
            115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
            180                 185                 190

Tyr Pro Leu Leu Ser Asn Gly Ser His Ala Tyr Tyr Arg Arg Ser Ala
    195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
            260                 265                 270

Arg Gly Thr Val Lys Pro Thr Glu Lys Asp Ser Glu Glu His Pro Phe
    275                 280                 285

Thr Ser Glu Gly Thr Leu Glu Gly Gly Phe Tyr Gly Pro Asn Ala Glu
290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
            340                 345                 350

Asp Ala Lys Thr Asn Ala Thr Thr Ser Thr Ala Ala Asn Thr Thr Thr
            355                 360                 365

Asp Thr Thr Ala Asn Thr Ile Thr Asp Glu Lys Asn Phe Lys Thr Glu
    370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
                405                 410                 415

Lys His His Thr Val Gly Asn Lys Arg Tyr Lys Val Glu Ala Cys Cys
```

```
                420                 425                 430
Ser Asn Leu Ser Tyr Val Lys Phe Gly Met Tyr Tyr Glu Asp Pro Leu
            435                 440                 445

Lys Glu Lys Glu Thr Glu Thr Glu Thr Glu Thr Glu Lys Asp Lys Glu
450                 455                 460

Lys Glu Lys Glu Lys Asp Lys Asp Lys Glu Lys Gln Thr Ala Ala Thr
465                 470                 475                 480

Thr Asn Thr Tyr Tyr Gln Phe Leu Leu Gly His Arg Thr Pro Lys Asp
                485                 490                 495

Asp Ile Pro Lys Thr Gly Ser Ala Lys Tyr His Gly Ser Trp Phe Gly
            500                 505                 510

Tyr Ile Thr Asp Gly Lys Thr Ser Tyr Ser Pro Ser Gly Asp Lys Lys
            515                 520                 525

Arg Asp Lys Asn Ala Val Ala Glu Phe Asn Val Asp Phe Ala Glu Lys
            530                 535                 540

Lys Leu Thr Gly Glu Leu Lys Arg His Asp Thr Gly Asn Pro Val Phe
545                 550                 555                 560

Ser Ile Glu Ala Asn Phe Asn Asn Ser Ser Asn Ala Phe Thr Gly Thr
                565                 570                 575

Ala Thr Ala Thr Asn Phe Val Ile Asp Gly Lys Asn Ser Gln Asn Lys
            580                 585                 590

Asn Thr Pro Ile Asn Ile Thr Thr Lys Val Asn Gly Ala Phe Tyr Gly
            595                 600                 605

Pro Lys Ala Ser Glu Leu Gly Gly Tyr Phe Thr Tyr Asn Gly Asn Ser
            610                 615                 620

Thr Ala Thr Asn Ser Glu Ser Ser Ser Thr Val Ser Ser Ser Ser Asn
625                 630                 635                 640

Ser Lys Asn Ala Arg Ala Ala Val Val Phe Gly Ala Arg Gln Gln Val
                645                 650                 655

Glu Thr Thr Lys
            660

<210> SEQ ID NO 11
<211> LENGTH: 914
<212> TYPE: PRT
<213> ORGANISM: Haemophilus influenzae

<400> SEQUENCE: 11

Met Thr Lys Lys Pro Tyr Phe Arg Leu Ser Ile Ile Ser Cys Leu Leu
1               5                   10                  15

Ile Ser Cys Tyr Val Lys Ala Glu Thr Gln Ser Ile Lys Asp Thr Lys
                20                  25                  30

Glu Ala Ile Ser Ser Glu Val Asp Thr Gln Ser Thr Glu Asp Ser Glu
            35                  40                  45

Leu Glu Thr Ile Ser Val Thr Ala Glu Lys Ile Arg Asp Arg Lys Asp
        50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
        115                 120                 125
```

-continued

```
Pro Gln Thr Gln Ser Tyr Val Gln Ser Pro Leu Val Ala Arg Ser
    130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
                165                 170                 175

Gly Ala Leu Ala Gly Ser Val Thr Phe Gln Ser Lys Ser Ala Ala Asp
                180                 185                 190

Ile Leu Glu Gly Asp Lys Ser Trp Gly Ile Gln Thr Lys Asn Ala Tyr
                195                 200                 205

Ser Ser Lys Asn Lys Gly Phe Thr His Ser Leu Ala Val Ala Gly Lys
    210                 215                 220

Gln Gly Gly Phe Asp Gly Val Ala Ile Tyr Thr Gln Arg Asn Ser Ile
225                 230                 235                 240

Glu Thr Gln Val His Lys Asp Ala Leu Lys Gly Val Gln Ser Tyr His
                245                 250                 255

Arg Leu Ile Ala Lys Pro Glu Asp Gln Ser Ala Tyr Phe Val Met Gln
                260                 265                 270

Asp Glu Cys Pro Lys Pro Asp Asp Tyr Asn Ser Cys Leu Pro Phe Ala
            275                 280                 285

Lys Arg Pro Ala Ile Leu Ser Ser Gln Arg Glu Thr Val Ser Val Ser
            290                 295                 300

Asp Tyr Thr Gly Ala Asn Arg Ile Lys Pro Asn Pro Met Lys Tyr Glu
305                 310                 315                 320

Ser Gln Ser Trp Phe Leu Arg Gly Gly Tyr His Phe Ser Glu Gln His
                325                 330                 335

Tyr Ile Gly Gly Ile Phe Glu Phe Thr Gln Gln Lys Phe Asp Ile Arg
                340                 345                 350

Asp Met Thr Phe Pro Ala Tyr Leu Arg Ser Thr Glu Lys Arg Asp Asp
                355                 360                 365

Ser Ser Gly Ser Phe Tyr Pro Lys Gln Asp Tyr Gly Ala Tyr Gln Arg
    370                 375                 380

Ile Glu Asp Gly Arg Gly Val Asn Tyr Ala Ser Gly Leu Tyr Phe Asp
385                 390                 395                 400

Glu His His Arg Lys Gln Arg Val Gly Ile Glu Tyr Ile Tyr Glu Asn
                405                 410                 415

Lys Asn Lys Ala Gly Ile Ile Asp Lys Ala Val Leu Ser Ala Asn Gln
                420                 425                 430

Gln Asn Ile Ile Leu Asp Ser Tyr Met Gln His Thr His Cys Ser Leu
            435                 440                 445

Tyr Pro Asn Pro Ser Lys Asn Cys Arg Pro Thr Arg Asp Lys Pro Tyr
    450                 455                 460

Ser Tyr Tyr His Ser Asp Arg Asn Val Tyr Lys Glu Lys His Asn Met
465                 470                 475                 480

Leu Gln Leu Asn Leu Glu Lys Lys Ile Gln Gln Asn Trp Leu Thr His
                485                 490                 495

Gln Ile Val Phe Asn Leu Gly Phe Asp Asp Phe Thr Ser Ala Leu Gln
                500                 505                 510

His Lys Asp Tyr Leu Thr Arg Arg Val Thr Ala Thr Lys Ser Ile
                515                 520                 525

Ser Glu Lys Ala Asn Glu Thr Arg Arg Asn Gly Tyr Lys Lys Gln Pro
530                 535                 540

Tyr Leu Tyr Pro Lys Pro Thr Val Gly Phe Val Val Gln Asp His Cys
```

-continued

```
         545                 550                 555                 560
Asp Tyr Lys Gly Asn Ser Ser Asn Tyr Arg Asp Cys Lys Val Arg Leu
                565                 570                 575
Ile Lys Gly Lys Asn Tyr Tyr Phe Ala Ala Arg Asn Asn Met Ala Leu
            580                 585                 590
Gly Lys Tyr Val Asp Leu Gly Leu Gly Ile Arg Tyr Asp Val Ser Arg
            595                 600                 605
Thr Lys Ala Asn Glu Ser Thr Ile Ser Val Gly Lys Phe Lys Asn Phe
        610                 615                 620
Ser Trp Asn Thr Gly Ile Val Ile Lys Pro Thr Glu Trp Leu Asp Leu
625                 630                 635                 640
Ser Tyr Arg Leu Ser Thr Gly Phe Arg Asn Pro Ser Phe Ala Glu Met
                645                 650                 655
Tyr Gly Trp Arg Tyr Gly Gly Asn Asn Ser Glu Val Tyr Val Gly Lys
                660                 665                 670
Phe Lys Pro Glu Thr Ser Arg Asn Gln Glu Phe Gly Leu Ala Leu Lys
            675                 680                 685
Gly Asp Phe Gly Asn Ile Glu Ile Ser His Phe Ser Asn Ala Tyr Arg
        690                 695                 700
Asn Leu Ile Ala Phe Ala Glu Glu Leu Asn Lys Asn Gly Thr Gly Lys
705                 710                 715                 720
Ala Asn Tyr Gly Tyr His Asn Ala Gln Asn Ala Lys Leu Val Gly Val
                725                 730                 735
Asn Ile Thr Ala Gln Leu Asp Phe Asn Gly Leu Trp Lys Arg Ile Pro
            740                 745                 750
Tyr Gly Trp Tyr Ala Thr Phe Ala Tyr Asn Arg Val Lys Val Lys Asp
            755                 760                 765
Gln Lys Ile Asn Ala Gly Leu Ala Ser Val Ser Ser Tyr Leu Phe Asp
        770                 775                 780
Ala Ile Gln Pro Ser Arg Tyr Ile Ile Gly Leu Gly Tyr Asp His Pro
785                 790                 795                 800
Ser Asn Thr Trp Gly Ile Asn Thr Met Phe Thr Gln Ser Lys Ala Lys
                805                 810                 815
Ser Gln Asn Glu Leu Leu Gly Lys Arg Ala Leu Gly Asn Asn Ser Arg
            820                 825                 830
Asp Val Lys Ser Thr Arg Lys Leu Thr Arg Ala Trp His Ile Leu Asp
        835                 840                 845
Val Ser Gly Tyr Tyr Met Ala Asn Lys Asn Ile Met Leu Arg Leu Gly
        850                 855                 860
Ile Tyr Asn Leu Phe Asn Tyr Arg Tyr Val Thr Trp Glu Ala Val Arg
865                 870                 875                 880
Gln Thr Ala Gln Gly Ala Val Asn Gln His Gln Asn Val Gly Ser Tyr
                885                 890                 895
Thr Arg Tyr Ala Ala Ser Gly Arg Asn Tyr Thr Leu Thr Leu Glu Met
            900                 905                 910
Lys Phe
```

<210> SEQ ID NO 12
<211> LENGTH: 654
<212> TYPE: PRT
<213> ORGANISM: Haemophilus influenzae

<400> SEQUENCE: 12

Met Lys Ser Val Pro Leu Ile Thr Gly Gly Leu Ser Phe Leu Leu Ser

-continued

```
  1               5              10              15
Ala Cys Ser Gly Gly Gly Ser Phe Asp Val Asp Val Ser Asn
             20                  25              30

Pro Ser Ser Lys Pro Arg Tyr Gln Asp Asp Thr Ser Asn Gln Arg
             35                  40              45

Thr Lys Ser Asp Leu Glu Lys Leu Phe Ile Pro Ser Leu Gly Gly Gly
 50                  55                  60

Met Lys Leu Val Ala Gln Asn Phe Ile Gly Ala Arg Glu Pro Ser Phe
 65                  70                  75                  80

Leu Asn Glu Asp Gly Tyr Met Ile Phe Ser Ser Leu Ser Thr Ile Glu
             85                  90                  95

Glu Asp Val Glu Lys Val Lys Asn Asn Asn Lys Asn Gly Gly Arg Leu
             100                 105             110

Ile Gly Ser Ile Glu Glu Pro Asn Gly Thr Ser Gln Asn Ser Asn Ser
             115                 120             125

Gln Glu Tyr Val Tyr Ser Gly Leu Tyr Tyr Ile Asp Ser Trp Arg Asp
             130                 135             140

Tyr Lys Lys Glu Glu Gln Lys Ala Tyr Thr Gly Tyr Tyr Gly Tyr Ala
145                  150                 155                 160

Phe Tyr Tyr Gly Asn Glu Thr Ala Lys Asn Leu Pro Val Lys Gly Val
                 165                 170                 175

Ala Lys Tyr Lys Gly Thr Trp Asn Phe Ile Thr Ala Thr Glu Asn Gly
                 180                 185                 190

Lys Arg Tyr Ser Leu Phe Ser Asn Ser Ile Gly Gln Ala Tyr Ser Arg
                 195                 200                 205

Arg Ser Ala Ile Ser Glu Asp Ile Tyr Asn Leu Glu Asn Gly Asp Ala
210                  215                 220

Gly Leu Ile Ser Glu Phe Ser Val Asp Phe Gly Lys Lys Glu Leu Thr
225                  230                 235                 240

Gly Glu Leu Tyr Tyr Asn Glu Arg Lys Thr Ser Val Asn Glu Ser Gln
                 245                 250                 255

Asn Thr Thr His Lys Leu Tyr Thr Leu Glu Ala Lys Val Tyr Ser Asn
                 260                 265                 270

Arg Phe Arg Gly Lys Val Lys Pro Thr Lys Thr Lys Ser Glu Asp His
                 275                 280                 285

Pro Phe Thr Ser Glu Gly Thr Leu Glu Gly Gly Phe Tyr Gly Pro Asn
                 290                 295                 300

Ala Glu Glu Leu Gly Gly Lys Phe Leu Ala Asn Asp Glu Lys Val Phe
305                  310                 315                 320

Gly Val Phe Ser Ala Lys Glu Asp Pro Gln Asn Pro Glu Asn Gln Lys
                 325                 330                 335

Leu Ser Thr Glu Thr Leu Ile Asp Gly Lys Leu Ile Thr Phe Lys Arg
                 340                 345                 350

Thr Asp Ala Thr Thr Asn Ala Thr Asp Ala Lys Thr Ser Ala Thr
                 355                 360                 365

Thr Asp Ala Thr Ser Thr Thr Ala Asn Lys Lys Thr Asp Ala Glu Asn
                 370                 375                 380

Phe Lys Thr Glu Asp Ile Pro Ser Phe Gly Glu Ala Asp Tyr Leu Leu
385                  390                 395                 400

Ile Gly Asn Gln Pro Ile Pro Leu Leu Pro Glu Lys Asn Thr Asp Asp
                 405                 410                 415

Phe Ile Ser Ser Lys His His Thr Val Gly Gly Lys Thr Tyr Lys Val
                 420                 425                 430
```

```
Glu Ala Cys Cys Lys Asn Leu Ser Tyr Val Lys Phe Gly Met Tyr Tyr
            435                 440                 445

Glu Asp Lys Asp Lys Asp Asn Lys Asn Glu Thr Asp Lys Glu Lys Gly
        450                 455                 460

Lys Glu Lys Pro Thr Thr Thr Thr Ser Ile Asn Thr Tyr Tyr Gln Phe
465                 470                 475                 480

Leu Leu Gly Leu Arg Thr Pro Lys Asp Glu Ile Pro Lys Glu Gly Ser
                485                 490                 495

Ala Lys Tyr His Gly Asn Trp Phe Gly Tyr Ile Ser Asp Gly Glu Thr
            500                 505                 510

Ser Tyr Ser Ala Ser Gly Asp Lys Glu Arg Ser Lys Asn Ala Val Ala
        515                 520                 525

Glu Phe Asp Val Ser Phe Ala Asn Lys Thr Leu Thr Gly Glu Leu Lys
    530                 535                 540

Arg His Asp Asn Gly Asn Thr Val Phe Lys Ile Asn Ala Glu Leu Asn
545                 550                 555                 560

Gly Ser Asn Asp Phe Thr Gly Thr Ala Thr Ala Thr Asn Phe Val Ile
                565                 570                 575

Asp Gly Asn Asn Ser Gln Thr Ser Asn Ala Lys Ile Asn Ile Thr Thr
            580                 585                 590

Lys Val Asn Gly Ala Phe Tyr Gly Pro Lys Ala Ser Glu Leu Gly Gly
        595                 600                 605

Tyr Phe Thr Tyr Asn Gly Lys Asn Pro Thr Ala Thr Asn Ser Glu Ser
    610                 615                 620

Ser Ser Thr Val Pro Ser Pro Asn Ser Pro Asn Ala Ser Ala Ala
625                 630                 635                 640

Val Val Phe Gly Ala Lys Lys Gln Val Glu Thr Thr Asn Lys
                645                 650

<210> SEQ ID NO 13
<211> LENGTH: 36
<212> TYPE: PRT
<213> ORGANISM: Haemophilus influenzae

<400> SEQUENCE: 13

Ala Glu Thr Gln Ser Ile Lys Asp Thr Lys Glu Ala Ile Ser Ser Glu
 1               5                  10                  15

Val Asp Thr Gln Ser Thr Glu Asp Ser Glu Leu Glu Thr Ile Ser Val
            20                  25                  30

Thr Ala Glu Lys
        35

<210> SEQ ID NO 14
<211> LENGTH: 36
<212> TYPE: PRT
<213> ORGANISM: Haemophilus influenzae

<400> SEQUENCE: 14

Ser Val Thr Ala Glu Lys Val Arg Asp Arg Lys Asp Asn Glu Val Thr
 1               5                  10                  15

Gly Leu Gly Lys Ile Ile Lys Thr Ser Glu Ser Ile Ser Arg Glu Gln
            20                  25                  30

Val Leu Asn Ile
        35

<210> SEQ ID NO 15
```

```
<211> LENGTH: 36
<212> TYPE: PRT
<213> ORGANISM: Haemophilus influenzae

<400> SEQUENCE: 15

Ser Arg Glu Gln Val Leu Asn Ile Arg Asp Leu Thr Arg Tyr Asp Pro
 1               5                  10                  15
Gly Ile Ser Val Val Glu Gln Gly Arg Gly Ala Ser Ser Gly Tyr Ser
            20                  25                  30
Ile Arg Gly Met
        35

<210> SEQ ID NO 16
<211> LENGTH: 36
<212> TYPE: PRT
<213> ORGANISM: Haemophilus influenzae

<400> SEQUENCE: 16

Gly Tyr Ser Ile Arg Gly Met Asp Arg Asn Arg Val Ala Leu Leu Val
 1               5                  10                  15
Asp Gly Leu Pro Gln Thr Gln Ser Tyr Val Val Gln Ser Pro Leu Val
            20                  25                  30
Ala Arg Ser Gly
        35

<210> SEQ ID NO 17
<211> LENGTH: 36
<212> TYPE: PRT
<213> ORGANISM: Haemophilus influenzae

<400> SEQUENCE: 17

Pro Leu Val Ala Arg Ser Gly Tyr Gly Thr Gly Ala Ile Asn Glu Ile
 1               5                  10                  15
Glu Tyr Glu Asn Val Lys Ala Val Glu Ile Ser Lys Gly Gly Ser Ser
            20                  25                  30
Ser Glu Tyr Gly
        35

<210> SEQ ID NO 18
<211> LENGTH: 36
<212> TYPE: PRT
<213> ORGANISM: Haemophilus influenzae

<400> SEQUENCE: 18

Ser Ser Ser Glu Tyr Gly Asn Gly Ala Leu Ala Gly Ser Val Thr Phe
 1               5                  10                  15
Gln Ser Lys Ser Ala Ala Asp Ile Leu Glu Gly Asp Lys Ser Trp Gly
            20                  25                  30
Ile Gln Thr Lys
        35

<210> SEQ ID NO 19
<211> LENGTH: 36
<212> TYPE: PRT
<213> ORGANISM: Haemophilus influenzae

<400> SEQUENCE: 19

Gly Ile Gln Thr Lys Asn Ala Tyr Ser Ser Lys Asn Lys Gly Phe Thr
 1               5                  10                  15
His Ser Leu Ala Val Ala Gly Lys Gln Gly Gly Phe Glu Gly Val Ala
            20                  25                  30
```

```
Ile Tyr Thr His
        35

<210> SEQ ID NO 20
<211> LENGTH: 36
<212> TYPE: PRT
<213> ORGANISM: Haemophilus influenzae

<400> SEQUENCE: 20

Gly Val Ala Ile Tyr Thr His Arg Asn Ser Ile Glu Thr Gln Val His
 1               5                  10                  15

Lys Asp Ala Leu Lys Gly Val Gln Ser Tyr Asp Arg Phe Ile Ala Thr
             20                  25                  30

Thr Glu Asp Gln
        35

<210> SEQ ID NO 21
<211> LENGTH: 36
<212> TYPE: PRT
<213> ORGANISM: Haemophilus influenzae

<400> SEQUENCE: 21

Ile Ala Thr Thr Glu Asp Gln Ser Ala Tyr Phe Val Met Gln Asp Glu
 1               5                  10                  15

Cys Leu Asp Gly Tyr Asp Lys Cys Lys Thr Ser Pro Lys Arg Pro Ala
             20                  25                  30

Thr Leu Ser Thr
        35

<210> SEQ ID NO 22
<211> LENGTH: 36
<212> TYPE: PRT
<213> ORGANISM: Haemophilus influenzae

<400> SEQUENCE: 22

Pro Ala Thr Leu Ser Thr Gln Arg Glu Thr Val Ser Val Ser Asp Tyr
 1               5                  10                  15

Thr Gly Ala Asn Arg Ile Lys Pro Asn Pro Met Lys Tyr Glu Ser Gln
             20                  25                  30

Ser Trp Phe Leu
        35

<210> SEQ ID NO 23
<211> LENGTH: 36
<212> TYPE: PRT
<213> ORGANISM: Haemophilus influenzae

<400> SEQUENCE: 23

Tyr Glu Ser Gln Ser Trp Phe Leu Arg Gly Gly Tyr His Phe Ser Glu
 1               5                  10                  15

Gln His Tyr Ile Gly Gly Ile Phe Glu Phe Thr Gln Gln Lys Phe Asp
             20                  25                  30

Ile Arg Asp Met
        35

<210> SEQ ID NO 24
<211> LENGTH: 36
<212> TYPE: PRT
<213> ORGANISM: Haemophilus influenzae

<400> SEQUENCE: 24
```

```
Lys Phe Asp Ile Arg Asp Met Thr Phe Pro Ala Tyr Leu Arg Pro Thr
  1               5                  10                  15

Glu Asp Lys Asp Leu Gln Ser Arg Pro Phe Tyr Pro Lys Gln Asp Tyr
             20                  25                  30

Gly Ala Tyr Gln
         35

<210> SEQ ID NO 25
<211> LENGTH: 36
<212> TYPE: PRT
<213> ORGANISM: Haemophilus influenzae

<400> SEQUENCE: 25

Asp Tyr Gly Ala Tyr Gln His Ile Gly Asp Gly Arg Gly Val Lys Tyr
  1               5                  10                  15

Ala Ser Gly Leu Tyr Phe Asp Glu His His Arg Lys Gln Arg Val Gly
             20                  25                  30

Ile Glu Tyr Ile
         35

<210> SEQ ID NO 26
<211> LENGTH: 36
<212> TYPE: PRT
<213> ORGANISM: Haemophilus influenzae

<400> SEQUENCE: 26

Gly Ile Glu Tyr Ile Tyr Glu Asn Lys Asn Lys Ala Gly Ile Ile Asp
  1               5                  10                  15

Lys Ala Val Leu Ser Ala Asn Gln Gln Asn Ile Ile Leu Asp Ser Tyr
             20                  25                  30

Met Arg His Thr
         35

<210> SEQ ID NO 27
<211> LENGTH: 36
<212> TYPE: PRT
<213> ORGANISM: Haemophilus influenzae

<400> SEQUENCE: 27

Asp Ser Tyr Met Arg His Thr His Cys Ser Leu Tyr Pro Asn Pro Ser
  1               5                  10                  15

Lys Asn Cys Arg Pro Thr Leu Asp Lys Pro Tyr Ser Tyr Tyr His Ser
             20                  25                  30

Asp Arg Asn Val
         35

<210> SEQ ID NO 28
<211> LENGTH: 36
<212> TYPE: PRT
<213> ORGANISM: Haemophilus influenzae

<400> SEQUENCE: 28

Ser Asp Arg Asn Val Tyr Lys Glu Lys His Asn Met Leu Gln Leu Asn
  1               5                  10                  15

Leu Glu Lys Lys Ile Gln Gln Asn Trp Leu Thr His Gln Ile Ala Phe
             20                  25                  30

Asn Leu Gly Phe
         35
```

```
<210> SEQ ID NO 29
<211> LENGTH: 36
<212> TYPE: PRT
<213> ORGANISM: Haemophilus influenzae

<400> SEQUENCE: 29

Thr His Gln Ile Ala Phe Asn Leu Gly Phe Asp Asp Phe Thr Ser Ala
 1               5                  10                  15
Leu Gln His Lys Asp Tyr Leu Thr Arg Arg Val Ile Ala Thr Ala Ser
            20                  25                  30
Ser Ile Ser Glu
        35

<210> SEQ ID NO 30
<211> LENGTH: 37
<212> TYPE: PRT
<213> ORGANISM: Haemophilus influenzae

<400> SEQUENCE: 30

Thr Ala Ser Ser Ile Ser Glu Lys Arg Gly Glu Ala Arg Arg Asn Gly
 1               5                  10                  15
Leu Gln Ser Ser Pro Tyr Leu Tyr Pro Thr Pro Lys Ala Glu Leu Val
            20                  25                  30
Gly Gly Asp Leu Cys
        35

<210> SEQ ID NO 31
<211> LENGTH: 36
<212> TYPE: PRT
<213> ORGANISM: Haemophilus influenzae

<400> SEQUENCE: 31

Leu Val Gly Gly Asp Leu Cys Asn Tyr Gln Gly Lys Ser Ser Asn Tyr
 1               5                  10                  15
Ser Asp Cys Lys Val Arg Leu Ile Lys Gly Lys Asn Tyr Tyr Phe Ala
            20                  25                  30
Ala Arg Asn Asn
        35

<210> SEQ ID NO 32
<211> LENGTH: 36
<212> TYPE: PRT
<213> ORGANISM: Haemophilus influenzae

<400> SEQUENCE: 32

Phe Ala Ala Arg Asn Asn Met Ala Leu Gly Lys Tyr Val Asp Leu Gly
 1               5                  10                  15
Leu Gly Met Arg Tyr Asp Val Ser Arg Thr Lys Ala Asn Glu Ser Thr
            20                  25                  30
Ile Ser Val Gly
        35

<210> SEQ ID NO 33
<211> LENGTH: 36
<212> TYPE: PRT
<213> ORGANISM: Haemophilus influenzae

<400> SEQUENCE: 33

Ser Thr Ile Ser Val Gly Lys Phe Lys Asn Phe Ser Trp Asn Thr Gly
 1               5                  10                  15
Ile Val Ile Lys Pro Thr Glu Trp Leu Asp Leu Ser Tyr Arg Leu Ser
```

```
                    20                  25                  30

Thr Gly Phe Arg
            35

<210> SEQ ID NO 34
<211> LENGTH: 36
<212> TYPE: PRT
<213> ORGANISM: Haemophilus influenzae

<400> SEQUENCE: 34

Leu Ser Thr Gly Phe Arg Asn Pro Ser Phe Ala Glu Met Tyr Gly Trp
  1               5                  10                  15

Arg Tyr Gly Gly Lys Asp Thr Asp Val Tyr Ile Gly Lys Phe Lys Pro
                 20                  25                  30

Glu Thr Ser Arg
            35

<210> SEQ ID NO 35
<211> LENGTH: 36
<212> TYPE: PRT
<213> ORGANISM: Haemophilus influenzae

<400> SEQUENCE: 35

Lys Pro Glu Thr Ser Arg Asn Gln Glu Phe Gly Leu Ala Leu Lys Gly
  1               5                  10                  15

Asp Phe Gly Asn Ile Glu Ile Ser His Phe Ser Asn Ala Tyr Arg Asn
                 20                  25                  30

Leu Ile Ala Phe
            35

<210> SEQ ID NO 36
<211> LENGTH: 36
<212> TYPE: PRT
<213> ORGANISM: Haemophilus influenzae

<400> SEQUENCE: 36

Tyr Arg Asn Leu Ile Ala Phe Ala Glu Glu Leu Ser Lys Asn Gly Thr
  1               5                  10                  15

Thr Gly Lys Gly Asn Tyr Gly Tyr His Asn Ala Gln Asn Ala Lys Leu
                 20                  25                  30

Val Gly Val Asn
            35

<210> SEQ ID NO 37
<211> LENGTH: 36
<212> TYPE: PRT
<213> ORGANISM: Haemophilus influenzae

<400> SEQUENCE: 37

Ala Lys Leu Val Gly Val Asn Ile Thr Ala Gln Leu Asp Phe Asn Gly
  1               5                  10                  15

Leu Trp Lys Arg Ile Pro Tyr Gly Trp Tyr Ala Thr Phe Ala Tyr Asn
                 20                  25                  30

Arg Val Lys Val
            35

<210> SEQ ID NO 38
<211> LENGTH: 36
<212> TYPE: PRT
<213> ORGANISM: Haemophilus influenzae
```

```
<400> SEQUENCE: 38

Ala Tyr Asn Arg Val Lys Val Lys Asp Gln Lys Ile Asn Ala Gly Leu
  1               5                  10                  15

Ala Ser Val Ser Ser Tyr Leu Phe Asp Ala Ile Gln Pro Ser Arg Tyr
                 20                  25                  30

Ile Ile Gly Leu
         35

<210> SEQ ID NO 39
<211> LENGTH: 36
<212> TYPE: PRT
<213> ORGANISM: Haemophilus influenzae

<400> SEQUENCE: 39

Ser Arg Tyr Ile Ile Gly Leu Asp Tyr Asp His Pro Ser Asn Thr Trp
  1               5                  10                  15

Gly Ile Lys Thr Met Phe Thr Gln Ser Lys Ala Lys Ser Gln Asn Glu
                 20                  25                  30

Leu Leu Gly Lys
         35

<210> SEQ ID NO 40
<211> LENGTH: 36
<212> TYPE: PRT
<213> ORGANISM: Haemophilus influenzae

<400> SEQUENCE: 40

Asn Glu Leu Leu Gly Lys Arg Ala Leu Gly Asn Asn Ser Arg Asn Val
  1               5                  10                  15

Lys Ser Thr Arg Lys Leu Thr Arg Ala Trp His Ile Leu Asp Val Ser
                 20                  25                  30

Gly Tyr Tyr Met
         35

<210> SEQ ID NO 41
<211> LENGTH: 30
<212> TYPE: PRT
<213> ORGANISM: Haemophilus influenzae

<400> SEQUENCE: 41

Ser Gly Tyr Tyr Met Val Asn Arg Ser Ile Leu Phe Arg Leu Gly Val
  1               5                  10                  15

Tyr Asn Leu Leu Asn Tyr Arg Tyr Val Thr Trp Glu Ala Val
                 20                  25                  30

<210> SEQ ID NO 42
<211> LENGTH: 23
<212> TYPE: PRT
<213> ORGANISM: Haemophilus influenzae

<400> SEQUENCE: 42

Leu Leu Asn Tyr Arg Tyr Val Thr Trp Glu Ala Val Arg Gln Thr Ala
  1               5                  10                  15

Gln Gly Ala Glu Phe Asp Ile
                 20

<210> SEQ ID NO 43
<211> LENGTH: 9
<212> TYPE: PRT
<213> ORGANISM: Haemophilus influenzae
```

```
<400> SEQUENCE: 43

Asp Asn Glu Val Thr Gly Leu Gly Lys
 1               5

<210> SEQ ID NO 44
<211> LENGTH: 16
<212> TYPE: PRT
<213> ORGANISM: Haemophilus influenzae

<400> SEQUENCE: 44

Glu Gln Val Leu Asn Ile Arg Asp Leu Thr Arg Tyr Asp Pro Gly Ile
 1               5                  10                  15

<210> SEQ ID NO 45
<211> LENGTH: 35
<212> TYPE: PRT
<213> ORGANISM: Haemophilus influenzae

<400> SEQUENCE: 45

Glu Gln Val Leu Asn Ile Arg Asp Leu Thr Arg Tyr Asp Pro Gly Ile
 1               5                  10                  15

Ser Val Val Glu Gln Gly Arg Gly Ala Ser Ser Gly Tyr Ser Ile Arg
                20                  25                  30

Gly Met Asp
        35

<210> SEQ ID NO 46
<211> LENGTH: 19
<212> TYPE: PRT
<213> ORGANISM: Haemophilus influenzae

<400> SEQUENCE: 46

Gly Ala Ile Asn Glu Ile Glu Tyr Glu Asn Val Lys Ala Val Glu Ile
 1               5                  10                  15

Ser Lys Gly

<210> SEQ ID NO 47
<211> LENGTH: 7
<212> TYPE: PRT
<213> ORGANISM: Haemophilus influenzae

<400> SEQUENCE: 47

Gly Ala Leu Ala Gly Ser Val
 1               5

<210> SEQ ID NO 48
<211> LENGTH: 15
<212> TYPE: PRT
<213> ORGANISM: Haemophilus influenzae

<400> SEQUENCE: 48

Ala Glu Thr Gln Ser Ile Lys Asp Thr Lys Glu Ala Ile Ser Cys
 1               5                  10                  15

<210> SEQ ID NO 49
<211> LENGTH: 14
<212> TYPE: PRT
<213> ORGANISM: Haemophilus influenzae

<400> SEQUENCE: 49

Cys Ser Gly Gly Gly Ser Phe Asp Val Asp Asn Val Ser Asn
 1               5                  10
```

```
<210> SEQ ID NO 50
<211> LENGTH: 31
<212> TYPE: PRT
<213> ORGANISM: Haemophilus influenzae

<400> SEQUENCE: 50

Leu Glu Gly Gly Phe Tyr Gly Pro Lys Gly Glu Leu Gly Phe Arg
 1               5                  10                  15

Phe Leu Ala Gly Asp Lys Lys Val Phe Gly Val Phe Ser Ala Lys
             20                  25                  30

<210> SEQ ID NO 51
<211> LENGTH: 23
<212> TYPE: PRT
<213> ORGANISM: Haemophilus influenzae

<400> SEQUENCE: 51

Thr Val Gly Lys Lys Thr Tyr Gln Val Glu Ala Cys Cys Ser Asn Leu
 1               5                  10                  15

Ser Tyr Val Lys Phe Gly Met
             20

<210> SEQ ID NO 52
<211> LENGTH: 23
<212> TYPE: PRT
<213> ORGANISM: Haemophilus influenzae

<400> SEQUENCE: 52

Ala Thr Val Lys Gly Ala Phe Tyr Gly Pro Lys Ala Ser Glu Leu Gly
 1               5                  10                  15

Gly Tyr Phe Thr Tyr Asn Gly
             20

<210> SEQ ID NO 53
<211> LENGTH: 35
<212> TYPE: PRT
<213> ORGANISM: Haemophilus influenzae

<400> SEQUENCE: 53

Met Lys Leu Ala Ala Leu Asn Leu Phe Asp Arg Asn Lys Pro Ser Leu
 1               5                  10                  15

Leu Asn Glu Asp Ser Tyr Met Ile Phe Ser Ser Arg Ser Thr Ile Glu
             20                  25                  30

Glu Asp Val
         35

<210> SEQ ID NO 54
<211> LENGTH: 35
<212> TYPE: PRT
<213> ORGANISM: Haemophilus influenzae

<400> SEQUENCE: 54

Ser Thr Ile Glu Glu Asp Val Lys Asn Asp Asn Gln Asn Gly Glu His
 1               5                  10                  15

Pro Ile Asp Ser Ile Val Asp Pro Arg Ala Pro Asn Ser Asn Glu Asn
             20                  25                  30

Arg His Gly
         35

<210> SEQ ID NO 55
<211> LENGTH: 35
```

```
<212> TYPE: PRT
<213> ORGANISM: Haemophilus influenzae

<400> SEQUENCE: 55

Ser Asn Glu Asn Arg His Gly Gln Lys Tyr Val Tyr Ser Gly Leu Tyr
 1               5                  10                  15

Tyr Ile Gln Ser Trp Ser Leu Arg Asp Leu Pro Asn Lys Lys Phe Tyr
            20                  25                  30

Ser Gly Tyr
        35

<210> SEQ ID NO 56
<211> LENGTH: 35
<212> TYPE: PRT
<213> ORGANISM: Haemophilus influenzae

<400> SEQUENCE: 56

Lys Lys Phe Tyr Ser Gly Tyr Tyr Gly Tyr Ala Tyr Tyr Phe Gly Asn
 1               5                  10                  15

Thr Thr Ala Ser Ala Leu Pro Val Gly Val Ala Thr Tyr Lys Gly
            20                  25                  30

Thr Trp Ser
        35

<210> SEQ ID NO 57
<211> LENGTH: 35
<212> TYPE: PRT
<213> ORGANISM: Haemophilus influenzae

<400> SEQUENCE: 57

Thr Tyr Lys Gly Thr Trp Ser Phe Ile Thr Ala Ala Glu Asn Gly Lys
 1               5                  10                  15

Asn Tyr Glu Leu Leu Arg Asn Ser Gly Gly Gln Ala Tyr Ser Arg
            20                  25                  30

Arg Ser Ala
        35

<210> SEQ ID NO 58
<211> LENGTH: 35
<212> TYPE: PRT
<213> ORGANISM: Haemophilus influenzae

<400> SEQUENCE: 58

Ala Tyr Ser Arg Arg Ser Ala Thr Pro Glu Asp Ile Asp Leu Asp Arg
 1               5                  10                  15

Lys Thr Gly Leu Thr Ser Glu Phe Thr Val Asn Phe Gly Thr Lys Lys
            20                  25                  30

Leu Thr Gly
        35

<210> SEQ ID NO 59
<211> LENGTH: 35
<212> TYPE: PRT
<213> ORGANISM: Haemophilus influenzae

<400> SEQUENCE: 59

Gly Thr Lys Lys Leu Thr Gly Gly Leu Tyr Tyr Asn Leu Arg Glu Thr
 1               5                  10                  15

Asp Ala Asn Lys Ser Gln Asn Arg Thr His Lys Leu Tyr Asp Leu Glu
            20                  25                  30
```

```
Ala Asp Val
        35

<210> SEQ ID NO 60
<211> LENGTH: 35
<212> TYPE: PRT
<213> ORGANISM: Haemophilus influenzae

<400> SEQUENCE: 60

Tyr Asp Leu Glu Ala Asp Val His Ser Asn Arg Phe Arg Gly Lys Val
 1               5                  10                  15

Lys Pro Thr Lys Lys Glu Ser Ser Glu Glu His Pro Phe Thr Ser Glu
            20                  25                  30

Gly Thr Leu
        35

<210> SEQ ID NO 61
<211> LENGTH: 35
<212> TYPE: PRT
<213> ORGANISM: Haemophilus influenzae

<400> SEQUENCE: 61

Phe Thr Ser Glu Gly Thr Leu Glu Gly Gly Phe Tyr Gly Pro Glu Gly
 1               5                  10                  15

Gln Glu Leu Gly Gly Lys Phe Leu Ala His Asp Lys Lys Val Leu Gly
            20                  25                  30

Val Phe Ser
        35

<210> SEQ ID NO 62
<211> LENGTH: 35
<212> TYPE: PRT
<213> ORGANISM: Haemophilus influenzae

<400> SEQUENCE: 62

Lys Val Leu Gly Val Phe Ser Ala Lys Glu Gln Gln Glu Thr Ser Glu
 1               5                  10                  15

Asn Lys Lys Leu Pro Lys Glu Thr Leu Ile Asp Gly Lys Leu Thr Thr
            20                  25                  30

Phe Lys Thr
        35

<210> SEQ ID NO 63
<211> LENGTH: 35
<212> TYPE: PRT
<213> ORGANISM: Haemophilus influenzae

<400> SEQUENCE: 63

Lys Leu Thr Thr Phe Lys Thr Thr Asn Ala Thr Ala Asn Ala Thr Thr
 1               5                  10                  15

Asp Ala Thr Thr Ser Thr Thr Ala Ser Thr Lys Thr Asp Thr Thr Thr
            20                  25                  30

Asn Ala Thr
        35

<210> SEQ ID NO 64
<211> LENGTH: 35
<212> TYPE: PRT
<213> ORGANISM: Haemophilus influenzae

<400> SEQUENCE: 64
```

```
Asp Thr Thr Thr Asn Ala Thr Asn Thr Glu Asn Phe Thr Thr Lys
 1               5                  10                  15

Asp Ile Pro Ser Leu Gly Glu Ala Asp Tyr Leu Leu Ile Asp Asn Tyr
                20                  25                  30

Pro Val Pro
        35
```

<210> SEQ ID NO 65
<211> LENGTH: 35
<212> TYPE: PRT
<213> ORGANISM: Haemophilus influenzae

<400> SEQUENCE: 65

```
Ile Asp Asn Tyr Pro Val Pro Leu Phe Pro Glu Ser Gly Asp Phe Ile
 1               5                  10                  15

Ser Ser Lys His His Thr Val Gly Lys Lys Thr Tyr Gln Val Glu Ala
                20                  25                  30

Cys Cys Ser
        35
```

<210> SEQ ID NO 66
<211> LENGTH: 36
<212> TYPE: PRT
<213> ORGANISM: Haemophilus influenzae

<400> SEQUENCE: 66

```
Cys Ser Asn Leu Ser Tyr Val Lys Phe Gly Met Tyr Tyr Glu Ala Pro
 1               5                  10                  15

Pro Lys Glu Glu Glu Lys Glu Lys Asp Lys Asp Lys Glu Lys
                20                  25                  30

Glu Lys Gln Ala
        35
```

<210> SEQ ID NO 67
<211> LENGTH: 35
<212> TYPE: PRT
<213> ORGANISM: Haemophilus influenzae

<400> SEQUENCE: 67

```
Lys Glu Lys Asp Lys Asp Lys Glu Lys Glu Lys Gln Ala Thr Thr Ser
 1               5                  10                  15

Ile Lys Thr Tyr Tyr Gln Phe Leu Leu Gly Leu Arg Thr Pro Ser Ser
                20                  25                  30

Glu Ile Pro
        35
```

<210> SEQ ID NO 68
<211> LENGTH: 35
<212> TYPE: PRT
<213> ORGANISM: Haemophilus influenzae

<400> SEQUENCE: 68

```
Thr Pro Ser Ser Glu Ile Pro Lys Glu Gly Ser Ala Lys Tyr His Gly
 1               5                  10                  15

Asn Trp Phe Gly Tyr Ile Ser Asp Gly Glu Thr Ser Tyr Ser Ala Ser
                20                  25                  30

Gly Asp Lys
        35
```

<210> SEQ ID NO 69

-continued

```
<211> LENGTH: 35
<212> TYPE: PRT
<213> ORGANISM: Haemophilus influenzae

<400> SEQUENCE: 69

Tyr Ser Ala Ser Gly Asp Lys Glu Arg Ser Lys Asn Ala Val Ala Glu
 1               5                  10                  15

Phe Asn Val Asn Phe Ala Glu Lys Thr Leu Thr Gly Glu Leu Lys Arg
            20                  25                  30

His Asp Thr
        35

<210> SEQ ID NO 70
<211> LENGTH: 35
<212> TYPE: PRT
<213> ORGANISM: Haemophilus influenzae

<400> SEQUENCE: 70

Glu Leu Lys Arg His Asp Thr Gln Asn Pro Val Phe Lys Ile Asn Ala
 1               5                  10                  15

Thr Phe Gln Ser Gly Lys Asn Asp Phe Thr Gly Thr Ala Thr Ala Lys
            20                  25                  30

Asp Leu Ala
        35

<210> SEQ ID NO 71
<211> LENGTH: 35
<212> TYPE: PRT
<213> ORGANISM: Haemophilus influenzae

<400> SEQUENCE: 71

Ala Thr Ala Lys Asp Leu Ala Ile Asp Gly Lys Asn Thr Gln Gly Thr
 1               5                  10                  15

Ser Lys Val Asn Phe Thr Ala Thr Val Asn Gly Ala Phe Tyr Gly Pro
            20                  25                  30

His Ala Thr
        35

<210> SEQ ID NO 72
<211> LENGTH: 26
<212> TYPE: PRT
<213> ORGANISM: Haemophilus influenzae

<400> SEQUENCE: 72

Phe Tyr Gly Pro His Ala Thr Glu Leu Gly Gly Tyr Phe Thr Tyr Asn
 1               5                  10                  15

Gly Asn Asn Pro Thr Asp Lys Asn Ser Ser
            20                  25

<210> SEQ ID NO 73
<211> LENGTH: 31
<212> TYPE: PRT
<213> ORGANISM: Haemophilus influenzae

<400> SEQUENCE: 73

Cys Pro Thr Asp Lys Asn Ser Ser Asn Ser Glu Lys Ala Arg Ala
 1               5                  10                  15

Ala Val Val Phe Gly Ala Lys Lys Gln Gln Val Glu Thr Thr Lys
            20                  25                  30

<210> SEQ ID NO 74
```

```
<211> LENGTH: 8
<212> TYPE: PRT
<213> ORGANISM: Haemophilus influenzae

<400> SEQUENCE: 74

Leu Glu Gly Gly Phe Tyr Gly Pro
  1               5

<210> SEQ ID NO 75
<211> LENGTH: 8
<212> TYPE: PRT
<213> ORGANISM: Haemophilus influenzae

<400> SEQUENCE: 75

Cys Ser Gly Gly Gly Ser Phe Asp
  1               5

<210> SEQ ID NO 76
<211> LENGTH: 6
<212> TYPE: PRT
<213> ORGANISM: Haemophilus influenzae

<400> SEQUENCE: 76

Tyr Val Tyr Ser Gly Leu
  1               5

<210> SEQ ID NO 77
<211> LENGTH: 11
<212> TYPE: PRT
<213> ORGANISM: Haemophilus influenzae

<400> SEQUENCE: 77

Cys Cys Ser Asn Leu Ser Tyr Val Lys Phe Gly
  1               5                  10

<210> SEQ ID NO 78
<211> LENGTH: 7
<212> TYPE: PRT
<213> ORGANISM: Haemophilus influenzae

<400> SEQUENCE: 78

Phe Leu Leu Gly His Arg Thr
  1               5

<210> SEQ ID NO 79
<211> LENGTH: 6
<212> TYPE: PRT
<213> ORGANISM: Haemophilus influenzae

<400> SEQUENCE: 79

Glu Phe Asn Val Asp Phe
  1               5

<210> SEQ ID NO 80
<211> LENGTH: 7
<212> TYPE: PRT
<213> ORGANISM: Haemophilus influenzae

<400> SEQUENCE: 80

Asn Ala Phe Thr Gly Thr Ala
  1               5

<210> SEQ ID NO 81
<211> LENGTH: 7
<212> TYPE: PRT
```

```
<213> ORGANISM: Haemophilus influenzae

<400> SEQUENCE: 81

Val Asn Gly Ala Phe Tyr Gly
 1               5

<210> SEQ ID NO 82
<211> LENGTH: 6
<212> TYPE: PRT
<213> ORGANISM: Haemophilus influenzae

<400> SEQUENCE: 82

Glu Leu Gly Gly Tyr Phe
 1               5

<210> SEQ ID NO 83
<211> LENGTH: 6
<212> TYPE: PRT
<213> ORGANISM: Haemophilus influenzae

<400> SEQUENCE: 83

Val Val Phe Gly Ala Arg
 1               5

<210> SEQ ID NO 84
<211> LENGTH: 6
<212> TYPE: PRT
<213> ORGANISM: Haemophilus influenzae

<400> SEQUENCE: 84

Val Val Phe Gly Ala Lys
 1               5

<210> SEQ ID NO 85
<211> LENGTH: 7
<212> TYPE: PRT
<213> ORGANISM: Haemophilus influenzae

<400> SEQUENCE: 85

Leu Glu Gly Gly Phe Tyr Gly
 1               5

<210> SEQ ID NO 86
<211> LENGTH: 103
<212> TYPE: DNA
<213> ORGANISM: Haemophilus influenzae

<400> SEQUENCE: 86
tatggaaact caaagtataa aagatacaaa agaagctata tcatctgaag tggacactca      60
aagtacagaa gattcagaat tagaaactat ctcagtcact gca                       103

<210> SEQ ID NO 87
<211> LENGTH: 97
<212> TYPE: DNA
<213> ORGANISM: Haemophilus influenzae

<400> SEQUENCE: 87
acctttgagt ttcatatttt ctatgttttc ttcgatatag tagacttcac ctgtgagttt      60
catgtcttct aagtcttaat ctttgataga gtcagtg                               97

<210> SEQ ID NO 88
<211> LENGTH: 115
<212> TYPE: DNA
```

<213> ORGANISM: Haemophilus influenzae

<400> SEQUENCE: 88

| | | |
|---|---|---|
| tatgaaagct actaaactgg ttctgggtgc tgttatcctg ggttccactc tgctggctgg | 60 | |
| ttgtagcgga ggtggttgtt ttgatgtaga taacgtctct aataccccct cttct | 115 | |

<210> SEQ ID NO 89
<211> LENGTH: 116
<212> TYPE: DNA
<213> ORGANISM: Haemophilus influenzae

<400> SEQUENCE: 89

| | |
|---|---|
| actttcgatg atttgaccaa gacccacgac aataggaccc aaggtgagac gaccgaccaa | 60 |
| catcgcctcc accaacaaaa ctacatctat tgcagagatt atgggggaga agattt | 116 |

<210> SEQ ID NO 90
<211> LENGTH: 109
<212> TYPE: DNA
<213> ORGANISM: Haemophilus influenzae

<400> SEQUENCE: 90

| | |
|---|---|
| tatgcgatat ctggcaacat tgttgttatc tctggcggtg ttaatcaccg ctggttgtag | 60 |
| cggaggtggt tcttttgatg tagataacgt ctctaatacc ccctcttct | 109 |

<210> SEQ ID NO 91
<211> LENGTH: 110
<212> TYPE: DNA
<213> ORGANISM: Haemophilus influenzae

<400> SEQUENCE: 91

| | |
|---|---|
| acgctataga ccgttgtaac aacaatagag accgccacaa ttagtggcga ccaacatcgc | 60 |
| ctccaccaag aaaactacat ctattgcaga gattatgggg gagaagattt | 110 |

<210> SEQ ID NO 92
<211> LENGTH: 117
<212> TYPE: DNA
<213> ORGANISM: Haemophilus influenzae

<400> SEQUENCE: 92

| | |
|---|---|
| tatgcaactg aacaaagtgc tgaaagggct gatgattgct ctgcctgtta tggcaatgct | 60 |
| ggttgtagcg gaggtggttc ttttgatgta gataacgtct ctaataccccc ctcttct | 117 |

<210> SEQ ID NO 93
<211> LENGTH: 119
<212> TYPE: DNA
<213> ORGANISM: Haemophilus influenzae

<400> SEQUENCE: 93

| | |
|---|---|
| acgttgactt gtttcacgac tttcccgact actaacgaga cggacaatac cgttaacgac | 60 |
| caacatcgcc tccaccaaga aaactacatc tattgcagag attatggggg agaagattt | 119 |

<210> SEQ ID NO 94
<211> LENGTH: 908
<212> TYPE: PRT
<213> ORGANISM: Haemophilus influenzae

<400> SEQUENCE: 94

Met Gln Gln Gln His Leu Phe Arg Leu Asn Ile Leu Cys Leu Ser Leu
 1               5                  10                  15

-continued

```
Met Thr Ala Leu Pro Val Tyr Ala Glu Asn Val Gln Ala Glu Gln Ala
         20                  25                  30

Gln Glu Lys Gln Leu Asp Thr Ile Gln Val Lys Ala Lys Lys Gln Lys
         35                  40                  45

Thr Arg Arg Asp Asn Glu Val Thr Gly Leu Gly Lys Leu Val Lys Ser
         50                  55                  60

Ser Asp Thr Leu Ser Lys Glu Gln Val Leu Asn Ile Arg Asp Leu Thr
 65                  70                  75                  80

Arg Tyr Asp Pro Gly Ile Ala Val Val Glu Gln Gly Arg Gly Ala Ser
                 85                  90                  95

Ser Gly Tyr Ser Ile Arg Gly Met Asp Lys Asn Arg Val Ser Leu Thr
                100                 105                 110

Val Asp Gly Val Ser Gln Ile Gln Ser Tyr Thr Ala Gln Ala Ala Leu
         115                 120                 125

Gly Gly Thr Arg Thr Ala Gly Ser Ser Gly Ala Ile Asn Glu Ile Glu
         130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
                180                 185                 190

Lys Thr Ala Tyr Ser Gly Lys Asp His Ala Leu Thr Gln Ser Leu Ala
         195                 200                 205

Leu Ala Gly Arg Ser Gly Gly Ala Glu Ala Leu Leu Ile Tyr Thr Lys
         210                 215                 220

Arg Arg Gly Arg Glu Ile His Ala His Lys Asp Ala Gly Lys Gly Val
225                 230                 235                 240

Gln Ser Phe Asn Arg Leu Val Leu Asp Glu Asp Lys Lys Glu Gly Gly
                245                 250                 255

Ser Gln Tyr Arg Tyr Phe Ile Val Glu Glu Glu Cys His Asn Gly Tyr
                260                 265                 270

Ala Ala Cys Lys Asn Lys Leu Lys Glu Asp Ala Ser Val Lys Asp Glu
         275                 280                 285

Arg Lys Thr Val Ser Thr Gln Asp Tyr Thr Gly Ser Asn Arg Leu Leu
         290                 295                 300

Ala Asn Pro Leu Glu Tyr Gly Ser Gln Ser Trp Leu Phe Arg Pro Gly
305                 310                 315                 320

Trp His Leu Asp Asn Arg His Tyr Val Gly Ala Val Leu Glu Arg Thr
                325                 330                 335

Gln Gln Thr Phe Asp Thr Arg Asp Met Thr Val Pro Ala Tyr Phe Thr
                340                 345                 350

Ser Glu Asp Tyr Val Pro Gly Ser Leu Lys Gly Leu Gly Lys Tyr Ser
         355                 360                 365

Gly Asp Asn Lys Ala Glu Arg Leu Phe Val Gln Gly Glu Gly Ser Thr
         370                 375                 380

Leu Gln Gly Ile Gly Tyr Gly Thr Gly Val Phe Tyr Asp Glu Arg His
385                 390                 395                 400

Thr Lys Asn Arg Tyr Gly Val Glu Tyr Val His Asn Ala Asp Lys
                405                 410                 415

Asp Thr Trp Ala Asp Tyr Ala Arg Leu Ser Tyr Asp Arg Gln Gly Ile
         420                 425                 430

Asp Leu Asp Asn Arg Leu Gln Gln Thr His Cys Ser His Asp Gly Ser
```

-continued

```
                435                 440                 445
Asp Lys Asn Cys Arg Pro Asp Gly Asn Lys Pro Tyr Ser Phe Tyr Lys
    450                 455                 460
Ser Asp Arg Met Ile Tyr Glu Glu Ser Arg Asn Leu Phe Gln Ala Val
465                 470                 475                 480
Phe Lys Lys Ala Phe Asp Thr Ala Lys Ile Arg His Asn Leu Ser Ile
                485                 490                 495
Asn Leu Gly Tyr Asp Arg Phe Lys Ser Gln Leu Ser His Ser Asp Tyr
                500                 505                 510
Tyr Leu Gln Asn Ala Val Gln Ala Tyr Asp Leu Ile Thr Pro Lys Lys
            515                 520                 525
Pro Pro Phe Pro Asn Gly Ser Lys Asp Asn Pro Tyr Arg Val Ser Ile
    530                 535                 540
Gly Lys Thr Thr Val Asn Thr Ser Pro Ile Cys Arg Phe Gly Asn Asn
545                 550                 555                 560
Thr Tyr Thr Asp Cys Thr Pro Arg Asn Ile Gly Gly Asn Gly Tyr Tyr
                565                 570                 575
Ala Ala Val Gln Asp Asn Val Arg Leu Gly Arg Trp Ala Asp Val Gly
            580                 585                 590
Ala Gly Ile Arg Tyr Asp Tyr Arg Ser Thr His Ser Glu Asp Lys Ser
            595                 600                 605
Val Ser Thr Gly Thr His Arg Asn Leu Ser Trp Asn Ala Gly Val Val
    610                 615                 620
Leu Lys Pro Phe Thr Trp Met Asp Leu Thr Tyr Arg Ala Ser Thr Gly
625                 630                 635                 640
Phe Arg Leu Pro Ser Phe Ala Glu Met Tyr Gly Trp Arg Ala Gly Glu
                645                 650                 655
Ser Leu Lys Thr Leu Asp Leu Lys Pro Glu Lys Ser Phe Asn Arg Glu
                660                 665                 670
Ala Gly Ile Val Phe Lys Gly Asp Phe Gly Asn Leu Glu Ala Ser Tyr
            675                 680                 685
Phe Asn Asn Ala Tyr Arg Asp Leu Ile Ala Phe Gly Tyr Glu Thr Arg
    690                 695                 700
Thr Gln Asn Gly Gln Thr Ser Ala Ser Gly Asp Pro Gly Tyr Arg Asn
705                 710                 715                 720
Ala Gln Asn Ala Arg Ile Ala Gly Ile Asn Ile Leu Gly Lys Ile Asp
                725                 730                 735
Trp His Gly Val Trp Gly Gly Leu Pro Asp Gly Leu Tyr Ser Thr Leu
                740                 745                 750
Ala Tyr Asn Arg Ile Lys Val Lys Asp Ala Asp Ile Arg Ala Asp Arg
            755                 760                 765
Thr Phe Val Thr Ser Tyr Leu Phe Asp Ala Val Gln Pro Ser Arg Tyr
    770                 775                 780
Val Leu Gly Leu Gly Tyr Asp His Pro Asp Gly Ile Trp Gly Ile Asn
785                 790                 795                 800
Thr Met Phe Thr Tyr Ser Lys Ala Lys Ser Val Asp Glu Leu Leu Gly
                805                 810                 815
Ser Gln Ala Leu Leu Asn Gly Asn Ala Asn Ala Lys Lys Ala Ala Ser
                820                 825                 830
Arg Arg Thr Arg Pro Trp Tyr Val Thr Asp Val Ser Gly Tyr Tyr Asn
            835                 840                 845
Ile Lys Lys His Leu Thr Leu Arg Ala Gly Val Tyr Asn Leu Leu Asn
    850                 855                 860
```

-continued

Tyr Arg Tyr Val Thr Trp Glu Asn Val Arg Gln Thr Ala Gly Gly Ala
865                 870                 875                 880

Val Asn Gln His Lys Asn Val Gly Val Tyr Asn Arg Tyr Ala Ala Pro
            885                 890                 895

Gly Arg Asn Tyr Thr Phe Ser Leu Glu Met Lys Phe
            900                 905

<210> SEQ ID NO 95
<211> LENGTH: 911
<212> TYPE: PRT
<213> ORGANISM: Haemophilus influenzae

<400> SEQUENCE: 95

Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
    50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
    210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Glu Tyr Ala
                245                 250                 255

Tyr Phe Ile Val Glu Asp Glu Cys Glu Gly Lys Asn Tyr Glu Thr Cys
            260                 265                 270

Lys Ser Lys Pro Lys Lys Asp Val Gly Lys Asp Glu Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln

```
                    325                 330                 335
Thr Phe Asp Thr Arg Asp Met Thr Val Pro Ala Phe Leu Thr Lys Ala
            340                 345                 350

Val Phe Asp Ala Asn Ser Lys Gln Ala Gly Ser Leu Pro Gly Asn Gly
            355                 360                 365

Lys Tyr Ala Gly Asn His Lys Tyr Gly Gly Leu Phe Thr Asn Gly Glu
            370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
            405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
            435                 440                 445

Asp Gly Ser Asp Lys Tyr Cys Arg Pro Ser Ala Asp Lys Pro Phe Ser
            450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
            485                 490                 495

Leu Ser Val Asn Leu Gly Phe Asp Arg Phe Asp Ser Asn Leu Arg His
            500                 505                 510

Gln Asp Tyr Tyr Tyr Gln His Ala Asn Arg Ala Tyr Ser Ser Lys Thr
            515                 520                 525

Pro Pro Lys Thr Ala Asn Pro Asn Gly Asp Lys Ser Lys Pro Tyr Trp
            530                 535                 540

Val Ser Ile Gly Gly Gly Asn Val Val Thr Gly Gln Ile Cys Leu Phe
545                 550                 555                 560

Gly Asn Asn Thr Tyr Thr Asp Cys Thr Pro Arg Ser Ile Asn Gly Lys
            565                 570                 575

Ser Tyr Tyr Ala Ala Val Arg Asp Asn Val Arg Leu Gly Arg Trp Ala
            580                 585                 590

Asp Val Gly Ala Gly Leu Arg Tyr Asp Tyr Arg Ser Thr His Ser Asp
            595                 600                 605

Asp Gly Ser Val Ser Thr Gly Thr His Arg Thr Leu Ser Trp Asn Ala
            610                 615                 620

Gly Ile Val Leu Lys Pro Ala Asp Trp Leu Asp Leu Thr Tyr Arg Thr
625                 630                 635                 640

Ser Thr Gly Phe Arg Leu Pro Ser Phe Ala Glu Met Tyr Gly Trp Arg
            645                 650                 655

Ser Gly Val Gln Ser Lys Ala Val Lys Ile Asp Pro Glu Lys Ser Phe
            660                 665                 670

Asn Lys Glu Ala Gly Ile Val Phe Lys Gly Asp Phe Gly Asn Leu Glu
            675                 680                 685

Ala Ser Trp Phe Asn Asn Ala Tyr Arg Asp Leu Ile Val Arg Gly Tyr
            690                 695                 700

Glu Ala Gln Ile Lys Asn Gly Lys Glu Glu Ala Lys Gly Asp Pro Ala
705                 710                 715                 720

Tyr Leu Asn Ala Gln Ser Ala Arg Ile Thr Gly Ile Asn Ile Leu Gly
            725                 730                 735

Lys Ile Asp Trp Asn Gly Val Trp Asp Lys Leu Pro Glu Gly Trp Tyr
            740                 745                 750
```

-continued

```
Ser Thr Phe Ala Tyr Asn Arg Val His Val Arg Asp Ile Lys Lys Arg
            755                 760                 765

Ala Asp Arg Thr Asp Ile Gln Ser His Leu Phe Asp Ala Ile Gln Pro
    770                 775                 780

Ser Arg Tyr Val Val Gly Leu Gly Tyr Asp Gln Pro Glu Gly Lys Trp
785                 790                 795                 800

Gly Val Asn Gly Met Leu Thr Tyr Ser Lys Ala Lys Glu Ile Thr Glu
                805                 810                 815

Leu Leu Gly Ser Arg Ala Leu Leu Asn Gly Asn Ser Arg Asn Thr Lys
            820                 825                 830

Ala Thr Ala Arg Arg Thr Arg Pro Trp Tyr Ile Val Asp Val Ser Gly
        835                 840                 845

Tyr Tyr Thr Ile Lys Lys His Phe Thr Leu Arg Ala Gly Val Tyr Asn
    850                 855                 860

Leu Leu Asn Tyr Arg Tyr Val Thr Trp Glu Asn Val Arg Gln Thr Ala
865                 870                 875                 880

Gly Gly Ala Val Asn Gln His Lys Asn Val Gly Val Tyr Asn Arg Tyr
                885                 890                 895

Ala Ala Pro Gly Arg Asn Tyr Thr Phe Ser Leu Glu Met Lys Phe
            900                 905                 910

<210> SEQ ID NO 96
<211> LENGTH: 915
<212> TYPE: PRT
<213> ORGANISM: Haemophilus influenzae

<400> SEQUENCE: 96

Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
    50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile Arg Thr Gly
```

```
                210                 215                 220
Arg His Ala Gly Glu Ile Arg Ala His Glu Ala Ala Gly Arg Gly Val
225                 230                 235                 240

Gln Ser Phe Asn Arg Leu Ala Pro Val Asp Asp Gly Ser Lys Tyr Ala
                245                 250                 255

Tyr Phe Ile Val Glu Glu Cys Lys Asn Gly Gly His Glu Lys Cys
                260                 265                 270

Lys Ala Asn Pro Lys Lys Asp Val Gly Glu Asp Lys Arg Gln Thr
                275                 280                 285

Val Ser Thr Arg Asp Tyr Thr Gly Pro Asn Arg Phe Leu Ala Asp Pro
290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu Arg Thr Gln Gln
                325                 330                 335

Thr Phe Asp Thr Arg Asp Met Thr Val Pro Ala Phe Leu Thr Lys Ala
                340                 345                 350

Val Phe Asp Ala Asn Gln Lys Gln Ala Gly Ser Leu Arg Gly Asn Gly
                355                 360                 365

Lys Tyr Ala Gly Asn His Lys Tyr Gly Gly Leu Phe Thr Ser Gly Glu
370                 375                 380

Asn Asn Ala Pro Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
                420                 425                 430

Gln Gly Ile Gly Leu Asp Asn His Phe Gln Gln Thr His Cys Ser Ala
                435                 440                 445

Asp Gly Ser Asp Lys Tyr Cys Arg Pro Ser Ala Asp Lys Pro Phe Ser
450                 455                 460

Tyr Tyr Lys Ser Asp Arg Val Ile Tyr Gly Glu Ser His Lys Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Tyr Asp Arg Phe Gly Ser Asn Leu Arg His
                500                 505                 510

Gln Asp Tyr Tyr Gln Ser Ala Asn Arg Ala Tyr Ser Leu Lys Thr
                515                 520                 525

Pro Pro Gln Asn Asn Gly Lys Lys Thr Ser Pro Asn Gly Arg Glu Lys
530                 535                 540

Asn Pro Tyr Trp Val Ser Ile Gly Arg Gly Asn Val Val Thr Arg Gln
545                 550                 555                 560

Ile Cys Leu Phe Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
                580                 585                 590

Gly Arg Trp Ala Asp Val Gly Ala Gly Leu Arg Tyr Asp Tyr Arg Ser
                595                 600                 605

Thr His Ser Asp Asp Gly Ser Val Ser Thr Gly Thr His Arg Thr Leu
                610                 615                 620

Ser Trp Asn Ala Gly Ile Val Leu Lys Pro Ala Asp Trp Leu Asp Leu
625                 630                 635                 640
```

-continued

```
Thr Tyr Arg Thr Ser Thr Gly Phe Arg Leu Pro Ser Phe Ala Glu Met
                645                 650                 655

Tyr Gly Trp Arg Ser Gly Asp Lys Ile Lys Ala Val Lys Ile Asp Pro
            660                 665                 670

Glu Lys Ser Phe Asn Lys Glu Ala Gly Ile Val Phe Lys Gly Asp Phe
        675                 680                 685

Gly Asn Leu Glu Ala Ser Trp Phe Asn Asn Ala Tyr Arg Asp Leu Ile
    690                 695                 700

Val Arg Gly Tyr Glu Ala Gln Ile Lys Asp Gly Lys Glu Gln Val Lys
705                 710                 715                 720

Gly Asn Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
            740                 745                 750

Glu Gly Trp Tyr Ser Thr Phe Ala Tyr Asn Arg Val Arg Val Arg Asp
        755                 760                 765

Ile Lys Lys Arg Ala Asp Arg Thr Asp Ile Gln Ser His Leu Phe Asp
    770                 775                 780

Ala Ile Gln Pro Ser Arg Tyr Val Val Gly Ser Gly Tyr Asp Gln Pro
785                 790                 795                 800

Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ala Arg Arg Thr Arg Pro Trp Tyr Ile Val
        835                 840                 845

Asp Val Ser Gly Tyr Tyr Thr Val Lys Lys His Phe Thr Leu Arg Ala
    850                 855                 860

Gly Val Tyr Asn Leu Leu Asn His Arg Tyr Val Thr Trp Glu Asn Val
865                 870                 875                 880

Arg Gln Thr Ala Ala Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
            900                 905                 910

Met Lys Phe
        915

<210> SEQ ID NO 97
<211> LENGTH: 598
<212> TYPE: PRT
<213> ORGANISM: Haemophilus influenzae

<400> SEQUENCE: 97

Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Glu Thr Val Gln Asp Met His Ser Lys Pro Lys Tyr Glu Asp Glu
        35                  40                  45

Lys Ser Gln Pro Glu Ser Gln Gln Asp Val Ser Glu Asn Ser Gly Ala
    50                  55                  60

Ala Tyr Gly Phe Ala Val Lys Leu Pro Arg Arg Asn Ala His Phe Asn
65                  70                  75                  80

Pro Lys Tyr Lys Glu Lys His Lys Pro Leu Gly Ser Met Asp Trp Lys
```

-continued

```
                85                  90                  95
Lys Leu Gln Arg Gly Glu Pro Asn Ser Phe Ser Glu Arg Asp Glu Leu
                100                 105                 110
Glu Lys Lys Arg Gly Ser Ser Glu Leu Ile Glu Ser Lys Trp Glu Asp
                115                 120                 125
Gly Gln Ser Arg Val Val Gly Tyr Thr Asn Phe Thr Tyr Val Arg Ser
                130                 135                 140
Gly Tyr Val Tyr Leu Asn Lys Asn Asn Ile Asp Ile Lys Asn Asn Ile
145                 150                 155                 160
Val Leu Phe Gly Pro Asp Gly Tyr Leu Tyr Tyr Lys Gly Lys Glu Pro
                165                 170                 175
Ser Lys Glu Leu Pro Ser Glu Lys Ile Thr Tyr Lys Gly Thr Trp Asp
                180                 185                 190
Tyr Val Thr Asp Ala Met Glu Lys Gln Arg Phe Glu Gly Leu Gly Ser
                195                 200                 205
Ala Ala Gly Gly Asp Lys Ser Gly Ala Leu Ser Ala Leu Glu Glu Gly
                210                 215                 220
Val Leu Arg Asn Gln Ala Glu Ala Ser Ser Gly His Thr Asp Phe Gly
225                 230                 235                 240
Met Thr Ser Glu Phe Glu Val Asp Phe Ser Asp Lys Thr Ile Lys Gly
                245                 250                 255
Thr Leu Tyr Arg Asn Asn Arg Ile Thr Gln Asn Asn Ser Glu Asn Lys
                260                 265                 270
Gln Ile Lys Thr Thr Arg Tyr Thr Ile Gln Ala Thr Leu His Gly Asn
                275                 280                 285
Arg Phe Lys Gly Lys Ala Leu Ala Ala Asp Lys Gly Ala Thr Asn Gly
                290                 295                 300
Ser His Pro Phe Ile Ser Asp Ser Asp Ser Leu Glu Gly Gly Phe Tyr
305                 310                 315                 320
Gly Pro Lys Gly Glu Glu Leu Ala Gly Lys Phe Leu Ser Asn Asp Asn
                325                 330                 335
Lys Val Ala Ala Val Phe Gly Ala Lys Gln Lys Asp Lys Lys Asp Gly
                340                 345                 350
Glu Asn Ala Ala Gly Pro Ala Thr Glu Val Ile Asp Ala Tyr Arg Ile
                355                 360                 365
Thr Gly Glu Glu Phe Lys Lys Glu Gln Ile Asp Ser Phe Gly Asp Val
                370                 375                 380
Lys Lys Leu Leu Val Asp Gly Val Glu Leu Ser Leu Leu Pro Ser Glu
385                 390                 395                 400
Gly Asn Lys Ala Ala Phe Gln His Glu Ile Glu Gln Asn Gly Val Lys
                405                 410                 415
Ala Thr Val Cys Cys Ser Asn Leu Asp Tyr Met Ser Phe Gly Lys Leu
                420                 425                 430
Ser Lys Glu Asn Lys Asp Asp Met Phe Leu Gln Gly Val Arg Thr Pro
                435                 440                 445
Val Ser Asp Val Ala Ala Arg Thr Glu Ala Asn Ala Lys Tyr Arg Gly
                450                 455                 460
Thr Trp Tyr Gly Tyr Ile Ala Asn Gly Thr Ser Trp Ser Gly Glu Ala
465                 470                 475                 480
Ser Asn Gln Glu Gly Gly Asn Arg Ala Glu Phe Asp Val Asp Phe Ser
                485                 490                 495
Thr Lys Lys Ile Ser Gly Thr Leu Thr Ala Lys Asp Arg Thr Ser Pro
                500                 505                 510
```

-continued

```
Ala Phe Thr Ile Thr Ala Met Ile Lys Asp Asn Gly Phe Ser Gly Val
        515                 520                 525
Ala Lys Thr Gly Glu Asn Gly Phe Ala Leu Asp Pro Gln Asn Thr Gly
    530                 535                 540
Asn Ser His Tyr Thr His Ile Glu Ala Thr Val Ser Gly Gly Phe Tyr
545                 550                 555                 560
Gly Lys Asn Ala Ile Glu Met Gly Gly Ser Phe Ser Phe Pro Gly Asn
                565                 570                 575
Ala Pro Glu Gly Lys Gln Glu Lys Ala Ser Val Val Phe Gly Ala Lys
            580                 585                 590
Arg Gln Gln Leu Val Gln
        595

<210> SEQ ID NO 98
<211> LENGTH: 711
<212> TYPE: PRT
<213> ORGANISM: Haemophilus influenzae

<400> SEQUENCE: 98

Met Asn Asn Pro Leu Val Asn Gln Ala Ala Met Val Leu Pro Val Phe
1               5                   10                  15
Leu Leu Ser Ala Cys Leu Gly Gly Gly Ser Phe Asp Leu Asp Ser
            20                  25                  30
Val Asp Thr Glu Ala Pro Arg Pro Ala Pro Lys Tyr Gln Asp Val Ser
        35                  40                  45
Ser Glu Lys Pro Gln Ala Gln Lys Asp Gln Gly Gly Tyr Gly Phe Ala
    50                  55                  60
Met Arg Leu Lys Arg Arg Asn Trp Tyr Pro Gly Ala Glu Glu Ser Glu
65                  70                  75                  80
Val Lys Leu Asn Glu Ser Asp Trp Glu Ala Thr Gly Leu Pro Thr Lys
                85                  90                  95
Pro Lys Glu Leu Pro Lys Arg Gln Lys Ser Val Ile Glu Lys Val Glu
            100                 105                 110
Thr Asp Gly Asp Ser Asp Ile Tyr Ser Ser Pro Tyr Leu Thr Pro Ser
        115                 120                 125
Asn His Gln Asn Gly Ser Ala Gly Asn Gly Val Asn Gln Pro Lys Asn
    130                 135                 140
Gln Ala Thr Gly His Glu Asn Phe Gln Tyr Val Tyr Ser Gly Trp Phe
145                 150                 155                 160
Tyr Lys His Ala Ala Ser Glu Lys Asp Phe Ser Asn Lys Lys Ile Lys
                165                 170                 175
Ser Gly Asp Asp Gly Tyr Ile Phe Tyr His Gly Glu Lys Pro Ser Arg
            180                 185                 190
Gln Leu Pro Ala Ser Gly Lys Val Ile Tyr Lys Gly Val Trp His Phe
        195                 200                 205
Val Thr Asp Thr Lys Lys Gly Gln Asp Phe Arg Glu Ile Ile Gln Pro
    210                 215                 220
Ser Lys Lys Gln Gly Asp Arg Tyr Ser Gly Phe Ser Gly Asp Gly Ser
225                 230                 235                 240
Glu Glu Tyr Ser Asn Lys Asn Glu Ser Thr Leu Lys Asp Asp His Glu
                245                 250                 255
Gly Tyr Gly Phe Thr Ser Asn Leu Glu Val Asp Phe Gly Asn Lys Lys
            260                 265                 270
Leu Thr Gly Lys Leu Ile Arg Asn Asn Ala Ser Leu Asn Asn Asn Thr
```

-continued

```
                275                 280                 285
Asn Asn Asp Lys His Thr Thr Gln Tyr Tyr Ser Leu Asp Ala Gln Ile
    290                 295                 300
Thr Gly Asn Arg Phe Asn Gly Thr Ala Thr Ala Thr Asp Lys Lys Glu
305                 310                 315                 320
Asn Glu Thr Lys Leu His Pro Phe Val Ser Asp Ser Ser Ser Leu Ser
                325                 330                 335
Gly Gly Phe Phe Gly Pro Gln Gly Glu Leu Gly Phe Arg Phe Leu
                340                 345                 350
Ser Asp Asp Gln Lys Val Ala Val Val Gly Ser Ala Lys Thr Lys Asp
                355                 360                 365
Lys Leu Glu Asn Gly Ala Ala Ala Ser Gly Ser Thr Gly Ala Ala Ala
    370                 375                 380
Ser Gly Gly Ala Ala Gly Thr Ser Ser Glu Asn Ser Lys Leu Thr Thr
385                 390                 395                 400
Val Leu Asp Ala Val Glu Leu Thr Leu Asn Asp Lys Lys Ile Lys Asn
                405                 410                 415
Leu Asp Asn Phe Ser Asn Ala Ala Gln Leu Val Val Asp Gly Ile Met
                420                 425                 430
Ile Pro Leu Leu Pro Lys Asp Ser Glu Ser Gly Asn Thr Gln Ala Asp
                435                 440                 445
Lys Gly Lys Asn Gly Gly Thr Glu Phe Thr Arg Lys Phe Glu His Thr
                450                 455                 460
Pro Glu Ser Asp Lys Lys Asp Ala Gln Ala Gly Thr Gln Thr Asn Gly
465                 470                 475                 480
Ala Gln Thr Ala Ser Asn Thr Ala Gly Asp Thr Asn Gly Lys Thr Lys
                485                 490                 495
Thr Tyr Glu Val Glu Val Cys Cys Ser Asn Leu Asn Tyr Leu Lys Tyr
                500                 505                 510
Gly Met Leu Thr Arg Lys Asn Ser Lys Ser Ala Met Gln Ala Gly Gly
                515                 520                 525
Asn Ser Ser Gln Ala Asp Ala Lys Thr Glu Gln Val Glu Gln Ser Met
530                 535                 540
Phe Leu Gln Gly Glu Arg Thr Asp Glu Lys Glu Ile Pro Thr Asp Gln
545                 550                 555                 560
Asn Val Val Tyr Arg Gly Ser Trp Tyr Gly His Ile Ala Asn Gly Thr
                565                 570                 575
Ser Trp Ser Gly Asn Ala Ser Asp Lys Glu Gly Asn Arg Ala Glu
                580                 585                 590
Phe Thr Val Asn Phe Ala Asp Lys Lys Ile Thr Gly Lys Leu Thr Ala
                595                 600                 605
Glu Asn Arg Gln Ala Gln Thr Phe Thr Ile Glu Gly Met Ile Gln Gly
    610                 615                 620
Asn Gly Phe Glu Gly Thr Ala Lys Thr Ala Glu Ser Gly Phe Asp Leu
625                 630                 635                 640
Asp Gln Lys Asn Thr Thr Arg Thr Pro Lys Ala Tyr Ile Thr Asp Ala
                645                 650                 655
Lys Val Lys Gly Gly Phe Tyr Gly Pro Lys Ala Glu Leu Gly Gly
                660                 665                 670
Trp Phe Ala Tyr Pro Gly Asp Lys Gln Thr Glu Lys Ala Thr Ala Thr
                675                 680                 685
Ser Ser Asp Gly Asn Ser Ala Ser Ser Ala Thr Val Phe Gly Ala
    690                 695                 700
```

Lys Arg Gln Gln Pro Val Gln
705                710

<210> SEQ ID NO 99
<211> LENGTH: 546
<212> TYPE: PRT
<213> ORGANISM: Haemophilus influenzae

<400> SEQUENCE: 99

Met His Phe Lys Leu Asn Pro Tyr Ala Leu Ala Phe Thr Ser Leu Phe
 1               5                  10                  15

Leu Val Ala Cys Ser Gly Gly Lys Gly Ser Phe Asp Leu Glu Asp Val
            20                  25                  30

Arg Pro Asn Lys Thr Thr Gly Val Ser Lys Glu Glu Tyr Lys Asp Val
        35                  40                  45

Glu Thr Ala Lys Lys Glu Lys Glu Gln Leu Gly Glu Leu Met Glu Pro
    50                  55                  60

Ala Leu Gly Tyr Val Val Lys Val Pro Val Ser Ser Phe Glu Asn Lys
65                  70                  75                  80

Lys Val Asp Ile Ser Asp Ile Glu Val Ile Thr Asn Gly Asn Leu Asp
                85                  90                  95

Asp Val Pro Tyr Lys Ala Asn Ser Ser Lys Tyr Asn Tyr Pro Asp Ile
            100                 105                 110

Lys Thr Lys Asp Ser Ser Leu Gln Tyr Val Arg Ser Gly Tyr Val Ile
        115                 120                 125

Asp Gly Glu His Ser Gly Ser Asn Glu Lys Gly Tyr Val Tyr Tyr Lys
    130                 135                 140

Gly Asn Ser Pro Ala Lys Glu Leu Pro Val Asn Gln Leu Leu Thr Tyr
145                 150                 155                 160

Thr Gly Ser Trp Asp Phe Thr Ser Asn Ala Asn Leu Asn Asn Glu Glu
                165                 170                 175

Gly Arg Pro Asn Tyr Leu Asn Asp Asp Tyr Tyr Thr Lys Phe Ile Gly
            180                 185                 190

Lys Arg Val Gly Leu Val Ser Gly Asp Ala Lys Pro Ala Lys His Lys
        195                 200                 205

Tyr Thr Ser Gln Phe Glu Val Asp Phe Ala Thr Lys Lys Met Thr Gly
    210                 215                 220

Lys Ser Asp Lys Glu Lys Thr Ile Tyr Thr Val Asn Ala Asp Ile Arg
225                 230                 235                 240

Gly Asn Arg Phe Thr Gly Ala Ala Thr Ala Ser Asp Lys Asn Lys Gly
                245                 250                 255

Lys Gly Glu Ser Tyr Asn Phe Phe Ser Ala Asp Ser Gln Ser Leu Glu
            260                 265                 270

Gly Gly Phe Tyr Gly Pro Lys Ala Glu Glu Met Ala Gly Lys Phe Val
        275                 280                 285

Ala Asn Asp Lys Ser Leu Phe Ala Val Phe Ser Ala Lys His Asn Gly
    290                 295                 300

Ser Asn Val Asn Thr Val Arg Ile Ile Asp Ala Ser Lys Ile Asp Leu
305                 310                 315                 320

Thr Asn Phe Ser Ile Ser Glu Leu Asn Asn Phe Gly Asp Ala Ser Val
                325                 330                 335

Leu Ile Ile Asp Gly Lys Lys Ile Lys Leu Ala Gly Ser Gly Phe Thr
            340                 345                 350

Asn Lys His Thr Ile Glu Ile Asn Gly Lys Thr Met Val Ala Val Ala

-continued

```
                355                 360                 365
Cys Cys Ser Asn Leu Glu Tyr Met Lys Phe Gly Gln Leu Trp Gln Gln
    370                 375                 380

Ala Glu Gly Gly Lys Pro Glu Asn Asn Ser Leu Phe Leu Gln Gly Glu
385                 390                 395                 400

Arg Thr Ala Thr Asp Lys Met Pro Lys Gly Gly Asn Tyr Lys Tyr Ile
                405                 410                 415

Gly Thr Trp Asp Ala Gln Val Ser Lys Glu Asn Asn Trp Val Ala Thr
                420                 425                 430

Ala Asp Asp Arg Lys Ala Gly Tyr Arg Thr Glu Phe Asp Val Asp
            435                 440                 445

Phe Gly Asn Lys Asn Leu Ser Gly Lys Leu Phe Asp Lys Asn Gly Val
    450                 455                 460

Asn Pro Val Phe Thr Val Asp Ala Lys Ile Asp Gly Asn Gly Phe Thr
465                 470                 475                 480

Gly Lys Ala Lys Thr Ser Asp Glu Gly Phe Ala Leu Asp Ser Gly Ser
                485                 490                 495

Ser Arg Tyr Glu Asn Val Lys Phe Asn Asp Val Ala Val Ser Gly Gly
            500                 505                 510

Phe Tyr Gly Pro Thr Ala Ala Glu Leu Gly Gly Gln Phe His His Lys
    515                 520                 525

Ser Glu Asn Gly Ser Val Gly Ala Val Phe Gly Ala Lys Gln Gln Val
530                 535                 540

Lys Lys
545

<210> SEQ ID NO 100
<211> LENGTH: 593
<212> TYPE: PRT
<213> ORGANISM: Haemophilus influenzae

<400> SEQUENCE: 100

Met His Phe Lys Leu Asn Pro Tyr Ala Leu Ala Phe Thr Ser Leu Phe
1               5                   10                  15

Leu Val Ala Cys Ser Gly Gly Lys Gly Ser Phe Asp Leu Glu Asp Val
                20                  25                  30

Arg Pro Asn Gln Thr Ala Lys Ala Glu Lys Ala Thr Thr Ser Tyr Gln
            35                  40                  45

Asp Glu Glu Thr Lys Lys Thr Lys Glu Glu Leu Asp Lys Leu Met
        50                  55                  60

Glu Pro Ala Leu Gly Tyr Glu Thr Gln Ile Leu Arg Arg Asn Lys Ala
65                  70                  75                  80

Pro Lys Thr Glu Thr Gly Glu Lys Arg Asn Glu Arg Val Val Glu Leu
                85                  90                  95

Ser Glu Asp Lys Ile Thr Lys Leu Tyr Gln Glu Ser Val Glu Ile Ile
                100                 105                 110

Pro His Leu Asp Glu Leu Asn Gly Lys Thr Thr Ser Asn Asp Val Tyr
            115                 120                 125

His Ser His Asp Ser Lys Arg Leu Asp Lys Asn Arg Asp Leu Lys Tyr
        130                 135                 140

Val Arg Ser Gly Tyr Val Tyr Asp Gly Ser Phe Asn Glu Ile Arg Arg
145                 150                 155                 160

Asn Asp Ser Gly Phe His Val Phe Lys Gln Gly Ile Asp Gly Tyr Val
                165                 170                 175
```

-continued

```
Tyr Tyr Leu Gly Val Thr Pro Ser Lys Glu Leu Pro Lys Gly Lys Val
            180                 185                 190

Ile Ser Tyr Lys Gly Thr Trp Asp Phe Val Ser Asn Ile Asn Leu Glu
        195                 200                 205

Arg Glu Ile Asp Gly Phe Asp Thr Ser Gly Asp Gly Lys Asn Val Ser
    210                 215                 220

Ala Thr Ser Ile Thr Glu Thr Val Asn Arg Asp His Lys Val Gly Glu
225                 230                 235                 240

Lys Leu Gly Asp Asn Glu Val Lys Gly Val Ala His Ser Ser Glu Phe
                245                 250                 255

Ala Val Asp Phe Asp Asn Lys Lys Leu Thr Gly Ser Leu Tyr Arg Asn
            260                 265                 270

Gly Tyr Ile Asn Arg Asn Lys Ala Gln Glu Val Thr Lys Arg Tyr Ser
        275                 280                 285

Ile Glu Ala Asp Ile Ala Gly Asn Arg Phe Arg Gly Lys Ala Lys Ala
    290                 295                 300

Glu Lys Ala Gly Asp Pro Ile Phe Thr Asp Ser Asn Tyr Leu Glu Gly
305                 310                 315                 320

Gly Phe Tyr Gly Pro Lys Ala Glu Glu Met Ala Gly Lys Phe Phe Thr
                325                 330                 335

Asn Asn Lys Ser Leu Phe Ala Val Phe Ala Ala Lys Ser Glu Asn Gly
            340                 345                 350

Glu Thr Thr Thr Glu Arg Ile Ile Asp Ala Thr Lys Ile Asp Leu Thr
        355                 360                 365

Gln Phe Asn Ala Lys Glu Leu Asn Asn Phe Gly Asp Ala Ser Val Leu
    370                 375                 380

Ile Ile Asp Gly Gln Lys Ile Asp Leu Ala Gly Val Asn Phe Lys Asn
385                 390                 395                 400

Ser Lys Thr Val Glu Ile Asn Gly Lys Thr Met Val Ala Val Ala Cys
                405                 410                 415

Cys Ser Asn Leu Glu Tyr Met Lys Phe Gly Gln Leu Trp Gln Lys Glu
            420                 425                 430

Gly Lys Gln Gln Val Lys Asp Asn Ser Leu Phe Leu Gln Gly Glu Arg
        435                 440                 445

Thr Ala Thr Asp Lys Met Pro Ala Gly Gly Asn Tyr Lys Tyr Val Gly
    450                 455                 460

Thr Trp Asp Ala Leu Val Ser Lys Gly Thr Asn Trp Ile Ala Glu Ala
465                 470                 475                 480

Asp Asn Asn Arg Glu Ser Gly Tyr Arg Thr Glu Phe Asp Val Asn Phe
                485                 490                 495

Ser Asp Lys Lys Val Asn Gly Lys Leu Phe Asp Lys Gly Gly Val Asn
            500                 505                 510

Pro Val Phe Thr Val Asp Ala Thr Ile Asn Gly Asn Gly Phe Ile Gly
        515                 520                 525

Ser Ala Lys Thr Ser Asp Ser Gly Phe Ala Leu Asp Ala Gly Ser Ser
    530                 535                 540

Gln His Gly Asn Ala Val Phe Ser Asp Ile Lys Val Asn Gly Gly Phe
545                 550                 555                 560

Tyr Gly Pro Thr Ala Gly Glu Leu Gly Gly Gln Phe His His Lys Ser
                565                 570                 575

Asp Asn Gly Ser Val Gly Ala Val Phe Gly Ala Lys Arg Gln Ile Glu
            580                 585                 590

Lys
```

```
<210> SEQ ID NO 101
<211> LENGTH: 18
<212> TYPE: PRT
<213> ORGANISM: Haemophilus influenzae

<400> SEQUENCE: 101

Glu Thr Gln Ser Ile Lys Asp Thr Lys Glu Ala Ile Ser Ser Glu Val
 1               5                  10                  15

Asp Thr

<210> SEQ ID NO 102
<211> LENGTH: 20
<212> TYPE: PRT
<213> ORGANISM: Haemophilus influenzae

<400> SEQUENCE: 102

Leu Gln Leu Asn Leu Glu Lys Lys Ile Gln Gln Asn Trp Leu Thr His
 1               5                  10                  15

Gln Ile Ala Phe
            20

<210> SEQ ID NO 103
<211> LENGTH: 23
<212> TYPE: PRT
<213> ORGANISM: Haemophilus influenzae

<400> SEQUENCE: 103

Met Thr Lys Lys Pro Tyr Phe Arg Leu Ser Ile Ile Ser Cys Leu Leu
 1               5                  10                  15

Ile Ser Cys Tyr Val Lys Ala
            20

<210> SEQ ID NO 104
<211> LENGTH: 17
<212> TYPE: PRT
<213> ORGANISM: Haemophilus influenzae

<400> SEQUENCE: 104

Met Lys Ser Val Pro Leu Ile Ser Gly Gly Leu Ser Phe Leu Leu Ser
 1               5                  10                  15

Ala

<210> SEQ ID NO 105
<211> LENGTH: 5144
<212> TYPE: DNA
<213> ORGANISM: Haemophilus influenzae

<400> SEQUENCE: 105
caacatctgc ccaagctata ttcgttaatg ataagcctat taatgataag cctattaatg      60
ataagaaaga aatttgtttt acgccatttt tcatatttta tccatgaact taaaaaattc     120
taagttgaca ttattacaaa aaagaacaa taatgcgaat tattatcaat tttgtataag     180
aatataattc tatgaaatct gtacctctta tctctggtgg actttccttt ttattaagtg     240
cttgtagcgg aggagggtct tttgatgtag ataacgtctc taatccctcc tcttctaaac     300
cacgttatca agacgatacc tcgaatcaaa gaacaaaatc tgatttgcaa agttgtcca     360 ttccttcttt aggggagggg atgaagttag tggctcagaa tcttcttggt aagaaagaac     420
ctagtctctt aaataatgaa gatggctata tgatattttc ctcactttct acgattgaag     480
```

| | |
|---|---|
| aggatgttac aaaagaaaat aaatctcagg aacccactat tggctcaata gacgagccta | 540 |
| gcaaaacaaa ttcaccccaa aatcatcatg gcaatatgta tattcgggtc tttattatat | 600 |
| tcaatcgtgg cgtaattcct caaatggcaa gttttattca ggttactatg gatatgcgta | 660 |
| ttactttggc aagcaaacag ccactacatt acctgtagat ggcgaagcaa cgtataaagg | 720 |
| aacttggcac ttcatcaccg caactgaaaa tggcaaaaag tattctttgt tcagtaatga | 780 |
| tagcggtcaa gcttatcgca gacgtagtgc aattccagaa gatattgatt tagaaaaaaa | 840 |
| tgattcaact aatggtgaca agggcttaat aagtgaattt agtgtcaatt ttggtacaaa | 900 |
| aaagctcact ggaaaacttt attataatga agagaaaaca gaacttaata atcaaaaga | 960 |
| tagaaaacat acactctaca atctagaagc tgaagtgtat agtaaccgat tcagggtac | 1020 |
| agtaaagcca accgaaaaag attctacaga tcatcccttt accagcgagg gaacattaga | 1080 |
| aggtggtttt tatgggccta aaggtgaaga actaggagga aagttttag ctggcgataa | 1140 |
| aaaagttttt ggggtattta gtgccaaaga aacggaagaa acaaaaaaga aagcgttatc | 1200 |
| caaggaaacc ttaattgatg gcaagctaac tacttttaaa acaaccaatg caacaaccaa | 1260 |
| tgcaacagcc aatgcaacaa ccagtacaac agccagtaca caaccgatg cagaaaactt | 1320 |
| tacgacgaaa gatataccaa gttttggtga agctgattac cttttaattg ataattaccc | 1380 |
| tgttcctctt ttacctgaga gtggtgattt cataagtagt aagcaccata ctgtaggaaa | 1440 |
| gaaaacctat caagtagaag catgttgcag taatctaagc tatgtgaaat ttggtatgtt | 1500 |
| ttatgaagac ccacttaaag aagaaaaaga caaagaaaaa gaagaagaca agaaaaaca | 1560 |
| aacggcggca acgaccaaca cttattatca attcttatta ggtctccgta ctgccagttc | 1620 |
| tgaaattcct aaaatgggaa acgtggaata tcgcggtaat tggtttggtt atattagtga | 1680 |
| tggcacgaca tcttactccc ccagtggtga taaggaacgc aataaaaatg ctcccgccga | 1740 |
| ttttaatgtt gattttgtca ataaaaagct aacaggcaca ttaaaacgac acgataatgg | 1800 |
| aaataccgta tttagtattg aggcaaactt taacagtggg aatgacttca ctggtaaagc | 1860 |
| aaccgcaaaa gatttagtaa tagatggtaa aagtacacaa gccacatcta aagtcaattt | 1920 |
| cacggcaaca gtaaaagggg catttatgg acctgatgct tctgaattag gcggttattt | 1980 |
| cacctataac ggaaaaaatc ctacagctac aaattcccca accgtatctt caccatccaa | 2040 |
| ttcagcaaat gctcgtgctg ccgttgtgtt tggagctaaa aaacaagtag acacaaccaa | 2100 |
| caagtagaaa aaaccaaata atggaatact aaaaatgact aaaaaaccct attttcgcct | 2160 |
| aagtattatt tcttgtcttt taatttcatg ctatgtaaaa gcagaaactc aaagtataaa | 2220 |
| agatacaaaa gaagctatat catctgaagt ggacactcaa agtacagaag attcagaatt | 2280 |
| agaaactatc tcagtcactg cagaaaaat aagagatcgt aaagataatg aagtaactgg | 2340 |
| acttggcaaa attataaaaa cgagtgaaag tatcagccga gaacaagtat taaatattcg | 2400 |
| tgatctaaca cgctatgatc caggcatttc agttgtagaa caaggtcgcg gtgcaagttc | 2460 |
| tggatattct attcgtggta tggacagaaa tagagttgct ttattagtag atggtttacc | 2520 |
| tcaaacgcaa tctatgtag tgcaaagccc tttagttgct cgttcaggat attctggcac | 2580 |
| tggtgcaatt aatgaaattg aatatgaaaa tgtaaaggcc gtcgaaataa gcaagggggg | 2640 |
| gagttcttct gagtatggta atggagcact agctggttct gtaacatttc aaagcaaatc | 2700 |
| cgcagccgat atcttagaag gagacaaatc atggggaatt caaactaaaa atgcttattc | 2760 |
| aagcaaaaat aaaggcttta cccattcttt agctgtagca ggaaaacaag gtggatttga | 2820 |
| aggggtcgcc atttcacactc aacgaaattc ggaggaaacc caagtccata aagatgcatt | 2880 |

```
aaaaggcgta caaagttatg agcgattcat cgccacaaca gataaatctt caggatactt    2940
tgtgatacaa ggtgagtgtc caaatggtga tgacaagtgt gcagccaaac cacctgcaaa    3000
gttatccccc caaagcgaaa ccgtaagcgt ttcagattat acggggcta accgtatcaa     3060
acctaatcca atgaaatatg aaagccagtc ttggttttta agaggagggt atcattttc     3120
tgaacaacac tatattggtg gtattttga attcacacaa caaaaatttg atatccgtga     3180
tatgacattt cccgcttatt taagatcaac agaaaaacgg gatgatagaa ctggcccttt    3240
ttatccaaag caagattatg gtgcatatca acgtattgag gatggccgag gcgttaacta    3300
tgcaagtggg ctttatttcg atgaacacca tagaaaacag cgtgtaggta ttgaatatat    3360
ttacgaaaat aagaacaaag cgggcatcat tgacaaagca gtgttaagtg ctaatcaaca    3420
aaacatcata cttgacagtt atatgcgaca tacgcattgc agtctttatc ctaatccaag    3480
taagaattgc cgcccgacac ttgataaacc ttattcatac tatcgttctg atagaaatgt    3540
ttataaagaa aaacataata tgttgcaatt gaatttagag aaaaaaattc aacaaaattg    3600
gcttactcat caaattgtct tcaatcttgg ttttgatgac tttacttcag cgcttcagca    3660
taaagattat ttaactcgac gtgttaccgc tacggcaaat attatttcag ggacagttgc    3720
tggtaaacga gaaatggtt acgaaaaaca accttactta tactcaaaac caaaagtaga    3780
ttttgtagga caagatcatt gtaattataa aggtagctcc tctaattaca gcgactgtaa    3840
agtgcggtta attaaaggga aaattatta tttcgcagca cgcaataata tggcattagg    3900
gaaatacatt gatttaggtt taggtattcg gtatgacgta tctcgtacaa aagctaatga    3960
atcaactatt agtgttggta aatttaaaaa tttctcttgg aatactggta ttgtcataaa    4020
accaacggaa tggcttgatc tttcttatcg cctttctact ggatttagaa atcctagttt    4080
tgctgaaatg tatggttggc ggtatggtgg caataatagc gatgtttatg taggtaaatt    4140
taagcctgaa acatctcgta accaagagtt tggtctcgct ctaaaagggg attttggtaa    4200
tattgagatc agtcatttta gtaatgctta tcgaaatctt atcgcctttg ctgaagaact    4260
tagtaaaaat ggaactactg gaaagggcaa ttatggatat cataatgcac aaaatgcaaa    4320
attagttggc gtaaatataa ctgcgcaatt agatttttaat ggtttatgga acgtattcc    4380
ctacggttgg tatgcaacat tgcttataa ccgagtaaaa gttaaagatc aaaaaatcaa    4440
tgctggtttg gcctccgtaa gcagttattt atttgatgcc attcagccca gccgttatat    4500
cattggttta ggctatgatc atccaagtaa tacttgggga attaatacaa tgtttactca    4560
atcaaaagca aaatctcaaa atgaattgct aggacaacgt gcattgggta acaattcaag    4620
gaatgtaaaa tcaacaagaa aacttactcg ggcatggcat atcttagatg tatcgggtta    4680
ttacatggcg aataaaaata ttatgcttcg attagggata tataatttat tcaactatcg    4740
ctatgttact tgggaagcgg tgcgtcaaac agcacaaggt gcggtcaatc aacatcaaaa    4800
tgttggtagc tatactcgct acgcagcatc aggacgaaac tataccttaa cattagaaat    4860
gaaattctaa attaaaatgc gccagatgga ctagatatgc tatatctata ccttactggc    4920
gcatcttttt ctgttctata atctgcttaa gtgaaaaacc aaacttggat tttttacaag    4980
atcttttcac gcatttattg taaaatctcc gacaattttt accgcacttt tctctattac    5040
aaaaacaata aggatccttt tgtgactctc tcaatctttg gcaagttgct gttacaactt    5100
cagatcaagt ttcagccagc gatcttaggc acttgggttc ggcc                    5144
```

<210> SEQ ID NO 106

```
<211> LENGTH: 168
<212> TYPE: PRT
<213> ORGANISM: Haemophilus influenzae

<400> SEQUENCE: 106

Met Lys Ser Val Pro Leu Ile Ser Gly Gly Leu Ser Phe Leu Leu Ser
 1               5                  10                  15

Ala Cys Ser Gly Gly Gly Ser Phe Asp Val Asp Asn Val Ser Asn Pro
             20                  25                  30

Ser Ser Ser Lys Pro Arg Tyr Gln Asp Asp Thr Ser Asn Gln Arg Thr
         35                  40                  45

Lys Ser Asp Leu Gln Lys Leu Ser Ile Pro Ser Leu Gly Gly Gly Met
     50                  55                  60

Lys Leu Val Ala Gln Asn Leu Gly Lys Lys Glu Pro Ser Leu Leu
 65                  70                  75                  80

Asn Asn Glu Asp Gly Tyr Met Ile Phe Ser Ser Leu Ser Thr Ile Glu
                 85                  90                  95

Glu Asp Val Thr Lys Glu Asn Lys Ser Gln Glu Pro Thr Ile Gly Ser
            100                 105                 110

Ile Asp Glu Pro Ser Lys Thr Asn Ser Pro Gln Asn His His Gly Asn
        115                 120                 125

Met Tyr Ile Arg Val Phe Ile Ile Phe Asn Arg Gly Val Ile Pro Gln
    130                 135                 140

Met Ala Ser Phe Ile Gln Val Thr Met Asp Met Arg Ile Thr Leu Ala
145                 150                 155                 160

Ser Lys Gln Pro Leu His Tyr Leu
                165

<210> SEQ ID NO 107
<211> LENGTH: 911
<212> TYPE: PRT
<213> ORGANISM: Haemophilus influenzae

<400> SEQUENCE: 107

Met Thr Lys Lys Pro Tyr Phe Arg Leu Ser Ile Ile Ser Cys Leu Leu
 1               5                  10                  15

Ile Ser Cys Tyr Val Lys Ala Glu Thr Gln Ser Ile Lys Asp Thr Lys
             20                  25                  30

Glu Ala Ile Ser Ser Glu Val Asp Thr Gln Ser Thr Glu Asp Ser Glu
         35                  40                  45

Leu Glu Thr Ile Ser Val Thr Ala Glu Lys Ile Arg Asp Arg Lys Asp
     50                  55                  60

Asn Glu Val Thr Gly Leu Gly Lys Ile Ile Lys Thr Ser Glu Ser Ile
 65                  70                  75                  80

Ser Arg Glu Gln Val Leu Asn Ile Arg Asp Leu Thr Arg Tyr Asp Pro
                 85                  90                  95

Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
        115                 120                 125

Pro Gln Thr Gln Ser Tyr Val Val Gln Ser Pro Leu Val Ala Arg Ser
    130                 135                 140

Gly Tyr Ser Gly Thr Gly Ala Ile Asn Glu Ile Glu Tyr Glu Asn Val
145                 150                 155                 160

Lys Ala Val Glu Ile Ser Lys Gly Gly Ser Ser Glu Tyr Gly Asn
                165                 170                 175
```

```
Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
            195                 200                 205

Ser Ser Lys Asn Lys Gly Phe Thr His Ser Leu Ala Val Ala Gly Lys
            210                 215                 220

Gln Gly Gly Phe Glu Gly Val Ala Ile Tyr Thr Gln Arg Asn Ser Glu
225                 230                 235                 240

Glu Thr Gln Val His Lys Asp Ala Leu Lys Gly Val Gln Ser Tyr Glu
            245                 250                 255

Arg Phe Ile Ala Thr Thr Asp Lys Ser Ser Gly Tyr Phe Val Ile Gln
            260                 265                 270

Gly Glu Cys Pro Asn Gly Asp Asp Lys Cys Ala Ala Lys Pro Pro Ala
            275                 280                 285

Lys Leu Ser Pro Gln Ser Glu Thr Val Ser Val Ser Asp Tyr Thr Gly
            290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
            325                 330                 335

Ile Phe Glu Phe Thr Gln Gln Lys Phe Asp Ile Arg Asp Met Thr Phe
            340                 345                 350

Pro Ala Tyr Leu Arg Ser Thr Glu Lys Arg Asp Asp Arg Thr Gly Pro
            355                 360                 365

Phe Tyr Pro Lys Gln Asp Tyr Gly Ala Tyr Gln Arg Ile Glu Asp Gly
            370                 375                 380

Arg Gly Val Asn Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
            405                 410                 415

Gly Ile Ile Asp Lys Ala Val Leu Ser Ala Asn Gln Gln Asn Ile Ile
            420                 425                 430

Leu Asp Ser Tyr Met Arg His Thr His Cys Ser Leu Tyr Pro Asn Pro
            435                 440                 445

Ser Lys Asn Cys Arg Pro Thr Leu Asp Lys Pro Tyr Ser Tyr Tyr Arg
            450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
            485                 490                 495

Asn Leu Gly Phe Asp Asp Phe Thr Ser Ala Leu Gln His Lys Asp Tyr
            500                 505                 510

Leu Thr Arg Arg Val Thr Ala Thr Ala Asn Ile Ile Ser Gly Thr Val
            515                 520                 525

Ala Gly Lys Arg Arg Asn Gly Tyr Glu Lys Gln Pro Tyr Leu Tyr Ser
            530                 535                 540

Lys Pro Lys Val Asp Phe Val Gly Gln Asp His Cys Asn Tyr Lys Gly
545                 550                 555                 560

Ser Ser Ser Asn Tyr Ser Asp Cys Lys Val Arg Leu Ile Lys Gly Lys
            565                 570                 575

Asn Tyr Tyr Phe Ala Ala Arg Asn Asn Met Ala Leu Gly Lys Tyr Ile
            580                 585                 590
```

-continued

```
Asp Leu Gly Leu Gly Ile Arg Tyr Asp Val Ser Arg Thr Lys Ala Asn
            595                 600                 605

Glu Ser Thr Ile Ser Val Gly Lys Phe Lys Asn Phe Ser Trp Asn Thr
        610                 615                 620

Gly Ile Val Ile Lys Pro Thr Glu Trp Leu Asp Leu Ser Tyr Arg Leu
625                 630                 635                 640

Ser Thr Gly Phe Arg Asn Pro Ser Phe Ala Glu Met Tyr Gly Trp Arg
                645                 650                 655

Tyr Gly Gly Asn Asn Ser Asp Val Tyr Val Gly Lys Phe Lys Pro Glu
            660                 665                 670

Thr Ser Arg Asn Gln Glu Phe Gly Leu Ala Leu Lys Gly Asp Phe Gly
        675                 680                 685

Asn Ile Glu Ile Ser His Phe Ser Asn Ala Tyr Arg Asn Leu Ile Ala
690                 695                 700

Phe Ala Glu Glu Leu Ser Lys Asn Gly Thr Thr Gly Lys Gly Asn Tyr
705                 710                 715                 720

Gly Tyr His Asn Ala Gln Asn Ala Lys Leu Val Gly Val Asn Ile Thr
                725                 730                 735

Ala Gln Leu Asp Phe Asn Gly Leu Trp Lys Arg Ile Pro Tyr Gly Trp
            740                 745                 750

Tyr Ala Thr Phe Ala Tyr Asn Arg Val Lys Val Lys Asp Gln Lys Ile
        755                 760                 765

Asn Ala Gly Leu Ala Ser Val Ser Ser Tyr Leu Phe Asp Ala Ile Gln
770                 775                 780

Pro Ser Arg Tyr Ile Ile Gly Leu Gly Tyr Asp His Pro Ser Asn Thr
785                 790                 795                 800

Trp Gly Ile Asn Thr Met Phe Thr Gln Ser Lys Ala Lys Ser Gln Asn
                805                 810                 815

Glu Leu Leu Gly Gln Arg Ala Leu Gly Asn Asn Ser Arg Asn Val Lys
            820                 825                 830

Ser Thr Arg Lys Leu Thr Arg Ala Trp His Ile Leu Asp Val Ser Gly
        835                 840                 845

Tyr Tyr Met Ala Asn Lys Asn Ile Met Leu Arg Leu Gly Ile Tyr Asn
850                 855                 860

Leu Phe Asn Tyr Arg Tyr Val Thr Trp Glu Ala Val Arg Gln Thr Ala
865                 870                 875                 880

Gln Gly Ala Val Asn Gln His Gln Asn Val Gly Ser Tyr Thr Arg Tyr
                885                 890                 895

Ala Ala Ser Gly Arg Asn Tyr Thr Leu Thr Leu Glu Met Lys Phe
            900                 905                 910
```

<210> SEQ ID NO 108
<211> LENGTH: 1993
<212> TYPE: DNA
<213> ORGANISM: Haemophilus influenzae

<400> SEQUENCE: 108

```
atatgaaatc tgtacctctt atctctggtg gactttcctt tttattaagt gcttgtagcg     60
ggggaggtgg ttcttttgat gtagatgacg tctctaatcc ctcctcttct aaaccacgtt    120
atcaagacga tacttcaagt tcaagaacaa aatctaaatt ggaaaatttg tccattcctt    180
ctttaggggg agggatgaag ttagtggctc agaatcttcg tgataggaca aaacctagtc    240
tcttaaatga agatgactat atgatatttt cctcactttc aacgattaaa gctgatgttg    300
aaaaagaaaa taaacactat acaagtccag ttggctcaat agacgagcct agtacaacaa    360
```

-continued

```
atccaaaaga aaatgatcat ggacaaagat atgtatattc aggactttat tatattccat      420
cgtggaattt aaacgatctt aaaaataaca agtattatta ttctggttac tatggatatg      480
cgtattactt tggcaagcaa acagccacta cattacctgt aaatggcaaa gtaacgtata      540
aaggaacttg gagcttcatc accgcagctg aaaatggcaa aaggtatcct tgttaagta       600 atggcagtca agcttatttt cgacgtagtg caattccaga agatattgat ttagaagtta      660
aaaatgatga gaatagagaa aaagggctag tgagtgaatt tagtgcagat tttgggacta      720
aaaaactgac aggaggactg ttttacacca aaagacaaac tcatattcaa aaccatgaaa      780
agaaaaaact ctatgatata gatgcccata tttatagtaa tagattcaga ggtaaagtaa      840
atcctaccca aaaagattct aaagaacatc cctttaccag cgagggaaca ttagaaggtg      900 gttttttacgg gcctgaaggt caagaattag gaggaaagtt tttagctggc gacaaaaaag    960
ttttgggggt atttagtgcc aaaggaacgg aagaaaacaa aaaattaccc aaagaaacct     1020
taattgatgg caagctaact actttctcta ctaaaacaac cgatgcaaaa accaatgcaa     1080
cagccaatgc aacaaccagt accgcagcca atacaacaac cgatacaaca gccaatacaa     1140
taaccgatgc agaaaacttt aagacgaaag atatatcaag ttttggtgaa gctgattacc     1200
ttttaattga taattacccct gttcctcttt tacctgagag tggtgatttc ataagtagta     1260
agcaccatac tgtaggaaag aaaacctatc aagtaaaagc atgttgcagt aatctaagct     1320
atgtgaaatt tggtatgtat tatgaagtcc cacctaaaga agaagaaaaa gacaaagaaa     1380
aaaaagaaaa agaaaagaa aaacaagcga caaatctatc gaacacttat tatcaattct      1440
tattaggtct ccgtactccc agttctgaaa ttcctaaagg aggaagtgca aaatatctcg     1500
gtagttggtt tggttatctg agcgatggtt caacatctta ctcccccagt ggtgataaga     1560
aacgcgagaa caatgctctc gccgagttta atgtaaattt tgtcgataaa acattaaaag     1620
gccaattaat acgacacgat aatcaaaata ccgttttac aattgatgca acctttaaag      1680
gtggtaagaa taacttcact ggtacagcaa ccgcaaacaa tgtagcgatt gatccccaaa     1740
gtacacaagg cacatctaac gtcaatttca cggcaacagt aaatgggca tttatgggc      1800 cgaacgctac agaattaggc ggttatttca cctataacgg aaatcctaca gataaaagtt     1860
cctcaaccgt accttcatca tccaattcaa aaaatgcaag agctgcagtt gtctttggtg     1920
cgagacaaca agtagaaaca accaaataat ggaatactaa aaatgactaa aaaagcttct     1980
agaagccgaa ttc                                                        1993
```

<210> SEQ ID NO 109
<211> LENGTH: 648
<212> TYPE: PRT
<213> ORGANISM: Haemophilus influenzae

<400> SEQUENCE: 109

```
Met Lys Ser Val Pro Leu Ile Ser Gly Gly Leu Ser Phe Leu Leu Ser
 1               5                  10                  15

Ala Cys Ser Gly Gly Gly Gly Ser Phe Asp Val Asp Asp Val Ser Asn
            20                  25                  30

Pro Ser Ser Ser Lys Pro Arg Tyr Gln Asp Asp Thr Ser Ser Ser Arg
        35                  40                  45

Thr Lys Ser Lys Leu Glu Asn Leu Ser Ile Pro Ser Leu Gly Gly Gly
    50                  55                  60

Met Lys Leu Val Ala Gln Asn Leu Arg Asp Arg Thr Lys Pro Ser Leu
65                  70                  75                  80
```

-continued

```
Leu Asn Glu Asp Asp Tyr Met Ile Phe Ser Ser Leu Ser Thr Ile Lys
                85                  90                  95
Ala Asp Val Glu Lys Glu Asn Lys His Tyr Thr Ser Pro Val Gly Ser
            100                 105                 110
Ile Asp Glu Pro Ser Thr Thr Asn Pro Lys Glu Asn Asp His Gly Gln
        115                 120                 125
Arg Tyr Val Tyr Ser Gly Leu Tyr Tyr Ile Pro Ser Trp Asn Leu Asn
    130                 135                 140
Asp Leu Lys Asn Asn Lys Tyr Tyr Ser Gly Tyr Gly Tyr Ala
145                 150                 155                 160
Tyr Tyr Phe Gly Lys Gln Thr Ala Thr Thr Leu Pro Val Asn Gly Lys
                165                 170                 175
Val Thr Tyr Lys Gly Thr Trp Ser Phe Ile Thr Ala Ala Glu Asn Gly
            180                 185                 190
Lys Arg Tyr Pro Leu Leu Ser Asn Gly Ser Gln Ala Tyr Phe Arg Arg
        195                 200                 205
Ser Ala Ile Pro Glu Asp Ile Asp Leu Glu Val Lys Asn Asp Glu Asn
    210                 215                 220
Arg Glu Lys Gly Leu Val Ser Glu Phe Ser Ala Asp Phe Gly Thr Lys
225                 230                 235                 240
Lys Leu Thr Gly Gly Leu Phe Tyr Thr Lys Arg Gln Thr His Ile Gln
                245                 250                 255
Asn His Glu Lys Lys Lys Leu Tyr Asp Ile Asp Ala His Ile Tyr Ser
            260                 265                 270
Asn Arg Phe Arg Gly Lys Val Asn Pro Thr Gln Lys Asp Ser Lys Glu
        275                 280                 285
His Pro Phe Thr Ser Glu Gly Thr Leu Glu Gly Gly Phe Tyr Gly Pro
    290                 295                 300
Glu Gly Gln Glu Leu Gly Gly Lys Phe Leu Ala Gly Asp Lys Lys Val
305                 310                 315                 320
Phe Gly Val Phe Ser Ala Lys Gly Thr Glu Glu Asn Lys Lys Leu Pro
                325                 330                 335
Lys Glu Thr Leu Ile Asp Gly Lys Leu Thr Thr Phe Ser Thr Lys Thr
            340                 345                 350
Thr Asp Ala Lys Thr Asn Ala Thr Ala Asn Ala Thr Thr Ser Thr Ala
        355                 360                 365
Ala Asn Thr Thr Thr Asp Thr Thr Ala Asn Thr Ile Thr Asp Ala Glu
    370                 375                 380
Asn Phe Lys Thr Lys Asp Ile Ser Ser Phe Gly Glu Ala Asp Tyr Leu
385                 390                 395                 400
Leu Ile Asp Asn Tyr Pro Val Pro Leu Leu Pro Glu Ser Gly Asp Phe
                405                 410                 415
Ile Ser Ser Lys His His Thr Val Gly Lys Lys Thr Tyr Gln Val Lys
            420                 425                 430
Ala Cys Cys Ser Asn Leu Ser Tyr Val Lys Phe Gly Met Tyr Tyr Glu
        435                 440                 445
Val Pro Pro Lys Glu Glu Lys Asp Lys Glu Lys Glu Lys Glu
    450                 455                 460
Lys Glu Lys Gln Ala Thr Asn Leu Ser Asn Thr Tyr Tyr Gln Phe Leu
465                 470                 475                 480
Leu Gly Leu Arg Thr Pro Ser Ser Glu Ile Pro Lys Gly Gly Ser Ala
                485                 490                 495
```

```
Lys Tyr Leu Gly Ser Trp Phe Gly Tyr Leu Ser Asp Gly Ser Thr Ser
            500                 505                 510

Tyr Ser Pro Ser Gly Asp Lys Lys Arg Glu Asn Asn Ala Leu Ala Glu
        515                 520                 525

Phe Asn Val Asn Phe Val Asp Lys Thr Leu Lys Gly Gln Leu Ile Arg
        530                 535                 540

His Asp Asn Gln Asn Thr Val Phe Thr Ile Asp Ala Thr Phe Lys Gly
545                 550                 555                 560

Gly Lys Asn Asn Phe Thr Gly Thr Ala Thr Asn Asn Val Ala Ile
                565                 570                 575

Asp Pro Gln Ser Thr Gln Gly Thr Ser Asn Val Asn Phe Thr Ala Thr
            580                 585                 590

Val Asn Gly Ala Phe Tyr Gly Pro Asn Ala Thr Glu Leu Gly Gly Tyr
        595                 600                 605

Phe Thr Tyr Asn Gly Asn Pro Thr Asp Lys Ser Ser Ser Thr Val Pro
        610                 615                 620

Ser Ser Ser Asn Ser Lys Asn Ala Arg Ala Ala Val Val Phe Gly Ala
625                 630                 635                 640

Arg Gln Gln Val Glu Thr Thr Lys
                645

<210> SEQ ID NO 110
<211> LENGTH: 1974
<212> TYPE: DNA
<213> ORGANISM: Haemophilus influenzae

<400> SEQUENCE: 110
gaattcggct tggatccata tgaaatctgt acctcttatc tctggtggac tttccttttt      60
actaagtgct tgtagcggag gggggtcttt tgatgtagat aacgtctcta atccatcctc     120
ttctaaacca cgttatcaag acgatacttc aagttcaaga acaaaatcta atttgaaaaa     180
gttgtccatt ccttctttag ggggagggat gaagttagtg gctcagaatc ttagtgataa     240
gaacaaacct agtctcttaa atgaagatga ctatatatca tattttttcct cactttctac     300 aattcaagat gatgttaaaa agaaaataa acgccataca aatccagttg gctcaataga     360
cgagcctaac gcaacaaatc cacccgaaaa gcatcatgga caaagatatg tatattcagg     420
gctttattat attccatcgt ggagtcattc ctcaaatggc aagctttatt taggttacta     480
tggatatgcg ttttattatg gtaataaaac tgcaacaaac ttgccagtaa gcggcatagc     540
taaatacaaa ggaacttggg attttattac tgcaactaaa aatggccaac gttattcttt     600
atttggtagc gcttttggag cttataatag acgcagtgct atttcagaag atatagataa     660
tttagaaaat aatctaaaga atggtgcggg attaactagt gaatttactg tcaattttgg     720
tacgaaaaag ctcactggaa aactttatta taatgaaagg gaaacaaatc ttaataaatt     780
acaaaagaga aaacatgaac tctatgatat agatgccgat atttatagta atagattcag     840
aggtaaagta aagccaacaa cccaaaaaga ttctcaagaa catcccttta ccagcgaggg     900
aacattagaa ggtggttttt atgggcctaa cggtgaagaa ttaggaggaa gttttttagc     960
tggcgataac cgagttttg gggtatttag tgccaaagaa gaagaaacaa agacaaaaa    1020 attatccaga gaaccttaa ttgatggcaa gctaattact tttaaaagaa ctgatgcaac    1080
aaccaataca gcagccaatg caaaaaccga tgaaaaaaac tttacgacga agatatacc    1140 aagttttggt gaagctgatt accttttaat tgataattac cctgttcctc ttttccctga    1200
agaaaatact aatgatttca taactagtag gcaccataag gtaggagata aaacctataa    1260
```

-continued

```
agtagaagca tgttgcaaga atctaagcta tgtgaaattt ggtatgtatt atgaagaccc    1320
attaaatgga gaaatggca agaaaaaga aaagaaaaa gaaaagaca agaaaaaca        1380 agcgacaaca tctatcaaga cttattatca attcttatta ggtcaccgta ctgccaaggc    1440
cgacatacct gcaacgggaa acgtgaaata tcgcggtaat tggtttggtt atattggtga    1500
tgacaagaca tcttactcca ctactggaga taaaaatgct gtcgccgagt ttgatgtaaa    1560
ttttgccgat aaaacattaa caggcacatt aaaacgacac gataatggaa atcccgtatt    1620
tacaattaat gcaagctttc aaagtggtaa gaatgacttc actggtacag caaccgcaaa    1680
caatgtagcg attgatcccc aaaatacaca accacatct agagtcaatt tcacggcaac    1740
agtaaacggg gcattttatg gacctaaggc tacagaatta ggcggttatt tcacttataa    1800
cggaaacaat cctacagata aaattcctc aaccgtttca ccatccaatt cagcaaatgc    1860
tcgtgctgcc gttgtgtttg cgctaaaaa acaagtagaa acaaccaaca agtaaaaaca    1920
accaagtaat ggaatactaa aaatgactaa aaagcttct agaaagccga attc           1974
```

<210> SEQ ID NO 111
<211> LENGTH: 631
<212> TYPE: PRT
<213> ORGANISM: Haemophilus influenzae

<400> SEQUENCE: 111

```
Met Lys Ser Val Pro Leu Ile Ser Gly Gly Leu Ser Phe Leu Leu Ser
  1               5                  10                  15

Ala Cys Ser Gly Gly Ser Phe Asp Val Asp Asn Val Ser Asn Pro
              20                  25                  30

Ser Ser Ser Lys Pro Arg Tyr Gln Asp Asp Thr Ser Ser Ser Arg Thr
          35                  40                  45

Lys Ser Asn Leu Lys Lys Leu Ser Ile Pro Ser Leu Gly Gly Gly Met
      50                  55                  60

Lys Leu Val Ala Gln Asn Leu Ser Asp Lys Asn Lys Pro Ser Leu Leu
  65                  70                  75                  80

Asn Glu Asp Asp Tyr Ile Ser Tyr Phe Ser Leu Ser Thr Ile Gln
                  85                  90                  95

Asp Asp Val Lys Lys Glu Asn Lys Arg His Thr Asn Pro Val Gly Ser
              100                 105                 110

Ile Asp Glu Pro Asn Ala Thr Asn Pro Pro Glu Lys His His Gly Gln
          115                 120                 125

Arg Tyr Val Tyr Ser Gly Leu Tyr Tyr Ile Pro Ser Trp Ser His Ser
      130                 135                 140

Ser Asn Gly Lys Leu Tyr Leu Gly Tyr Tyr Gly Tyr Ala Phe Tyr Tyr
 145                 150                 155                 160

Gly Asn Lys Thr Ala Thr Asn Leu Pro Val Ser Gly Ile Ala Lys Tyr
                 165                 170                 175

Lys Gly Thr Trp Asp Phe Ile Thr Ala Thr Lys Asn Gly Gln Arg Tyr
             180                 185                 190

Ser Leu Phe Gly Ser Ala Phe Gly Ala Tyr Asn Arg Arg Ser Ala Ile
         195                 200                 205

Ser Glu Asp Ile Asp Asn Leu Glu Asn Leu Lys Asn Gly Ala Gly
     210                 215                 220

Leu Thr Ser Glu Phe Thr Val Asn Phe Gly Thr Lys Lys Leu Thr Gly
 225                 230                 235                 240

Lys Leu Tyr Tyr Asn Glu Arg Glu Thr Asn Leu Asn Lys Leu Gln Lys
```

```
                    245                 250                 255
Arg Lys His Glu Leu Tyr Asp Ile Asp Ala Asp Ile Tyr Ser Asn Arg
                260                 265                 270
Phe Arg Gly Lys Val Lys Pro Thr Thr Gln Lys Asp Ser Gln Glu His
            275                 280                 285
Pro Phe Thr Ser Glu Gly Thr Leu Glu Gly Phe Tyr Gly Pro Asn
        290                 295                 300
Gly Glu Glu Leu Gly Gly Lys Phe Leu Ala Gly Asp Asn Arg Val Phe
305                 310                 315                 320
Gly Val Phe Ser Ala Lys Glu Glu Thr Lys Asp Lys Lys Leu Ser
                325                 330                 335
Arg Glu Thr Leu Ile Asp Gly Lys Leu Ile Thr Phe Lys Arg Thr Asp
                340                 345                 350
Ala Thr Thr Asn Thr Ala Ala Asn Ala Lys Thr Asp Glu Lys Asn Phe
                355                 360                 365
Thr Thr Lys Asp Ile Pro Ser Phe Gly Glu Ala Asp Tyr Leu Leu Ile
            370                 375                 380
Asp Asn Tyr Pro Val Pro Leu Phe Pro Glu Glu Asn Thr Asn Asp Phe
385                 390                 395                 400
Ile Thr Ser Arg His His Lys Val Gly Asp Lys Thr Tyr Lys Val Glu
                405                 410                 415
Ala Cys Cys Lys Asn Leu Ser Tyr Val Lys Phe Gly Met Tyr Tyr Glu
                420                 425                 430
Asp Pro Leu Asn Gly Glu Asn Gly Lys Glu Lys Glu Lys Glu Lys Glu
            435                 440                 445
Lys Asp Lys Glu Lys Gln Ala Thr Thr Ser Ile Lys Thr Tyr Tyr Gln
        450                 455                 460
Phe Leu Leu Gly His Arg Thr Ala Lys Ala Asp Ile Pro Ala Thr Gly
465                 470                 475                 480
Asn Val Lys Tyr Arg Gly Asn Trp Phe Gly Tyr Ile Gly Asp Asp Lys
                485                 490                 495
Thr Ser Tyr Ser Thr Thr Gly Asp Lys Asn Ala Val Ala Glu Phe Asp
            500                 505                 510
Val Asn Phe Ala Asp Lys Thr Leu Thr Gly Thr Leu Lys Arg His Asp
        515                 520                 525
Asn Gly Asn Pro Val Phe Thr Ile Asn Ala Ser Phe Gln Ser Gly Lys
530                 535                 540
Asn Asp Phe Thr Gly Thr Ala Thr Ala Asn Asn Val Ala Ile Asp Pro
545                 550                 555                 560
Gln Asn Thr Gln Thr Thr Ser Arg Val Asn Phe Thr Ala Thr Val Asn
                565                 570                 575
Gly Ala Phe Tyr Gly Pro Lys Ala Thr Glu Leu Gly Gly Tyr Phe Thr
                580                 585                 590
Tyr Asn Gly Asn Asn Pro Thr Asp Lys Asn Ser Ser Thr Val Ser Pro
            595                 600                 605
Ser Asn Ser Ala Asn Ala Arg Ala Ala Val Val Phe Gly Ala Lys Lys
        610                 615                 620
Gln Val Glu Thr Thr Asn Lys
625                 630
```

<210> SEQ ID NO 112
<211> LENGTH: 1951
<212> TYPE: DNA
<213> ORGANISM: Haemophilus influenzae

<400> SEQUENCE: 112

```
atgaaatctg tacctcttat ctctggtgga ctttcccttt tattaagtgc ttgtagcggg      60
ggaggtggtt cttttgatgt agatgacgtc tctaatccct cctcttctaa accacgttat     120
caagacgata cctcgagtca agaacaaaa tctaatttgg aaaagttgtc cattccttct      180
ttaggaggag ggatgaaatt ggtggctcag aatctgagtg gtaataaaga acctagtttc    240
ttaaatggaa atgactatat gatatttttcc tcacgttcta cgattaaaga tgatgttgaa    300
aataacaata caaacggggg ggactatatt ggctcaatag acgagcctag tacaacaaat   360
ccactcgaaa agcatcatgg acaaaggtat gtatattcag ggctttatta tattcaatcg   420
tggagtctaa gagatttacc aaagaagttt tattcaggtt actatggata tgcgtattac   480
tttggcaagg aaacagccac tacattacct gtaaatggcg aagcaacgta taaggaact    540
tgggatttca tcactgcaac tagaaatggc aaaagttatt ctttgttaag taataaccga   600
caagcttatt ccaaacgtag tgcaattcca gaagacattg atttagaaaa tgatccaaag   660
aatggtgaga cgagattaac tagtgaattt actgtgaatt ttggtacgaa aaagctcaca   720
ggtggacttt attaccattt acgtaaaaca atgctaatg aaaaccaaaa tagaaaacat    780
aaactctaca atctagaagc tgatgtgtat agcaaccgat tcagaggtaa agtaaagcca   840
accaaagagt cttctgaaga acatcccttt accagcgagg gaacattaga aggtggtttt    900
tatgggccta atgctgaaga actagggga aaattttttag ctagcgataa aaagttttt    960
ggggtattta gtgccaaaga acagcaagaa acggaagaaa acaaaaaatt actcaaagaa  1020
accttaattg atggcaagct aactactttc tctactaaaa aaaccaatgc aacaaccgat   1080
gcaacaacca gtacaacaac cagtacagca accaatgcaa cagccgatgc agaaaacttt   1140
acgacaaaag atatatcaag ttttggtgaa gctgattatc ttttaattga taattaccct   1200
gttcctcttt tacctgaaaa tactaatgat ttcataagca gtaagcacca tgaggtagga   1260
ggtaaacact ataagtggaa gcatgttgc aagaatctaa gctatgtgaa atttggtata   1320
tattatgagg ataatgagaa gaacaccaaa attgaaacag aacaatacca ccaatttttg  1380
ttaggtctcc gtactcccag ttctcaaatt cctgcaacgg gaaacgtgaa atatcgcggt   1440
agttggtttg gttatatttgg tgatgacaag acatcttact ccactactgg agataaaat   1500
gctctcgccg agtttgatgt aaatttaccc gataaaaagc taacaggcga attaaaacga  1560
gccgataatc aaaataccgt atttagaatt aatgcagact ttaaaaataa tgataatgcc  1620
ttcaaaggta cagcaaccgc agaaaatttt gtaatagatg gtaacaatag tcaaactgga  1680
aatacccaaa ttaatattaa aactgaagta atgggggcat tttatggtcc gaacgctaca  1740
gaattaggcg gttatttcac ttataacgga aaaaatccta cagataaaaa ttctgaaagt  1800
tcctcaaccg taccttcacc acccaattca ccaaatgcaa gagctgcagt tgtctttggt   1860
gctaaaaaac aagtagaaaa aaacaacaag taaaacaac caagtaatgg aatactaaaa  1920
atgactaaaa aagcttctag aagccgaatt c                                  1951
```

<210> SEQ ID NO 113
<211> LENGTH: 630
<212> TYPE: PRT
<213> ORGANISM: Haemophilus influenzae

<400> SEQUENCE: 113

```
Met Lys Ser Val Pro Leu Ile Ser Gly Gly Leu Ser Leu Leu Leu Ser
  1               5                  10                  15
```

-continued

```
Ala Cys Ser Gly Gly Gly Ser Phe Asp Val Asp Val Ser Asn
             20                  25                  30

Pro Ser Ser Lys Pro Arg Tyr Gln Asp Thr Ser Ser Gln Arg
         35                  40                  45

Thr Lys Ser Asn Leu Glu Lys Leu Ser Ile Pro Ser Leu Gly Gly Gly
     50                  55                  60

Met Lys Leu Val Ala Gln Asn Leu Ser Gly Asn Lys Glu Pro Ser Phe
 65                  70                  75                  80

Leu Asn Gly Asn Asp Tyr Met Ile Phe Ser Ser Arg Ser Thr Ile Lys
                 85                  90                  95

Asp Val Glu Asn Asn Asn Thr Asn Gly Gly Asp Tyr Ile Gly Ser
             100                 105                 110

Ile Asp Glu Pro Ser Thr Thr Asn Pro Leu Glu Lys His His Gly Gln
         115                 120                 125

Arg Tyr Val Tyr Ser Gly Leu Tyr Tyr Ile Gln Ser Trp Ser Leu Arg
     130                 135                 140

Asp Leu Pro Lys Lys Phe Tyr Ser Gly Tyr Tyr Gly Tyr Ala Tyr Tyr
145                 150                 155                 160

Phe Gly Lys Glu Thr Ala Thr Thr Leu Pro Val Asn Gly Glu Ala Thr
                 165                 170                 175

Tyr Lys Gly Thr Trp Asp Phe Ile Thr Ala Thr Arg Asn Gly Lys Ser
             180                 185                 190

Tyr Ser Leu Leu Ser Asn Asn Arg Gln Ala Tyr Ser Lys Arg Ser Ala
         195                 200                 205

Ile Pro Glu Asp Ile Asp Leu Glu Asn Asp Pro Lys Asn Gly Glu Thr
     210                 215                 220

Arg Leu Thr Ser Glu Phe Thr Val Asn Phe Gly Thr Lys Lys Leu Thr
225                 230                 235                 240

Gly Gly Leu Tyr Tyr His Leu Arg Lys Thr Asn Ala Asn Glu Asn Gln
                 245                 250                 255

Asn Arg Lys His Lys Leu Tyr Asn Leu Glu Ala Asp Val Tyr Ser Asn
             260                 265                 270

Arg Phe Arg Gly Lys Val Lys Pro Thr Lys Glu Ser Ser Glu Glu His
         275                 280                 285

Pro Phe Thr Ser Glu Gly Thr Leu Glu Gly Gly Phe Tyr Gly Pro Asn
     290                 295                 300

Ala Glu Glu Leu Gly Gly Lys Phe Leu Ala Ser Asp Lys Lys Val Phe
305                 310                 315                 320

Gly Val Phe Ser Ala Lys Glu Gln Gln Glu Thr Glu Glu Asn Lys Lys
                 325                 330                 335

Leu Leu Lys Glu Thr Leu Ile Asp Gly Lys Leu Thr Thr Phe Ser Thr
             340                 345                 350

Lys Lys Thr Asn Ala Thr Thr Asp Ala Thr Thr Ser Thr Thr Thr Ser
         355                 360                 365

Thr Ala Thr Asn Ala Thr Ala Asp Ala Glu Asn Phe Thr Thr Lys Asp
     370                 375                 380

Ile Ser Ser Phe Gly Glu Ala Asp Tyr Leu Leu Ile Asp Asn Tyr Pro
385                 390                 395                 400

Val Pro Leu Leu Pro Glu Asn Thr Asn Asp Phe Ile Ser Ser Lys His
                 405                 410                 415

His Glu Val Gly Gly Lys His Tyr Lys Val Glu Ala Cys Cys Lys Asn
             420                 425                 430
```

```
Leu Ser Tyr Val Lys Phe Gly Ile Tyr Tyr Glu Asp Asn Glu Lys Asn
        435                 440                 445

Thr Lys Ile Glu Thr Glu Gln Tyr His Gln Phe Leu Leu Gly Leu Arg
        450                 455                 460

Thr Pro Ser Ser Gln Ile Pro Ala Thr Gly Asn Val Lys Tyr Arg Gly
465                 470                 475                 480

Ser Trp Phe Gly Tyr Ile Gly Asp Asp Lys Thr Ser Tyr Ser Thr Thr
                485                 490                 495

Gly Asp Lys Asn Ala Leu Ala Glu Phe Asp Val Asn Phe Thr Asp Lys
                500                 505                 510

Lys Leu Thr Gly Glu Leu Lys Arg Ala Asp Asn Gln Asn Thr Val Phe
            515                 520                 525

Arg Ile Asn Ala Asp Phe Lys Asn Asn Asp Asn Ala Phe Lys Gly Thr
530                 535                 540

Ala Thr Ala Glu Asn Phe Val Ile Asp Gly Asn Asn Ser Gln Thr Gly
545                 550                 555                 560

Asn Thr Gln Ile Asn Ile Lys Thr Glu Val Asn Gly Ala Phe Tyr Gly
                565                 570                 575

Pro Asn Ala Thr Glu Leu Gly Gly Tyr Phe Thr Tyr Asn Gly Lys Asn
                580                 585                 590

Pro Thr Asp Lys Asn Ser Glu Ser Ser Ser Thr Val Pro Ser Pro Pro
            595                 600                 605

Asn Ser Pro Asn Ala Arg Ala Ala Val Val Phe Gly Ala Lys Lys Gln
        610                 615                 620

Val Glu Lys Asn Asn Lys
625                 630

<210> SEQ ID NO 114
<211> LENGTH: 1955
<212> TYPE: DNA
<213> ORGANISM: Haemophilus influenzae

<400> SEQUENCE: 114
atgaaatctg tacctcttat ctctggtgga ctttcctttt tactaagtgc ttgtagcgga      60
ggggggtctt ttgatgtaga taacgtctct aataccccct cttctaaacc acgttatcaa     120
gacgatacct cgaatcaaag aacaaaatct aaattggaaa agttgtccat tccttcttta     180
ggaggaggga tgaagttagt tgtgcaaaat tttgctggtg ctaaagaacc tagtttctta     240
aatgaaaatg actatatatc atattttccc tcactttcta tgattaaaga tgatgttgaa     300
aataacaata aaaataagga tactccaatt ggctcaatag acgagcctag agcaccaaat     360
tcaaacgaaa atcatcaaaa tcatcatgga cagcaatatg tatattcggg tctttattat     420
attccatcgt ggcgtctaat aaatttacca ataagttttt attcaggtta ctatggatat     480
gcgtattact ttggcaagca aactgccact acattacctg taaatggcga agcaacgtat     540
aaaggaactt ggagcttcat caccgcaact gaaagaggca aaaattattc tttgttcaat     600
aatagaggtc aagcttattc tcgacgtagt gctactccag gagatattga tttagaaaac     660
ggtgacgcag gcttaacaag tgaatttact gtcaattttg gtacaaaaaa gctcactgga     720
gaaccttatt ataatgaaag ggaaacaaat cttaatcaat caaagataga aaacataaaa     780
ctctacgatc tagaagctga tgtgtatagc aaccgattca gaggtacagt aaagccaacc     840
aaaaaagagt cttctgaaga acatcccttt accagcgagg gaacattaga aggtggtttt     900
tatgggccta atgctgaaga actaggggga aaatttttag ctagcgataa aaaagttttt     960
```

-continued

```
ggggtattta gtgccaaaga aacggaagaa aaaccaaaat tacccaaaga aaccttaatt      1020
gatggcaagc taactacttt ctctaaaaca accgatacaa caaccaataa aacaaccagt      1080
gcaaaaacca atacagaaaa ctttacgaca aaagatatac caagttttgg tgaagctgat      1140
tatcttttaa ttgataatta ccctattccg cttttacctg agagtggtga tttcataagt      1200
agtaagcacc atgaggtagg aggtaaacgc tataaagtgg aagcatgttg caagaatcta      1260
tgctatgtga aatttggtat gtattatgag gataaagaga caacaaaaa tgaaacagac       1320 aaagaaaaag aaaaacaaac gacaacatct atcaagactt attatcaatt cttattaggt      1380
ctccggactc ccagttctga aattcctaaa atgggaaacg tgacatatcg cggtagttgg      1440
tttggttata ttggtgatga caagacatct tactccgcta caggagataa acgacaagat      1500
aaaaatgctc ccgccgagtt taatgctgat tttaacaata aaaagctaac aggcacatca      1560
aaacgacacg ataatcaaaa tcccgtgttt aacattaagg caacctttca aaatggtcgg      1620
aatgactttg aaggtacagc aaccgcagaa aattttgtaa tagatggtaa agatagtcaa      1680
ggaaataccc caattaatat tacaactaaa gtaaacgggg cattttatgg acctgatgct      1740
tctgaattag gcggttattt cacctataac ggaaaagaca ctataactaa aaatactgaa      1800
agttcctcaa ccgtaccttc accacccaat tcaccaaatg caagagctgc agttgtgttt      1860
ggagctaaaa aacaagtaga aacaaccaac aagtagaaaa aaacaaataa tggaatacta      1920
aaatgactaa aaaagcttc tagaaagccg aattc                                  1955
```

<210> SEQ ID NO 115
<211> LENGTH: 631
<212> TYPE: PRT
<213> ORGANISM: Haemophilus influenzae

<400> SEQUENCE: 115

```
Met Lys Ser Val Pro Leu Ile Ser Gly Gly Leu Ser Phe Leu Leu Ser
  1               5                  10                  15

Ala Cys Ser Gly Gly Gly Ser Phe Asp Val Asp Asn Val Ser Asn Thr
                 20                  25                  30

Pro Ser Ser Lys Pro Arg Tyr Gln Asp Asp Thr Ser Asn Gln Arg Thr
             35                  40                  45

Lys Ser Lys Leu Glu Lys Leu Ser Ile Pro Ser Leu Gly Gly Met
         50                  55                  60

Lys Leu Val Val Gln Asn Phe Ala Gly Ala Lys Glu Pro Ser Phe Leu
 65                  70                  75                  80

Asn Glu Asn Asp Tyr Ile Ser Tyr Phe Ser Ser Leu Ser Met Ile Lys
                 85                  90                  95

Asp Asp Val Glu Asn Asn Lys Asn Lys Asp Thr Pro Ile Gly Ser
                100                 105                 110

Ile Asp Glu Pro Arg Ala Pro Asn Ser Asn Glu Asn His Gln Asn His
            115                 120                 125

His Gly Gln Gln Tyr Val Tyr Ser Gly Leu Tyr Tyr Ile Pro Ser Trp
        130                 135                 140

Arg Leu Ile Asn Leu Pro Asn Lys Phe Tyr Gly Tyr Tyr Gly Tyr
145                 150                 155                 160

Ala Tyr Tyr Phe Gly Lys Gln Thr Ala Thr Thr Leu Pro Val Asn Gly
                165                 170                 175

Glu Ala Thr Tyr Lys Gly Thr Trp Ser Phe Ile Thr Ala Thr Glu Arg
            180                 185                 190

Gly Lys Asn Tyr Ser Leu Phe Asn Asn Arg Gly Gln Ala Tyr Ser Arg
```

-continued

```
                195                 200                 205
Arg Ser Ala Thr Pro Gly Asp Ile Asp Leu Glu Asn Gly Asp Ala Gly
    210                 215                 220

Leu Thr Ser Glu Phe Thr Val Asn Phe Gly Thr Lys Lys Leu Thr Gly
225                 230                 235                 240

Glu Pro Tyr Tyr Asn Glu Arg Glu Thr Asn Leu Asn Gln Ser Lys Asp
                245                 250                 255

Arg Lys His Lys Leu Tyr Asp Leu Glu Ala Asp Val Tyr Ser Asn Arg
            260                 265                 270

Phe Arg Gly Thr Val Lys Pro Thr Lys Glu Ser Glu His
        275                 280                 285

Pro Phe Thr Ser Glu Gly Thr Leu Gly Gly Phe Tyr Gly Pro Asn
290                 295                 300

Ala Glu Glu Leu Gly Gly Lys Phe Leu Ala Ser Asp Lys Lys Val Phe
305                 310                 315                 320

Gly Val Phe Ser Ala Lys Glu Thr Glu Lys Pro Lys Leu Pro Lys
                325                 330                 335

Glu Thr Leu Ile Asp Gly Lys Leu Thr Thr Phe Ser Lys Thr Thr Asp
            340                 345                 350

Thr Thr Thr Asn Lys Thr Thr Ser Ala Lys Thr Asn Thr Glu Asn Phe
            355                 360                 365

Thr Thr Lys Asp Ile Pro Ser Phe Gly Glu Ala Asp Tyr Leu Leu Ile
        370                 375                 380

Asp Asn Tyr Pro Ile Pro Leu Leu Pro Glu Ser Gly Asp Phe Ile Ser
385                 390                 395                 400

Ser Lys His His Glu Val Gly Gly Lys Arg Tyr Lys Val Glu Ala Cys
                405                 410                 415

Cys Lys Asn Leu Cys Tyr Val Lys Phe Gly Met Tyr Tyr Glu Asp Lys
            420                 425                 430

Glu Asn Asn Lys Asn Glu Thr Asp Lys Glu Lys Glu Lys Gln Thr Thr
            435                 440                 445

Thr Ser Ile Lys Thr Tyr Tyr Gln Phe Leu Leu Gly Leu Arg Thr Pro
        450                 455                 460

Ser Ser Glu Ile Pro Lys Met Gly Asn Val Thr Tyr Arg Gly Ser Trp
465                 470                 475                 480

Phe Gly Tyr Ile Gly Asp Asp Lys Thr Ser Tyr Ser Ala Thr Gly Asp
                485                 490                 495

Lys Arg Gln Asp Lys Asn Ala Pro Ala Glu Phe Asn Ala Asp Phe Asn
            500                 505                 510

Asn Lys Lys Leu Thr Gly Thr Ser Lys Arg His Asp Asn Gln Asn Pro
            515                 520                 525

Val Phe Asn Ile Lys Ala Thr Phe Gln Asn Gly Arg Asn Asp Phe Glu
        530                 535                 540

Gly Thr Ala Thr Ala Glu Asn Phe Val Ile Asp Gly Lys Asp Ser Gln
545                 550                 555                 560

Gly Asn Thr Pro Ile Asn Ile Thr Thr Lys Val Asn Gly Ala Phe Tyr
                565                 570                 575

Gly Pro Asp Ala Ser Glu Leu Gly Gly Tyr Phe Thr Tyr Asn Gly Lys
            580                 585                 590

Asp Thr Ile Thr Lys Asn Thr Glu Ser Ser Thr Val Pro Ser Pro
        595                 600                 605

Pro Asn Ser Pro Asn Ala Arg Ala Ala Val Val Phe Gly Ala Lys Lys
610                 615                 620
```

-continued

Gln Val Glu Thr Thr Asn Lys
625                 630

<210> SEQ ID NO 116
<211> LENGTH: 100
<212> TYPE: DNA
<213> ORGANISM: Haemophilus influenzae

<400> SEQUENCE: 116
tctaacttga cattattaca aaaaaagatc aataatgcga attattatca attttgtatg    60
agtatataat tctatgaaat ctgtacctct tatctctggt                          100

<210> SEQ ID NO 117
<211> LENGTH: 100
<212> TYPE: DNA
<213> ORGANISM: Haemophilus influenzae

<400> SEQUENCE: 117
tctaacttga cattattaca aaaaaagatc aataatgcga attattatca attttgtatg    60
agtatataat tctatgaaat ctgtacctct tatctctggt                          100

<210> SEQ ID NO 118
<211> LENGTH: 99
<212> TYPE: DNA
<213> ORGANISM: Haemophilus influenzae

<400> SEQUENCE: 118
tctaagttga cattattaca aaaaaagaac aataatgcga attattatca attttgtata    60
agtattaatt ctatgaaatc tgtacctctt atctctggt                           99

<210> SEQ ID NO 119
<211> LENGTH: 100
<212> TYPE: DNA
<213> ORGANISM: Haemophilus influenzae

<400> SEQUENCE: 119
tctaagttga cattattaca aaaaaagaac aataatgcga attattatca attttgtata    60
agaatataat tctatgaaat ctgtacctct tatctctggt                          100

<210> SEQ ID NO 120
<211> LENGTH: 35
<212> TYPE: DNA
<213> ORGANISM: Haemophilus influenzae

<400> SEQUENCE: 120
ggatccatat gaaatctgta cctcttatct ctggt                               35

<210> SEQ ID NO 121
<211> LENGTH: 61
<212> TYPE: DNA
<213> ORGANISM: Haemophilus influenzae

<400> SEQUENCE: 121
gtagaaacaa ccaaataatg gaatactaaa aatgactaaa aaccctatt ttcgcctaag     60 t                                                                    61

<210> SEQ ID NO 122
<211> LENGTH: 61
<212> TYPE: DNA
<213> ORGANISM: Haemophilus influenzae

```
<400> SEQUENCE: 122
gtagaaacaa ccaaataatg gaatactaaa aatgactaaa aaaccctatt ttcgcctaag    60
t                                                                   61

<210> SEQ ID NO 123
<211> LENGTH: 61
<212> TYPE: DNA
<213> ORGANISM: Haemophilus influenzae

<400> SEQUENCE: 123
gtagaaacaa ccaagtaatg gaatactaaa aatgactaaa aaaccctatt ttcgcctaag    60
t                                                                   61

<210> SEQ ID NO 124
<211> LENGTH: 78
<212> TYPE: DNA
<213> ORGANISM: Haemophilus influenzae

<400> SEQUENCE: 124
gtagaaacaa ccaacaagta aaacaacca agtaatggaa tactaaaaat gactaaaaaa    60
ccctattttc gcctaagt                                                 78

<210> SEQ ID NO 125
<211> LENGTH: 43
<212> TYPE: DNA
<213> ORGANISM: Haemophilus influenzae

<400> SEQUENCE: 125
gtagaaacaa ccaaataatg gaatactaaa aatgactaaa aaa                     43

<210> SEQ ID NO 126
<211> LENGTH: 60
<212> TYPE: DNA
<213> ORGANISM: Haemophilus influenzae

<400> SEQUENCE: 126
gtagaaacaa ccaacaagta aaacaacca agtaatggaa tactaaaaat gactaaaaaa    60

<210> SEQ ID NO 127
<211> LENGTH: 60
<212> TYPE: DNA
<213> ORGANISM: Haemophilus influenzae

<400> SEQUENCE: 127
gtagaaaaaa acaactagta aaacaacca agtaatggaa tactaaaaat gactaaaaaa    60

<210> SEQ ID NO 128
<211> LENGTH: 60
<212> TYPE: DNA
<213> ORGANISM: Haemophilus influenzae

<400> SEQUENCE: 128
gtagaaacaa ccaacaagta gaaaaaaaca ataatggaa tactaaaaat gactaaaaaa    60

<210> SEQ ID NO 129
<211> LENGTH: 35
<212> TYPE: DNA
<213> ORGANISM: Haemophilus influenzae

<400> SEQUENCE: 129
```
tctagaagct tttttagtca tttttagtat tccat                                    35

<210> SEQ ID NO 130
<211> LENGTH: 58
<212> TYPE: DNA
<213> ORGANISM: Haemophilus influenzae

<400> SEQUENCE: 130
tatgtgttct ggtggtggtt ctttcgacgt tgacaacgtt tctaacactc cctcttct      58

<210> SEQ ID NO 131
<211> LENGTH: 59
<212> TYPE: DNA
<213> ORGANISM: Haemophilus influenzae

<400> SEQUENCE: 131
acacaagacc accaccaaga aagctgcaac tgttgcaaag attgtgaggg agaagattt    59

<210> SEQ ID NO 132
<211> LENGTH: 9
<212> TYPE: PRT
<213> ORGANISM: Haemophilus influenzae

<400> SEQUENCE: 132

Asn Pro Ala Ser Thr Thr Asn Lys Asp
 1               5

<210> SEQ ID NO 133
<211> LENGTH: 17
<212> TYPE: PRT
<213> ORGANISM: Haemophilus influenzae

<400> SEQUENCE: 133

Asn Pro Ala Ser Thr Thr Ser Leu Glu Gly Gly Phe Tyr Gly Pro Lys
 1               5                  10                  15
Asp

<210> SEQ ID NO 134
<211> LENGTH: 16
<212> TYPE: PRT
<213> ORGANISM: Haemophilus influenzae

<400> SEQUENCE: 134

Asn Pro Ala Ser Thr Thr Ser Leu Glu Gly Gly Phe Tyr Gly Lys Asp
 1               5                  10                  15

<210> SEQ ID NO 135
<211> LENGTH: 16
<212> TYPE: PRT
<213> ORGANISM: Haemophilus influenzae

<400> SEQUENCE: 135

Asn Pro Ala Ser Thr Thr Leu Glu Gly Gly Phe Tyr Gly Pro Lys Asp
 1               5                  10                  15

<210> SEQ ID NO 136
<211> LENGTH: 15
<212> TYPE: PRT
<213> ORGANISM: Haemophilus influenzae

<400> SEQUENCE: 136

Asn Pro Ala Ser Thr Thr Leu Glu Gly Gly Phe Tyr Gly Lys Asp
 1               5                  10                  15

```
<210> SEQ ID NO 137
<211> LENGTH: 35
<212> TYPE: DNA
<213> ORGANISM: Haemophilus influenzae

<400> SEQUENCE: 137
tctagaagct tttttagtca tttttagtat tccat                                35

<210> SEQ ID NO 138
<211> LENGTH: 4
<212> TYPE: PRT
<213> ORGANISM: Haemophilus influenzae

<400> SEQUENCE: 138

Met Thr Lys Lys
  1

<210> SEQ ID NO 139
<211> LENGTH: 5
<212> TYPE: PRT
<213> ORGANISM: Haemophilus influenzae

<400> SEQUENCE: 139

Glu Gln Val Leu Asn
  1               5

<210> SEQ ID NO 140
<211> LENGTH: 9
<212> TYPE: PRT
<213> ORGANISM: Haemophilus influenzae

<400> SEQUENCE: 140

Asp Ile Arg Asp Leu Thr Arg Tyr Asp
  1               5

<210> SEQ ID NO 141
<211> LENGTH: 18
<212> TYPE: PRT
<213> ORGANISM: Haemophilus influenzae

<400> SEQUENCE: 141

Gly Ala Ile Asn Glu Ile Glu Tyr Glu Asn Val Lys Ala Val Glu Ile
  1               5                  10                  15

Ser Lys

<210> SEQ ID NO 142
<211> LENGTH: 5
<212> TYPE: PRT
<213> ORGANISM: Haemophilus influenzae

<400> SEQUENCE: 142

Val Tyr Asn Leu Phe
  1               5

<210> SEQ ID NO 143
<211> LENGTH: 9
<212> TYPE: PRT
<213> ORGANISM: Haemophilus influenzae

<400> SEQUENCE: 143

Leu Asn Tyr Arg Tyr Val Thr Trp Glu
  1               5
```

<210> SEQ ID NO 144
<211> LENGTH: 9
<212> TYPE: PRT
<213> ORGANISM: Haemophilus influenzae

<400> SEQUENCE: 144

Cys Ser Gly Gly Gly Ser Phe Asp
 1               5

<210> SEQ ID NO 145
<211> LENGTH: 9
<212> TYPE: PRT
<213> ORGANISM: Haemophilus influenzae

<400> SEQUENCE: 145

Cys Leu Gly Gly Gly Ser Phe Asp
 1               5

<210> SEQ ID NO 146
<211> LENGTH: 8
<212> TYPE: PRT
<213> ORGANISM: Haemophilus influenzae

<400> SEQUENCE: 146

Leu Ser Gly Gly Phe Phe Gly Pro
 1               5

<210> SEQ ID NO 147
<211> LENGTH: 10
<212> TYPE: PRT
<213> ORGANISM: Haemophilus influenzae

<400> SEQUENCE: 147

Met Lys Ser Val Pro Leu Ile Ser Gly Ser
 1               5                  10

<210> SEQ ID NO 148
<211> LENGTH: 647
<212> TYPE: PRT
<213> ORGANISM: Haemophilus influenzae

<400> SEQUENCE: 148

Met Lys Ser Val Pro Leu Ile Ser Gly Gly Leu Ser Phe Leu Leu Ser
 1               5                  10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
        50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Lys Asn Gly Ala Asp Leu Ile Gly Ser
            100                 105                 110

Ile Asp Glu Pro Ser Thr Thr Asn Pro Pro Glu Lys His His Gly Gln
        115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr

-continued

```
              145                 150                 155                 160
          Tyr Gly Asn Lys Thr Ala Thr Asn Leu Pro Val Asn Gly Val Ala Lys
                          165                 170                 175
          Tyr Lys Gly Thr Trp Asp Phe Ile Thr Ala Thr Lys Asn Gly Lys Arg
                          180                 185                 190
          Tyr Pro Leu Leu Ser Asn Gly Ser His Ala Tyr Arg Arg Ser Ala
                          195                 200                 205
          Ile Pro Glu Asp Ile Asp Leu Glu Asn Asp Ser Lys Asn Gly Asp Ile
                          210                 215                 220
          Gly Leu Ile Ser Glu Phe Ser Ala Asp Phe Gly Thr Lys Lys Leu Thr
          225                 230                 235                 240
          Gly Gln Leu Ser Tyr Thr Lys Arg Lys Thr Asn Asn Gln Pro Tyr Glu
                          245                 250                 255
          Lys Lys Lys Leu Tyr Asp Ile Asp Ala Asp Ile Tyr Ser Asn Arg Phe
                          260                 265                 270
          Arg Gly Thr Val Lys Pro Thr Glu Lys Asp Ser Glu Glu His Pro Phe
                          275                 280                 285
          Thr Ser Glu Gly Thr Leu Glu Gly Gly Phe Tyr Gly Pro Asn Ala Glu
                          290                 295                 300
          Glu Leu Gly Gly Lys Phe Leu Ala Thr Asp Asn Arg Val Phe Gly Val
          305                 310                 315                 320
          Phe Ser Ala Lys Glu Thr Glu Thr Lys Lys Glu Ala Leu Ser Lys
                          325                 330                 335
          Glu Thr Leu Ile Asp Gly Lys Leu Ile Thr Phe Ser Thr Lys Lys Thr
                          340                 345                 350
          Asp Ala Lys Thr Asn Ala Thr Thr Ser Thr Ala Ala Asn Thr Thr Thr
                          355                 360                 365
          Asp Thr Thr Ala Asn Thr Ile Thr Asp Glu Lys Asn Phe Lys Thr Glu
                          370                 375                 380
          Asp Ile Ser Ser Phe Gly Glu Ala Asp Tyr Leu Leu Ile Asp Lys Tyr
          385                 390                 395                 400
          Pro Ile Pro Leu Leu Pro Asp Lys Asn Thr Asn Asp Phe Ile Ser Ser
                          405                 410                 415
          Lys His His Thr Val Gly Asn Lys Arg Tyr Lys Val Glu Ala Cys Cys
                          420                 425                 430
          Ser Asn Leu Ser Tyr Val Lys Phe Gly Met Tyr Tyr Glu Asp Pro Leu
                          435                 440                 445
          Lys Glu Lys Glu Thr Glu Thr Glu Thr Glu Thr Glu Lys Asp Lys Glu
                          450                 455                 460
          Lys Glu Lys Glu Lys Asp Lys Asp Lys Glu Lys Gln Thr Ala Ala Thr
          465                 470                 475                 480
          Thr Asn Thr Tyr Tyr Gln Phe Leu Leu Gly His Arg Thr Pro Lys Asp
                          485                 490                 495
          Asp Ile Pro Lys Thr Gly Ser Ala Lys Tyr His Gly Ser Trp Phe Gly
                          500                 505                 510
          Tyr Ile Thr Asp Gly Lys Thr Ser Tyr Ser Pro Ser Gly Asp Lys Lys
                          515                 520                 525
          Arg Asp Lys Asn Ala Val Ala Glu Phe Asn Val Asp Phe Ala Glu Lys
                          530                 535                 540
          Lys Leu Thr Gly Glu Leu Lys Arg His Asp Thr Gly Asn Pro Val Phe
          545                 550                 555                 560
          Ser Ile Glu Ala Asn Phe Asn Asn Ser Ser Asn Ala Phe Thr Gly Thr
                          565                 570                 575
```

-continued

```
Ala Thr Ala Thr Asn Phe Val Ile Asp Gly Lys Asn Ser Gln Asn Lys
            580                 585                 590

Asn Thr Pro Ile Asn Ile Thr Thr Lys Val Asn Gly Ala Phe Tyr Gly
        595                 600                 605

Pro Lys Ala Ser Glu Leu Gly Gly Tyr Phe Thr Tyr Asn Gly Asn Ser
        610                 615                 620

Thr Ala Thr Asn Ser Glu Ser Ser Ser Thr Val Ser Ser Ser Ser Asn
625                 630                 635                 640

Ser Lys Asn Ala Arg Ala Ala
                645

<210> SEQ ID NO 149
<211> LENGTH: 547
<212> TYPE: PRT
<213> ORGANISM: Haemophilus influenzae

<400> SEQUENCE: 149

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
            20                  25                  30

Pro Ser Ser Lys Pro Arg Tyr Gln Asp Asp Thr Ser Asn Gln Arg Lys
        35                  40                  45

Lys Ser Asn Leu Lys Lys Leu Phe Ile Pro Ser Leu Gly Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
            100                 105                 110

Ile Asp Glu Pro Ser Thr Thr Asn Pro Pro Glu Lys His His Gly Gln
        115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
            180                 185                 190

Tyr Pro Leu Leu Ser Asn Gly Ser His Ala Tyr Tyr Arg Arg Ser Ala
        195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
            260                 265                 270

Arg Gly Thr Val Lys Pro Thr Glu Lys Asp Ser Glu Glu His Pro Phe
        275                 280                 285

Thr Ser Glu Gly Thr Leu Glu Gly Gly Phe Tyr Gly Pro Asn Ala Glu
```

-continued

```
            290                 295                 300
Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
            340                 345                 350

Asp Ala Lys Thr Asn Ala Thr Thr Ser Thr Ala Ala Asn Thr Thr Thr
                355                 360                 365

Asp Thr Thr Ala Asn Thr Ile Thr Asp Glu Lys Asn Phe Lys Thr Glu
370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
                405                 410                 415

Lys His His Thr Val Gly Asn Lys Arg Tyr Lys Val Glu Ala Cys Cys
                420                 425                 430

Ser Asn Leu Ser Tyr Val Lys Phe Gly Met Tyr Tyr Glu Asp Pro Leu
                435                 440                 445

Lys Glu Lys Glu Thr Glu Thr Glu Thr Glu Thr Glu Lys Asp Lys Glu
            450                 455                 460

Lys Glu Lys Glu Lys Asp Lys Asp Lys Glu Lys Gln Thr Ala Ala Thr
465                 470                 475                 480

Thr Asn Thr Tyr Tyr Gln Phe Leu Leu Gly His Arg Thr Pro Lys Asp
                485                 490                 495

Asp Ile Pro Lys Thr Gly Ser Ala Lys Tyr His Gly Ser Trp Phe Gly
                500                 505                 510

Tyr Ile Thr Asp Gly Lys Thr Ser Tyr Ser Pro Ser Gly Asp Lys Lys
                515                 520                 525

Arg Asp Lys Asn Ala Val Ala Glu Phe Asn Val Asp Phe Ala Glu Lys
                530                 535                 540

Lys Leu Thr
545

<210> SEQ ID NO 150
<211> LENGTH: 529
<212> TYPE: PRT
<213> ORGANISM: Haemophilus influenzae

<400> SEQUENCE: 150

Met Lys Ser Val Pro Leu Ile Ser Gly Gly Leu Ser Phe Leu Leu Ser
1               5                   10                  15

Ala Cys Ser Gly Gly Ser Phe Asp Val Asp Asn Val Ser Asn Thr
                20                  25                  30

Pro Ser Ser Lys Pro Arg Tyr Gln Asp Thr Ser Asn Gln Arg Lys
            35                  40                  45

Lys Ser Asn Leu Lys Lys Leu Phe Ile Pro Ser Leu Gly Gly Met
    50                  55                  60

Lys Leu Val Ala Gln Asn Leu Arg Gly Asn Lys Glu Pro Ser Phe Leu
65              70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
                100                 105                 110
```

```
Ile Asp Glu Pro Ser Thr Thr Asn Pro Pro Glu Lys His His Gly Gln
        115                 120                 125
Lys Tyr Val Tyr Ser Gly Leu Tyr Tyr Thr Pro Ser Trp Ser Leu Asn
    130                 135                 140
Asp Ser Lys Asn Lys Phe Tyr Leu Gly Tyr Tyr Gly Tyr Ala Phe Tyr
145                 150                 155                 160
Tyr Gly Asn Lys Thr Ala Thr Asn Leu Pro Val Asn Gly Val Ala Lys
                165                 170                 175
Tyr Lys Gly Thr Trp Asp Phe Ile Thr Ala Thr Lys Asn Gly Lys Arg
            180                 185                 190
Tyr Pro Leu Leu Ser Asn Gly Ser His Ala Tyr Tyr Arg Arg Ser Ala
        195                 200                 205
Ile Pro Glu Asp Ile Asp Leu Glu Asn Asp Ser Lys Asn Gly Asp Ile
    210                 215                 220
Gly Leu Ile Ser Glu Phe Ser Ala Asp Phe Gly Thr Lys Lys Leu Thr
225                 230                 235                 240
Gly Gln Leu Ser Tyr Thr Lys Arg Lys Thr Asn Asn Gln Pro Tyr Glu
                245                 250                 255
Lys Lys Lys Leu Tyr Asp Ile Asp Ala Asp Ile Tyr Ser Asn Arg Phe
            260                 265                 270
Arg Gly Thr Val Lys Pro Thr Glu Lys Asp Ser Glu Glu His Pro Phe
        275                 280                 285
Thr Ser Glu Gly Thr Leu Glu Gly Gly Phe Tyr Gly Pro Asn Ala Glu
    290                 295                 300
Glu Leu Gly Gly Lys Phe Leu Ala Thr Asp Asn Arg Val Phe Gly Val
305                 310                 315                 320
Phe Ser Ala Lys Glu Thr Glu Glu Thr Lys Lys Glu Ala Leu Ser Lys
                325                 330                 335
Glu Thr Leu Ile Asp Gly Lys Leu Ile Thr Phe Ser Thr Lys Lys Thr
            340                 345                 350
Asp Ala Lys Thr Asn Ala Thr Thr Ser Thr Ala Ala Asn Thr Thr Thr
        355                 360                 365
Asp Thr Thr Ala Asn Thr Ile Thr Asp Glu Lys Asn Phe Lys Thr Glu
    370                 375                 380
Asp Ile Ser Ser Phe Gly Glu Ala Asp Tyr Leu Leu Ile Asp Lys Tyr
385                 390                 395                 400
Pro Ile Pro Leu Leu Pro Asp Lys Asn Thr Asn Asp Phe Ile Ser Ser
                405                 410                 415
Lys His His Thr Val Gly Asn Lys Arg Tyr Lys Val Glu Ala Cys Cys
            420                 425                 430
Ser Asn Leu Ser Tyr Val Lys Phe Gly Met Tyr Tyr Glu Asp Pro Leu
        435                 440                 445
Lys Glu Lys Glu Thr Glu Thr Glu Thr Glu Thr Glu Lys Asp Lys Glu
    450                 455                 460
Lys Glu Lys Glu Lys Asp Lys Asp Lys Glu Lys Gln Thr Ala Ala Thr
465                 470                 475                 480
Thr Asn Thr Tyr Tyr Gln Phe Leu Leu Gly His Arg Thr Pro Lys Asp
                485                 490                 495
Asp Ile Pro Lys Thr Gly Ser Ala Lys Tyr His Gly Ser Trp Phe Gly
            500                 505                 510
Tyr Ile Thr Asp Gly Lys Thr Ser Tyr Ser Pro Ser Gly Asp Lys Lys
        515                 520                 525
Arg
```

<210> SEQ ID NO 151
<211> LENGTH: 463
<212> TYPE: PRT
<213> ORGANISM: Haemophilus influenzae

<400> SEQUENCE: 151

Met Lys Ser Val Pro Leu Ile Ser Gly Gly Leu Ser Phe Leu Leu Ser
 1               5                  10                  15

Ala Cys Ser Gly Gly Ser Phe Asp Val Asp Asn Val Ser Asn Thr
            20                  25                  30

Pro Ser Ser Lys Pro Arg Tyr Gln Asp Asp Thr Ser Asn Gln Arg Lys
        35                  40                  45

Lys Ser Asn Leu Lys Leu Phe Ile Pro Ser Leu Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
            100                 105                 110

Ile Asp Glu Pro Ser Thr Thr Asn Pro Pro Glu Lys His His Gly Gln
        115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
            180                 185                 190

Tyr Pro Leu Leu Ser Asn Gly Ser His Ala Tyr Tyr Arg Arg Ser Ala
        195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
            260                 265                 270

Arg Gly Thr Val Lys Pro Thr Glu Lys Asp Ser Glu Glu His Pro Phe
        275                 280                 285

Thr Ser Glu Gly Thr Leu Glu Gly Gly Phe Tyr Gly Pro Asn Ala Glu
    290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
            340                 345                 350

Asp Ala Lys Thr Asn Ala Thr Thr Ser Thr Ala Ala Asn Thr Thr Thr
        355                 360                 365

Asp Thr Thr Ala Asn Thr Ile Thr Asp Glu Lys Asn Phe Lys Thr Glu

```
            370                 375                 380
Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
                405                 410                 415

Lys His His Thr Val Gly Asn Lys Arg Tyr Lys Val Glu Ala Cys Cys
                420                 425                 430

Ser Asn Leu Ser Tyr Val Lys Phe Gly Met Tyr Tyr Glu Asp Pro Leu
                435                 440                 445

Lys Glu Lys Glu Thr Glu Thr Glu Thr Glu Lys Asp Lys
450                 455                 460

<210> SEQ ID NO 152
<211> LENGTH: 430
<212> TYPE: PRT
<213> ORGANISM: Haemophilus influenzae

<400> SEQUENCE: 152

Met Lys Ser Val Pro Leu Ile Ser Gly Gly Leu Ser Phe Leu Leu Ser
1               5                   10                  15

Ala Cys Ser Gly Gly Ser Phe Asp Val Asp Asn Val Ser Asn Thr
                20                  25                  30

Pro Ser Ser Lys Pro Arg Tyr Gln Asp Thr Ser Asn Gln Arg Lys
                35                  40                  45

Lys Ser Asn Leu Lys Lys Leu Phe Ile Pro Ser Leu Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Leu Ser Thr Ile Glu
                85                  90                  95

Lys Asp Val Lys Asp Asn Asn Lys Asn Gly Ala Asp Leu Ile Gly Ser
                100                 105                 110

Ile Asp Glu Pro Ser Thr Thr Asn Pro Pro Glu Lys His His Gly Gln
            115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
                180                 185                 190

Tyr Pro Leu Leu Ser Asn Gly Ser His Ala Tyr Tyr Arg Arg Ser Ala
            195                 200                 205

Ile Pro Glu Asp Ile Asp Leu Glu Asn Asp Ser Lys Asn Gly Asp Ile
            210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
                260                 265                 270

Arg Gly Thr Val Lys Pro Thr Glu Lys Asp Ser Glu Glu His Pro Phe
                275                 280                 285
```

```
Thr Ser Glu Gly Thr Leu Glu Gly Gly Phe Tyr Gly Pro Asn Ala Glu
    290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
                340                 345                 350

Asp Ala Lys Thr Asn Ala Thr Thr Ser Thr Ala Ala Asn Thr Thr Thr
                355                 360                 365

Asp Thr Thr Ala Asn Thr Ile Thr Asp Glu Lys Asn Phe Lys Thr Glu
                370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
                405                 410                 415

Lys His His Thr Val Gly Asn Lys Arg Tyr Lys Val Glu Ala
                420                 425                 430

<210> SEQ ID NO 153
<211> LENGTH: 417
<212> TYPE: PRT
<213> ORGANISM: Haemophilus influenzae

<400> SEQUENCE: 153

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
                35                  40                  45

Lys Ser Asn Leu Lys Lys Leu Phe Ile Pro Ser Leu Gly Gly Gly Met
            50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
                100                 105                 110

Ile Asp Glu Pro Ser Thr Thr Asn Pro Pro Glu Lys His His Gly Gln
            115                 120                 125

Lys Tyr Val Tyr Ser Gly Leu Tyr Tyr Thr Pro Ser Trp Ser Leu Asn
            130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
                180                 185                 190

Tyr Pro Leu Leu Ser Asn Gly Ser His Ala Tyr Tyr Arg Arg Ser Ala
            195                 200                 205

Ile Pro Glu Asp Ile Asp Leu Glu Asn Asp Ser Lys Asn Gly Asp Ile
        210                 215                 220

Gly Leu Ile Ser Glu Phe Ser Ala Asp Phe Gly Thr Lys Lys Leu Thr
225                 230                 235                 240
```

```
Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
            260                 265                 270

Arg Gly Thr Val Lys Pro Thr Glu Lys Asp Ser Glu His Pro Phe
        275                 280                 285

Thr Ser Glu Gly Thr Leu Glu Gly Gly Phe Tyr Gly Pro Asn Ala Glu
    290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
                340                 345                 350

Asp Ala Lys Thr Asn Ala Thr Thr Ser Thr Ala Ala Asn Thr Thr Thr
                355                 360                 365

Asp Thr Thr Ala Asn Thr Ile Thr Asp Glu Lys Asn Phe Lys Thr Glu
            370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn Asp Phe Ile Ser Ser
                405                 410                 415

Lys

<210> SEQ ID NO 154
<211> LENGTH: 411
<212> TYPE: PRT
<213> ORGANISM: Haemophilus influenzae

<400> SEQUENCE: 154

Met Lys Ser Val Pro Leu Ile Ser Gly Gly Leu Ser Phe Leu Leu Ser
 1               5                  10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
        50                  55                  60

Lys Leu Val Ala Gln Asn Leu Arg Gly Asn Lys Glu Pro Ser Phe Leu
 65                 70                  75                  80

Asn Glu Asp Asp Tyr Ile Ser Tyr Phe Ser Ser Leu Ser Thr Ile Glu
                85                  90                  95

Lys Asp Val Lys Asp Asn Lys Asn Gly Ala Asp Leu Ile Gly Ser
            100                 105                 110

Ile Asp Glu Pro Ser Thr Thr Asn Pro Pro Glu Lys His His Gly Gln
        115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
            180                 185                 190
```

```
Tyr Pro Leu Leu Ser Asn Gly Ser His Ala Tyr Tyr Arg Arg Ser Ala
        195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
                260                 265                 270

Arg Gly Thr Val Lys Pro Thr Glu Lys Asp Ser Glu Glu His Pro Phe
            275                 280                 285

Thr Ser Glu Gly Thr Leu Glu Gly Gly Phe Tyr Gly Pro Asn Ala Glu
        290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
                340                 345                 350

Asp Ala Lys Thr Asn Ala Thr Thr Ser Thr Ala Ala Asn Thr Thr Thr
                355                 360                 365

Asp Thr Thr Ala Asn Thr Ile Thr Asp Glu Lys Asn Phe Lys Thr Glu
            370                 375                 380

Asp Ile Ser Ser Phe Gly Glu Ala Asp Tyr Leu Leu Ile Asp Lys Tyr
385                 390                 395                 400

Pro Ile Pro Leu Leu Pro Asp Lys Asn Thr Asn
                405                 410

<210> SEQ ID NO 155
<211> LENGTH: 404
<212> TYPE: PRT
<213> ORGANISM: Haemophilus influenzae

<400> SEQUENCE: 155

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
                100                 105                 110

Ile Asp Glu Pro Ser Thr Thr Asn Pro Pro Glu Lys His His Gly Gln
            115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
```

```
                145                 150                 155                 160
Tyr Gly Asn Lys Thr Ala Thr Asn Leu Pro Val Asn Gly Val Ala Lys
                    165                 170                 175

Tyr Lys Gly Thr Trp Asp Phe Ile Thr Ala Thr Lys Asn Gly Lys Arg
            180                 185                 190

Tyr Pro Leu Leu Ser Asn Gly Ser His Ala Tyr Tyr Arg Arg Ser Ala
        195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
            260                 265                 270

Arg Gly Thr Val Lys Pro Thr Glu Lys Asp Ser Glu Glu His Pro Phe
        275                 280                 285

Thr Ser Glu Gly Thr Leu Glu Gly Gly Phe Tyr Gly Pro Asn Ala Glu
    290                 295                 300

Glu Leu Gly Gly Lys Phe Leu Ala Thr Asp Asn Arg Val Phe Gly Val
305                 310                 315                 320

Phe Ser Ala Lys Glu Thr Glu Thr Lys Lys Glu Ala Leu Ser Lys
                325                 330                 335

Glu Thr Leu Ile Asp Gly Lys Leu Ile Thr Phe Ser Thr Lys Lys Thr
            340                 345                 350

Asp Ala Lys Thr Asn Ala Thr Thr Ser Thr Ala Ala Asn Thr Thr Thr
        355                 360                 365

Asp Thr Thr Ala Asn Thr Ile Thr Asp Glu Lys Asn Phe Lys Thr Glu
    370                 375                 380

Asp Ile Ser Ser Phe Gly Glu Ala Asp Tyr Leu Leu Ile Asp Lys Tyr
385                 390                 395                 400

Pro Ile Pro Leu

<210> SEQ ID NO 156
<211> LENGTH: 365
<212> TYPE: PRT
<213> ORGANISM: Haemophilus influenzae

<400> SEQUENCE: 156

Met Lys Ser Val Pro Leu Ile Ser Gly Gly Leu Ser Phe Leu Leu Ser
  1               5                  10                  15

Ala Cys Ser Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
        35                  40                  45

Lys Ser Asn Leu Lys Lys Leu Phe Ile Pro Ser Leu Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
            100                 105                 110

Ile Asp Glu Pro Ser Thr Thr Asn Pro Pro Glu Lys His His Gly Gln
```

```
                115                 120                 125
Lys Tyr Val Tyr Ser Gly Leu Tyr Tyr Thr Pro Ser Trp Ser Leu Asn
130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
                180                 185                 190

Tyr Pro Leu Leu Ser Asn Gly Ser His Ala Tyr Arg Arg Ser Ala
                195                 200                 205

Ile Pro Glu Asp Ile Asp Leu Glu Asn Asp Ser Lys Asn Gly Asp Ile
210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
                260                 265                 270

Arg Gly Thr Val Lys Pro Thr Glu Lys Asp Ser Glu Glu His Pro Phe
                275                 280                 285

Thr Ser Glu Gly Thr Leu Glu Gly Gly Phe Tyr Gly Pro Asn Ala Glu
                290                 295                 300

Glu Leu Gly Gly Lys Phe Leu Ala Thr Asp Asn Arg Val Phe Gly Val
305                 310                 315                 320

Phe Ser Ala Lys Glu Thr Glu Glu Thr Lys Lys Glu Ala Leu Ser Lys
                325                 330                 335

Glu Thr Leu Ile Asp Gly Lys Leu Ile Thr Phe Ser Thr Lys Lys Thr
                340                 345                 350

Asp Ala Lys Thr Asn Ala Thr Thr Ser Thr Ala Ala Asn
                355                 360                 365

<210> SEQ ID NO 157
<211> LENGTH: 310
<212> TYPE: PRT
<213> ORGANISM: Haemophilus influenzae

<400> SEQUENCE: 157

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
        50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
                100                 105                 110

Ile Asp Glu Pro Ser Thr Thr Asn Pro Pro Glu Lys His His Gly Gln
            115                 120                 125
```

```
Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
            180                 185                 190

Tyr Pro Leu Leu Ser Asn Gly Ser His Ala Tyr Tyr Arg Arg Ser Ala
        195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala Asp Ile Tyr Ser Asn Arg Phe
                260                 265                 270

Arg Gly Thr Val Lys Pro Thr Glu Lys Asp Ser Glu His Pro Phe
            275                 280                 285

Thr Ser Glu Gly Thr Leu Glu Gly Gly Phe Tyr Gly Pro Asn Ala Glu
    290                 295                 300

Glu Leu Gly Gly Lys Phe
305             310

<210> SEQ ID NO 158
<211> LENGTH: 265
<212> TYPE: PRT
<213> ORGANISM: Haemophilus influenzae

<400> SEQUENCE: 158

Met Lys Ser Val Pro Leu Ile Ser Gly Gly Leu Ser Phe Leu Leu Ser
  1               5                  10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
                100                 105                 110

Ile Asp Glu Pro Ser Thr Thr Asn Pro Pro Glu Lys His His Gly Gln
            115                 120                 125

Lys Tyr Val Tyr Ser Gly Leu Tyr Tyr Thr Pro Ser Trp Ser Leu Asn
    130                 135                 140

Asp Ser Lys Asn Lys Phe Tyr Leu Gly Tyr Tyr Gly Tyr Ala Phe Tyr
145                 150                 155                 160

Tyr Gly Asn Lys Thr Ala Thr Asn Leu Pro Val Asn Gly Val Ala Lys
                165                 170                 175

Tyr Lys Gly Thr Trp Asp Phe Ile Thr Ala Thr Lys Asn Gly Lys Arg
            180                 185                 190
```

-continued

```
Tyr Pro Leu Leu Ser Asn Gly Ser His Ala Tyr Tyr Arg Arg Ser Ala
            195                 200                 205

Ile Pro Glu Asp Ile Asp Leu Glu Asn Asp Ser Lys Asn Gly Asp Ile
    210                 215                 220

Gly Leu Ile Ser Glu Phe Ser Ala Asp Phe Gly Thr Lys Lys Leu Thr
225                 230                 235                 240

Gly Gln Leu Ser Tyr Thr Lys Arg Lys Thr Asn Asn Gln Pro Tyr Glu
                245                 250                 255

Lys Lys Lys Leu Tyr Asp Ile Asp Ala
            260                 265

<210> SEQ ID NO 159
<211> LENGTH: 123
<212> TYPE: PRT
<213> ORGANISM: Haemophilus influenzae

<400> SEQUENCE: 159

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
    50                  55                  60

Lys Leu Val Ala Gln Asn Leu Arg Gly Asn Lys Glu Pro Ser Phe Leu
65                  70                  75                  80

Asn Glu Asp Asp Tyr Ile Ser Tyr Phe Ser Ser Leu Ser Thr Ile Glu
                85                  90                  95

Lys Asp Val Lys Asp Asn Asn Lys Asn Gly Ala Asp Leu Ile Gly Ser
            100                 105                 110

Ile Asp Glu Pro Ser Thr Thr Asn Pro Pro Glu
        115                 120

<210> SEQ ID NO 160
<211> LENGTH: 82
<212> TYPE: PRT
<213> ORGANISM: Haemophilus influenzae

<400> SEQUENCE: 160

Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
                20                  25                  30

Pro Ser Ser Lys Pro Arg Tyr Gln Asp Asp Thr Ser Asn Gln Arg Lys
            35                  40                  45

Lys Ser Asn Leu Lys Lys Leu Phe Ile Pro Ser Leu Gly Gly Gly Met
    50                  55                  60

Lys Leu Val Ala Gln Asn Leu Arg Gly Asn Lys Glu Pro Ser Phe Leu
65                  70                  75                  80

Asn Glu
```

TRANSFERRIN RECEPTOR GENES

REFERENCE TO RELATED APPLICATION

This application is a continuation of U.S. patent application Ser. No. 08/649,518 filed May 17, 1996 (now U.S. Pat. No. 6,361,779), which itself is a continuation-in-part of U.S. patent application Ser. No. 08/483,577, filed Jun. 7, 1995 (now U.S. Pat. No. 6,015,698), which itself is a continuation-in-part of U.S. patent application Ser. No. 08/337,483, filed Nov. 8, 1994 (now U.S. Pat. No. 5,922,562), which itself is a continuation-in-part of U.S. patent application Ser. No. 08/175,116 filed Dec. 29, 1993 (now abandoned), which itself is a continuation-in-part of U.S. patent application Ser. No. 08/148,968, filed Nov. 8, 1993 (now abandoned).

FIELD OF INVENTION

The present invention is related to the molecular cloning of genes encoding transferrin receptor and in particular to the cloning of transferrin receptor genes from *Haemophilus influenzae*.

BACKGROUND OF THE INVENTION

Encapsulated *Haemophilus influenzae* type b strains are the major cause of bacterial meningitis and other invasive infections in young children. However, the non-encapsulated or non-typable *H. influenzae* (NTHi) are responsible for a wide range of human diseases including otitis media, epiglottitis, pneumonia, and tracheobronchitis. Vaccines based upon *H. influenzae* type b capsular polysaccharide conjugated to diphtheria toxoid (Berkowitz et al., 1987. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure), tetanus toxoid (Classon et al., 1989 and U.S. Pat. No. 4,496,538), or *Neisseria meningitidis* outer membrane protein (Black et al., 1991) have been effective in reducing *H. influenzae* type b-induced meningitis, but not NTHi-induced disease (Bluestone, 1982).

Otitis media is the most common illness of early childhood with 60–70% of all children of less than 2 years of age experiencing between one and three ear infections. Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures such as tonsillectomies, adenoidectomies and insertion of tympanostomy tubes. Furthermore, many of the causative organisms of otitis media are becoming resistant to antibiotic treatment. An effective prophylactic vaccine against otitis media is thus desirable. Non-typable strains of *H. influenzae* are also important pathogens responsible for pneumonia in the elderly and other individuals who are particularly susceptible to respiratory infections. There is thus a need for antigens from *H. influenzae* which are useful as components in immunogenic preparations that provide protection against the many serotypes of *H. influenzae*.

Iron is an essential nutrient for the growth of many bacteria. Several human pathogens, such as *H. influenzae*, *Branhamella catarrhalis*, *N. meningitidis*, *N. gonorrhoeae* and non-pathogenic commensal *Neisseria* strains, can utilize human transferrin as an iron source (Schryvers, 1988; Schryvers and Lee, 1989; Mickelsen and Sparling, 1981). The bacterial transferrin receptor (TfR) is composed of two chains, Tbp1 and Tbp2. In strains of *H. influenzae*, the molecular weight of Tbp1 is approximately 100,000, whereas the molecular weight of Tbp2 is variable, ranging from 60,000 to 90,000, depending upon the strain (Schryvers and Gray-Owen, 1992; Holland et al., 1992). Expression of *H. influenzae* transferrin receptor is thought to be iron-and/or hemin-regulated (Morton et al., 1993) and a putative fur-binding site (Braun and Hantke, 1991) has been identified upstream of tbp2. This sequence is found in the promoter region of genes which are negatively regulated by iron, including *N. meningitidis* TfR (Legrain et al., 1993). The promoter is followed by the tbp2 and Tbp1 genes, an arrangement found in other bacterial TfR operons (Legrain et al, 1993; Wilton et al., 1993). Antibodies which block the access of the transferrin receptor to its iron source may prevent bacterial growth. In addition, antibodies against TfR that are opsonizing or bactericidal may also provide protection by alternative mechanisms. Thus, the transferrin receptor, fragments thereof, its constituent chains, or peptides derived therefrom are vaccine candidates to protect against *H. influenzae* disease. Mice immunized with *N. meningitidis* TfR proteins in Freund's adjuvant were protected from homologous challenge and the anti-TfR antisera were bactericidal and protective in a passive transfer assay (Danve et al., 1993). Pigs immunized with recombinant *A. pleuropneumoniae* Tbp2 were protected against homologous challenge but not heterologous challenge (Rossi-Campos et al., 1992). These data indicate the efficacy of TfR-based vaccines in protection from disease. It would be desirable to provide the sequence of the DNA molecule that encodes transferrin receptor and peptides corresponding to portions of the transferrin receptor and vectors containing such sequences for diagnosis, immunization and the generation of diagnostic and immunological reagents.

Poliovirus is an enterovirus, a genus of the family Picornaviridae. There are three distinct serotypes of the virus, and multiple strains within each serotype. Virulent strains are causative agents of paralytic poliomyelitis. Attenuated strains, which have reduced potential to cause paralytic disease, and inactivated virulent strains, are used as vaccines. Infection with the virus induces long-lasting, protective, mucosal immunity. Inoculation with inactivated poliovirus vaccines can also induce a mucosal immune response.

The structure of poliovirus is known, and is highly conserved among strains and serotypes. The structures of several other picornaviruses (viruses belonging to genera of the family Picornaviridae) have also been determined, and have been shown to be closely related to the structure of poliovirus. It is possible to express foreign epitopes on the capsid of polioviruses (Murdin et al, 1992) and this work has been extended to other picornaviruses. Epitopes which have been expressed are usually short, well defined, contiguous epitopes, and most have been expressed within poliovirus neutralisation antigenic site I (NAgI) or the equivalent site on other picornaviruses. This site includes the loop linking beta strands B and C (the BC loop) of poliovirus capsid protein VP1. The BC loop of VP1 is a surface-exposed loop of nine amino acids which can be replaced and extended with at least twenty-five heterologous amino acids (Murdin et al, 1991). Hybrid or chimeric polioviruses expressing transferrin receptor epitopes, which grow to a high titre and are immunogenic, would be useful as vaccines and as tools for the generation of immunological reagents.

SUMMARY OF THE INVENTION

The present invention is directed towards the provision of purified and isolated nucleic acid molecules encoding a transferrin receptor of a strain of *Haemophilus* or a fragment or an analog of the transferrin receptor protein. The nucleic acid molecules provided herein are useful for the specific detection of strains of *Haemophilus*, and for diagnosis of infection by *Haemophilus*. The purified and isolated nucleic acid molecules provided herein, such as DNA, are also useful for expressing the TfR genes by recombinant DNA means for providing, in an economical manner, purified and isolated transferrin receptor subunits, fragments or analogs thereof. The transferrin receptor, subunits or fragments thereof or analogs thereof, as well as nucleic acid molecules encoding the same and vectors containing such nucleic acid molecules, are useful in immunogenic compositions against diseases caused by *Haemophilius*, the diagnosis of infection by *Haemophilus* and as tools for the generation of immunological reagents. Monoclonal antibodies or mono-specific antisera (antibodies) raised against the transferrin receptor protein produced in accordance with aspects of the present invention are useful for the diagnosis of infection by *Haemophilus*, the specific detection of *Haemophilus* (in for example in vitro and in vivo assays) and for the treatment of diseases caused by *Haemophilus*.

Peptides corresponding to portions of the transferrin receptor or analogs thereof are useful immunogenic compositions against disease caused by *Haemophilus*, the diagnosis of infection by *Haemophilus* and as tools for the generation of immunological reagents. Monoclonal antibodies or antisera raised against these peptides, produced in accordance with aspects of the present invention, are useful for the diagnosis of infection by *Haemophilus*, the specific detection of *Haemophilus* (in, for example, in vitro and in vivo assays) and for use in passive immunization as a treatment of disease caused by *Haemophilus*.

In accordance with one aspect of the present invention, there is provided a purified and isolated nucleic acid molecule encoding a transferrin receptor protein of a strain of *Haemophilus*, more particularly, a strain of *H. influenzae*, specifically a strain of *H. influenzae* type b, such as *H. influenzae* type b strain DL63, Eagan or MinnA, or a non-typable strain of *H. influenzae*, such as *H. influenzae* strain PAK 12085, SB33, SB12, SB29, SB30 or SB32, or a fragment or an analog of the transferrin receptor protein.

In one preferred embodiment of the invention, the nucleic acid molecule may encode only the Tbp1 protein of the *Haemophilus* strain or only the Tbp2 protein of the *Haemophilus* strain. In another preferred embodiment of the invention, the nucleic acid may encode a fragment of the transferrin receptor protein of a strain of *Haemophilus* having a conserved amino acid sequence which is conserved among bacteria that produce transferrin receptor protein. Such conserved amino acid sequence may have an amino acid sequence contained within the amino acid sequence of the peptides shown in Tables 2 and 3 below for *Haemophilus influenzae* type b strain Eagan as well as corresponding peptides of other strains of *Haemophilus influenzae*.

In another aspect of the present invention, there is provided a purified and isolated nucleic acid molecule having a DNA sequence selected from the group consisting of (a) any one of the DNA sequences set out in FIG. 3, 4, 5, 6, 7, 8, 9, 10 or 11 (SEQ ID NOS: 1, 2, 3, 4, 105, 108, 110, 112, 114) or the complementary DNA sequence of any one of said sequences; (b) a DNA sequence encoding one of the amino acid sequences set out in FIG. 3, 4, 5, 6, 7, 8, 9, 10, 11 or 31 (SEQ ID NOS: 5, 6, 7, 8, 9, 10, 11, 12, 106, 107, 109, 111, 113, 115) or the complementary DNA sequence thereto; and (c) a DNA sequence which hybridizes under stringent conditions to any one of the DNA sequences defined in (a) or (b). The DNA sequence defined in (c) preferably has at least about 90% sequence identity with any one of the DNA sequences defined in (a) and (b).

In an additional aspect, the present invention includes a vector adapted for transformation of a host, comprising a nucleic acid molecule as provided herein. The vector may be one having the characteristics of plasmid DS-712-1-3 having ATCC accession number 75603 or plasmid JB-1042-7-6 having ATCC accession number 75607.

The plasmids may be adapted for expression of the encoded transferrin receptor, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the transferrin receptor protein or the fragment or analog of the transferrin receptor protein. In specific embodiments of this aspect of the invention, the nucleic acid molecule may encode substantially all the transferrin receptor protein, only the Tbp1 protein or only the Tbp2 protein of the *Haemophilus* strain. The expression means may include a nucleic acid portion encoding a leader sequence for secretion from the host of the transferrin receptor protein or the fragment or the analog of the transferrin receptor protein. The expression means also may include a nucleic acid portion encoding a lipidation signal for expression from the host of a lipidated form of the transferrin receptor protein or the fragment or the analog of the transferrin receptor protein. The expression plasmid may have the identifying characteristics of plasmid JB-1468-29, JB-1600-1 or JB-1424-2-8. The host may be selected from, for example, *Escherichia coli, Bacillus, Haemophilus*, fungi, yeast or baculovirus and Semliki Forest virus expression systems may be used.

In an additional aspect of the invention, there is provided a transformed host containing an expression vector as provided herein. Such host may selected from JB-1476-2-1, JB-1437-4-1 and JB-1607-1-1. The invention further includes a recombinant transferrin receptor protein or fragment or analog thereof producible by the transformed host.

As described in more detail below, there has been produced Tbp1 and Tbp2 protein receptors separate from each other. Further aspects of the present invention, therefore, provide an isolated and purified Tbp1 protein of a strain of *Haemophilus* free from the Tbp2 protein of the *Haemophilus* strain and an isolated and purified Tbp2 protein of a strain of *Haemophilus* free from the Tbp1 protein of the *Haemophilus* strain. The *Haemophilus* strain may be *H. influenzae* type b or a non-typable strain of *H. influenzae*.

The present invention further provides synthetic peptides corresponding to portions of the transferrin receptor. Accordingly, in a further aspect of the invention, there is provided a synthetic peptide having no less than six amino acids and no more than 150 amino acids and containing an amino acid sequence corresponding to a portion only of a transferrin receptor protein of a strain of bacteria or of an analog the transferrin receptor protein. The bacterial strain preferably is a *Haemophilus* strain, particularly a *H. influenzae* strain, specifically a strain of *H. influenzae* type b or a non-typable strain of *H. influenzae*.

The peptides provided herein may comprise an amino acid sequence which is conserved among bacteria that produces transferrin receptor protein, including strains of *Haemophilus*. The peptide may include an amino acid sequence LEGGFYGP (SEQ ID NO: 74) or LEGGFYG (SEQ ID NO: 85). The peptides provided herein may have an amino acid sequence selected from those presented in Table 2 or 3 below for the Eagan strain of *H. influenzae* type b and corresponding amino acid sequences for other strains of *H. influenzae*.

In accordance with another aspect of the invention, an immunogenic composition is provided which comprises at least one active component selected from at least one nucleic acid molecule as provided herein, at least one recombinant protein as provided herein, at least one of the purified and isolated Tbp1 or Tbp2 proteins, as provided herein, at least one synthetic peptide, as provided herein, at least one purified and isolated truncated Tbp2 protein, as provided herein and a live vector, as provided herein, and a pharmaceutically acceptable carrier therefor or vector therefor. The at least one active component produces an immune response when administered to a host.

The immunogenic compositions provided herein may be formulated as a vaccine for in vivo administration to protect against diseases caused by bacterial pathogens that produce transferrin receptors. For such purpose, the compositions may be formulated as a microparticle, capsule or liposome preparation. Alternatively, the compositions may be provided in combination with a targeting molecule for delivery to specific cells of the immune system or to mucosal surfaces. The immunogenic composition may comprise a plurality of active components to provide protection against disease caused by a plurality of species of transferrin receptor producing bacteria. The immunogenic compositions may further comprise an adjuvant.

In accordance with another aspect of the invention, there is provided a method for inducing protection against infection or disease caused by *Haemophilus* or other bacteria that produce transferrin receptor protein, comprising the step of administering to a susceptible host, such as a human, an effective amount of the immunogenic composition as recited above.

In accordance with another aspect of the invention, an antiserum or antibody specific for the recombinant protein, the isolated and purified Tbp1 protein or Tbp2 protein, synthetic peptide or the immunogenic composition, is provided.

In a further aspect, there is provided a live vector for delivery of transferrin receptor to a host, comprising a vector containing the nucleic acid molecule as described above. The vector may be selected from *Salmonella*, BCG, adenovirus, poxvirus, vaccinia and poliovirus. The vector may specifically be poliovirus and the nucleic acid molecule may code for a fragment of transferrin receptor having an amino acid sequence of LEGGFYGP (SEQ ID NO: 74) or LEGGFYG (SEQ ID NO: 85). The present invention further includes a plasmid vector having the identifying characteristics of pT7TBP2A, pT7TBP2B, pT7TBP2C or pT7TBP2D (ATCC designation Nos. 75931, 75932, 75933, 75934).

An additional aspect of the invention provides a strain of *Haemophilus* that does not produce transferrin receptor protein. Such strain may comprise a gene encoding transferrin receptor which is functionally disabled, such as by insertional mutagenesis. The *Haemophilus* strain may be one that has been attenuated and the attenuated strain may comprise the vector for delivery of transferrin receptor.

As mentioned above, one aspect of the invention provides novel Tbp1 or Tbp2 protein of a strain of *Haemophilus*, preferably a strain of *Haemophilius influenzae*, which is isolated and purified and free from the other. A yet further aspect of the present invention provides a method for producing such proteins. Accordingly, in this yet further aspect, the present invention provides a method of producing an isolated and purified Tbp1 or Tbp2 protein of a strain of *Haemophilus*, comprising the steps of (a) providing a recombinant host expressing, in inclusion bodies, Tbp1 or Tbp2 protein, but not both; (b) growing the host to provide a cell mass; (c) disrupting the cell mass to provide a cell lysate; (d) fractionating the cell lysate to provide a first supernatant and a first pellet, the first supernatant comprising substantially a large proportion of soluble host proteins; (e) separating the first supernatant from the first pellet; (f) selectively extracting the first pellet to remove substantially all soluble host proteins and host membrane proteins therefrom to provide a second supernatant and an extracted pellet containing the inclusion bodies; (g) separating the second supernatant from the extracted pellet; (h) solubilizing the extracted pellet to provide a solubilized extract; and (i) fractionating the solubilized extract to provide a Tbp1 or Tbp2 protein containing fraction.

The cell lysate may be fractionated to provide the first supernatant and first pellet may be effected by at least one detergent extraction.

The solubilized extract may be fractionated by gel filtration to provide the Tbp1 or Tbp2 protein containing fraction, which may be subsequently dialyzed to remove at least the detergent and provide a further purified solution of Tbp1 or Tbp2 protein.

BRIEF DESCRIPTION OF DRAWINGS

The present invention will be further understood from the following description with reference to the drawings, in which:

FIG. 1A shows the restriction map of two plasmid clones (pBHT1 and pBHT2) of the transferrin receptor operon of *Haemophilus influenzae* type b strain DL63.

FIG. 1B shows the restriction map of clones S-4368-3-3 and JB-901-5-3 containing TfR genes from *H. influenzae* type b strain Eagan.

FIG. 1C shows the restriction map of clone DS-712-1-3 containing the transferrin receptor gene from *H. influenzae* type b strain MinnA.

FIG. 1D shows the restriction map of clone JB-1042-7-6 containing the transferrin receptor gene from the non-typable *H. influenzae* strain PAK 12085.

FIG. 2 illustrates the organization and restriction maps of the cloned Tbp1 and Tbp2 genes of identified strains and the genetic organization of the TfR operon with two genes (tbp1 and tbp2) in tandem forming an operon under the transcriptional regulation of a single promoter and also depicts the 3.0 kb DNA fragment of pBHIT2 used to probe libraries for TfR genes from the *Haemophilus* strains.

FIGS. 3A to 3Q show the nucleotide sequences of the transferrin receptor genes (SEQ ID NO: 1) and their deduced amino acid sequences (SEQ ID NO: 5—Tbp1 and SEQ ID NO: 6—Tbp2) from *H. influenzae* type b, strain DL63. The underlined amino acid sequences correspond to peptides of Tbp1 identified by amino acid sequencing. The putative signal sequences are indicated by double overlining and correspond to residues 1 to 17 for Tbp2 and 1 to 23 for Tbp1.

FIGS. 4A to 4Q show the nucleotide sequences of the transferrin receptor genes (SEQ ID NO: 2) and their deduced amino acid sequences (SEQ ID NO: 7—Tbp1 and SEQ ID NO: 8—Tbp2) from *H. influenzae* type b strain Eagan. Putative −35, −10 and ribosomal binding site sequences are overlined.

FIGS. 5A to 5Q show the nucleotide sequences of the transferrin receptor genes (SEQ ID NO: 3) and their deduced amino acid sequences (SEQ ID NO: 9—Tbp1 and SEQ ID NO: 10—Tbp2) from *H. influenzae* type b strain MinnA. Putative −35, −10 and ribosomal binding site sequences are overlined.

FIGS. 6A to 6Q show the nucleotide sequences of the transferrin receptor genes (SEQ ID NO: 4) and their deduced amino acid sequences (SEQ ID NO. 11—Tbp1 and SEQ ID NO. 12—Tbp2) from the non-typable *H. influenzae* strain PAK 12085. Putative −35, −10 and ribosomal binding site sequences are overlined.

FIGS. 7A to 7N show the nucleotide sequences of the transferrin receptor genes (SEQ ID NO: 105) and their deduced amino acid sequences (SEQ ID NO. 106—Tbp1 and SEQ ID NO. 107—Tbp2) from the non-typable *H. influenzae* strain SB33.

FIGS. 8A to 8G show the nucleotide sequence of the Tbp2 gene (SEQ ID NO: 108) and the deduced amino acid sequence (SEQ ID NO: 109—Tbp2) from non-typable strain *H. influenzae* strain SB12.

FIGS. 9A to 9G show the nucleotide sequence of the Tbp2 gene (SEQ ID NO: 110) and the deduced amino acid sequence (SEQ ID NO: 111—Tbp2) from non-typable strain *H. influenzae* strain SB29.

FIGS. 10A to 10G show the nucleotide sequence of the Tbp2 gene (SEQ ID NO: 112) and the deduced amino acid sequence (SEQ ID NO: 113—Tbp2) from non-typable strain *H. influenzae* strain SB30.

FIGS. 11A to 11G show the nucleotide sequence of the Tbp2 gene (SEQ ID NO: 114) and the deduced amino acid sequence (SEQ ID NO: 115—Tbp2) from non-typable strain *H. influenzae* strain SB32.

FIG. 12A shows the nucleotide sequences of the promoter regions and 5'-end of the tbp2 genes from *H. influenzae* strains Eagan (SEQ ID NO: 116), MinnA (SEQ ID NO: 117), PAK 12085 (SEQ ID NO: 118) and SB33 (SEQ ID NO: 119). The coding strand primer used to amplify tbp2 genes by PCR is underlined (SEQ ID NO: 120).

FIG. 12B shows the nucleotide sequence of the intergenic region and 5'-end of the Tbp1 genes from *H. influenzae* strains Eagan (SEQ ID NO: 121), MinnA (SEQ ID NO: 122), DL63 (SEQ ID NO: 123), PAK 12085 (SEQ ID NO: 124), SB12 (SEQ ID NO: 125), SB29 (SEQ ID NO: 126), SB30 (SEQ ID NO: 127), and SB32 (SEQ ID NO: 128). The non-coding strand primer used to amplify the tbp2 genes by PCR is underlined (SEQ ID NO: 129).

Figure 13:
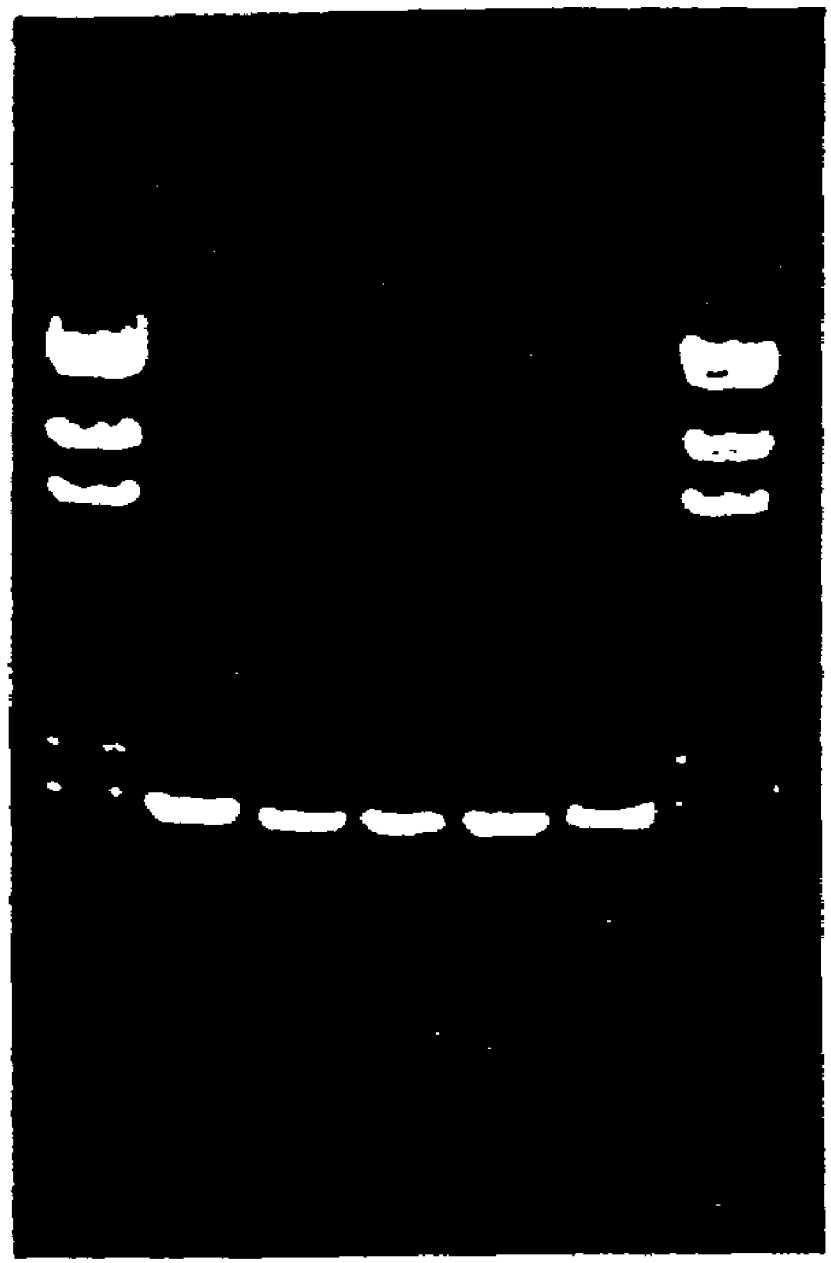

FIG. 13 shows the agarose gel analysis of PCR amplified tbp2 genes from non-typable *H. influenzae* strains SB12, SB29, SB30, SB32 and SB33. Lane 1 is SB33, lane 2 is SB12, lane 3 is SB29, lane 4 is SB30, lane 5 is SB32.

FIGS. 14A to 14C show a comparison of the amino acid sequences of Tbp1 from *H. influenzae* strains Eagan, DL63, PAK 12085 and SB33 (SEQ ID NOS: 7, 5, 11 and 106), *N. meningitidis* strains B16B6 and M982 (SEQ ID NOS: 94 and 95), and *N. gonorrhoeae* strain FA19 (SEQ ID NO: 96).

FIGS. 15A to 15D show a comparison of the amino acid sequence of Tbp2 from *H. influenzae* strains Eagan, DL63, PAK 12085, SB12, SB29, SB30 and SB32 (SEQ ID NOS: 8, 6, 12, 109, 110, 112, 114), *N. meningitidis* strains B16B6 and M982 (SEQ ID NOS: 97 and 98), *N. gonorrhoeae* strain FA19, and *Actinobacillus pleuropneumoniae* strains AP205 and AP37 (SEQ ID NOS: 99 and 100).

Figure 16A:
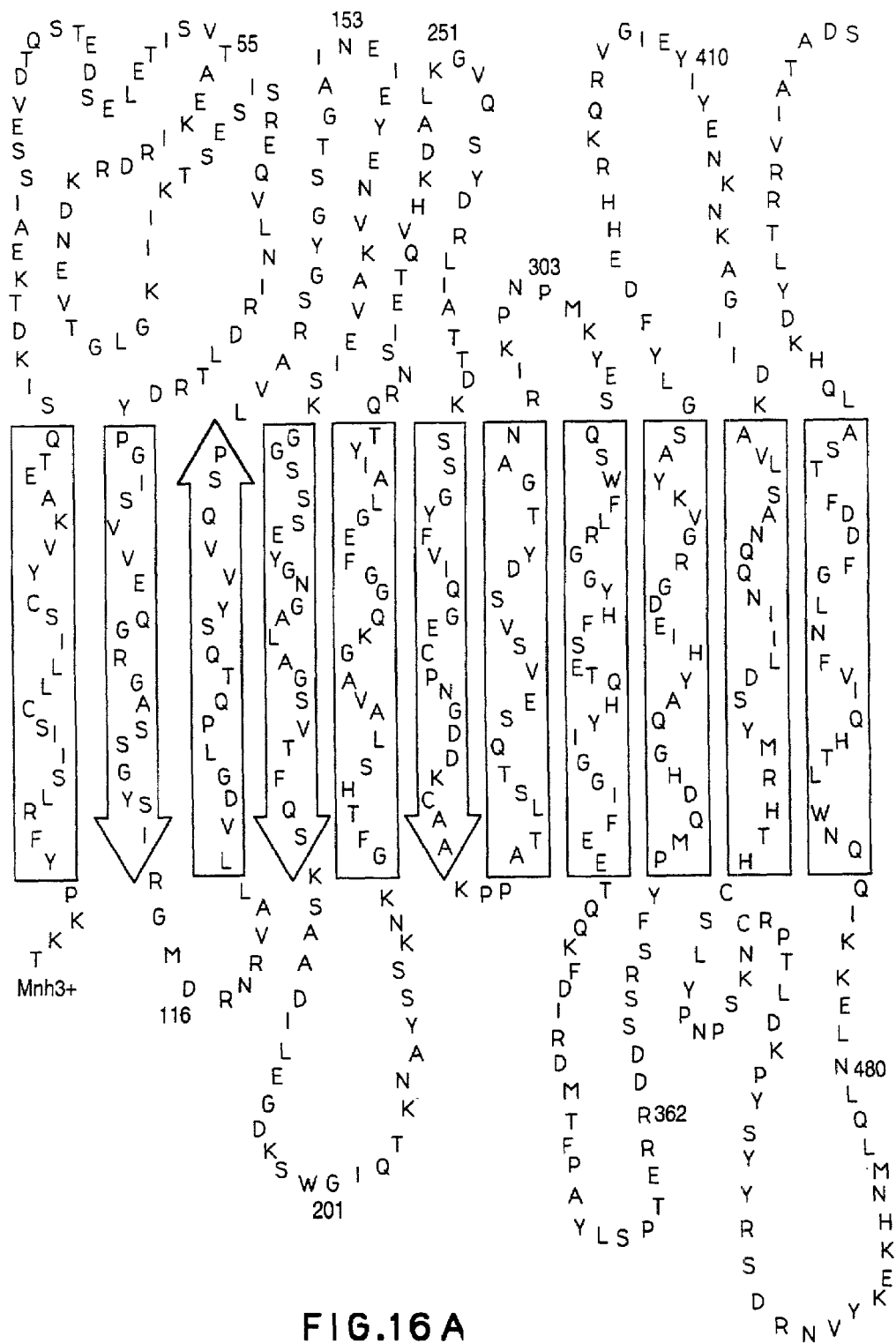
Figure 16B:
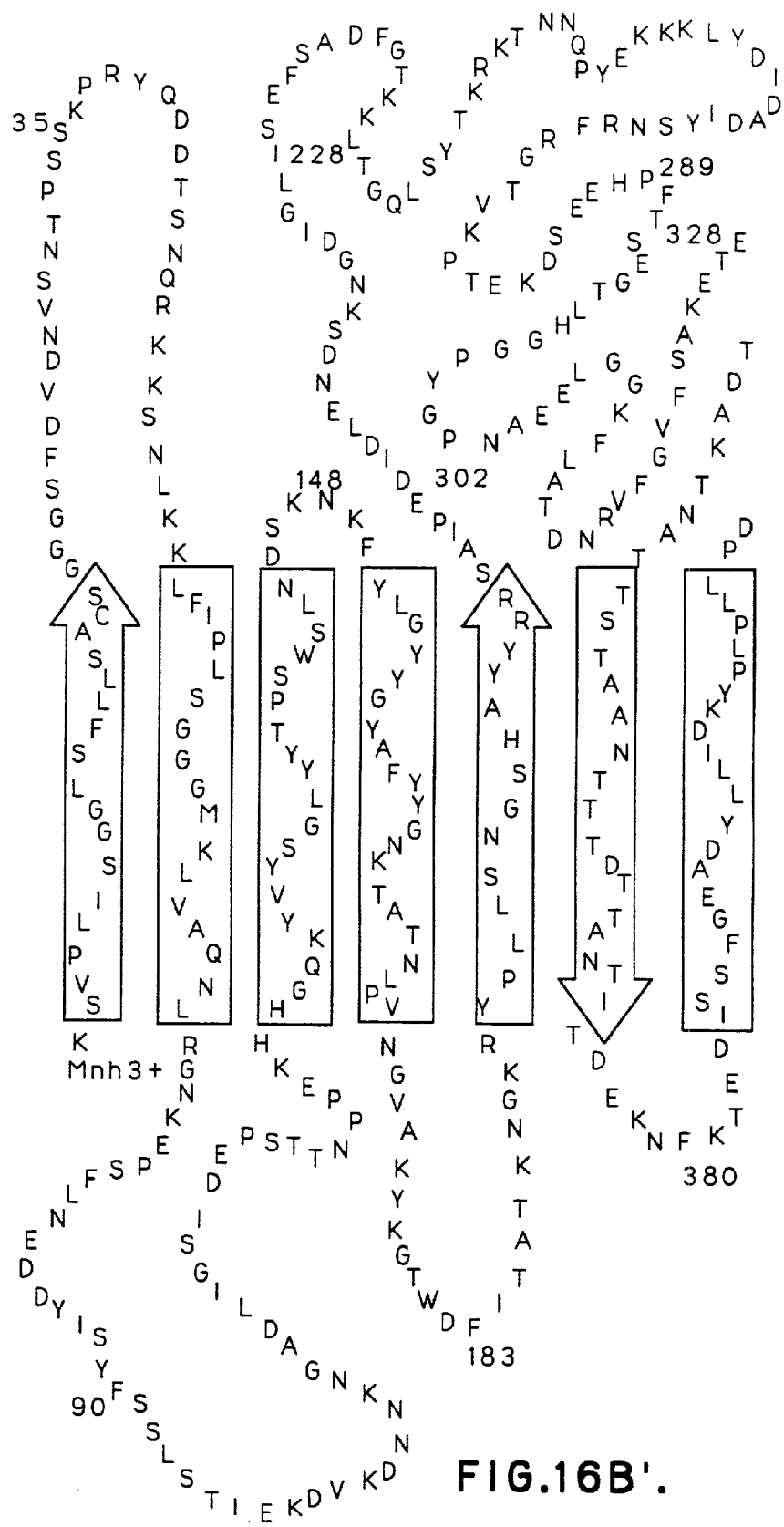

FIGS. 16A' and 16A" show the predicted secondary structure of *H. influenzae* Tbp1 protein and FIGS. 16B' and 16B" show the predicted secondary structure of *H. influenzae* Tbp2 protein.

Figure 17:
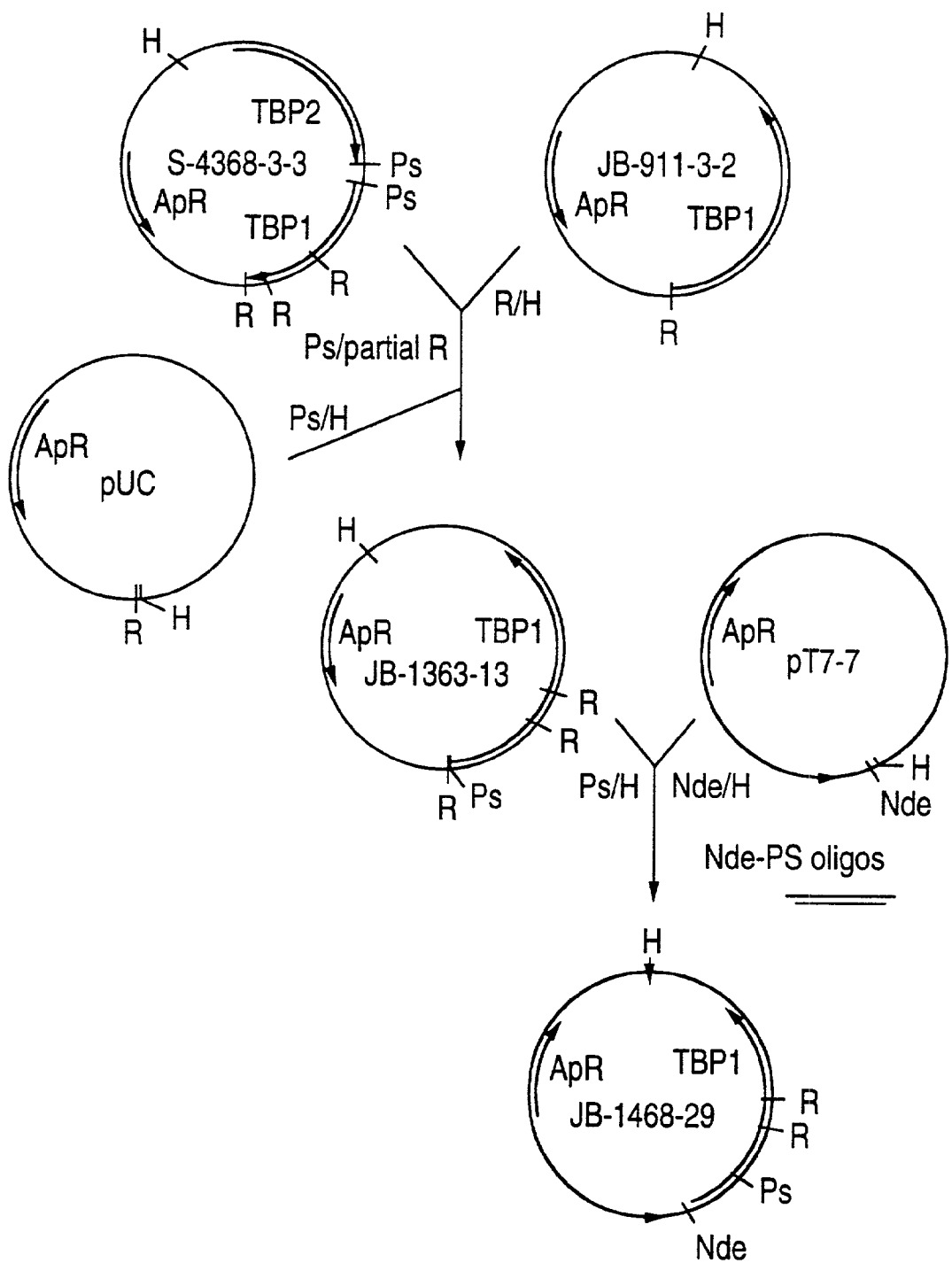

FIG. 17 shows the construction scheme of plasmid JB-1468-29 which expresses *H. influenzae* type b Eagan Tbp1 from *E. coli*.

Figure 18:
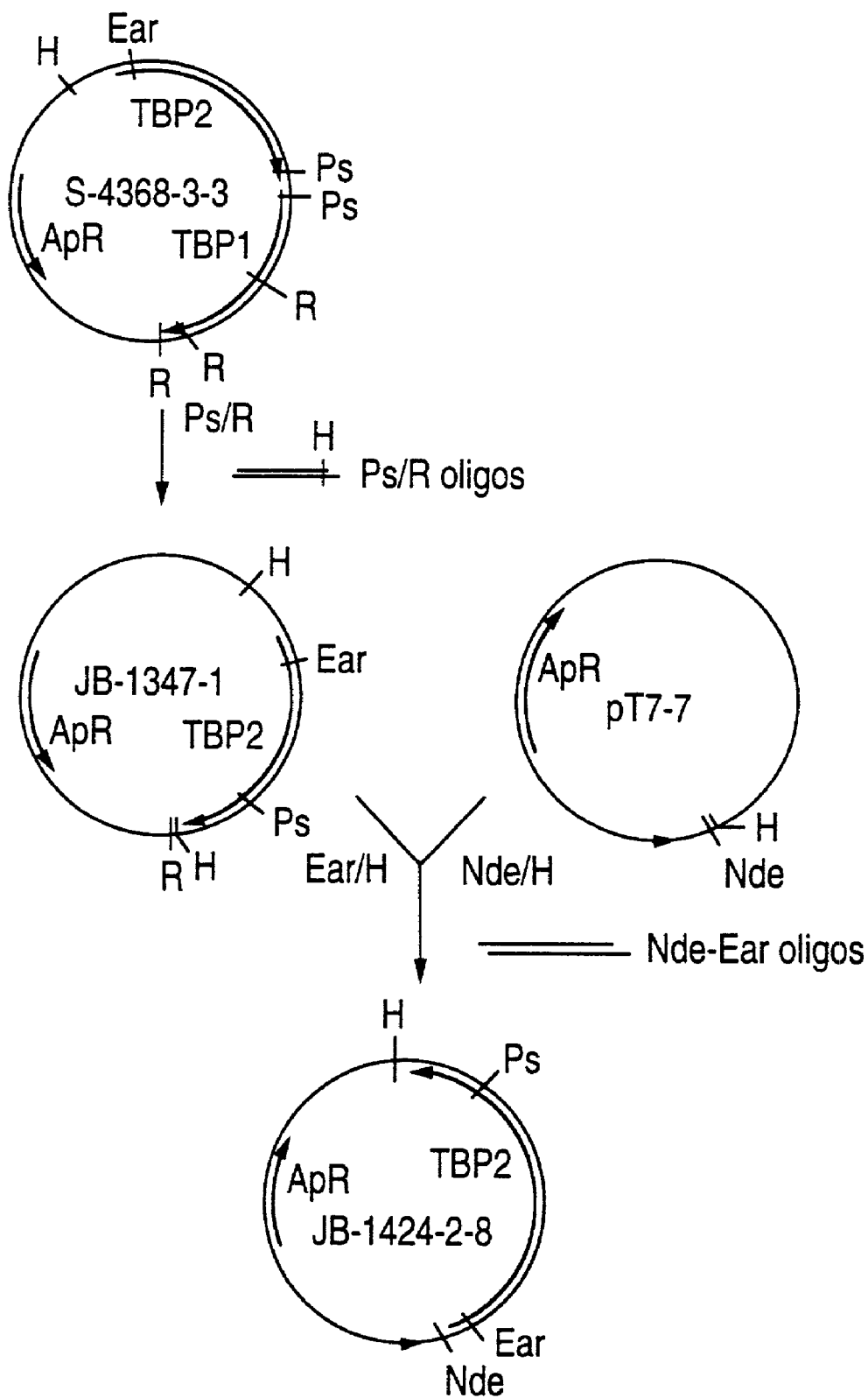

FIG. 18 shows the construction scheme of plasmid JB-1424-2-8 which expresses *H. influenzae* type b Eagan Tbp2 from *E. coli*.

FIG. 19 shows the oligonucleotide pairs (SEQ ID NOS: 130, 131) used to construct plasmid JB-1424-2-8.

FIGS. 20A and 20B show the sequence of oligonucleotide pairs A (SEQ ID NOS: 86, 87), B (SEQ ID NOS: 88, 89), C (SEQ ID NOS: 90, 91) and D (SEQ ID NOS: 92, 93) for constructing Tbp1 and Tbp2 expression plasmids.

Figure 21:
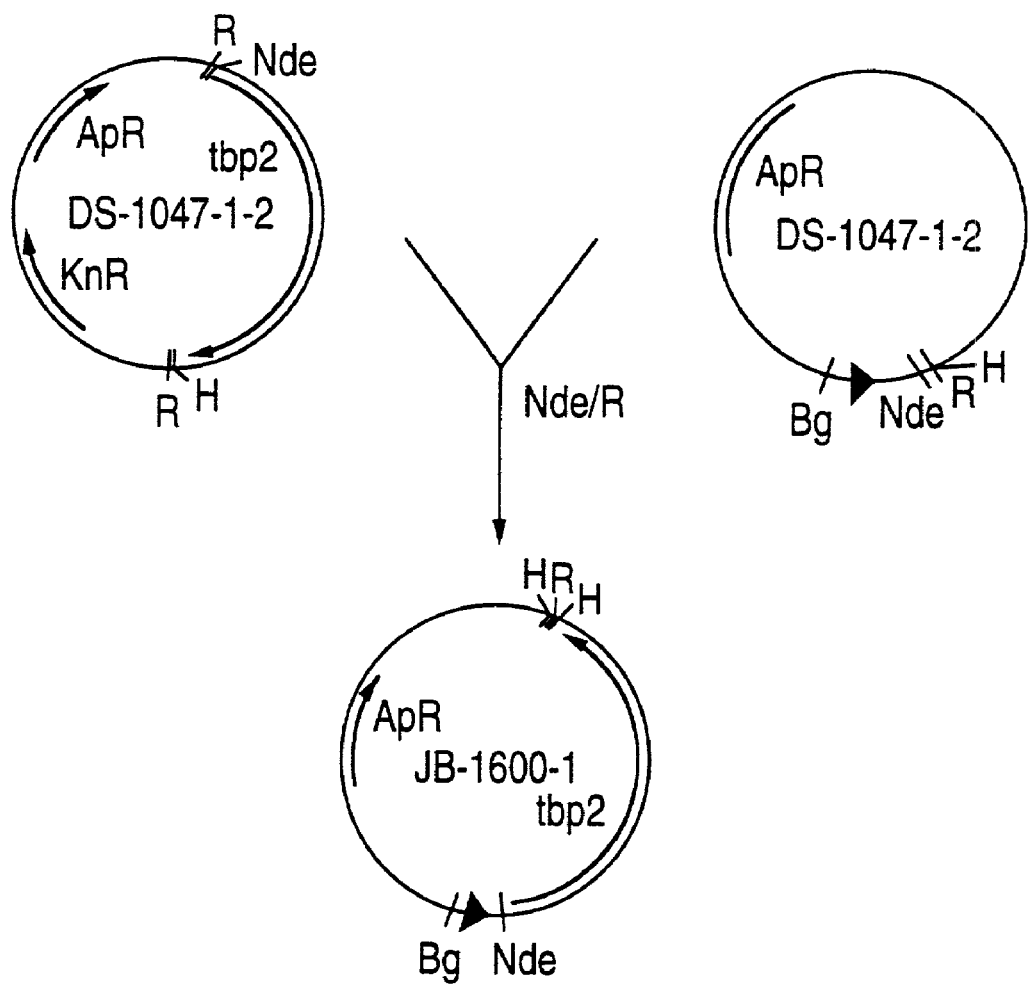

FIG. 21 shows the construction scheme of plasmid JB-1600-1 which expresses *H. influenzae* strain SB12 Tbp2 from *E. coli*.

Figure 22:

FIG. 22 shows SDS-PAGE gels of products from the expression of *Haemophilus* type b Eagan Tbp1 protein, Eagan Tbp2 protein, and non-typable *H. influenzae* SB12 Tbp2 protein from *E. coli*. Lane 1, JB-1476-2-1 (T7/Eagan Tbp1) at $t_0$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_0$; lane 5, JB-1437-4-1 at t=4h induction; lane 6, JB-1607-1-1 (T7/SB12 Tbp2) at $t_0$; lane 7, JB-1607-1-1 at t=4 h induction.

Figure 23:
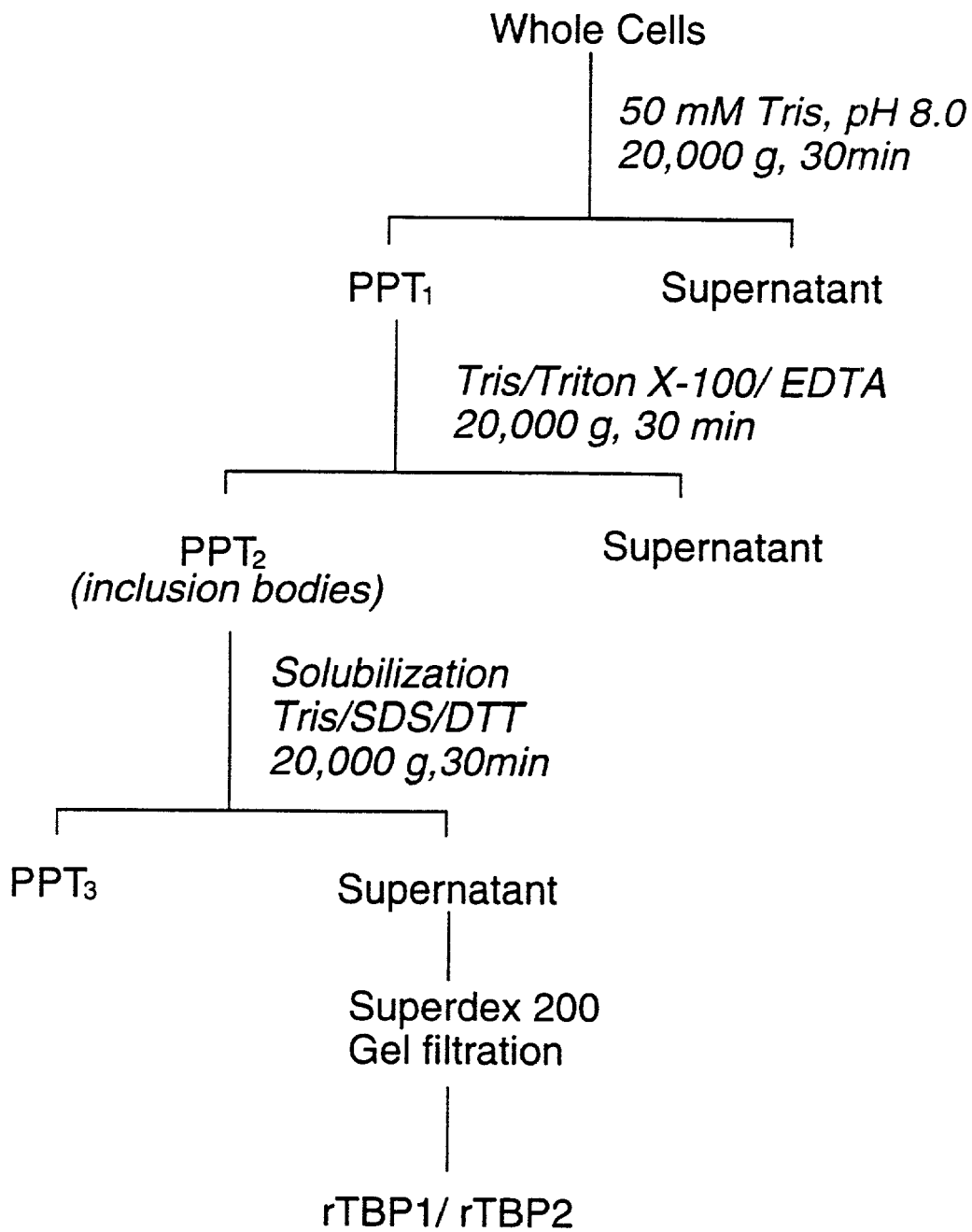

FIG. 23 shows a purification scheme for recombinant Tbp1 and Tbp2 expressed from *E. coli*.

FIG. 24 shows an analysis of the purity of recombinant Tbp1 and Tbp2 purified by the scheme of FIG. 23. Lane 1 contains molecular weight size markers (106, 80, 49.5, 32.5, 27.5 and 18.5 kDa), Lane 2 is *E. Coli* whole cell lysate. Lane 3 is solubilized inclusion bodies. Lane 4 is purified Tbp1 or Tbp2.

Figure 25A:
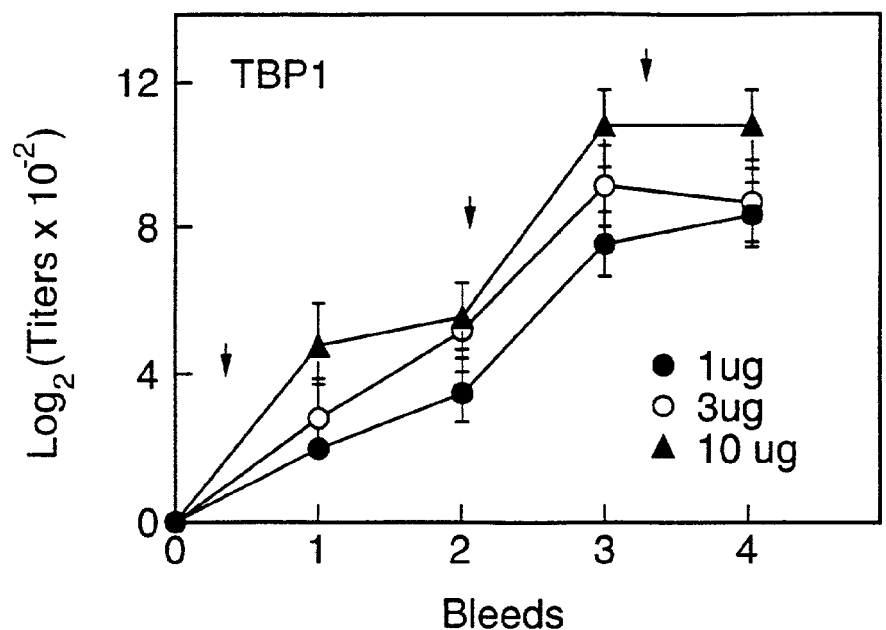
Figure 25B:
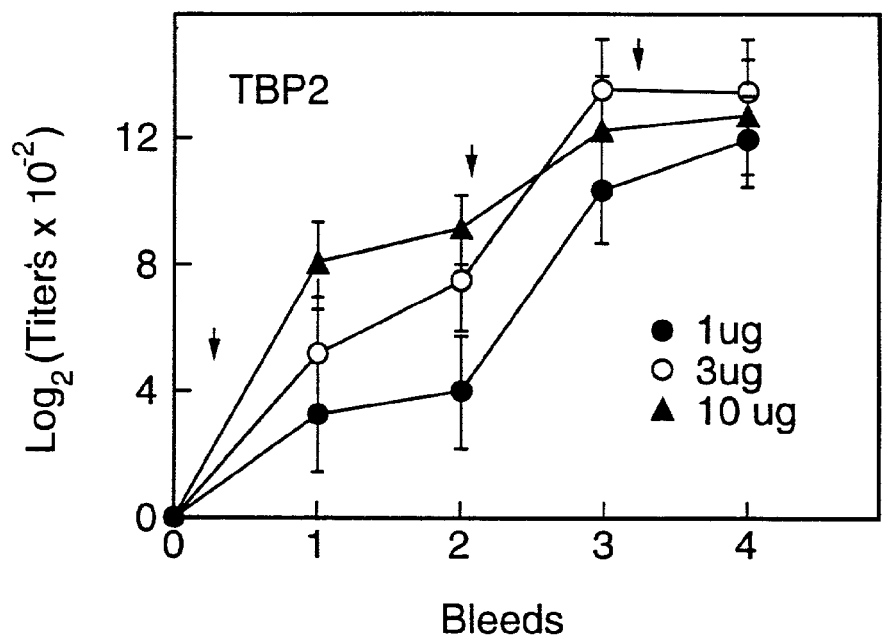

FIG. 25 shows the immunogenicity of rTbp1 (upper panel) and rTbp2 (lower panel) in mice.

Figure 26:
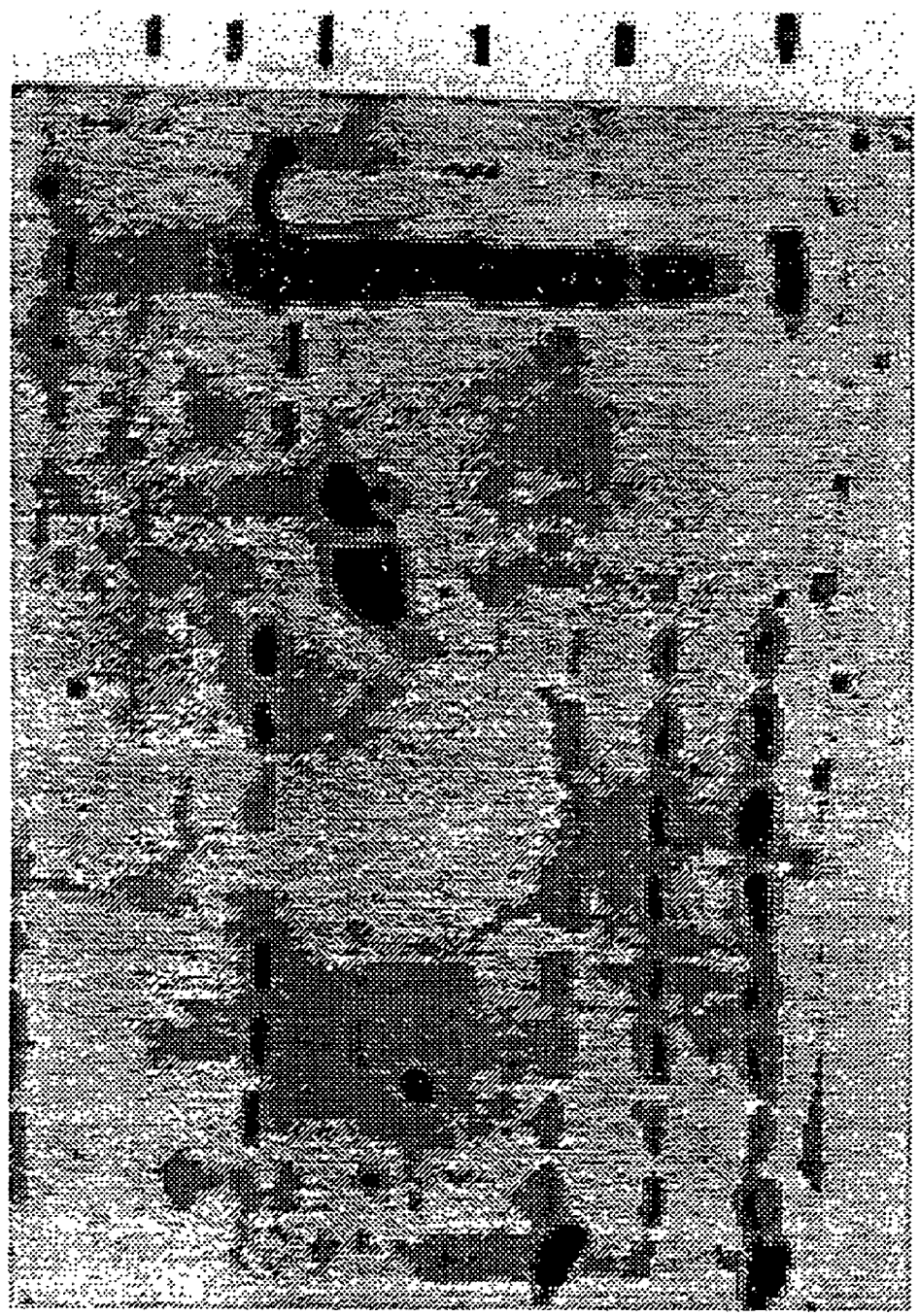

FIG. 26 shows the reactivity of anti-Eagan rTbp1 antisera with various *H. influenzae* strains on a Western blot. Lane 1, BL21/DE3; lane 2, SB12−EDDA; lane 3, SB12+EDDA; lane 4, SB29−EDDA; lane 5, SB29+EDDA; lane 6, SB33−EDDA; lane 7, SB33+EDDA; lane 8, Eagan−EDDA; lane 9, Eagan+EDDA; lane 10, *B. catarrhalis* 4223−EDDA; lane 11, *B. catarrhalis* 4223+EDDA; lane 12, *N. meningitidis* 608−EDDA; lane 13, *N. meningitidis* 608+EDDA; lane 14, induced JB-1476-2-1 expressing recombinant Eagan Tbp1; lane 15, molecular weight markers. Specific ~95 kDa bands reacted with the anti-Tbp1 antisera in lanes 3, 4, 5, 7, 8 and 9, corresponding to *H. influenzae* strains SB12, SB29, SB33 and Eagan; ~110 kDa bands in lanes 10 and 11, corresponding to *B. catarrhalis* strain 4223; and ~80 kDa bands in lanes 12 and 13, corresponding to *N. meningitidis* 608.

Figure 27:
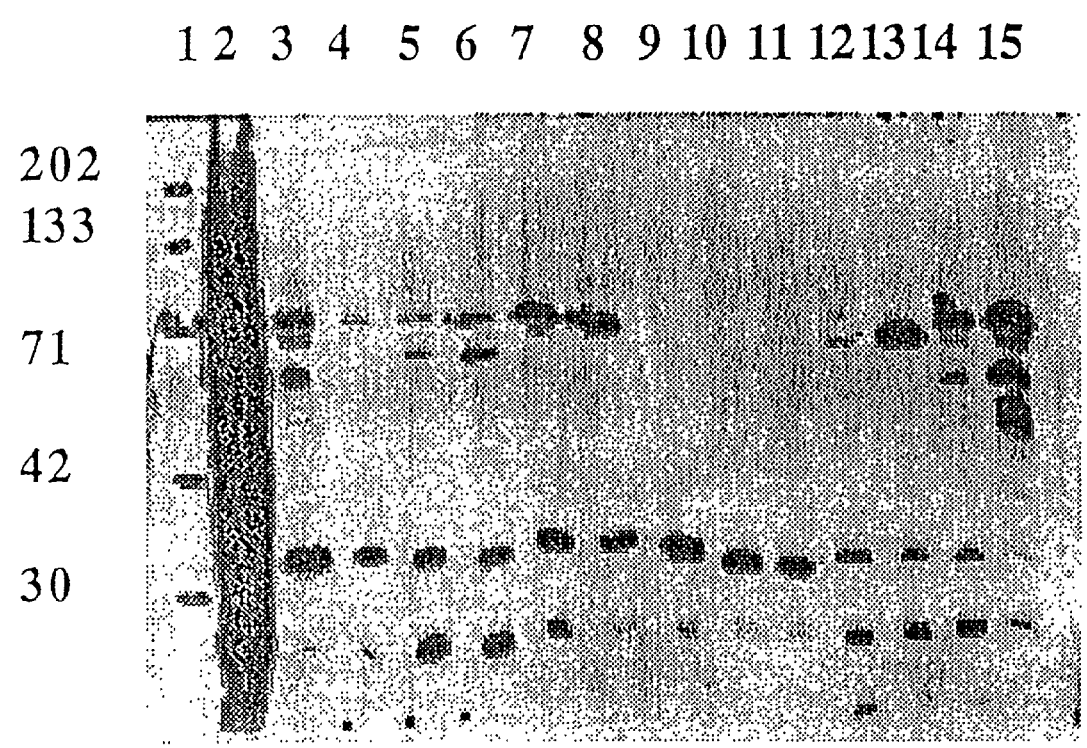

FIG. 27 shows the reactivity of anti-Eagan rTbp2 antisera with various *H. influenzae* strains on a Western blots. Lane 1, molecular weight markers; lane 2, induced JB-1437-4-1 expressing recombinant Eagan Tbp2; lane 3, SB12−EDDA; lane 4, SB12+EDDA; lane 5, SB29−EDDA; lane 6, SB29+ EDDA; lane 7, SB30−EDDA; lane 8, SB30+EDDA; lane 9, SB32−EDDA; lane 10, SB33−EDDA; lane 11, SB33+ EDDA; lane 12, PAK−EDDA; lane 13, PAK+EDDA; lane 14, Eagan−EDDA; lane 15, Eagan+EDDA. Specific bands of 60–70 kDa were reactive with the anti-Tbp2 antisera in lanes, 3, 6, 7, 8, 13, 14 and 15, i.e. strains SB12, SB29, SB30, PAK and Eagan.

Figure 28:
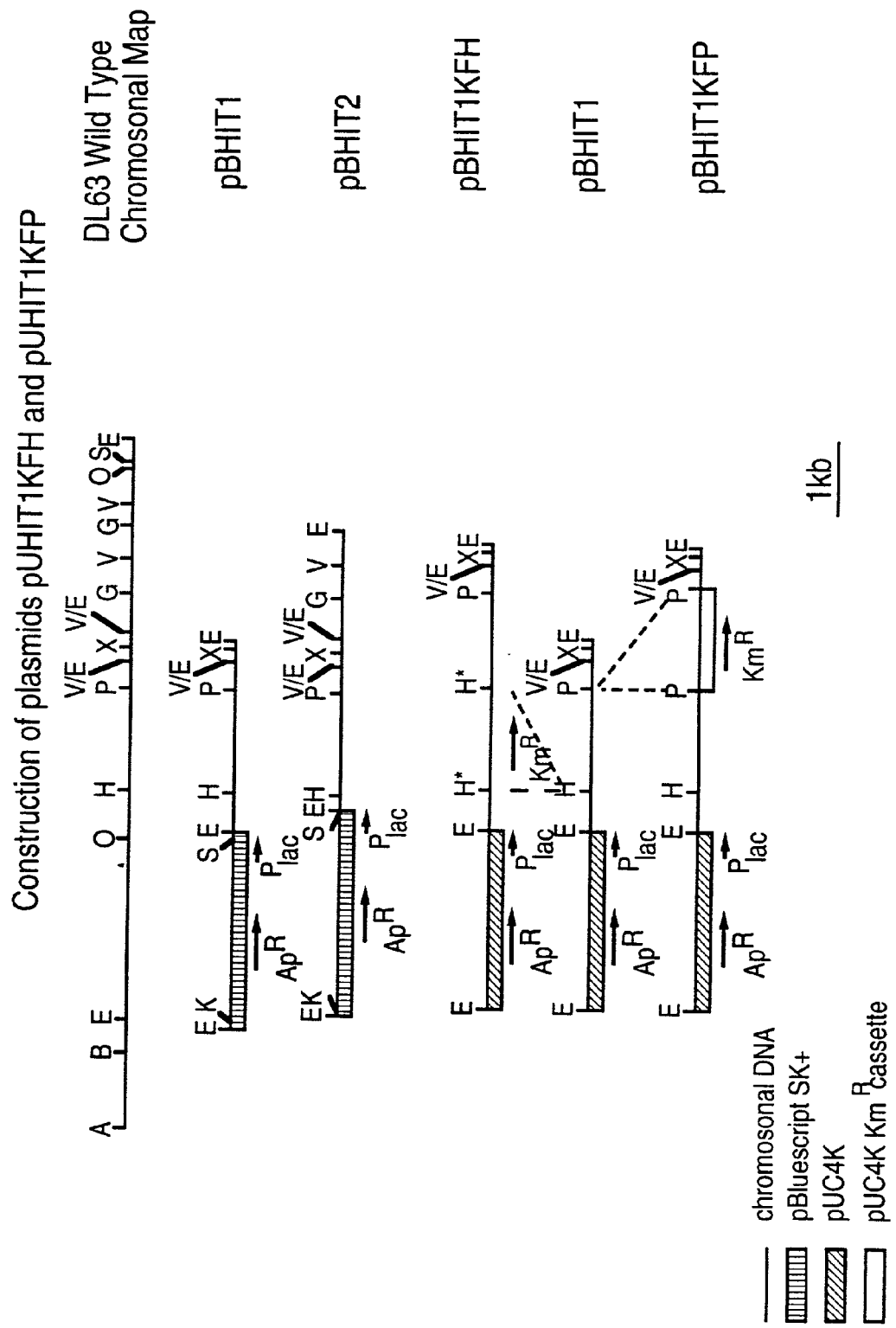

FIG. 28 shows the construction of plasmids pUHIT1KFH and pUHIT1KFP used to generate strains of *H. influenzae* that do not produce transferrin receptor.

Figure 29:
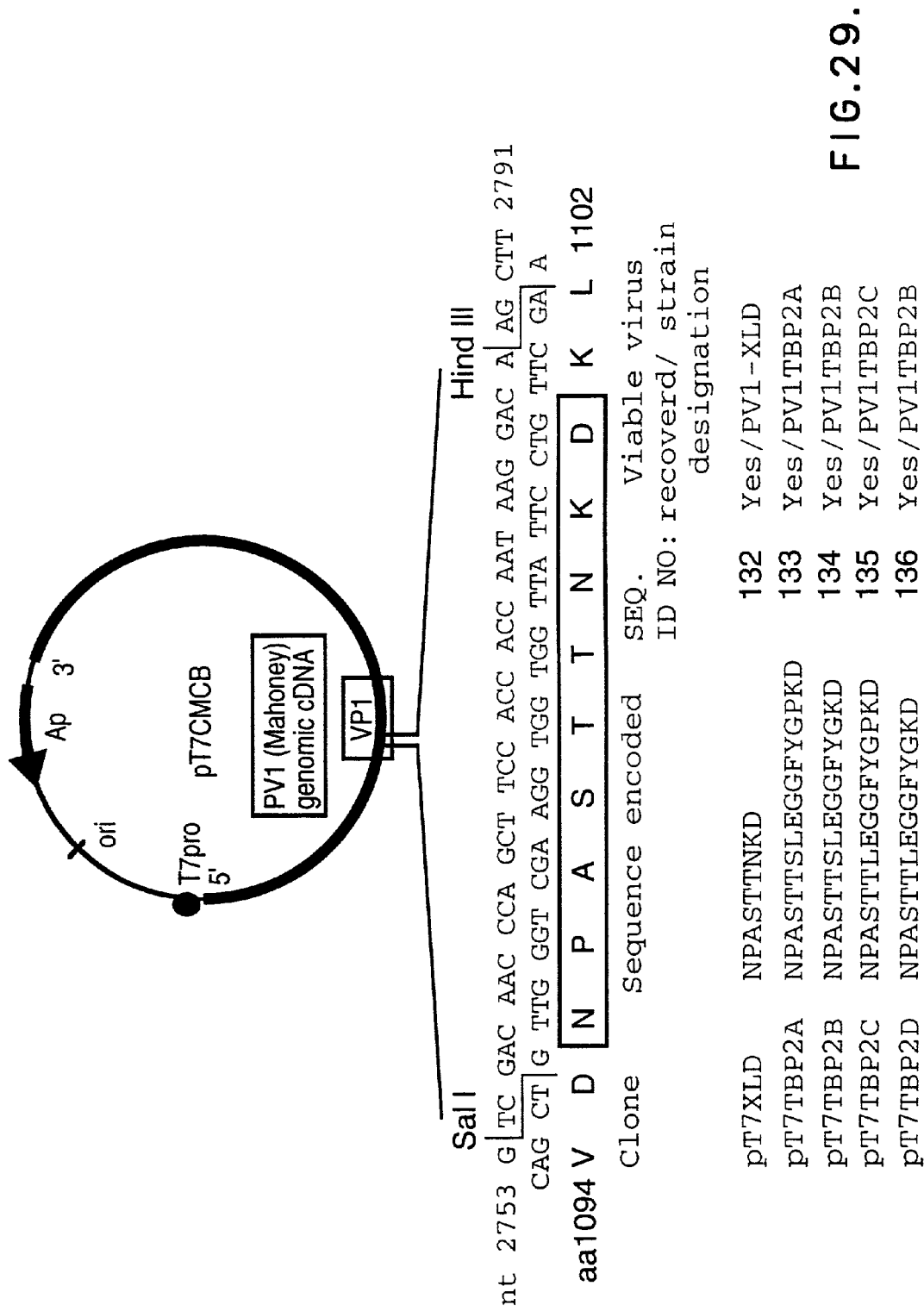

FIG. 29 shows the construction of plasmids encoding chimeric polioviruses expressing an epitope derived from transferrin receptor protein that is conserved among bacteria that produce transferrin receptor protein.

FIG. 30 is a Western blot showing the reactivity of antisera produced by immunization of rabbits with poliovirus chimeras expressing an epitope derived from transferrin receptor protein that is conserved among bacteria that produce transferrin receptor protein. Panel A shows a Coomassie Brilliant Blue-stained gel showing purified recombinant Tbp2 from *H. influenzae* strain SB12 expressed in *E. coli* (lane 1), purified Tbp2 from *Branhamella catarrhalis* strain 4223 (lane 2), a whole cell lysate of iron-limited *B. catarrhalis* strain 4223 (lane 3), a whole cell lysate of *E. coli* JM109 grown under non-iron limited conditions (lane 5). Panel B shows results of a Western blot of a replicate gel using a pool of the sera collected on day 27 from rabbits immunised with PV1TBP2A (rabbits 40, 41 and 42). Panel C shows the results for a pool of prebleed sera from the same, which displayed minimal specific reactivity.

FIGS. 31A and 31B illustrate a number of truncated analogues of transferrin receptor protein Tbp2 of the Eagan strain. On the Figure, there are identified a number of clones which contain the nucleic acid molecules encoding the respective truncated analogs (The encoding nucleic molecule for the Tbp2 protein is shown in FIG. 4). The specific clones and the SEQ ID nos. for the encoded truncated Tbp2 analogs are contained in Table 8.

FIGS. 32A and 32B show the binding of truncated Tbp2 proteins to transferrin.

In some of the above Figures, the following abbreviations have been used to designate particular site specific restriction endonucleases: R, Eco RI; Ps, Pst I; H, Hind III; Bg, Bgl II; Nde, Nde I; Ear, Ear I; and Sau, Sau3A I.

In FIG. 28, the following abbreviations have been used to designate particular site specific restriction endonucleases: A, Acc I; B Bam HI; E, Eco RI; O, Xho I; H, Hind III; Ps, Pst I; V, Eco RV; X, Xba I, G, Bgl II; S, Sal I; K, Kpn I; and S*, Sac I.

GENERAL DESCRIPTION OF THE INVENTION

Any *Haemophilus* strain may be conveniently used to provide the purified and isolated nucleic acid which may be in the form of DNA molecules, comprising at least a portion of the nucleic acid coding for a transferrin receptor as typified by embodiments of the present invention. Such strains are generally available from clinical sources and from bacterial culture collections, such as the American Type Culture Collection.

According to an aspect of the invention, the transferrin receptor protein may be isolated from *Haemophilus* strains by the methods described by Schryvers (1989), Ogunnaviwo and Schryvers (1992) and U.S. Pat. No. 5,141,743, the subject matter of which is hereby incorporated by reference. Although the details of an appropriate process are provided in patent U.S. Pat. No. 5,141,743, a brief summary of such process is as follows. Isolation of transferrin receptor is achieved by isolating a membrane fraction from a bacterial strain expressing transferrin binding activity and purifying the transferrin receptor by an affinity method involving the sequential steps of prebinding of transferrin to the transferrin receptor in the membrane fraction, solubilising the membrane, immobilising the transferrin and separating the transferrin receptor from the immobilised transferrin. Alternatively, the receptor proteins may be isolated by a modification of the above method in which the prebinding step is avoided and a high concentration of salt is included in the solubilization buffer to allow direct isolation with immobilized transferrin as described in Ogunnariwo and Schryvers (1992).

In this application, the term "transferrin receptor" is used to define a family of Tbp1 and/or Tbp2 proteins which includes those having variations in their amino acid sequences including those naturally occurring in various strains of, for example, *Haemophilus*. Other bacterial sources of transferrin receptor include, but are not limited to, species of *Neisseria, Branhamella, Pasteurella* and *Actinobacillus*. Some, if not all, of these bacteria contain both Tbp1 and Tbp2. The purified and isolated DNA molecules comprising at least a portion coding for transferrin receptor of the present invention also include those encoding functional analogs of transferrin receptor. In this application, a first protein or peptide is a "functional analog" of a second protein if the first protein is immunologically related to and/or has the same function as the second protein or peptide. The functional analog may be, for example, a fragment of the protein, such as those shown in FIG. 31, or a substitution, addition or deletion mutant thereof.

In one particular embodiment, the transferrin receptor was isolated from *H. influenzae* type b strain DL63 and purified by affinity chromatography methods, as described by Schryvers (1989), Ogunnariwo and Schryvers (1992) and in U.S. Pat. No. 5,141,743. The isolated and purified transferrin receptor was used to generate anti-TfR antisera in rabbits. Chromosomal DNA from *H. influenzae* type b strain DL63 was mechanically sheared, EcoRI linkers added, and a λZAP expression library constructed. The library was screened with the anti-TfR rabbit antisera and two positive clones (pBHIT1 and pBHIT2) were obtained which had overlapping restriction maps (FIG. 1A and FIG. 2). The clones were sequenced and two large open reading frames were identified (FIG. 2). The nucleotide sequences of the transferrin receptor genes Tbp1 and Tbp2 (SEQ ID NO: 1) from *H. influenzae* DL63 and their deduced amino acid sequences (SEQ ID NO: 5—Tbp1 and SEQ ID NO: 6—Tbp2) are shown in FIG. 3. The sequence analysis showed the TfR operon to consist of two genes (Tbp1 and Tbp2) arranged in tandem and transcribed from a single promoter (as particularly shown in FIG. 2 and FIG. 3). The Tbp2 protein tends to vary in molecular weight depending on the species whereas the Tbp1 protein tends to have a more consistent molecular weight with some variability across the various bacteria which have TfR genes. The molecular weight of Tbp1 is usually in the range of 94 to 106,000 whereas the molecular weight of Tbp2 varies considerably from 58 to 98 000.

Amino acid sequencing of the N-termini and cyanogen bromide fragments of transferrin receptor from *H. influenzae* DL63 was performed. The N-terminus of Tbp2 was blocked but amino acid sequences were identified by sequencing of Tbp1 and are indicated by underlining within the protein sequence of FIG. 3. These peptide sequences are Glu Thr Gln Ser Ile Lys Asp Thr Lys Glu Ala Ile Ser Ser Glu Val Asp Thr (as shown in FIG. 3, SEQ ID NO: 101) and Leu Gln Leu Asn Leu Glu Lys Lys Ile Gln Gln Asn Trp Leu Thr His Gln Ile Ala Phe (as shown in FIG. 3; SEQ ID NO: 102). The signal sequence of Tbp1 and the putative signal sequence of Tbp2 are indicated by double overligning in FIG. 3. The putative signal sequence for Tbp1 is Met Thr Lys Lys Pro Tyr Phe Arg Leu Ser Ile Ile Ser Cys Leu Leu Ile Ser Cys Tyr Val Lye Ala (SEQ ID NO: 103). The putative signal sequence for Tbp2 is Met Lys Ser Val Pro Leu Ile Ser Gly Gly Leu Ser Phe Leu Leu Ser Ala (SEQ ID NO: 104). The derived amino acid sequence of the N-terminal region of Tbp2 indicates that it is a lipoprotein.

Figure 1A:
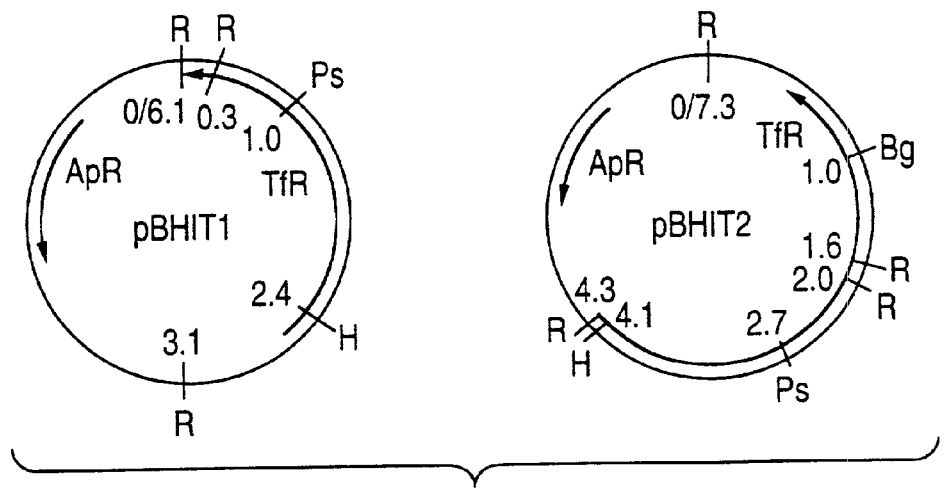
Figure 1B:
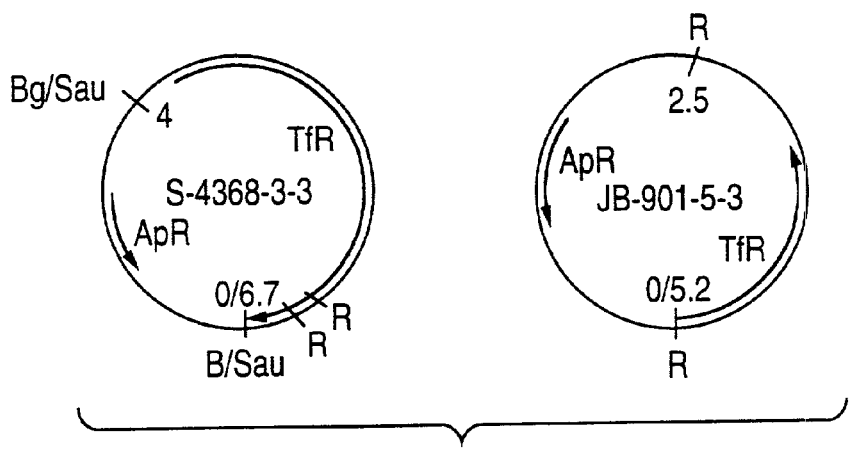
Figure 2:
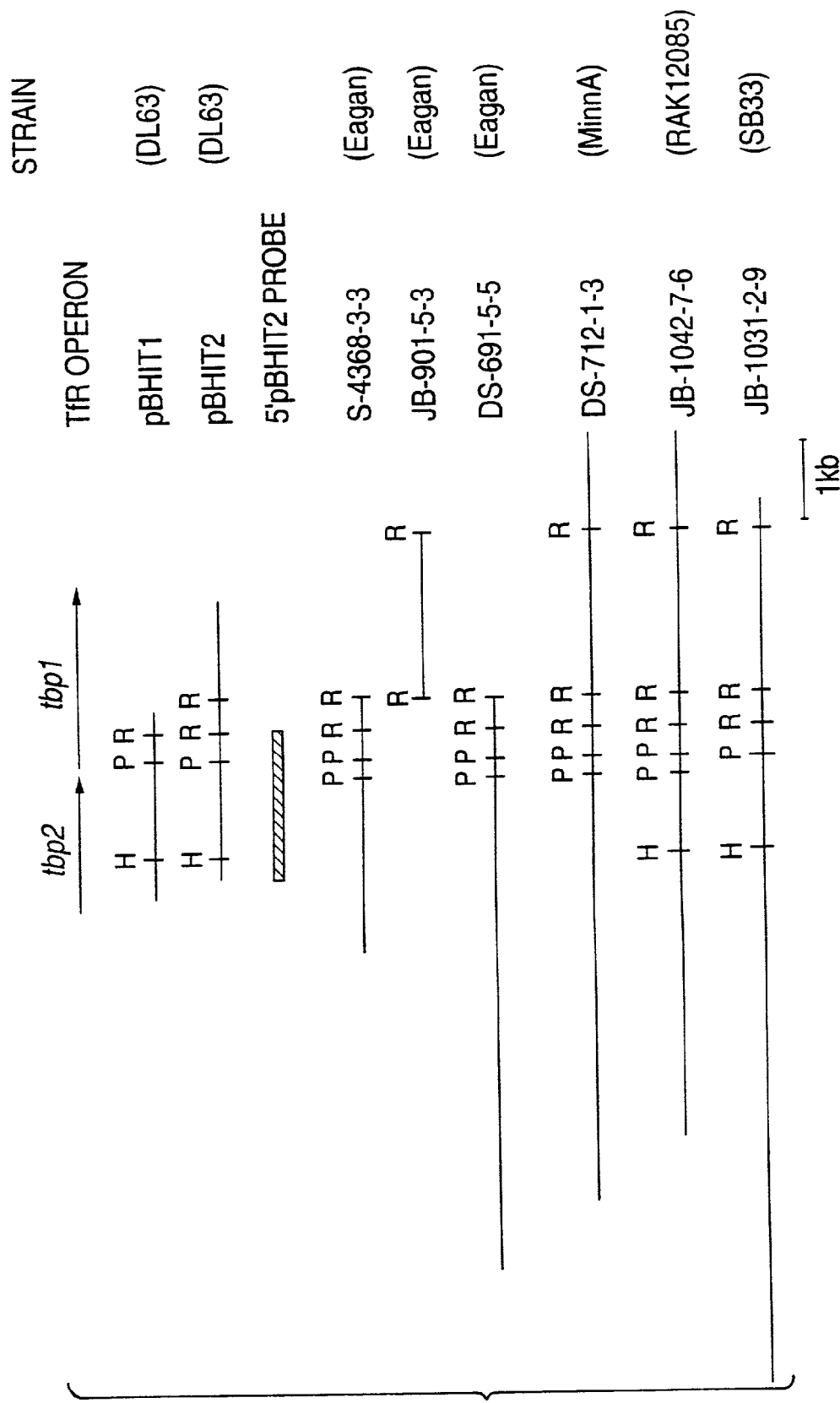

Chromosomal DNA from *H. influenzae* type b strain Eagan was prepared and libraries were generated. The first library was constructed from DNA partially digested with Sau3A I, size-fractionated for ~5–10 kb fragments, and cloned into a pUC-based plasmid. The second library was constructed from Eco RI-restricted chromosomal DNA fragments cloned into λZAP. Both libraries were probed with a 5'-fragment of the pBHIT clone as shown in FIG. 2 and partial clones of the TfR genes of *H. influenzae* Eagan termed S-4368-3-3 and JB-901-5-3 were obtained. Thus, referring to FIGS. 1B and 2, there is illustrated according to further aspects of the present invention, plasmid clones S-4368-3-3 and JB-901-5-3 encoding Tbp1 and Tbp2 from *H. influenzae* type b strain Eagan. The DNA sequences of the Tbp1 and Tbp2 genes (SEQ ID NO: 2) from *H. influenzae* type b strain Eagan and their deduced amino acid sequences (SEQ ID NOS: 7 and 8) are shown in FIG. 4 with the Tbp2 sequence being the first gene in the operon. In FIG. 4, putative –35, –10 and ribosomal binding site sequences are overlined.

Figures 1C, 1D:
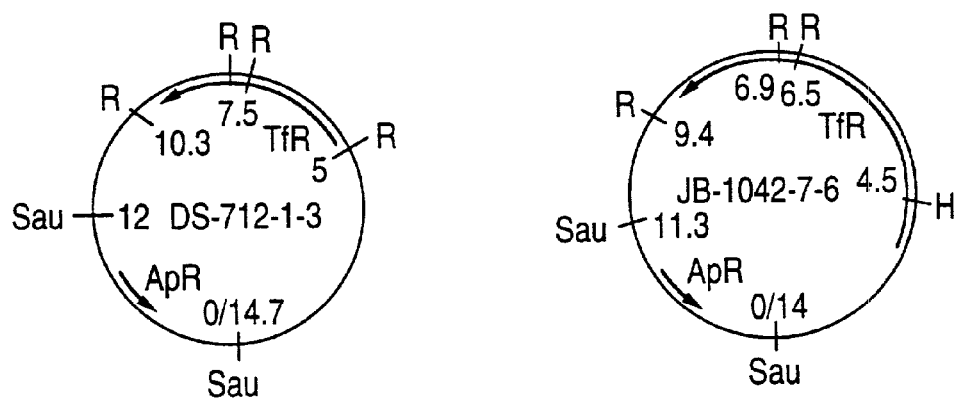

Chromosomal DNA from *H. influenzae* type b strain MinnA was prepared and the DNA partially digested with Sau3A I, size-fractionated for 10–20 kb fragments, and cloned into the BamHI site of EMBL3. The library was probed with the 5'-fragment of the pBHIT clone (FIG. 2) and a full-length clone encoding TfR (DS-712-1-3) was obtained. Referring to FIG. 1C and 2, there is illustrated according to additional aspects of the present invention, plasmid clone DS 712-1-3 encoding Tbp1 and Tbp2 from *H. influenzae* type b strain MinnA. The DNA sequences of Tbp1 and Tbp2 (SEQ ID NO: 3) and their deduced amino acid sequences (SEQ ID NO: 9—Tbp1 and SEQ ID NO: 10—Tbp2) from *H. influenzae* type b strain MinnA are shown in FIG. 5 where the Tbp2 sequence is first in the operon. In FIG. 5, Putative –35, –10 and ribosomal binding site sequences are overlined.

Chromosomal DNA from the non-typable *H. influenzae* strain PAK 12085 was prepared. The DNA was partially digested with Sau3A I, size-fractionated for 10–20 kb fragments, and cloned into the BamH I site of EMBL3. The library was probed with the fragments of the pBHIT clone (FIG. 2) and a full-length clone encoding TfR (JB-1042-7-6) was obtained. The restriction map of clone JB-1042-7-6 is shown in FIG. 1D and 2 and the nucleotide sequences of the Tbp1 and Tbp2 genes (SEQ ID NO: 4) from *H. influenzae* PAK 12085 and their deduced amino acid sequences are shown in FIG. 6 (SEQ ID NOS: 11, 12), with the Tbp2 sequence first. In FIG. 6, Putative –35, –10 and ribosomal binding site sequences are overlined.

Chromosomal DNA from the otitis-media derived non-typable *H. influenzae* strain SB33 was prepared. The DNA was partially digested with Sau3A I, size-fractionated for 10–20 kb fragments, and cloned into the BamH I site of EMBL3. The library was probed with the fragments of the pBHIT clone (FIG. 2) and a full-length clone encoding TfR (JB-1031-2-9) was obtained. The restriction map of clone JB-1031-2-9 is shown in FIG. 2 and the nucleotide sequences of the Tbp1 and Tbp2 genes (SEQ ID NO: 105) from *H. influenzae* SB33 and their deduced amino acid sequences are shown in FIG. 7 (SEQ ID NOS: 106, 107), with the Tbp2 sequence first. The SB33 tbp2 gene was found to have a single base deletion which resulted in a frame-shift at residue 126 and premature truncation of the resulting protein at residue 168.

PCR amplification of the tbp2 genes from otitis media-derived NTHi strains SB12, SB29, SB30 and SB32 was performed and the genes sequenced.

The nucleotide sequence of the tbp2 genes from non-typable *H. influenzae* strains SB12 (SEQ ID NO: 105), SB29 (SEQ ID NO: 108), SB30 (SEQ ID NO: 110) and SB32 (SEQ ID NO: 112) are shown in FIGS. 8, 9, 10 and 11 respectively.

All of the amplified tbp2 genes were found to encode full-length Tbp2 proteins indicating that the defective tbp2 gene of strain SB33 was atypical.

The three *H. influenzae* b strains all had identical short intergenic sequences of only 13 bp between tbp2 and Tbp1, but the NTHi strains PAK 12085 and SB33 had longer intergenic sequences of 27 bp (FIG. 12).

Strain SB12 had a 13 bp intergenic sequence identical to that found in the *H. influenzae* b strains while strains SB29, SB30 and SB32 contained longer intergenic sequences (27–30 bp) as found in the other NTHi strains PAK 12085 and SB33 (FIG. 2B). All nine strains have a common core conserved 13 bp sequence between their tbp2 and tbp1 genes.

A pentapeptide sequence near the amino terminus of *H. influenzae* Tbp1 was identified (FIG. 12) which is similar to the TonB box. The tonB gene of *H. influenzae* has been recently cloned and sequenced (Jarosik et al., 1994).

The amino acid sequences of Tbp1 from *H. influenzae* strains Eagan/MinnA, DL63, PAK 12085 and SB33 strains are compared in FIG. 14. The Tbp1 proteins of Eagan and MinnA are identical and 912 amino acids in length, that of DL63 has 914 residues, that of PAK 12085 has 914 residues, and that of SB33 has 911 residues. The *H. influenzae* Tbp1 proteins are highly conserved with 95–100% sequence identity. The amino acid sequences of Tbp2 from *H. influenzae* strains Eagan/MinnA, DL63, PAK 12085 SB12, SB29, SB30 and SB32 are compared in FIG. 15. The Tbp2 proteins of Eagan and MinnA are identical and contain 660 amino acids, that of DL63 has 644 residues, and that of PAK 12085 has 654 residues. There is a single base deletion in the SB33 tbp2 gene which results in a frame-shift at residue 126 and premature trunction of the resulting protein at residue 168. The missing base was confirmed by direct sequencing of PCR amplified chromosomal DNA. With the exception of Eagan and MinnA which are identical, the Tbp2 protein sequences are less conserved with only 66–70% identity, but there are several short segments of conserved sequence which can be identified in FIG. 15. The PCR amplified tbp2 genes from strains SB12, SB29, SB30 and SB32 were all found to encode full-length Tbp2 proteins. There was sequence and size heterogeneity amongst the deduced Tbp2 proteins wherein SB12 had 648 amino acids, SB29 had 631 residues, SB30 had 630 residues and SB32 had 631 residues.

Putative secondary structures of Eagan Tbp1 and Tbp2 were determined (FIGS. 16A and 16B). Both proteins have several transmembrane domains, with Tbp1 traversing the membrane 20 times and Tbp2 crossing it 12 times. Three exposed conserved epitopes were identified in the Tbp1 amino-terminal region (DNEVTGLGK—SEQ ID NO: 43, EQVLN/DIRDLTRYD—SEQ ID NOS: 139 and 140, and GAINEIEYENVKAVEISK—SEQ ID NO: 141) and one in the C-terminal region (GI/VYNLF/LNYRYVTWE—SEQ ID NOS: 142 and 143). Only three small conserved regions can be identified within the Tbp2 proteins of the human pathogens: CS/LGGG(G)SFD—SEQ ID NOS: 75, 144 and 145 at the N-terminal, LE/SGGFY/FGP—SEQ ID NOS: 74 and 146 located internally, and VVFGAR/K—SEQ ID NOS: 83 and 84 at the C-terminus The discovery that the Tbp2 amino acid sequence varies between strains of *Haemophilus* allows for the grouping of *Haemophilus* into sub-groups defined by the same Tbp2 amino acid sequence. This discovery allows the rational selection of a minimal number of Tbp1 and/or Tbp2 sequences or synthetic peptides representing epitopes shared by such subtypes within strains of *Haemophilus* to be used in immunogenic compositions for, for example, immunization against the diseases caused by *Haemophilus* and other bacteria that produce transferrin receptor with sequence similarities to Tbp1 and Tbp2 from *Haemophilus* species. Thus, a minimal number of transferrin receptor, analogs, fragments, and/or peptides, may be used to immunize against many or all strains of *Haemophilus* and other bacterial pathogens that produce transferrin receptor.

Furthermore, the amino acid sequences of the transferrin receptor from a range of bacterial pathogens (*H. influenzae* type b, non-typable *H. influenzae, Neisseria meningitidis, Neisseria gonorrhoeae* and *Actinobacillus (Haemophilus) pleuropneumoniae*) were compared as shown in FIGS. 14 and 15. This analysis revealed regions of Tbp1 and Tbp2 which are conserved between all of these bacteria. Some of such conserved sequences are contained in peptides in Tables 2 and 3. In particular the sequences DNEVTGLGK (SEQ ID: 43), EQVLNIRDLTRYDPGI (SEQ ID NO: 44), EQVLNIRDLTRYDPGISVVEQG RGASSGYSIRGMD (SEQ ID NO: 45), GAINEIEYENVKAVEISKG (SEQ ID NO: 46) and GALAGSV (SEQ ID NO: 47) are conserved in Tbp1 (Table 1 and FIG. 14). Particular conserved sequences in Tbp2 include LEGGFYGP (SEQ ID NO: 74), CSGGGSFD (SEQ ID NO: 75) YVYSGL (SEQ ID NO: 76), CCSNLSYVKFG (SEQ ID NO: 77), FLLGHRT (SEQ ID NO: 78), EFNVOF (SEQ ID NO: 79), NAFTGTA (SEQ ID NO: 80), VNGAFYG (SEQ ID NO: 81), ELGGYF (SEQ ID NO: 82), VVFGAR (SEQ ID NO: 83) and VVFGAK (SEQ ID NO: 84) (Table 2 and FIG. 15).

The discovery of conserved sequences within the transferrin receptor of a range of bacterial pathogens allows the selection of a minimal number of antigens having particular amino acid sequences (including in the form of synthetic peptides) to immunize against the disease caused by pathogens that have transferrin receptors. Such bacteria in addition to those recited above include other species of *Neisseria*, such as *Neisseria gonorrhoeae*, and *Branhamella*, including *Branhamella catarrhalis*. Such conserved amino acid sequences among many bacterial pathogens permits the generation of TfR specific antibodies, including monoclonal antibodies, that recognize most if not all transferrin receptors. Antiserum was raised against peptides corresponding to conserved portions of the transferrin receptor. This antiserum recognized the transferrin receptor in *Branhamella catarrhalis*. Such antisera are useful for the detection and neutralization of most if not all bacteria that produce TfR protein and are also useful for passive immunization against the diseases caused by such pathogens. Diagnostic assays and kits using such conserved amino acid sequences are useful to detect many if not all bacteria that produce transferrin receptor.

Epitopes containing the afore-mentioned amino acid sequences can be delivered to cells of the immune system by the use of synthetic peptides containing such sequences, or by the use of live vectors expressing such sequences, or by the direct administration of nucleic acid molecules encoding the amino acid sequence.

Some peptides containing conserved amino acid sequences within the Tbp1 proteins of *H. influenzae* type b strains Eagan, MinnA, DL63 and the nontypable strain PAK 12085 are shown in Table 2. Antibodies to some of these peptides were raised in guinea pigs (Table 4). Peptides containing conserved amino acid sequences within the Tbp2 proteins of *H. influenzae* type b strains Eagan, Minn A, DL63 and the nontypable strain PAK 12085 are shown in Table 3. Antibodies to some of these peptides were raised in guinea pigs (Table 4).

The coding sequences of the Tbp1 and Tbp2 genes may be cloned into appropriate expression vectors to produce recombinant proteins. Recombinant Tbp1 and Tbp2 were expressed from *E. coli* using the T7 expression system. The Tbp1 gene encoding the mature Eagan Tbp1 protein was cloned in-frame behind the T7 promoter generating plasmid JB-1468-29, as shown in FIG. 17. When introduced into BL21/DE3 cells and induced with IPTG or lactose, Eagan Tbp1 protein was expressed as shown in FIG. 22.

The tbp2 gene encoding the mature Tbp2 protein was cloned in-frame behind the T7 promotor generating plasmid JB-1424-2-8 as shown in FIG. 18. When introduced into *E. coli* cells and induced as above, Tbp2 protein was expressed as shown in FIG. 22.

The tbp2 gene from strain NTHi SB12 was amplified by PCR. The resultant amplified DNA contains the authentic *H. influenzae* Tbp2 signal sequence before the mature protein. The SB12 tbp2 gene encoding the signal sequence and the mature protein was cloned into the pT7-7 expression system as shown in FIG. 21. When the resultant plasmid (JB-1600-1) was introduced into *E. coli* BL21/DE3 cells and induced, SB12 Tbp2 was expressed, as shown in FIG. 22.

Recombinant proteins Tbp1 and Tbp2 produced in *E. coli* as inclusion bodies were purified by the scheme shown in FIG. 23. The purified proteins were at least about 70% pure as shown in FIG. 24. Immunogenicity studies were performed in mice with the purified recombinant Tbp1 and Tbp2 proteins. Both proteins elicited a good immune response in mice at 3–10 μg doses (FIG. 25).

Antisera raised to recombinant Tbp1 or Tbp2 derived from one *H. influenzae* strain are cross-reactive with other strains, making these potentially useful diagnostic reagents (FIGS. 26 and 27).

Plasmids pUHIT1KFH and pUHITKFP shown in FIG. 28, contain a selectable antibiotic resistance marker cloned within the transferrin receptor operon and were constructed to insertionally inactivate the transferrin receptor operon. These plasmids were used to transform *Haemophilus* to generate strains that do not produce transferrin receptor Tbp1 and/or Tbp2 as described in Example 19. Such strains are useful as negative controls (since they do not produce TfR) in in vitro and in vivo detection and diagnostic embodiments. Such strains are also expected to be attenuated for in viva growth and are useful as live vaccines to provide protection against diseases caused by *Haemophilus*.

As discussed above, epitopes of transferrin receptor proteins can be delivered to cells of the immune system by the use of live vectors expressing such amino acid sequences and the live vector may be poliovirus. Referring to FIG. 29 there is illustrated the construction of hybrid polioviruses expressing an epitope of transferrin receptor protein including the conserved epitope from Tbp2 LEGGFYGP (SEQ ID NO: 74). Such viruses were recognized by antibodies raised against a peptide incorporating the amino acid sequence LEGGFYGP (SEQ ID NO: 74) (Table 5) indicating that the viruses expressed this sequence in an antigenically recognisable form. PV1TBP2A and PV1TBP2B were also neutralized by rabbit antisera raised against *H. influenzae* strain DL63 tbp2, indicating that at least these two viruses expressed the sequence in a form recognisable to antibodies raised against the protein. All viruses were neutralisable by anti-PV1 sera, indicating that the changes in polio neutralization antigenic site I had not significantly affected other antigenic sites on the viruses. Furthermore, rabbit antiserum produced by immunization with poliovirus chimera PV1TBP2A or PV1TBP2B recognized a peptide incorporating the amino acid sequence LEGGFYGP (SEQ ID NO: 74). This indicates that the sequences expressed by PV1TB2A and PV1TBP2B are immunogenic and elicit antibodies capable of recognizing the same sequence in the context of a synthetic peptide.

Figure 30:
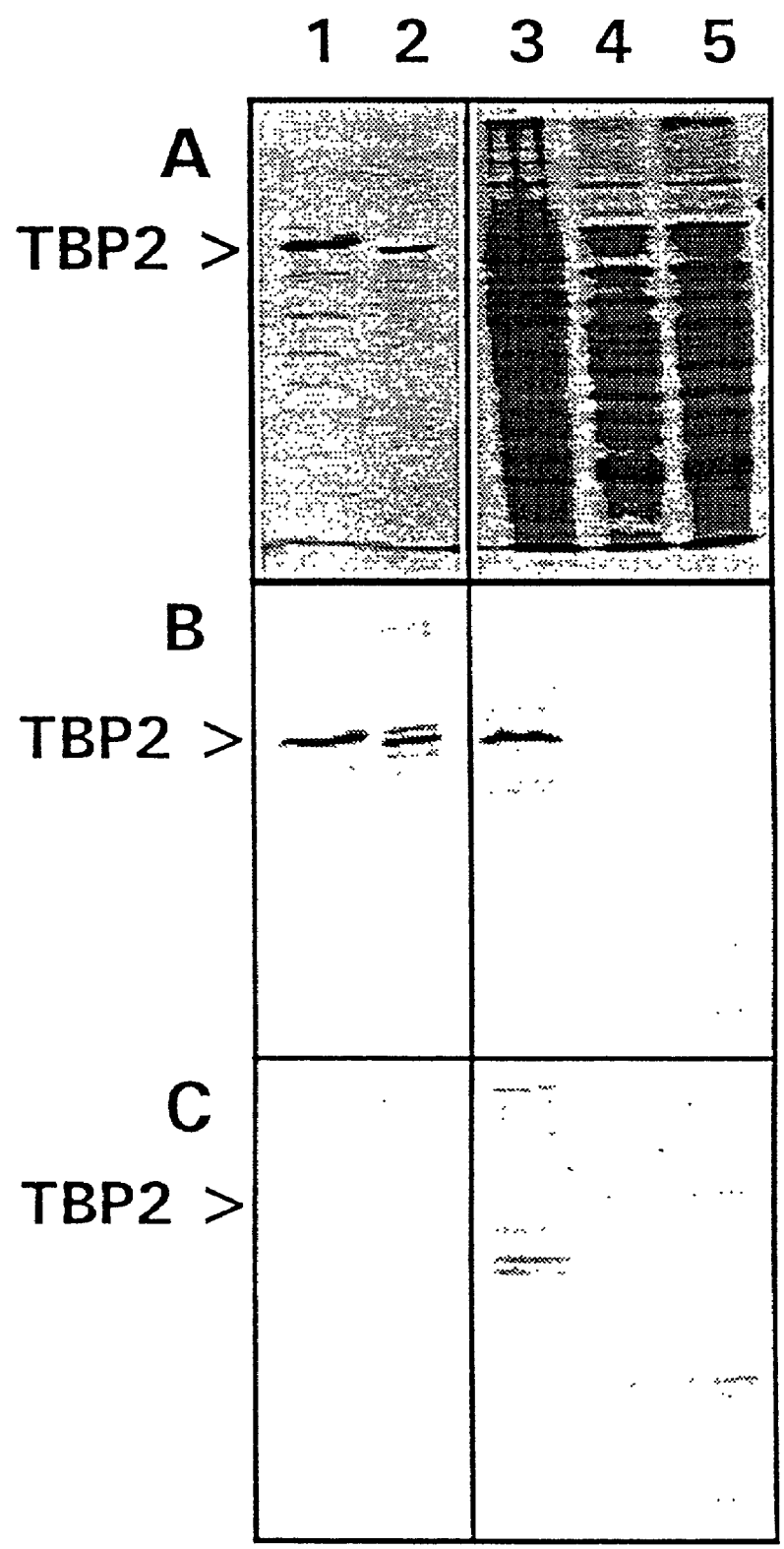

Referring to FIG. 30, panel A shows an SDS PAGE gel showing purified recombinant tbp2 from *H. influenzae* strain SB12 expressed in *E. coli* (lane 1), tbp2 from *Branhamella catarrhalis* strain 4223 (lane 2), a whole cell lysate of iron-limited *B. catarrhalis* strain 4223 (land 3), a whole cell lysate of iron-limited *E. coli* JM109 (lane 4), and a whole cell lysate of *E. coli* JM109 grown under non-iron limited conditions (lane 5). Panel B shows results of a Western blot of a replicate gel using a pool of sera from rabbits immunized with PV1TBP2A. There was a strong reaction with the purified transferrin-binding proteins in lanes 1 and 2, and with a similar sized band in lane 3. There was no significant reaction with any *E. coli* proteins (lanes 4 and 5). Panel C shows the results for a pool of prebleed sera from the same rabbits, which displayed minimal specific reactivity. These results show that PV1TBP2A is able to induce antisera specific for transferrin binding proteins from *H. influenzae* and *B. catarrhalis*, and that the antisera can distinguish *B. catarrhalis* from *E. coli*, which does not express an equivalent protein.

Guinea pig anti-Eagan rTbp1, anti-Eagan rTbp2, and anti-SB12 rTbp2 antisera were used to screen a panel of *H. influenzae* strains for antigenic conservation of the Tbp1 and Tbp2 proteins. Of 33 strains screened by Western blot with anti-Eagan rTbp1 antisera, all had a reactive band of ~100 kDa. Of 89 strains screened by Western blot with anti-Eagan rTbp2 antisera, 85 had a reactive band of 60–90 kDa. Of 86 strains screened by Western blot with anti-SB12 rTbp2 antisera, 82 had a reactive band of 60–90 kDa. Only one strain was not recognized by either anti-Eagan rTbp2 or anti-SB12 rTbp2 antisera, and that was NTHi strain SB33 which has a defective tbpB gene. These data indicate that transferrin receptor proteins are highly conserved in strains of *H. influenzae* and support the use of these proteins as antigens and in immunogenic compositions, including vaccines, for immunization against disease cause by *H. influenzae* and diagnosis thereof.

The infant rat model of bacteremia (Loeb et al, 1987) was used to assess the protective abililty of anti-Eagan rTbp1 and anti-Eagan rTbp2 antisera. Anti-Eagan rTbp1 antisera raised in either rabbits or guinea pigs was not protective in this model but anti-Eagan rTbp2 antisera raised in rabbits or guinea pigs was protective (Table 7). These data indicate the use for rTbp2 proteins as protective antigens against disease caused by *H. influenzae*.

The chinchilla model of otitis media (Barenksamp et al, 1986) was used to assess the protective ability of SB12 rTbp2. Data indicated that compared with the control group, the immunized animals had less severe disease.

In further embodiments, there is provided a number of truncated analogues at transferrin receptor protein Tbp2 as shown in Table 8 and FIG. 31 below, and nucleic acid molecules encoding the same. Some of such truncated analogues are highly expressed in recombinant expression systems (such as *E. coli*) and represent appropriate antisera and immunogens in diagnostic and vaccination embodiments of the invention.

The purified and isolated DNA molecules comprising at least a portion coding for a transferrin receptor of a species of *Haemophilus* typified by the embodiments described herein are advantageous as:

nucleic acid probes for the specific identification of *Haemophilus* strains in vitro or in vivo.

the products encoded by the DNA molecules are useful as diagnostic reagents, antigens for the production of *Haemophilus*-specific antisera, for vaccination against the diseases caused by species of *Haemophilus* and (for example) detecting infection by *Haemophilus*.

peptides corresponding to portions of the transferrin receptor as typified by the embodiments described herein are advantageous as diagnostic reagents, antigens for the production of *Haemophilus*-specific antisera, for vaccination against the diseases caused by species of *Haemophilus* and (for example) for detecting infection by *Haemophilus*.

The transferrin receptor encoded by the nucleic acid molecules of the present invention, fragments and analogs thereof, and peptides containing sequences corresponding to portions of the transferrin receptor that are conserved between various isolates of *Haemophilus* and other bacteria that produce transferrin receptor, are useful in diagnosis of and immunization against diseases caused by any bacterial strain that produces transferrin receptor. In particular, peptides containing the sequences LEGGFYGP are conserved in the transferrin receptor proteins of many bacterial pathogens that produce transferrin receptor and are appropriate for diagnosis of and immunization against diseases caused by bacteria that produce transferrin receptor. Such bacteria include but are not limited to species of *Haemophilus*, *Neisseria* (including *N. meningitidis* and *N. gonorrhoeae*) and *Branhamella* (including *B. catarrhalis*).

It is clearly apparent to one skilled in the art, that the various embodiments of the present invention have many applications in the fields of vaccination, diagnosis, treatment of, for example, *Haemophilus* infections, and infections with other bacterial pathogens that produce transferrin receptor and the generation of immunological reagents. A further non-limiting discussion of such uses is further presented below.

1. Vaccine Preparation and Use

Immunogenic compositions, suitable to be used as vaccines, may be prepared from immunogenic transferrin receptor, analogs and fragments thereof and/or peptides as disclosed herein. The vaccine elicits an immune response which produces antibodies, including anti-transferrin receptor antibodies and antibodies that are opsonizing or bactericidal. Should the vaccinated subject be challenged by *Haemophilus* or other bacteria that produce a transferrin receptor, the antibodies bind to the transferrin receptor and thereby prevent access of the bacteria to an iron source which is required for viability. Furthermore, opsonizing or bactericidal anti-TfR antibodies may also provide protection by alternative mechanisms.

Vaccines containing peptides are generally well known in the art, as exemplified by U.S. Pat. Nos. 4,601,903; 4,599,231; 4,599,230; and 4,596,792; all of which references are incorporated herein by reference. Immunogenic compositions including vaccines may be prepared as injectables, as liquid solutions or emulsions. The transferrin receptor, analogs and fragments thereof and/or peptides may be mixed with pharmaceutically acceptable excipients which are compatible with the transferrin receptor, fragments analogs or peptides. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include strain B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the transferrin receptor, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the transferrin receptor, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

The nucleic acid molecules encoding the transferrin receptor of the present invention may also be used directly for immunization by administration of the DNA directly, for example by injection for genetic immunization or by constructing a live vector such as Salmonella, BCG, adenovirus, poxvirus, vaccinia or poliovirus. A discussion of some live vectors that have been used to carry heterologous antigens to the immune system are discussed in for example O'Hagan (1992). Processes for the direct injection of DNA into test subjects for genetic immunization are described in, for example, Ulmer et al., 1993.

The use of peptides in vivo may first require their chemical modification since the peptides themselves may not have a sufficiently long serum and/or tissue half-life and/or sufficient immunogenicity. Such chemically modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

Examples of side chain modifications contemplated by the present invention include modification of amino groups such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butylglycine, norvaline, phenylglycine, ornithine, sarcosine, 4-amino-3-hydroxy-6-methylhepanoic acid, 2-thienyl alanine and/or D-isomers of amino acids.

Immunogenicity can be significantly improved if the antigens are co-administered with adjuvants, commonly used as an 0.05 to 1.0 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminim phosphate (collectively commonly referred to as alum) are routinely used as adjuvants in human and veterinary vaccines. The efficacy of alum in increasing antibody responses to diptheria and tetanus toxoids is will established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller 1989, describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. 1989, reported in vivo priming of virus-lpecific cytotoxic T lymphocytes with synthetic lipopeptide vaccine which comprised of modified synthetic peptides derived from influenza virus nucleoprotein by linkage to a lipopeptide, N-palmityl-s-(2,3-bis(palmitylxy)-(2RS)-propyl-[R]-cysteine (TPC).

2. Immunoassays

The transferrin receptor, analogs and fragments thereof and/or peptides of the present invention are useful as immunogens, as antigens in immunoassays including enzyme-linked immunosorbent assays (ELISA), RIAs and other non-enzyme linked antibody binding assays or procedures known in the art for the detection of anti-bacterial, *Haemophilus*, TfR and/or peptide antibodies. In ELISA assays, the transferrin receptor, analogs, fragments and/or peptides corresponding to portions of TfR protein are immobilized onto a selected surface, for example a surface capable of binding proteins or peptides such as the wells of a polystyrene microtiter plate. After washing to remove incompletely adsorbed transferrin receptor, analogs, fragments and/or peptides, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface. Preferably, the selected peptides are from the conserved regions of Table 2 or Table 3 to enhance the cross-species detection unless one particular bacterial species is to be detected. In that event, a polypeptide is selected which is unique to the TfR of that particular species. Normally, the peptides are in the range of 12 residues and up and preferably 14 to 30 residues. It is understood however, that a mixture of peptides may be used either as an immunogen in a vaccine or as a diagnostic agent. There may be circumstances where a mixture of peptides from the conserved regions and/or from the non-conserved regions are used to provide cross-species protection and/or diagnosis. In this instance, the mixture of peptide immunogens is commonly referred to as a "cocktail" preparation for use as a vaccine or diagnostic agent.

The immobilizing surface is then contacted with a sample such as clinical or biological materials to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from 2 to 4 hours, at temperatures such as of the order of 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound transferrin receptor, analogs, fragments and/or peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a visible spectra spectrophotometer.

3. Use of Sequences as Hybridization Probes

The nucleotide sequences of the present invention, comprising the sequence of the transferrin receptor gene, now allow for the identification and cloning of the transferrin receptor genes from any species of *Haemophilus* and other bacteria that have transferrin receptor genes.

The nucleotide sequences comprising the sequence of the transferrin receptor genes of the present invention are useful for their ability to selectively form duplex molecules with complementary stretches of other TfR genes. Depending on the application, a variety of hybridization conditions may be employed to achieve varying degrees of selectivity of the probe toward the other TfR genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90k homology.

In a clinical diagnostic embodiment, the nucleic acid sequences of the TfR genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing TfR gene sequences.

The nucleic acid sequences of TfR genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e. g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the TfR genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. As with the selection of peptides, it is preferred to select nucleic acid sequence portions which are conserved among species of *Haemophilus*, such as nucleic acid sequences encoding the conserved peptide sequence of FIGS. 8, 9, 13 and 14 and particularly listed in Tables 2 and 3. The selected probe may be at least 18 bp and may be in the range of 30 bp to 90 bp long.

4. Expression of the Transferrin Receptor Genes

Plasmid vectors containing replicon and control sequences which are derived from species compatible with the host cell may be used for the expression of the transferrin receptor genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems (Chang et al., 1978: Itakura et al., 1977 Goeddel et al., 1979; Goeddel et al., 1980) and other microbial promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the transferrin receptor genes, fragment analogs or variants thereof include *E. coli, Bacillus* species, *Haemophilus*, fungi, yeast or the baculovirus expression system may be used.

In accordance with this invention, it is preferred to make the protein by recombinant methods, particularly when the naturally occurring TfR protein as purified from a culture of a species of *Haemophilus* may include trace amounts of toxic materials or other contaminants. This problem can be avoided by using recombinantly produced TfR protein in heterologous systems which can be isolated from the host in a manner to minimize comtaminants in the purified material.

Particularly desirable hosts for expression in this regard include Gram positive bacteria which do not have LPS and are therefore endotoxin free. Such hosts include species of *Bacillus* and may be particularly useful for the production of non-pyrogenic transferrin receptor, fragments or analogs thereof. Furthermore, recombinant methods of production permit the manufacture of Tbp1 or Tbp2 or fragments thereof separate from one another which is distinct from the normal combined proteins present in *Haemophilus*.

5 Biological Deposits

Certain plasmids that contain at least a portion coding for a transferrin receptor from strains of *Haemophilus influenzae* that are described and referred to herein have been deposited with the American Type Culture Collection (ATCC) located at 10801 University Boulevard, Manassas, Va. 20110-2209, USA pursuant to the Budapest Treaty and prior to the filing of this application. Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

Deposit Summary

| Clone | ATCC Designation | Date Deposited |
|---|---|---|
| DS-712-1-3 | 75603 | Nov. 4, 1993 |
| JB-1042-7-6 | 75607 | Nov. 4, 1993 |
| JB-1424-2-8 | 75937 | Oct. 27, 1994 |
| JB-1600-1 | 75935 | Oct. 27, 1994 |
| JB-1468-29 | 75936 | Oct. 27, 1994 |
| pT7TBP2A | 75931 | Oct. 27, 1994 |
| pT7TBP2B | 75932 | Oct. 27, 1994 |
| pT7TBP2C | 75933 | Oct. 27, 1994 |
| pT7TBP2D | 75934 | Oct. 27, 1994 |

Strains of *Haemophilus*

Hib strain Eagan is available from Connaught Laboratories Limited, 1755 Steeles Ave. W., Willowdale, Ontario, Canada M2R 3T4.

Hib strain MinnA was obtained from the collection of Dr. Robert Munson, Department of Microbiology and Immunology, Washington University School of Medicine, Children's Hospital, St. Louis, Mis. 63110.

Hib strain DL63 was obtained from the collection of Dr. Eric Hansen, Department of Microbiology, University of Texas Southwestern Medical Center, 5323 Harry Hines Boulevard, Dallas, Tex. 75235-9048.

PAK 12085 was obtained from the collection of Dr. Robert Munson (supra).

SB12, 29, 30, 32 and 33 were obtained from the collection of Dr. Stephen Barenkamp, Department of Pediatrics, School of Medicine, Saint Louis University Medical Centre, St. Louis, Mo. 63104.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used but not explicitly described in this disclosure and these Examples are amply reported in the scientific literature and are well within the ability of those skilled in the art.

Example 1

This Example illustrates the preparation of chromosomal DNA from *H. influenzae* strains DL63, Eagan, MinnA, and PAK 12085, and SB33.

*H. influenzae* strains were grown on Mueller-Hinton agar or in brain heart infusion broth as described by Harkness et al 1992.

A. Chromosomal DNA extraction from *Haemophilus influenzae* type b DL63

Chromosomal DNA was prepared as follows. Two hundred and fifty ml of culture were pelleted by centrifugation at 8,000 rpm in a Beckman J14 rotor for 15 minutes. The pellet was washed with 200 ml of 50 mM Tris-HCl, pH 8.0, centrifuged as before, resuspended in 12.5 ml of 50 mM Tris-HCl, 50 mM EDTA, pH 8.0, and frozen at −20° C. Then 1.25 ml of a 10 mg/ml lysozyme solution in 0.25M Tris-HCl, pH 8.0, was added to the frozen cell pellet. The pellet was thawed and incubated on ice for 45 minutes. Next, 2.5 ml of a solution of 1 mg/ml proteinase K in 0.5% SDS, 0.4M EDTA, 50 mM Tris-HCl, pH 7.5 was added and the mixture incubated at 50° C. for 1 hour with occasional mixing. The lysate was extracted once with 15 ml of Tris-buffered phenol, then 1.5 ml of 3M sodium acetate and 30 ml of ethanol were added to precipitate the DNA. The DNA was spooled on a glass rod, then dissolved in 12.5 ml of 50 mM Tris-HCl, 1 mM EDTA, pH 7.5 containing 0.2 mg/ml RNAse A by rocking overnight. The sample was extracted once with an equal volume of chloroform, precipitated, and spooled as above. The DNA was dissolved in 2 ml of 50 mM Tris-HCl, 1mM EDTA, pH 7.5 and stored at 4° C.

B. Chromosomal DNA extraction from *Haemophilus influenzae* type b Eagan

Fifty ml of culture were pelleted by centrifugation, the pellet resuspended in 25 ml of TE (10 mM Tris, 1 mM EDTA, pH 7.5), and 2×5 ml aliquots used for chromosomal DNA preparation. To each aliquot was added 0.6 ml of 10% sarkosyl and 0.15 ml of 20 mg/ml proteinase K and the samples incubated at 37° C. for 1 hour. The lysate was extracted once with Tris-saturated phenol and three times with chloroform:isoamyl alcohol (24:1). The aqueous phases were pooled for a final volume of 7 ml. Then 0.7 ml of 3M sodium acetate (pH 5.2) and 4.3 ml of isopropanol were added to precipitate the DNA which was spooled, rinsed with 70% ethanol, dried, and resuspended in 1 ml of water.

C. Chromosomal DNA extraction from *Haemophilus influenzae* Eagan, MinnA, PAK 12085 and SB33

Cells were pelleted from 50 ml of culture by centrifugation at 5000 rpm for 15–20 minutes, at 4° C. The cell pellet was resuspended in 10 ml of TE (10 mM Tris-HCl, 1 mM EDTA, pH 7.5), pronase and SDS were added to final concentrations of 500 μg/ml and 1%, respectively. The sample was incubated at 37° C. for 4 hours until a clear lysate was obtained. The lysate was extracted once with Tris-saturated phenol, once with Tris-saturated phenol/chloroform (1:1), and once with chloroform. The final aqueous phase was dialysed for 24 hours against 2×500 ml of 1M NaCl at 4° C., changing the buffer once, and for 24 hours against 2×500 ml of TE at 4° C., changing the buffer once. The final dialysate was aliquotted for use.

Example 2

This Example illustrates the preparation of chromosomal libraries.

A. *H. influenzae* DL63-λZAP Library

100 μg of *H. influenzae* DL63 chromosomal DNA in TE was mechanically sheared in a 1 ml syringe with a 25 gauge needle. The sheared DNA was made blunt-ended by adding water to a final volume of 405 μl, 45 μl of 10×S1 nuclease buffer (2M NaCl, 500 mM NaOAc, pH 4.5, 10 mM $ZnSO_4$, 5% glycerol), and 1.7 μl of S1 nuclease at 100 U/μl and incubating at 37° C. for 15 min. The sample was extracted once with phenol/chloroform and once with chloroform and 1 ml of ethanol was added to precipitate the DNA. The sample was incubated on ice for 10 min or at −20° C. overnight and the DNA was harvested by centrifugation in a microfuge for 30 minutes. The DNA was washed with 70% ethanol and dried. The Eco RI sites in the DNA sequence were methylated using standard procedures. To this methylated DNA was added 5 μl of 100 mM $MgCl_2$, 8 μl of dNTP mix (2.5 mM each of dATP, dCTP, dGTP, and dTTP), and 4 μl of 5 U/μl Klenow. The mixture was incubated at 12° C. for 30 minutes. 450 μl of STE (0.1M NaCl, 10 mM Tris-HCl, 1 mM EDTA, pH 8.0) were added, and the mixture extracted once with phenol/chloroform, and once with chloroform, before adding 1 ml of ethanol to precipitate the DNA. The sample was incubated on ice for 10 min or at −20° C. overnight. The DNA was harvested by centrifugation in a microfuge for 30 minutes, washed with 70% ethanol and dried.

The DNA was resuspended in 7 μl of TE and to the solution was added 14 μl of phosphorylated Eco RI linkers (200 ng/μl), 3 μl of 10× ligation buffer, 3 μl of 10 mM ATP, and 3 μl of T4 DNA ligase (4 U/μl). The sample was incubated at 4° C. overnight, then incubated at 68° C. for 10 minutes to inactivate the ligase. To the mixture was added 218 μl of $H_2O$, 45 μl of 10× Universal buffer, and 7 μl of Eco RI at 30 U/μl. After incubation at 37° C. for 1.5 hours, 1.5 μl of 0.5M EDTA was added, and the mixture placed on ice.

The DNA was size fractionated on a sucrose gradient, pooling fractions containing DNA of 6–10 kb. The pooled DNA was ethanol precipitated and resuspended in 5 μl of TE buffer. 200 ng of insert DNA was ligated for 2–3 days at 4° C. with 1 μg of ZAP II vector in a final volume of 5 μl. The ligation mixture was packaged using Gigapack II Gold (Stratagene) and plated on *E. coli* SURE cells on NZY plates. The library was titrated, amplified, and stored at 4° C. under 0.3% chloroform.

B. *H. influenzae* Eagan-pUC Library

Chromosomal DNA prepared from *H. influenzae* Eagan by the method in Example 1C was digested with Sau3A I for 2, 5, and 10 minutes and samples electrophoresed on a preparative agarose gel. Gel slices which included DNA fragments between 3–10 kb in length were excised and the DNA extracted by the standard freeze-thaw procedure. Plasmid DNA from pUC 8:2 (pUC 8 with additional Bgl II and Xba I restriction enzyme sites in the multiple cloning site) was digested with BamH I and Bgl II, and dephosphorylated with calf alkaline phosphatase (CAP). The fragments of *H. influenzae* Eagan DNA were ligated into pUC and the mixture used to transform *E. coli* JM109 cells.

C. *H. influenzae* Eagan-λZAP Library

Chromosomal DNA from *H. influenzae* Eagan prepared as in Example 1B was digested with Eco RI and size fractionated on a preparative agarose gel. Gel slices corresponding to DNA fragments of 7–23 kb were excised and DNA was electroeluted overnight in dialysis tubing containing 3 ml of TAE (40 mM Tris-acetate, 1 mM EDTA) at 14V. The DNA was precipitated twice and resuspended in water before being ligated overnight with Eco RI digested λZAP II DNA. The ligation mixture was packaged using the Gigapack II packaging kit (Stratagene) and plated on *E. coli* XL1-Blue cells. The library was titrated, amplified, and stored at 4° C. under 0.3% chloroform.

D. EMBL3 Libraries

*H. influenzae* MinnA chromosomal DNA (10 μg) was prepared as in Example 1C and digested with Sau3A I (40 units) for 2, 4, and 6 minutes then size-fractionated on a 10–30% sucrose gradient in TNE buffer (20 mM Tris-HCl, 5 mM NaCl, 1 mM EDTA, pH 8). Fractions containing DNA fragments greater than 5 kb were pooled and precipitated. In a second experiment, chromosomal DNA (2.6 μg) was digested with Sau3A I (4 units) for 1, 2, and 3 minutes and size-fractionated by preparative agarose gel electrophoresis. Gel slices containing DNA fragments of 10–20 kb were excised and DNA extracted by a standard freeze/thaw technique. The size- fractionated DNA from the two experiments was pooled for ligation with BamH I arms of EMBL3 (Promega). The ligation mixture was packaged using the Gigapack II packaging kit and plated on *E. coli* LE392 cells. The library was titrated, then amplified and stored at 4° C. under 0.3% chloroform.

Chromosomal DNA from *H. influenzae* PAK 12085 or SB33 prepared as in Example 1C was digested with Sau3A I (0.5 units/10 μg DNA) at 37° C. for 15 minutes and size-fractionated by agarose gel electrophoresis. Gel slices corresponding to DNA fragments of 15–23 kb were excised and DNA was electroeluted overnight in dialysis tubing containing 3 ml of TAE at 14V. The DNA was precipitated twice and resuspended in water before overnight ligation with EMBL3 BamH I arms (Promega). The ligation mixture was packaged using the Lambda in vitro packaging kit (Amersham) according to the manufacturer's instructions and plated onto *E. coli* NM539 cells. The library was titrated, then amplified, and stored at 4° C. in the presence of 0.3%. chloroform.

Example 3

This Example illustrates screening of the libraries

A. *H. influenzae* DL63-λZAP Expression Library

Tbp1 and Tbp2 proteins were affinity purified on solid phase human transferrin (hTf). Briefly, a 20 ml hTf-Sepharose column was prepared according to the manufacturer's protocol for coupling protein ligands to CNBr-activated Sepharose (Sigma). The resulting matrix was washed with 3 column volumes of 50 mM Tris-HCl, 1M NaCl, 6M guanidine-HCl, pH 8.0 to remove non-covalently bound hTf. The column was then equilibrated with 50 mM Tris-HCl, pH 8.0 and bound hTf was iron loaded using 1 ml of 10 mg/ml $FeCl_3$ in buffer containing 100 mM each of sodium citrate and sodium bicarbonate, pH 8.6, followed by 2 column volumes of 50 mM Tris-HCl, 1M NaCl, pH 8.0. Total bacterial membranes (300 mg total protein) were prepared from *H. influenzae* strain DL63 grown on iron deficient media as described previously (Schryvers et al., 1989). Membranes were diluted to 2 mg/ml in 50 mM Tris-HCl, 1M NaCl, pH 8.0 and solubilized by the addition of EDTA to 15 mM and Sarkosyl NL97 to 1.5%. After centrifugation at 40,000×g for 1 hour, the supernatant was applied to the hTf column and the column washed with 10 column volumes of 50 mM Tris-HCl, 1M NaCl, 10 mM EDTA, 0.5% Sarkosyl, pH 8.0. The receptor proteins were eluted using 2M GnHCl in the same buffer and the eluted fractions were dialysed extensively against 25 mM ammonium bicarbonate buffer (5 buffer changes), lyophilized, and stored at −20° C. Isolated proteins were used to generate transferrin receptor-specific antisera in New Zealand White rabbits using standard techniques. Briefly, rabbits were immunized 3 times subcutaneously, at intervals of two weeks, using complete Freund's adjuvant for the first injection and incomplete Freund's adjuvant for subsequent injections.

The DL63 λZAP library was plated on *E. coli* SURE cells and plaques were transferred onto nitrocellulose membranes which had been pre-soaked in 10 mM IPTG to induce expression from the pBluescript lacZ promoter. Filters were blocked using 0.5% skim milk in 50 mM Tris-HCl, 150 mM NaCl, pH 7.5, prior to being probed with the polyclonal anti-TfR antisera and horse radish peroxidase-conjugated goat anti-rabbit IgG. Plaques were purified by 3 rounds of screening and recombinant pBluescript plasmids (pBHIT1 and pBHIT2; FIGS. 1A and 2) were recovered by the in vivo excision procedure (Short et al., 1988).

B. Eagan, MinnA, and PAK 12085 Non-expression Libraries (i) Screening of *H. influenzae* Eagan-pUC Library Colony lifts onto nitrocellulose were performed using standard techniques and the filters were probed with the 5'pBHIT2 probe of the transferrin receptor gene illustrated in FIG. 2. The probe was labelled with digoxigenin (dig, Boehringer Mannheim) following the manufacturer's specifications. Several putative clones were dot blotted onto nitrocellulose and submitted to second round screening using the same 5'pBHIT2 probe. Second round putatives were analysed by restriction enzyme mapping and clone S-4368-3-3 (FIG. 1B, FIG. 2) was selected for sequence analysis.

(ii) Screening *H. influenzae* Eagan-λZAP Library

The phage library was plated using standard techniques on XLI Blue cells (Stratagene) using LB plates and a 0.7% agarose overlay layer. Plaques were lifted onto nitrocellulose using standard protocols and the filters were baked at 80° C., for 2 hours, under vacuum, to fix the DNA. The 5'pBHIT2 probe of the transferrin receptor gene (FIG. 2) was labelled with digoxigenin and the filters were pre-hybridized for 4 hours at 42° C., then hybridized with the labelled probe at 42° C., overnight. The filters were washed at 68° C. and after autoradiography, several plaques were selected for second round screening. In vivo excision of phagemid DNA from second round putatives was performed according to protocols provided with the λZAP system (Promega). Four clones with identical ~2.5 kb Eco RI inserts were obtained of which JB-901-5-3 in FIG. B, FIG. 2 is an example. Putative plaques were also amplified and phage DNA was purified from 500 ml of culture. Insert DNA was excised by digestion with Xba I and was cloned into pUC 8:2 (pUC 8 containing additional Bgl II and Xba I sites in its multiple cloning site) which had been digested with Xba I and dephosphorylated. Clone JB-911-3-2 (FIG. 17) contains the 3'-half of the *H. influenzae* Eagan TfR operon.

(iii) Screening EMBL 3 Libraries

The *H. influenzae* MinnA library was plated onto LE392 cells on NZCYM plates using 0.7% top agarose in NZCYM as overlay. Plaque lifts onto nitrocellulose filters were performed following standard procedures, and filters were processed and probed with the 5'pBHIT2 probe (FIG. 2) labelled with digoxigenin. Putative plaques were plated and submitted to second and third rounds of screening using the same procedures. Phage DNA was prepared from 500 ml of culture using standard techniques, the insert DNA excised by Sal I digestion, and cloned into pUC to generate clone DS-712-1-3 (FIGS. 1C and 2).

The *H. influenzae* PAK 12085 library was plated on LE392 cells on NZCYM plates using 0.7% agarose in NZCYM as overlay. Plaques were lifted onto nitrocellulose and filters were processed and probed with the digoxigenin-labelled 5'pBHIT2 probe (FIG. 2). Putative plaques were plated and subjected to a second round of screening using the same procedures. Phage DNA was prepared from 500 ml cultures by standard techniques, the DNA insert was excised by digestion with Sal I, and cloned into pUC to generate clone JB-1042-7-6 (FIG. 1D and 2).

The *H. influenzae* SB33 library was plated on LE392 cells on NZCYM plates using 0.7% agarose in NZCYM as overlay. Plaques were lifted onto nitrocellulose and filters were processed and probed with the digoxigenin-labelled 5'pBHIT2 probe (FIG. 2). Putative plaques were plated and subjected to a second round of screening using the same procedures. Phage DNA was prepared from 500 ml cultures by standard techniques, the DNA insert was excised by digestion with Sal I, and cloned into pUC to generate clone JB-1031-2-9 (FIG. 2).

Example 4

This Example illustrates the sequencing of the Tbp1 and Tbp2 genes of the TfR operon.

Plasmid DNA from clones pBHIT 1, pBHIT 2, S-4368-3-3, JB-901-5-3, DS-712-1-3, JB-1042-7-6 and JB-1031-2-9 was prepared using standard techniques. Oligonucleotide sequencing primers of 17–25 bases in length were synthesized on the ABI model 380B DNA Synthesizer and purified by chromatography using OPC cartridges obtained from Applied Biosystems Inc., and used in accordance with the manufactures recommendations. Samples were sequenced using the ABI model 370A DNA Sequencer and dye terminator chemistry according to manufacturers' protocols. The sequence of the TfR operon from strain DL63 is illustrated in FIG. 3, that of strain Eagan in FIG. 4, that of strain MinnA in FIG. 5, that of PAK 12085 in FIG. 6 and that of SB33 in FIG. 7.

Example 5

This Example illustrates the PCR amplification of the tbp2 genes from non-typable *H. influenzae* strains SB12, SB29, SB30, and SB32.

Chromosomal DNA from non-typable *H. influenzae* strains SB12, SB29, SB30, and SB32 was prepared as described aobve. The TfR genes are arranged as an operon with tbp2 followed by Tbp1 (see FIGS. 12A and 12B). Oligonucleotides were synthesized to the 5'-end of the tbp2 and the reverse complement of the 5'-end of the tbp1 coding sequences. The primers were: GGATCCATAT-GAAATCTGT ACCTCTTATCTCTGGT (SEQ ID NO:

120) corresponding to MKSVPLISGS (SEQ ID NO: 147) from the leader sequence of Tbp2 and TCTA-GAAGCTTTTTTAGTCATTTTTAGTATTCCAT (SEQ ID NO: 137) which is the reverse complement of the leader sequence MTKK (SEQ ID NO: 138) of Tbp1 and a part of the intergenic sequence (FIGS. 12A and 12B). PCR amplification was performed in buffer containing 10 mM Tris/HCl pH 8.3, 50 mM potassium chloride and 1.5 mM magnesium chloride. Each 100 µl reaction mixture contained 5 ng of chromosomal DNA, 1 µg of each primer, 5 units amplitaq DNA polymerase (Perkin Elmer Cetus) and 0.4 mM dNTPs (Perkin Elmer Cetus). The cycling conditions were 25 cycles of 94° C. for 1.0 min, 45° C. for 2.0 min and 72° C. for 1.5 min. Specific 2 kb fragments were amplified for each sample (FIG. 13). SB33 DNA was used as a positive control (Lane 1). Chromosomal DNA used for amplification of the Tbp2 gene were lane 1, SB33; lane 2, SB12; lane 3, SB29; lane 4, SB30; and lane 5, SB32. The fragments were cloned into the TA cloning vector (Invitrogen) and their nucleotide sequences determined. The nucleic acid sequences of Tbp2 from strains SB12 (SEQ ID NO: 108), SB29 (SEQ ID NO: 110), SB30 (SEQ ID NO: 112) and SB32 (SEQ ID NO: 114) are shown in FIGS. 8, 9 10 and 11 respectively.

Example 6

This Example illustrates the comparison of the amino acid sequences of transferrin the identification of potentially exposed epitopes of transferrin receptor proteins by secondary structure analysis.

Referring to FIG. 14, there is shown a comparison of the amino acid sequence of Tbp1 from *H. influenzae* type b Eagan, DL63, non-typable *H. influenzae* strains PAK 12085 and SB33, *N. meningitidis* strains B16B6 and M982 (Legrain et al., 1993) and *N. gonorrhoeae* FA19 (Cornelissen et al., 1992). This analysis revealed regions of Tbp1 which are conserved among all these bacteria.

Referring to FIG. 15, there is shown a comparison of the amino acid sequence of Tbp2 from *H. influenzae* type b strains Eagan, DL63, non-typable *H. influenzae* PAK 12085, SB12, SB29, SB30 and SB32, *N. meningitidis* strains B16B6 and M982, *N. gonorrhoeae* FA19 and *Actinobacillus* (*Haemophilus*) *pleuropneumoniae* (Gerlach et al., 1992) 205 and 37. This analysis revealed regions of Tbp2 which are conserved among all these bacteria.

Protein secondary structure analyses were performed using the Chou and Fasman algorithms (1978) and hydrophilicity/hydrophobicity plots were performed using the Hopp algorithm (1986). The values were derived from the averages of heptapeptide windows and are plotted at the midpoint of each fragment. FIG. 16A illustrates the predicted secondary structure of Tbp1 from *H. influenzae* type b Eagan and FIG. 16B illustrates the predicted secondary structure of Tbp2 from *H. inffluenzae* type b Eagan. The predicted secondary structures depicted in FIGS. 16A and 16B were arrived at using the procedures described above. However, the inventors have not yet been able to verify that the secondary structure is accurately depicted by these Figures.

Conserved epitopes of Tbp1 and Tbp2 proteins from several different bacteria were identified by sesquence alignment as shown in FIGS. 14 and 15 respectively. Some such conserved epitopes include:

| TBP1 | DNEVTGLGK | SEQ ID NO:43 |
| TBP1 | EQVLNIRLTRYDPGI | SEQ ID NO:44 |
| TBP1 | GAINEIEYENVKAVEISKG | SEQ ID NO:45 |
| TBP1 | GALAGSV | SEQ ID NO:46 |
| TBP2 | LEGGFYGP | SEQ ID NO:74 |
| TBP2 | CSGGGSFD | SEQ ID NO:75 |
| TBP2 | YVYSGL | SEQ ID NO:76 |
| TBP2 | CCSNLSYVKFG | SEQ ID NO:77 |
| TBP2 | FLLGHRT | SEQ ID NO:78 |
| TBP2 | EFNVDF | SEQ ID NO:79 |
| TBP2 | NAFTGTA | SEQ ID NO:80 |
| TBP2 | VNGAFYG | SEQ ID NO:81 |
| TBP2 | LEGGYF | SEQ ID NO:82 |
| TBP2 | VVFGAR | SEQ ID NO:83 |

Furthermore, in combination with the predicted secondary structures, four conserved exposed epitopes were identified on Tbp1 and two were identified on Tbp2. These are:

| Tbp1 | DNEVTGLGK | SEQ ID NO:43 |
| Tbp1 | EQVLN/DIRDLTRYD | SEQ ID NOS:139 and 140 |
| Tbp1 | GAINEIEYENVKAVEISK | SEQ ID NO:141 |
| Tbp1 | GI/VYNLF/LNYRYVTWE | SEQ ID NOS:142 and 143 |
| Tbp2 | CS/LGGG(G)SFD | SEQ ID NOS:75, 144 and 145 |
| Tbp2 | LE/SGGFY/FGP | SEQ ID NOS:74 and 146 |

Proteins, polypeptides or peptides containing the aforementioned conserved amino acid sequences are particularly useful as detecting means in diagnostic embodiments and as immunogens to detect or protect from diseases caused by bacteria that produce transferrin receptor protein. For immunization, the particularly indicated amino acid sequences may be presented to the immune system as proteins or peptides or a live delivery vehicle, such as *Salmonella*, BCG, adenovirus, poxcvirus, vaccinia or poliovirus may be used.

Example 7

This Example illustrates the construction of plasmid JB-1468-29 which expresses Eagan Tbp1 from *E. coli*.

Plasmids S-4368-3-3 (FIGS. 1B and 2) and JB-911-3-2 (FIG. 17) contain the 5'- and 3'-parts of the Eagan tbp1 gene, respectively. FIG. 17 illustrates the construction scheme for plasmid JB-1468-29. The oligonucleotide sequences used in the construction of JB-1468-29 are shown in FIG. 20, (SEQ ID NOS: 86 and 87). Plasmid JB-1468-29 was introduced into *E. coli* strain BL21/DE3 by electroporation to generate strain JB-1476-2-1.

JB-1476-2-1 was grown in YT medium and induced with IPTG following standard protocols. For preparation of Tbp1 for immunogenicity and other studies, strain JB-1476-2-1 was grown overnight in NZCYM media containing 3% glucose. A 1:40 inoculum was added to fresh NZCYK media without glucose, and the culture grown to $A_{578}$=0.3. Lactose was added to 1% and the culture was induced for 4 hours. SDS-PAGE analysis of whole cell lysates of JB-1476-2-1 is shown in FIG. 22. Lane 1, JB-14176-2-1 (T7/Eagan Tbp1) at $t_0$; lane 2, JB-1476-2-1 at t=4h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_0$; lane 5, JB-1437-4-1 at t=4 h induction; lane 6, JB-1607-1-1 (T7/SB12 Tbp2) at $t_0$; lane 7, JB-1607-1-1 at t=4 h induction.

Example 8

This Example illustrates the construction of plasmid JB-1424-2-8 which expresses Eagan Tbp2 from *E. coli*.

Referring to FIG. 18, there is shown plasmid S-4368-3-3 which contains the entire tbp2 gene from *H. influenzae* type b Eagan. FIG. 18 illustrates plasmid JB-1424-2-8 and FIG. 19 shows the oligonucleotides used. Plasmid JB-1424-2-8 was introduced into *E. coli* strain BL21/DE3 by electroporation to generate *E. coli* strain JB-1437-4-1. Upon induction with IPTG or lactose, Tbp2 was expressed by *E. coli* JB-1437-4-1 as shown in FIG. 22. Lane 1, JB-1476-2-1 (T7/Eagan Tbp1) at $t_0$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_0$; lane 5, JB-1437-4-1 at t=4 h induction; lane 6, JB-1607-1-1 (T7/SB12 Tbp2) at $t_0$; lane 7, JB-1607-1-1 at t=4 h induction.

Example 9

This Example illustrates the construction of plasmids which encode a lipoprotein leader sequence before the Tbp2 sequence.

Oligonucleotides used for the construction of plasmids with lipoprotein leader sequences derived from *E. coli* lpp (SEQ ID NOS: 88 and 89), rlpB (SEQ ID NOS: 90 and 91), and pal (SEQ ID NOS: 92 and 93) preceeding Tbp2 are shown in FIG. 20. Plasmids constructed and corresponding strains generated are illustrated in Table 1 below.

Example 10

This Example illustrates the construction of plasmid JB-1600-1 which expresses SB12 Tbp2 from *E. coli*.

Plasmid DS-1047-1-2 (FIG. 21) contains the PCR-amplified SB12 tbp2 gene. The tbp2 gene was excised as a Nde I to EcoR I restriction fragment and inserted into the pT7-7 expression vector to generate plasmid JB-1600-1. Electroporation into BL21/DE3 cells yielded *E. coli* strain JB-1607-1-1 which expresses SB12 Tbp2. Upon induction with IPTG or lactose, SB12 Tbp2 was expressed, as shown in FIG. 22. Lane 1, JB-1476-2-1 (T7/Eagan Tbp1) at $t_0$; lane 2, JB-1476-2-1 at t=4 h induction; lane 3, molecular weight markers of 200 kDa, 116 kDa, 97.4 kDa, 66 kDa, 45 kDa and 31 kDa; lane 4, JB-1437-4-1 (T7/Eagan Tbp2) at $t_0$; lane 5, JB-1437-4-1 at t=4 h induction; lane 6, JB-1607-1-1 (T7/SB12 Tbp2) at $t_0$; lane 7, JB-1607-1-1 at t=4 h induction.

Example 11

This Example illustrates the extraction and purification of Tbp1 and Tbp2.

The purification scheme for Tbp1 and Tbp2 is shown in FIG. 23. Both recombinant proteins are expressed as inclusion bodies in *E. coli* and the purification schemes are identical. Cells from a 500 ml culture, prepared as described in Example 7 for Tbp1 and in Example 8 for Tbp2, were resuspended in 50 ml of 50 mM Tris-HCl, pH 8.0, and disrupted by sonication (3×10 min, 70% duty circle). The extract was centrifuged at 20,000×g for 30 min and the resultant supernatant which contained >95% of the soluble *E. coli* proteins was discarded.

The remaining pellet (FIG. 23, $PPT_1$) was further extracted in 50 ml of 50 mM Tris, pH 8.0 containing 0.5% Triton X-100 and 10 mM EDTA. After centrifugation at 20,000×g for 30 min, the supernatant containing residual soluble proteins and the majority of the membrane proteins, was discarded. The resultant pellet (FIG. 23, $PPT_2$) obtained after the above extraction, contained the inclusion bodies. The Tbp1 and Tbp2 proteins were solubilized in 50 mM Tris, pH 8.0, containing 0.1% SDS and 5 mM DTT. After centrifugation, the resultant supernatant was further purified on a Superdex 200 gel filtration column equilibrated in 50 mM Tris, pH 8.0, containing 0.1% SDS and 5 mM DTI. The fractions were analysed by SDS PAGE and those containing purified Tbp1 or Tbp2 were dialysed overnight at 4° C. against 50 mM Tris, pH 8.0 and then centrifuged at 20,000×g for 30 min. The protein remained soluble under these conditions and the purified Tbp1 and Tbp2 were stored at −20° C.

The SDS-PAGE analysis of the purification process is shown in FIG. 24. Lanes 1, prestained molecular weight protein markers (106, 80, 49.5, 32.5, 27.5, 18.5 kDa); lanes 2, *E.coli* whole cell lysates; lanes 3, solubilized inclusion bodies; lanes 4, purified Tbp1 or Tbp2.

In an alternative method for extraction and purification of recombinant rTbp1 and rTbp2, cells from a 500 mL culture, prepared as described in Example 7 for Tbp1 and Example 8 for Tbp2, were resuspended in 40 mL of 50 mM Tris-HCl, pH 8.0, containing 5 mM AEBSF (4-(2-aminoethyl)benzenesulfonylfluoride) and disrupted by sonication (3×10 min, 70% duty circle). After centrifugation at 20,000×g for 30 min, the resultant pellet was further extracted at room temperature for 1 hour in 40 mL 50 mM Tris-HCl, pH 8.0, containing 10 mM EDTA and 0.5% Triton X-100. After centrifugation as described above, the resultant pellet contained the rTbp1 or rTbp2 inclusion bodies. rTbp1 or rTbp2 was then solubilized in 50 mM Tris-HCl, pH 8.0, containing 6 M guanidine and 5 mM DTT. After centrifugation, the resultant supernatant was further purified on a Superdex 200 gel filtration column equilibrated in 50 mM Tris-HCl, pH 8.0, containing 2 M guanidine and 5 mM DTT. The fractions were analyzed by SDS-PAGE and those containing purified rTbp1 or rTbp2 were pooled. Triton X-100 was added into the pooled solution to a final concentration of 0.1% and the solution was dialyzed against 50 mM Tris-HCl, pH 8.0 overnight at 40° C. The protein remained soluble under these conditions and the purified rTbp1 and rTbp2 were stored at 4° C.

Example 12

This Example illustrates immunogenicity studies of recombinant Tbp1 and Tbp2 in mice.

Groups of five Balb/c mice were injected subcutaneously (s.c.) on days 1, 29 and 43 with purified rTbp1 or rTbp2 (1 μg to 10 μg), prepared as described in Example 11, in the presence of $AlPO_4$ (1.5 mg per dose). Blood samples were taken on days 14, 28, 42 and 56 for analysis of the anti-rTbp1 and anti-rTbp2 antibody titers by EIA. The results of the immunogenicity studies are illustrated in FIG. 25.

Example 13

This Example illustrates the development of EIAs for determination of anti-rTbp1 and anti-rTbp2 antibodies in mouse sera.

Anti-rTbp1 and anti-rTbp2 antibody titres were determined essentially as described by Panezutti et al. (1993). Microtiter wells were coated with 0.5 μg of rTbp1 or rTbp2, prepared as described in Example 11, for 16 h at room temperature, then blocked with 0.1% (w/v) BSA in PBS. The sera were serially diluted, added to the wells, then incubated for one hour at room temperature. Affinity-purified F(ab')$_2$ fragments of goat anti-mouse IgG (Fc specific) antibody conjugated to horseradish peroxidase were used as second antibody. The reactions were developed using tetramethylbenzidine (TMB/H$_2$O$_2$) and the absorbance was measured at 450 nm (using 540 nm as a reference wavelength) in a Flow Multiskan MCC microplate reader. The reactive titer of an antiserum was defined as the reciprocal of the dilution consistently showing a two-fold increase in absorbance over that obtained with the pre-immune serum sample.

Example 14

This Example illustrates the cross-reactivity of anti-Tbp1 antisera, produced by immunization with recombinant Eagan Tbp1, with various strains of *H. influenzae*.

Whole cell lysates of *H. influenzae* strains grown in BHI media supplemented with NAD and heme (Harkness et al., 1992) ±EDDA were separated by SDS PAGE gel, transferred to nitrocellulose membrane, and probed with guinea pig anti-Tbp1 antisera raised to purified recombinant Eagan Tbp1 (FIG. 26). Lane 1, BL21/DE3; lane 2, SB12–EDDA; lane 3, SB12+EDDA; lane 4, SB29–EDDA; lane 5, SB29+EDDA; lane 6, SB33–EDDA; lane 7, SB33+EDDA; lane 8, Eagan–EDDA; lane 9, Eagan+EDDA; lane 10, *B. catarrhalis* 4223–EDDA; lane 11, *B. catarrhalis* 4223+EDDA; lane 12, *N. meningitidis* 608–EDDA; lane 13, *N. meningitidis* 608+EDDA; lane 14, induced JB-1476-2-1 expressing recombinant Eagan Tbp1; lane 5, molecular weight markers. Specific ~95 kDa bands reacted with the anti-Tbp1 antisera in lanes 3, 4, 5, 7, 8 and 9, corresponding *H. influenzae* strains SB12, SB29, SB33 and Eagan; ~110 kDa bands in lanes 10 and 11, corresponding *B. catarrhalis* strain 4223; and ~80 kDa bands in lanes 12 and 13, corresponding to *N. meningitidis* 608.

Example 15

This Example illustrates the cross-reactivity of anti-Tbp2 antisera, produced by immunization with recombinant Eagan Tbp2, with various strains of *H. influenzae*.

Whole cell lysates of *H. influenzae* strains grown in BHI media supplemented with NAD and heme (Harkness et al., 1992) ±EDDA were separated on an SDS PAGE gel, transferred to nitrocellulose membrane, and probed with guinea pig anti-Tbp2 antisera raised to purified recombinant Eagan Tbp2 (FIG. 27). Lane 1, molecular weight markers; lane 2, induced JB-1437-4-1 expressing recombinant Eagan Tbp2; lane 3, SB12–EDDA; lane 4, SB12+EDDA; lane 5, SB29–EDDA; lane 6, SB29+EDDA; lane 7, SB30–EDDA; lane 8, SB30+EDDA; lane 9, SB32–EDDA; lane 10, SB33–EDDA; lane 11, SB33+EDDA; lane 12, PAK–EDDA; lane 13, PAK+EDDA; lane 14, Eagan–EDDA; lane 15, Eagan+EDDA. Specific bands of about 60–70 kDa were reactive with the anti-Tbp2 antisera in lanes 3, 6, 7, 8, 13, 14 and 15, corresponding to *Haemophilus* strains SB12, SB29, SB30, PAK and Eagan.

Example 16

This Example illustrates the synthesis of synthetic peptides corresponding to conserved regions in Tbp2 and Tbp1.

The deduced amino acid sequences of Tbp1 and Tbp2 were compared as shown in FIGS. 14 and 15 respectively. This comparison identified regions of amino acid sequence conservation within the transferrin receptor described above and, as shown in Tables 2 and 3, peptides were synthesized containing a portion of the transferrin receptor. Such synthesis may be effected by expression in a suitable host of recombinant vectors containing nucleic acid encoding said peptides or by standard peptide synthesis.

Briefly, peptides were synthesized using an ABI 430A peptide synthesizer and optimized t-Boc chemistry using the conditions recommended by the manufacturer, and peptides were cleaved from the resin using hydrofluoric acid (HF). The peptides were purified by reverse-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 ml/minute. All synthetic peptides used in biochemical and immunological studies were >95% pure as judged by analytical HPLC. Amino acid composition analyses were performed on a Waters Pico-Tag system and were in good agreement with the theoretical compositions.

Example 17

This Example illustrates the immunogenicity of synthetic peptides in test animals.

Guinea pigs were immunized intramuscularly with 100 μg of peptide, prepared as described in Example 16, emulsified in Freund's complete adjuvant on day 0 followed by boosters on days +14 and +28 using the same amount of peptide emulsified in Freund's incomplete adjuvant. Sera samples were obtained on day 42+ and antibody titres determined by enzyme-linked immunosorbent assay (ELISA). Briefly, microtiter wells (Nunc-Immunoplate, Nunc, Denmark) were coated with 500 ng of any one particular peptide in 50 μL of coating buffer (15 mM Na$_2$CO$_3$, 35 mM NaHCO$_3$, pH 9.6) for 16 hours at room temperature. The plates were then blocked with 0.1% (w/v) BSA in phosphate buffer saline (PBS) for 30 minutes at room temperature. The antisera were serially diluted, added to the wells and incubated for 1 hour at room temperature. After removal of the antisera, the plates were washed five times with PBS containing 0.1% (w/v) Tween-20 and 0.1% (w/v) BSA. F(ab')$_2$ from goat anti-guinea pig IgG antibodies conjugated to horseradish peroxidase (Jackson ImmunoResearch Labs Inc., PA) were diluted (1/8,000) with washing buffer, and added onto the microtiter plates. After 1 hour of incubation at room temperature, the plates were washed five times with the washing buffer. The plates were developed using the substrate tetramethylbenzidine (TMB) in H$_2$O$_2$ (ADI, Toronto), the reaction was stopped with 1N H$_2$SO$_4$ and the optical density was measured at 450 nm using a Titretek Multiskan II (Flow Labs., Virginia). Two irrelevant peptides of 32 amino acid residues were included as negative controls in these ELISAs. Assays were performed in triplicate, and the reactive titer of each antiserum was defined as the dilution consistently showing a 2-fold increase in absorbance value over those obtained from the negative controls. The antisera raised in guinea pigs were monospecific for the peptide used for immunization. The titres of the sera obtained following immunization are shown in Table 4.

Peptides of the present invention comprise single copies of any of those shown in Tables 2 and 3 or peptides containing multiple copies of analogs thereof. A peptide may further comprise multiples of different peptides selected from those shown in Tables 2 and 3 or analogs thereof and include suitable carrier molecules. It is preferred that the peptides from conserved regions be used to develop antibodies because an immuno- or other type of binding assay can then be used to detect several species of *Haemophilus*. Tables 2 and 3 therefore set out several other conserved regions of transferrin receptor to identify other peptides which would be useful in diagnosis, immunization and medical treatment.

Guinea pig anti-Eagan rTbp1, anti-Eagan rTbp2, and anti-SB12 rTbp2 antisera were used to screen a panel of *H. influenzae* strains for antigenic conservation of the Tbp1 and Tbp2 proteins. Of 33 strains screened by Western blot with anti-Eagan rTbp1 antisera, all had a reactive band of ~100 kDa. Of 89 strains screened by Western blot with anti-Eagan rTbp2 antisera, 85 had a reactive band of 60–90 kDa. Of 86 strains screened by Western blot with anti-SB12 rTbp2 antisera, 82 had a reactive band of 60–90 kDa. Only one strain was not recognized by either anti-Eagan rTbp2 or anti-SB12 rTbp2 antisera, and that was NTHi strain SB33 which has a defective tbpB gene. These data indicate that transferrin receptor proteins are highly conserved in strains of *H. influenzae* and support the use of these proteins as antigens and in immunogenic compositions, including vaccines, for immunization against disease cause by *H. influenzae* and diagnosis thereof.

Example 18

This Example describes the ability of antiserum raised against peptides corresponding to conserved portions of transferrin receptor to recognize the transferrin receptor of *Branhamella catarrhalis*.

Guinea pigs were immunized with peptide, corresponding to conserved portions of transferrin receptor, and antisera obtained are described in Example 17. A whole-cell extract of *Branhamella catarrhalis* was immunoblotted with the peptide-specific antiserum which specifically recognized the transferrin receptor from this bacterium. Anti-peptide antiserum from a guinea pig immunized with the Tbp2 N-terminal peptide and peptide TBP2-25 specifically recognized Tbp2 protein from *Branhamella catarrhalis* and recombinant Tbp2 expressed by plasmid clone pBHIT2 in *E. coli*. Clone pBHIT2 expresses a truncated version of Tbp2 starting at amino acid 80. (i.e. NKKFYSG SEQ ID NO: 105). Therefore, the Tbp2 protein from pBHIT2 can only be recognized by antibodies raised against the second epitope LEGGFYGP (TBP2-25). This analysis shows that peptides corresponding to conserved sequences between transferrin receptor are useful in detecting most, if not all, bacteria that produce transferrin receptor and as components in immunogenic compositions, including vaccines to produce an immune response against transferrin receptor and protect against diseases caused by such bacteria.

The sera from these rabbits were tested by ELISA against a peptide incorporating the sequence LEGGFYGP (SEQ ID NO: 74) or against *H. influenzae* strain DL63, Tbp2. ELISA plates were coated with the peptide or the protein then blocked with 5% skim milk. Serial two-fold dilutions of sera in phosphate buffered saline, 0.05% tween-20, and 1% dried milk were incubated on the plates for two hours at 37° C., following which the plates were washed five times in phosphate buffered saline with 0.05% tween-20. Washed plates were probed with a horse-radish peroxidase (HRPO)-conjugated donkey anti-rabbit IgG for 30 minutes at room temperature, then washed five times in phosphate buffered saline with 0.05% tween-20. HRPO-substrate was added to all wells for 30 minutes at room temperature in the dark, then color developement was halted by the addition of 50 ul 1M sulphuric acid. Color was measured by determining absorbance at 450 nm.

Example 19

This Example illustrates the generation of *H. influenzae* strains that do not produce transferrin receptor.

A 2.55 Eco RI fragment of the insert from pBHIT1 was subcloned into the Eco RI site of pUC4K, resulting in removal of the Tn903 kanamycin resistance (kan) cassette from this vector (pUHIT1; FIG. 28). This subcloning step facilitated the subsequent insertion of either a HincII or PstI pUC4K fragment containing the kan cassette into the Hind III or Pst I sites of pUHIT1 as both are unique sites in this construction to produce pUHIT1KFH and pUHIT1KFP, FIG. 28. Following digestion with Eco RI to remove the interrupted gene sequences, the constructs were introduced into the *H. influenzae* wild type genome by transformation using M-IV media as described previously (Barcak et al., 1991) and transformants were selected on BHINH agar containing 20 μg/ml kanamycin.

Example 20

This Example illustrates the construction of polioviruses expressing an epitope of a transferrin receptor.

A cDNA clone of bases 1175 to 2956 of the poliovirus type 1, Mahoney strain (PV1-M) genome was cut with restriction enzymes Sau I and Hind III. These enzymes excise a fragment containing bases 2754 to 2786, which encodes PV1-M amino acids 1094 to 1102, as shown in FIG. 29. In this application, we use the four-digit code for poliovirus amino-acids; for example, 1095 is amino acid 95 of capsid protein VP1. New hybrid cDNA clones encoding both poliovirus and transferrin receptor amino-acid sequences were constructed by replacing the excised fragment with synthetic oligonucleotides coding for amino acids from *H. influenzae* Tbp2. The new hybrid cDNA clones were cut with restriction enzymes Nhe I and SnaB I, which excise a hybrid fragment, including the transferrin receptor DNA sequences, from poliovirus base 2471 to 2956. A cDNA clone, for example pT7XLD or pT7CMCB, of the entire genome of PV1-M was cut with Nhe I and SnaBI to excise a fragment from poliovirus base 2471 to 2956. This was then replaced with a hybrid fragment including the transferrin receptor DNA sequences to produce a hybrid cDNA clone of the genome of PV1-M with bases 2754 to 2786 replaced by bases encoding a hybrid BC loop including transferrin receptor amino acids, as shown in FIG. 29.

The plasmid pT7XLD and clones derived from pT7XLD, such as pT7CMCB, contain a promoter sequence for the enzyme T7 RNA polymerase at the 5' end of the PV1-M cDNA. RNA transcripts of the PV1-M cDNA, including any bases encoding transferrin receptor amino acids, were prepared using T7 RNA polymerase as described by van der Werf et al. Transfection of Vero cells with these RNA transcripts produced four viable hybrid viruses, designated PV1TBP2A, PV1TBP2B, PV1TBP2C and PV1TBP2D. Transfection with transcripts of pT7CMCB yielded a transfection-derived wild-type poliovirus designated PV1XLD (FIG. 29).

The antigenic characteristics of PV1TBP2A, PV1TBP2B, PV1TBP2C and PV1TBP2D are shown in Table 5. All were neutralized by guinea-pig antisera raised against a peptide incorporating the sequence LEGGFYGP (SEQ ID NO: 74), indicating that the viruses expressed this sequence in an antigenically recognisable form. To produce the antisera female guinea pigs were immunized IM with a 500 ul volume containing 200 ug peptide formulated in aluminum phosphate (3 mg/ml). Animals were immunized on days 1, 14, 28 and 42 and bled on days 0, 28, 42 and 56. Sera were from the day 56 bleed. PV1TBP2A and PV1TBP2B were also neutralized by rabbit antisera raised against *H. influenzae* strain DL63 Tbp2, indicating that at least these two viruses expressed the sequence in a form recognisable to antibodies raised against the protein. All viruses were neutralisable by anti-PV1 sera, indicating that the changes in polio neutralization antigenic site I had not significantly affected other antigenic sites on the viruses.

Example 21

This Example illustrates the use of poliovirus hybrids to induce high titer antisera against Tbp2.

Rabbits were inoculated with CsCl-purified PV1TBP2A (rabbits #40, 41, 42). Note that, although the viruses used were live, poliovirus does not replicate in rabbits and that any response observed is effectively the response to an inactivated antigen. On day 1, rabbits were inoculated with 1 ug of virus in Freund's complete adjuvant subcutaneously on the back, and, on day 14, the rabbits were boosted with 1 ug of virus in Freund's incomplete adjuvant inoculated subcutaneously on the back. The rabbits were bled on day 0 (prebleed) and on day 27. The dose of virus per inoculation was $2.5 \times 10^8$ pfu, which was determined from $A_{260}$ values to be approximately $3.0 \times 10^{11}$ virions. This equivalent to 0.5 pmol of virus or 30 pmol of the LEGGFYG (SEQ ID NO: 74) epitope, since each virion expresses 60 copies of the epitope.

Example 22

This Example illustrates the protection of relevant animal models from disease caused by *H. influenzae*.

The infant rat model of bacteremia (Loeb et al, 1987) was used to assess the protective abililty of anti-Eagan rTbp1 and anti-Eagan rTbp2 antisera. Anti-Eagan rTbp1 antisera raised in either rabbits or guinea pigs was not protective in this model but anti-Eagan rTbp2 antisera raised in rabbits or guinea pigs was protective (Table 7). These data indicate the use for rTbp2 proteins as protective antigens.

The chinchilla model of otitis media (Barenkamp et al, 1986) was used to assess the protective ability of SB12 rTbp2. Data indicated that compared with the control group, the immunized animals had less severe disease.

The ability of recombinant Tbp2 (rTbp2) to prevent nasopharyngeal colonization was determined in chinchillas. *H. influenzae* strain 12 was grown on supplemented Mueller Hinton agar containing 10–100 µg mL$^{-1}$ of streptomycin until spontaneous str$^R$ colonies were obtained. Strain 12 resistant to 100 µg mL$^{-1}$ of streptomycin was used in the colonization model which enabled the specific culture of *H. influenzae* bacteria from nasal ravages.

Chinchillas (3–4 month old or 1–2 year old) were immunized 3 times (i.m.) with either 30 µg of rTbp2 in alum, or $2 \times 10^9$ cfu inactivated strain 12 whole cells in alum, or alum alone on days 0, 14 and 28. On day 44, animals were lightly anesthetized using ketamine HCl. Intranasal inoculations were performed via passive inhalation (50 µL per nare, total 0.1 ml per animal) of freshly cultured streptomycin resistant NTHi strain 12 in BHI medium supplemented with hemin and nicotinamide adenine dinucleotide (NAD). The dose of bacterial challenge was $1 \times 10^8$ cfu per animal.

Nasopharyngeal lavage was performed on days 5 and 9 post inoculation. Secretions were obtained from anesthetized chinchillas by irrigating the nasopharynx with 1 ml of sterile diluent (diluent: 50 mL BHI, 100 mL saline, 200 µg NAD and 25 µL of 1% hemin) and collecting fluid out of the contralateral nares. Normally about 500 µL of fluid was collected from each animal and 25 µL of sample was plated on chocolate agar plate in the presence of 1 mg streptomycin. The results are shown in Table 10. On both 5-day and 9-day post challenge, 25 µL of undiluted nasal lavage fluid were plated in the presence of streptomycin. Although a few animals in the two positive control groups (whole cell immunization and convalescent) had a positive nasopharyngeal colonization on 5 days post challenge, all bacteria were cleared from these animals by day 9, and none of the animals from these two groups developed ear infection. Thus, rTbp2 was shown to partially protect chinchillas against NTHi colonization.

Example 23

This Example describes the generation of truncated analogues of transferrin receptor protein Tbp2.

Figure 32:
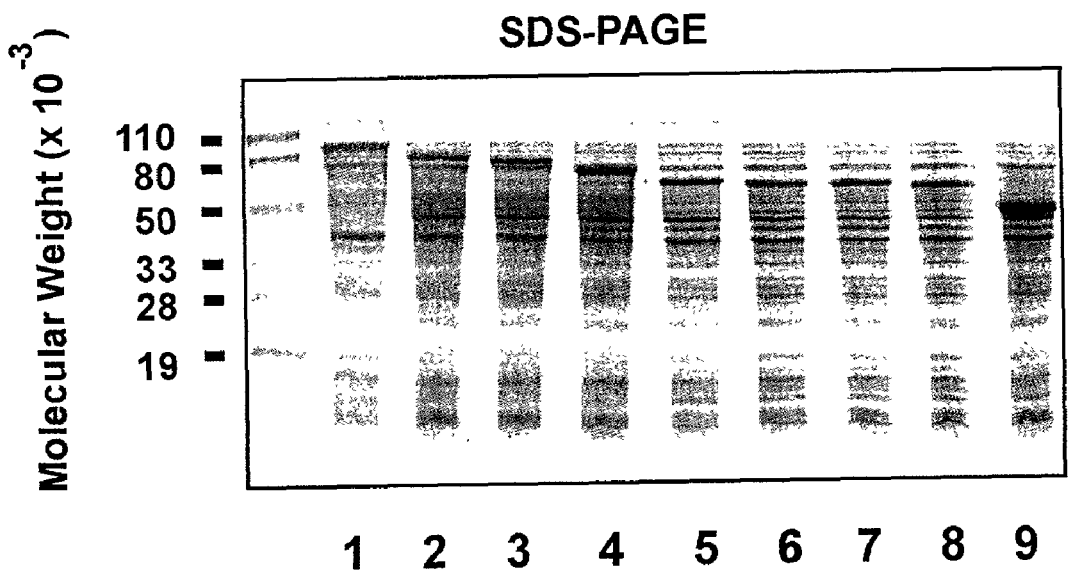
Figure 32:
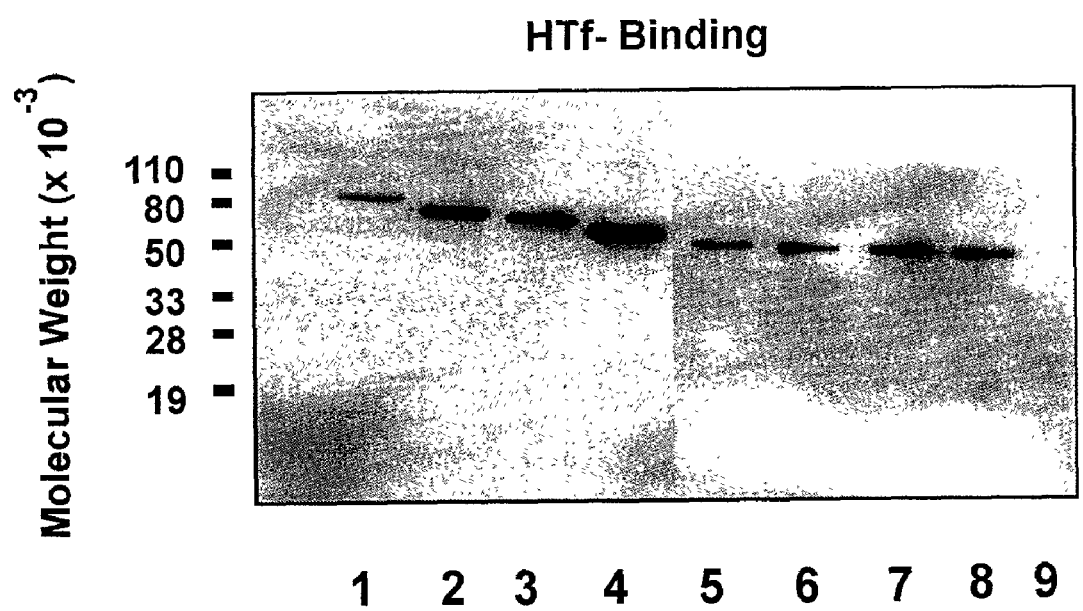

*H. influenzae* Tbp2 is produced in low amounts by *E. coli*. The Eagan tbpB gene was truncated from its 3'-end using an Erase-a-base kit to produce a number of truncated analogues of Tbp2 as shown in FIG. 31 and Table 8. The truncated genes were expressed in *E. coli* BL21 (DE3) from the T7 promoter. The percentage of the remaining mature Eagan rTbp2 is indicated and the expression level of the truncated clones is compared with that of the full-length Eagan rTbp2 clone (Table 8). Binding of the truncated clones to human transferrin (Tf) was measured using the assay described by Morton and Williams (1990) (FIG. 32). The data indicate that the yield of Eagan rTbp2 can be significantly increased by truncation of the carboxy region of the protein. The data also indicate that the transferrin binding site may be located between residues 348 and 446 of the mature Eagan Tbp2 protein (Table 3 and FIG. 32). However, the transferrin preservation of the Tf binding site in the truncated rTbp2 may not be necessary for its use as a protective immunogen.

The infant rat model of bacteremia (Loeb et al, 1987) was used to assess the protective ability of anti-truncated analogues of transferrin receptor protein Tbp2 and the results are shown in Table 9. Animals were considered to be protected if they had <10 cfu in 2 µl of blood.

SUMMARY OF THE DISCLOSURE

In summary of this disclosure, the present invention provides purified and isolated DNA molecules containing transferrin receptor genes, the sequences of these transferrin receptor genes and the derived amino acid sequences thereof. The invention also provides peptides corresponding to portions of the transferrin receptor. The genes, DNA sequences, recombinant proteins and peptides are useful for diagnosis, immunization and the generation of diagnostic and immunological reagents. Vaccines based upon expressed recombinant Tbp1 and/or Tbp2, portions thereof, or peptides derived from the provided sequences can be prepared for prevention of diseases caused by bacterial pathogens that produce transferrin receptor. Modifications are possible within the scope of this invention.

TABLE 1

| leader | 1st residue | plasmid | strain |
|---|---|---|---|
| *E. coli* lpp | Cys | JB-1360-1R-10 | JB-1407-1-1 |
| *E. coli* lpp | Ser | JB-1366-1R-7 | JB-1407-3-1 |

TABLE 1-continued

| leader | 1st residue | plasmid | strain |
|---|---|---|---|
| *E. coli* pal | Cys | JB-1360-3-10 | JB-1407-2-1 |
| *E. coli* pal | Ser | JB-1366-3R-5 | JB-1407-4-4 |
| *E. coli* rlpB | Cys | JB-1399-1 | JB-1437-1-1 |
| *E. coli* rlpB | Ser | JB-1378-7 | JB-1407-5-1 |

TABLE 2

PREDICTED ANTIGENIC Tbp1 PEPTIDES

| PEPTIDE | RESIDUES[1] | SEQUENCES | SEQ ID NO: |
|---|---|---|---|
| TBP1-N | 1—36 | AETQSIKDTKEAISSEVDTQSTEDSELETISVTAEK | 13 |
| TBP1-2 | 31—66 | SVTAEKVRDRKDNEVTGLGKIIKTSESISREQVLNI | 14 |
| TBP1-3 | 59—94 | SREQVLNIRDLTRYDPGISVVEQGRGASSGYSIRGM | 15 |
| TBP1-4 | 88—123 | GYSIRGMDRNRVALLVDGLPQTQSYVVQSPLVARSG | 16 |
| TBP1-5 | 117—152 | PLVARSGYGTGAINEIEYENVKAVEISKGGSSSEYG | 17 |
| TBP1-6 | 147—182 | SSSEYGNGALAGSVTFQSKSAADILEGDKSWGIQTK | 18 |
| TBP1-7 | 179—214 | GIQTKNAYSSKNKGFTHSLAVAGKQGGFEGVAIYTH | 19 |
| TBP1-8 | 208—243 | GVAIYTHRNSIETQVHKDALKGVQSYDRFIATTEDQ | 20 |
| TBP1-9 | 236—271 | IATTEDQSAYFVMQDECLDGYDKCKTSPKRPATLST | 21 |
| TBP1-10 | 266—301 | PATLSTQRETVSVSDYTGANRIKPNPMKYESQSWFL | 22 |
| TBP1-11 | 293—328 | YESQSWFLRGGYHFSEQHYIGGIFEFTQQKFDIRDM | 23 |
| TBP1-12 | 322—357 | KFDIRDMTFPAYLRPTEDKDLQSRPFYPKQDYGAYQ | 24 |
| TBP1-13 | 352—387 | DYGAYQHIGDGRGVKYASGLYFDEHHRKQRVGIEYI | 25 |
| TBP1-14 | 383—418 | GIEYIYENKNKAGIIDKAVLSANQQNIILDSYMRHT | 26 |
| TBP1-15 | 412—447 | DSYMRHTHCSLYPNPSKNCRPTLDKPYSYYHSDRNV | 27 |
| TBP1-16 | 443—478 | SDRNVYKEKHNMLQLNLEKKIQQNWLTHQIAFNLGP | 28 |
| TBP1-17 | 469—504 | THQIAFNLGFDDFTSALQHKDYLTRRVIATASSISE | 29 |
| TBP1-M | 498—534 | TASSISEKRGEARRNGLQSSPYLYPTPKAELVGGDLC | 30 |
| TBP1-19 | 528—563 | LVGGDLCNYQGKSSNYSDCKVRLIKGKNYYFAARNN | 31 |
| TBP1-20 | 558—593 | FAARNNMALGKYVDLGLGMRYDVSRTKANESTISVG | 32 |
| TBP1-21 | 588—623 | STISVGKFKNFSWNTGIVIKPTEWLDLSYRLSTGFR | 33 |
| TBP1-22 | 618—653 | LSTGFRNPSFAEMYGWRYGGKDTDVYIGKFKPETSR | 34 |
| TBP1-23 | 648—683 | KPETSRNQEFGLALKGDFGNIEISHFSNAYRNLIAF | 35 |
| TBP1-24 | 677—712 | YRNLIAFAEELSKNGTTGKGNYGYHNAQNAKLVGVN | 36 |
| TBP1-25 | 706—741 | AKLVGVNITAQLDFNGLWKRIPYGWYATFAYNRVKV | 37 |
| TBP1-26 | 735—770 | AYNRVKVKDQKINAGLASVSSYLFDAIQPSRYIIGL | 38 |
| TBP1-27 | 764—799 | SRYIIGLDYDHPSNTWGIKTMFTQSKAKSQNELLGK | 39 |
| TBP1-28 | 794—829 | NELLGKRALGNNSRNVKSTRKLTRAWHILDVSGYYM | 40 |
| TBP1-29 | 825—854 | SGYYMVNRSILFRLGVYNLLNYRYVTWEAV | 41 |
| TBP1-30 | 843—865 | LLNYRYVTWEAVRQTAQGAEFDI | 42 |

TABLE 2-continued

PREDICTED ANTIGENIC Tbp1 PEPTIDES

| PEPTIDE | RESIDUES[1] | SEQUENCES | SEQ ID NO: |
|---|---|---|---|
| TBP1-31 | 42–50 | DNEVTGLGK | 43 |
| TBP1-32 | 61–76 | EQVLNIRDLTRYDPGI | 44 |
| TBP1-33 | 61–95 | EQVLNIRDLTRYDPGISVVEQGRGASSGYSIRGMD | 45 |
| TBP1-34 | 128–146 | GAINEIEYENVKAVEISKG | 46 |
| TBP1-35 | 155–161 | GALAGSV | 47 |
| TBP1-1 | 1–14 | AETQSIKDTKEAISC[2] | 48 |

[1]Residue number from the sequence of Tbp1 of *H. influenzae* type b strain Eagan (as shown in FIG. 8).
[2]Cysteine added to facilitate coupling to a carrier protein, for example KLH.

TABLE 3

PREDICTED CONSERVED ANTIGENIC Tbp2 PEPTIDES

| PEPTIDE | RESIDUES[1] | SEQUENCES | SEQ ID NO: |
|---|---|---|---|
| TBP2-1 | 18–31 | CSGGGSFDVDNVSN | 49 |
| TBP2-2 | 231–261 | LEGGFYGPKGEELGFRFLAGDKKVFGVFSAK | 50 |
| TBP2-3 | 358–380 | TVGKKTYQVEACCSNLSYVKFGM | 51 |
| TBP2-4 | 527–549 | ATVKGAFYGPKASELGGYFTYNG | 52 |
| TBP2-5 | 1–36 | MKLAALNLFDRNKPSLLNEDSYMIFSSRSTIEEDV | 53 |
| TBP2-6 | 29–64 | STIEEDVKNDNQNGEHPIDSIVDPRAPNSNENRHG | 54 |
| TBP2-7 | 57–92 | SNENRHGQKYVYSGLYYIQSWSLRDLPNKKFYSGY | 55 |
| TBP2-8 | 85–120 | KKFYSGYYGYAYYFGNTTASALPVGGVATYKGTWS | 56 |
| TBP2-9 | 113–148 | TYKGTWSFITAAENGKNYELLRNSGGGQAYSRRSA | 57 |
| TBP2-10 | 141–176 | AYSRRSATPEDIDLDRKTGLTSEFTVNFGTKKLTG | 58 |
| TBP2-11 | 169–204 | GTKKLTGGLYYNLRETDANKSQNRTHKLYDLEADV | 59 |
| TBP2-12 | 197–232 | YDLEADVHSNRFRGKVKPTKKESSEEHPFTSEGTL | 60 |
| TBP2-13 | 225–260 | FTSEGTLEGGFYGPEGQELGGKFLAHDKKVLGVFS | 61 |
| TBP2-14 | 253–288 | KVLGVFSAKEQQETSENKKLPKETLIDGKLTTFKT | 62 |
| TBP2-15 | 281–316 | KLTTFKTTNATANATTDATTSTTASTKTDTTTNAT | 63 |
| TBP2-16 | 309–344 | DTTTNATANTENFTTKDIPSLGEADYLLIDNYPVP | 64 |
| TBP2-17 | 337–372 | IDNYPVPLFPESGDFISSKHHTVGKKTYQVEACCS | 65 |
| TBP2-M | 360–406 | CSNLSYVKFGMYYEAPPKEEEKEKEKDKDKEKEKQ | 66 |
| TBP2-19 | 393–428 | KEKDKDKEKEKQATTSIKTYYQFLLGLRTPSSEIP | 67 |
| TBP2-20 | 421–456 | TPSSEIPKEGSAKYHGNWFGYISDGETSYSASGDK | 68 |
| TBP2-21 | 449–484 | YSASGDKERSKNAVAEFNVNFAEKTLTGELKRHDT | 69 |
| TBP2-22 | 477–512 | ELKRHDTQNPVFKINATFQSGKNDFTGTATAKDLA | 70 |
| TBP2-23 | 505–540 | ATAKDLAIDGKNTQGTSKVNFTATVNGAFYGPHAT | 71 |
| TBP2-24 | 533–559 | FYGPHATELGGYFTYNGNNPTDKNSS | 72 |
| TBP2-C | 553–581 | CPTDKNSSSNSEKARAAVVFGAKKQQVETTK | 73 |
| TBP2-25 | 231–238 | LEGGFYGP | 74 |

TABLE 3-continued

PREDICTED CONSERVED ANTIGENIC Tbp2 PEPTIDES

| PEPTIDE | RESIDUES[1] | SEQUENCES | SEQ ID NO: |
|---|---|---|---|
| TBP2-26 | 18–25 | CSGGGSFD | 75 |
| TBP2-27 | 130–134 | YVYSGL | 76 |
| TBP2-28 | 345–355 | CCSNLSYVKFG | 77 |
| TBP2-29 | 401–407 | FLLGHRT | 78 |
| TBP2-30 | 450–456 | EFNVDF | 79 |
| TBP2-31 | 485–491 | NAFTGTA | 80 |
| TBP2-32 | 516–522 | VNGAFYG | 81 |
| TBP2-33 | 527–532 | ELGGYF | 82 |
| TBP2-34 | 562–566 | VVFGAR | 83 |
| TBP2-35 | 562–568 | VVFGAK | 84 |
| TBP2-36 | 231–238 | LEGGFYG | 85 |

[1]Residue number from the sequence of Tbp2 of *H. infLuenzae* type B Eagan strain (as shown in FIG. 9).

TABLE 4

Guinea pig antibody responses to Tbp1 and Tbp2 peptides

| PEPTIDE | SEQ ID | SEQUENCES | TITRE |
|---|---|---|---|
| TBP1-N | 13 | AETQSIKDTKEAISSEVDTQSTEDS ELETISVTAEK | 500 |
| TBP1-M | 30 | TASSISEKRGEARRNGLQSSPYLYP TPKAELVGGDLC | 1562500 |
| TBP1-1 | 48 | AETQSIKDTKEAISC | <100 |
| TBP2-1 | 49 | CSGGGSFDVDNVSN | 2500 |
| TBP2-2 | 50 | LEGGFYGPKGEELGFRFLAGDKKVF GVFSAK | 12500 |
| TBP2-3 | 51 | TVGKKTYQVEACCSNLSYVKFGM | 62500 |
| TBP2-4 | 52 | ATVKGAFYGPKASELGGYFTYNG | <100 |
| TBP2-M | 66 | CSNLSYVKFGMYYEAPPKEEEKEKE KDKDKEKEKQA | 2500 |
| TBP2-C | 73 | CPTDKNSSSNSEKARAAVVFGAKKQ QVETTK | 312500 |

TABLE 5

Neutralizing activity of anti-Tbp2 and anti-peptide sera against polio/Tbp2 hybrid viruses

| | Neutralizing Titre v. Virus[b] | | | | |
|---|---|---|---|---|---|
| Sera[a] | PV1TBP2A | PV1TBP2B | PV1TBP2C | PV1TBP2D | PV1XLD |
| Rb @PV1 | >40,9600 | 25,844 | 20,480 | 16,763 | >40,960 |
| Rb 516 D0 | <4 | <4 | <4 | <4 | <4 |
| Rb 516 D42 | 40 | 20 | <4 | <4 | <4 |
| GP561, 562 D0 pool | <4 | <4 | <4 | <4 | <4 |

TABLE 5-continued

Neutralizing activity of anti-Tbp2 and anti-peptide sera against polio/Tbp2 hybrid viruses

| Sera[a] | Neutralizing Titre v. Virus[b] | | | | |
|---|---|---|---|---|---|
| | PV1TBP2A | PV1TBP2B | PV1TBP2C | PV1TBP2D | PV1XLD |
| GP 561 D56 | >2048 | >2048 | >2048 | 1164 | <4 |
| GP 562 D56 | >2048 | >2048 | 25 | 10 | <4 |
| GP558, 559, 560 D56 pool | <4 | <4 | <4 | <4 | <4 |

[a]Rb @PV1 is pool of rabbit immune sera raised against PV1XLD. Rabbit 516 was immunised with three successive 3 μg dses of recombinant *H. influenzae* DL63 transferrin binding protein 2 on days 1, 14 and 28. Serum was collected on days 0 (D0) and 42 (D42). Guinea-pigs were immunized with four successive doses of 200 μg of peptide on days 1, 14, 28 and 42. Sera were collected on day 0 (D0) and day 56 (D56). Guinea-Pigs 561 and 562 received a peptide containing the sequence LEGGFYGP(SEQ ID NO:74). Guinea-pigs 558, 559 and 556 received a control peptide with an unrelated sequence.

[b]Titre is the inverse dilution of serum giving a 50% endpoint in a virus neutralization assay versus 100 $TCID_{50}$ of virus.

TABLE 6

Peptide-specific IgG titres of rabbits immunised with PV1TBP2A or PV1TBP2B

| RABBIT (ANTIGEN) | PEPTIDE-SPECIFIC IgG TITRES[a] | |
|---|---|---|
| | PREBLEED | DAY 27 |
| 40 (PV1TBP2A) | <20 | 640 |
| 41 (PV1TBP2A) | <20 | 640 |
| 42 (PV1TBP2A) | <20 | 2560 |
| 43 (PV1TBP2B) | <20 | 160 |
| 44 (PV1TBP2B) | <20 | 1280 |
| 45 (PV1TBP2B) | <20 | 1280 |
| 10 (PV1 Mahoney) | | <20[b] |
| 11 (PV1 Mahoney) | | <20 |

[a]Titres are the reciprocal of the greatest dilution of sera giving an $A_{450}$ of at least twice the background value. The background value was the mean $A_{450}$ of wells assayed in the absence of rabbit sera.

[b]Titres for rabbits 10 and 11 refer to sera taken on day 42 after three immunisations with PV1 Mahoney. Rabbits 10 and 11 were immunised as rabbits 40 to 45, except that an additional booster dose was administered on day 28.

TABLE 7

Infant Rat Protection studies with anti-rTbp1 and anti-rTbp2 antisera

| Antisera | # animals protected | # animals infected |
|---|---|---|
| rabbit anti-rTbp1 | 0/10 | 10/10 |
| pre-bleed | 0/10 | 10/10 |
| rabbit-anti MinnA | 10/10 | 0/10 |
| gp anti-rTbp1 | 0/10 | 10/10 |
| pre-bleed | 0/10 | 10/10 |
| gp anti-MinnA | 10/10 | 0/10 |
| rabbit anti-rTbp2 | 8/10 | 2/10 |
| pre-bleed | 0/10 | 10/10 |
| rabbit anti-MinnA | 10/10 | 0/10 |
| gp anti-rTbp2 | 10/10 | 0/10 |
| pre-bleed | 0/10 | 10/10 |
| gp anti-MinnA | 10/10 | 0/10 |

Antisera were raised in guinea pigs and rabbits to Eagan rTbp1 and Eagan rTbp2 proteins. Infant rats were immunized s.c. with 0.1 ml of antisera and 24 h later were challenged i.p. with 350 cfu of *H. influenzae* type b strain MinnA. Blood was collected 20 h post-challenge and plated on chocolate agar.

TABLE 8

Truncated Eagan rTbp2 clones

| Clone | SEQ ID NO: | % Tbp2 | Expression | Tf binding |
|---|---|---|---|---|
| | | 100% | + | + |
| DS-1461-8-1 | 148 | 98% | ND | ND |
| DS-1466-1-1 | 149 | 83% | + | + |
| DS-1466-1-14 | 150 | 80% | + | + |
| DS-1466-2-6 | 151 | 69% | + | + |
| DS-1466-3-4 | 152 | 63% | + | + |
| DS-1466-3-1 | 153 | 62% | + | + |
| DS-1644-7-9 | 154 | 61% | + | + |
| DS-1466-1-4 | 155 | 60% | + | + |
| DS-1457-3-1 | 156 | 54% | ++ | − |
| DS-1466-4-1 | 157 | 45% | ++ | − |
| DS-1466-5-1 | 158 | 38% | ++ | − |
| DS-1466-4-3 | 159 | 16% | ND | ND |
| DS-1466-1-18 | 160 | 10% | ND | ND |

TABLE 9

Protection of infant rats by truncated rTbp2

| Antiserum | Animals protected[1] | Animals protected[2] |
|---|---|---|
| pre-bleed | 0/10 | 0/10 |
| anti-rTbp2 (100%) | 7/8 | 9/10 |
| anti-rTbp2 (83%) | 7/8 | 8/10 |
| anti-rTbp2 (80%) | 5/8 | 10/10 |
| anti-rTbp2 (69%) | 3/8 | 2/10 |
| anti-rTbp2 (60%) | 7/8 | 8/10 |
| anti-rTbp2 (54%) | 6/8 | 6/10 |
| anti-*E. coli* | 0/8 | 0/10 |
| anti-*H. influenzae* | 6/6 | 10/10 |

[1]Rabbit antiserum

[2]Guinea pig antiserum

TABLE 10

Protective Ability of rTbp2 against NTHi Nasopharyngeal Colonization in Chinchillas

| Antigens | # of animals showed positive nasopharyngeal colonization/total # animals | |
|---|---|---|
| | 5-day post | 9-day post |
| alum | 8/10 | 10/10 |
| rTbp2 + alum | 6/10 ($\rho$ = 0.628) | 6/10 ($\rho$ = 0.0433)* |
| whole cell + alum | 3/8 ($\rho$ = 0.145) | 0/8 ($\rho$ = 0.00002)* |
| convalescent | 1/6 ($\rho$ = 0.035) | 0/6 ($\rho$ = 0.0001)* |

LIST OF REFERENCES

Barcak et al., (1991) Methods Enzymol. 204: 321–342.
Berkowitz et al., (1987) J. Pediatr. 110:509.
Black et al., (1991) Pediatr. Infect. Dis. J. 10:97.
Bluestone, N. (1982) Engl. J. Med. 306:1399.
Chang et al., (1978) Nature 375:615.
Chou, et al., (1978). Annual Reviews of Biochemistry 47, 251–276.
Claesson et al., (1989) J. Pediatr. 114:97.
Cornelissen et al., (1992) J. Bacteriol. 174:5788
Danve, et al., (1993). Vaccine 11, 1214–1220.
Deres et al., (1989) Nature 342:651.
Gerlach, et al., (1992) Infect. Immun. 608:325
Goeddel et al., (1979) Nature 281:544.
Goeddel et al., (1980) Nucl. Acids Res. 8:4057
Harkness et al., (1992) J. Bacteriol. 174:2425.
Holland et al., (1992) Infect. Immun. 60:2986.
Hopp, T. P. (1986) Journal of Immunological Methods 88, 1–18.
Itakura et al., (1977) Science 198:1056.
Jarosik et al., (1994). Infection and Immunity 62, 2470–2477.
Legrain et al., (1993). Gene 130:73
Lockhoff et al., (1991) Chem. Int. Ed. Engl. 30:1611.
Mickelsen and Sparling, (1981) Infect. Immun. 33:555.
Morton et al., (1993) Infection and Immunity 61, 4033–4037.
Murdin et al., (1992) J. Gen. Viral 73: 607.
Murdin et al., (1991) Microbial Pathogenesis 10:27.
Nixon-George et al., (1990) J. Immunol. 14:4798.
Ogunnariwo, and Schryvers, (1992) Avian Dis. 36:655.
O'Hagan (1992) Clin Pharmokinet. 22:1.
Panezutti et al., (1993) Infection and Immunity 61, 1867–1872.
Roosi-Campos et al., (1992) Vaccine 10, 512–518.
Schryvers, (1988) Molec. Microbiol. 2:467.
Schryvers and Lee, (1989) Can. J. Microbiol. 35:409.
Schryvers and Gray-Owen, (1992) J. Infect. Dis. 165 suppl 1:S103.
Schryvers (1989) Med. Microbiol. 29:121.
Short et al., (1988) Nucl. Acids Res. 16:7583.
Ulmer et al., (1993) Curr. Opinion Invest. Drugs. 2 (9): 983–989.
Van der Werf et al., (1986) Proc. Natl. Acad. Sci. 83: 2330.
Weismuller et al., (1989) Vaccine 8:29.
Wilton et al., (1993) FEMS Microbiology Letters 107, 59–66.
Loeb et al, 1987 Infect. Immun. 55:2612–2618.
Barenkamp et al, 1988 Infect. Immun. 52:572–578.
Morton and Williams 1990—J. Gen. Microbiol. 136:927–933.
U.S. Pat. No. 4,855,283
U.S. Pat. No. 4,258,029
U.S. Pat. No. 4,496,538
U.S. Pat. No. 4,599,230
U.S. Pat. No. 4,599,231
U.S. Pat. No. 4,601,903
U.S. Pat. No. 5,141,743
U.S. Pat. No. 4,596,792
U.S. Pat. No. 4,952,496
U.S. Pat. No. 5,194,254
WO 92/17167

We claim:

1. An immunogenic composition comprising not more than one synthetic peptide having no less than six amino acids and no more than 150 amino acids, and a pharmaceutically acceptable carrier thereof; wherein the synthetic peptide is comprised of the amino acid sequence, LEGGFYGP (SEQ ID NO: 74) or LEGGFYG (SEQ ID NO: 85), and which produces an immune response when administered to a host.

2. The immunogenic composition of claim 1, wherein the synthetic peptide is selected from the group consisting of:
LEGGFYGPKGEELGFRFLAGDKKVFGVFSAK (SEQ ID NO: 50),
FTSEGTLEGGFYGPEGQELGGKFLAHDKKVLGVFS (SEQ ID NO: 61) and
LEGGFYGP (SEQ ID NO: 74).

3. The immunogenic composition of claim 2, wherein the synthetic peptide is LEGGFYGP (SEQ ID NO: 74).

4. An immunogenic composition consisting essentially of:
(a) a synthetic peptide having no less than six amino acids and no more than 150 amino acids and comprised of the amino acid sequence, LEGGFYGP (SEQ ID NO: 74) or LEGGFYG (SEQ ID NO: 85),
(b) an adjuvant, and
(c) a pharmaceutically acceptable carrier thereof; and which produces an immune response when administered to a host.

5. An immunogenic composition consisting essentially of:
(a) a synthetic peptide having an amino acid sequence selected from the group consisting of:
LEGGFYOPKGEELGFRFLAGDKKVFGVFSAK (SEQ ID NO: 50),
FTSEGTLEGGFYGPEGQELGGKFLAHDKKVLGVFS (SEQ ID NO: 61) and
LEGGFYGP (SEQ ID NO: 74),
(b) an adjuvant, and
(c) a pharmaceutically acceptable carrier thereof; and which produces an immune response when administered to a host.

6. An immunogenic composition consisting essentially of:
(a) the synthetic peptide having the amino acid sequence LEGGFYGP (SEQ ID NO: 74),
(b) an adjuvant, and
(c) a pharmaceutically acceptable carder thereof; and which produces an immune response when administered to a host.

* * * * *